US012064567B2

(12) United States Patent
Erbey, II et al.

(10) Patent No.: US 12,064,567 B2
(45) Date of Patent: *Aug. 20, 2024

(54) PERCUTANEOUS URINARY CATHETER

(71) Applicant: Roivios Limited, Nassau (BS)

(72) Inventors: John R. Erbey, II, Milton, GA (US); Bryan J. Tucker, Chapel Hill, NC (US); Jacob L. Upperco, Atlanta, GA (US)

(73) Assignee: Roivios Limited, Nassau (BS)

( * ) Notice: Subject to any disclaimer, the term of this patent is extended or adjusted under 35 U.S.C. 154(b) by 320 days.

This patent is subject to a terminal disclaimer.

(21) Appl. No.: 17/520,850

(22) Filed: Nov. 8, 2021

(65) Prior Publication Data

US 2022/0054798 A1 Feb. 24, 2022

Related U.S. Application Data

(63) Continuation of application No. 16/206,207, filed on Nov. 30, 2018, now Pat. No. 11,229,771, which is a
(Continued)

(51) Int. Cl.
*A61M 25/00* (2006.01)
*A61F 2/04* (2013.01)
(Continued)

(52) U.S. Cl.
CPC ............ *A61M 25/0074* (2013.01); *A61F 2/04* (2013.01); *A61M 1/74* (2021.05); *A61M 1/76* (2021.05);
(Continued)

(58) Field of Classification Search
CPC ............ A61M 27/008; A61M 25/0017; A61M 25/007; A61M 2210/1085;
(Continued)

(56) References Cited

U.S. PATENT DOCUMENTS 1,870,942 A 8/1932 Beatty
2,285,980 A 6/1942 Jeckel
(Continued)

FOREIGN PATENT DOCUMENTS

AU 2013332448 A1 4/2015
CA 1243581 A 10/1988
(Continued)

OTHER PUBLICATIONS

Mordi et al., "Renal and Cardiovascular Effects of sodium-glucose cotransporter 2 (SGLT2) inhibition with loop Diuretics in diabetic patents with Chronic Heart Failure (REEDE-CHF): protocol for a randomised controlled double-blind cross-over trail". BJM open, 2017, vol. 7, pp. 1-9.
(Continued)

*Primary Examiner* — Adam Marcetich
(74) *Attorney, Agent, or Firm* — The Webb Law Firm

(57) ABSTRACT

A percutaneous urinary catheter configured to be deployed in a urinary tract, including: (a) a proximal portion; and (b) a distal portion including a retention portion configured to be deployed in a kidney and/or a renal pelvis, the retention portion including one or more drainage holes leading to one or more lumen(s) within the proximal portion, wherein the retention portion, when deployed, defines a three-dimensional shape sized and positioned to maintain patency of fluid flow between the kidney and/or renal pelvis and a proximal end of the catheter by inhibiting mucosal tissue from appreciably occluding the one or more drainage holes when negative pressure is applied through the catheter.

38 Claims, 86 Drawing Sheets

Related U.S. Application Data continuation-in-part of application No. 15/879,770, filed on Jan. 25, 2018, now Pat. No. 11,040,180, which is a continuation-in-part of application No. 15/687,064, filed on Aug. 25, 2017, now Pat. No. 10,765,834, which is a continuation-in-part of application No. 15/411,884, filed on Jan. 20, 2017, now Pat. No. 10,512,713, which is a continuation-in-part of application No. 15/214,955, filed on Jul. 20, 2016, now Pat. No. 10,307,564, said application No. 15/879,770 is a continuation-in-part of application No. 15/687,083, filed on Aug. 25, 2017, now Pat. No. 10,926,062, which is a continuation-in-part of application No. 15/411,884, filed on Jan. 20, 2017, now Pat. No. 10,512,713, said application No. 15/879,770 is a continuation-in-part of application No. 15/745,823, filed as application No. PCT/US2016/043101 on Jul. 20, 2016, now abandoned.

(60) Provisional application No. 62/300,025, filed on Feb. 25, 2016, provisional application No. 62/278,721, filed on Jan. 14, 2016, provisional application No. 62/260,966, filed on Nov. 30, 2015, provisional application No. 62/194,585, filed on Jul. 20, 2015, provisional application No. 62/489,789, filed on Apr. 25, 2017, provisional application No. 62/489,831, filed on Apr. 25, 2017.

(51) Int. Cl.
  *A61M 1/00* (2006.01)
  *A61M 25/04* (2006.01)
  *A61M 25/06* (2006.01)
  *A61M 25/10* (2013.01)
  *A61M 27/00* (2006.01)

(52) U.S. Cl.
  CPC .......... *A61M 25/007* (2013.01); *A61M 25/04* (2013.01); *A61M 25/065* (2013.01); *A61M 25/10* (2013.01); *A61M 27/002* (2013.01); *A61F 2002/047* (2013.01); *A61F 2002/048* (2013.01); *A61M 1/84* (2021.05); *A61M 2205/0266* (2013.01); *A61M 2205/3303* (2013.01); *A61M 2210/1082* (2013.01); *A61M 2210/1085* (2013.01); *A61M 2210/1089* (2013.01); *A61M 2230/207* (2013.01)

(58) Field of Classification Search
  CPC .......... A61M 2210/1082; A61M 25/04; A61M 1/84; A61M 2210/1089; A61B 5/201
  See application file for complete search history.

(56) References Cited

U.S. PATENT DOCUMENTS

| | | |
|---|---|---|
| 2,649,092 A | 8/1953 | Wallace |
| 3,108,595 A | 10/1963 | Overment |
| 3,397,699 A | 8/1968 | Kohl |
| 3,561,431 A | 2/1971 | Pannier, Jr. |
| 3,707,967 A | 1/1973 | Kitrilakis |
| 3,875,941 A | 4/1975 | Adair |
| 3,938,529 A | 2/1976 | Gibbons |
| 3,938,530 A | 2/1976 | Santomieri |
| 3,943,929 A | 3/1976 | Patel |
| 4,265,243 A | 5/1981 | Taylor |
| 4,306,557 A | 12/1981 | North |
| 4,324,663 A | 4/1982 | Hirel et al. |
| 4,349,029 A | 9/1982 | Mott |
| 4,425,124 A | 1/1984 | Womack |
| 4,437,856 A | 3/1984 | Valli |
| 4,531,933 A | 7/1985 | Norton et al. |
| 4,568,338 A | 2/1986 | Todd |
| 4,571,241 A | 2/1986 | Christopher |
| 4,575,371 A | 3/1986 | Nordqvist et al. |
| 4,629,015 A | 12/1986 | Fried et al. |
| 4,681,564 A | 7/1987 | Landreneau |
| 4,710,169 A | 12/1987 | Christopher |
| 4,738,667 A | 4/1988 | Galloway |
| 4,813,935 A | 3/1989 | Haber et al. |
| 4,834,724 A | 5/1989 | Geiss et al. |
| 4,932,938 A | 6/1990 | Goldberg et al. |
| 4,935,004 A | 6/1990 | Cruz |
| 4,945,895 A | 8/1990 | Takai et al. |
| 4,950,228 A | 8/1990 | Knapp, Jr. et al. |
| 4,957,479 A | 9/1990 | Roemer |
| 5,009,639 A | 4/1991 | Keymling |
| 5,011,488 A | 4/1991 | Ginsburg |
| 5,041,093 A | 8/1991 | Chu |
| 5,044,902 A | 9/1991 | Malbec |
| 5,059,169 A | 10/1991 | Zilber |
| 5,078,684 A | 1/1992 | Yasuda |
| 5,098,440 A | 3/1992 | Hillstead |
| 5,116,309 A | 5/1992 | Coll |
| 5,141,502 A | 8/1992 | Macaluso, Jr. |
| 5,193,533 A | 3/1993 | Body et al. |
| 5,256,146 A | 10/1993 | Ensminger et al. |
| 5,370,690 A | 12/1994 | Barrett |
| 5,401,257 A | 3/1995 | Chevalier, Jr. et al. |
| 5,451,215 A | 9/1995 | Wolter |
| 5,451,218 A | 9/1995 | Moore |
| 5,505,717 A | 4/1996 | Moore |
| 5,514,112 A | 5/1996 | Chu et al. |
| 5,523,092 A | 6/1996 | Hanson et al. |
| 5,536,274 A | 7/1996 | Neuss |
| 5,540,701 A | 7/1996 | Sharkey et al. |
| 5,554,144 A | 9/1996 | Wallace et al. |
| 5,562,622 A | 10/1996 | Tihon |
| 5,599,291 A | 2/1997 | Balbierz et al. |
| 5,647,843 A | 7/1997 | Mesrobian et al. |
| 5,662,713 A | 9/1997 | Andersen et al. |
| 5,709,874 A | 1/1998 | Hanson et al. |
| 5,727,555 A | 3/1998 | Chait |
| 5,769,821 A | 6/1998 | Abrahamson et al. |
| 5,785,641 A | 7/1998 | Davis |
| 5,795,319 A | 8/1998 | Ali |
| 5,865,764 A | 2/1999 | Moorhead |
| 5,873,865 A | 2/1999 | Horzewski et al. |
| 5,895,398 A | 4/1999 | Wensel et al. |
| 5,902,336 A | 5/1999 | Mishkin |
| 5,915,386 A | 6/1999 | Lloyd et al. |
| 5,957,867 A | 9/1999 | Lloyd et al. |
| 5,972,019 A | 10/1999 | Engelson et al. |
| 5,989,207 A | 11/1999 | Hughes |
| 6,066,113 A | 5/2000 | Overtoom |
| 6,090,069 A | 7/2000 | Walker |
| 6,111,520 A | 8/2000 | Allen et al. |
| 6,200,485 B1 | 3/2001 | Kitaevich et al. |
| 6,214,037 B1 | 4/2001 | Mitchell et al. |
| 6,283,940 B1 | 9/2001 | Mulholland |
| 6,332,892 B1 | 12/2001 | Desmond, III et al. |
| 6,364,868 B1 | 4/2002 | Ikeguchi |
| 6,402,736 B1 | 6/2002 | Brown et al. |
| 6,442,415 B1 | 8/2002 | Bis et al. |
| 6,461,346 B1 | 10/2002 | Buelna |
| 6,478,778 B1 | 11/2002 | Jacobsen et al. |
| 6,482,222 B1 | 11/2002 | Bruckheimer et al. |
| 6,500,158 B1 | 12/2002 | Ikeguchi |
| 6,558,350 B1 | 5/2003 | Hart et al. |
| 6,569,150 B2 | 5/2003 | Teague et al. |
| 6,620,202 B2 | 9/2003 | Bottcher et al. |
| 6,648,863 B2 | 11/2003 | Reever |
| 6,676,623 B2 | 1/2004 | Whitmore, III |
| 6,685,744 B2 | 2/2004 | Gellman et al. |
| 6,699,216 B2 | 3/2004 | Ikeguchi |
| 6,702,834 B1 | 3/2004 | Boylan et al. |
| 6,764,519 B2 | 7/2004 | Whitmore, III |
| 6,780,322 B1 | 8/2004 | Bissler et al. |
| 6,837,868 B1 | 1/2005 | Fajnsztajn |
| 7,025,753 B2 | 4/2006 | Reever |

(56) References Cited

U.S. PATENT DOCUMENTS

| | | |
|---|---|---|
| 7,037,345 B2 | 5/2006 | Bottcher et al. |
| 7,044,981 B2 | 5/2006 | Liu et al. |
| 7,316,663 B2 | 1/2008 | Whitmore, III |
| 7,329,226 B1 | 2/2008 | Ni et al. |
| 7,396,366 B2 | 7/2008 | Ward |
| 7,507,218 B2 | 3/2009 | Aliski et al. |
| 7,550,978 B2 | 6/2009 | Joy et al. |
| 7,603,170 B2 | 10/2009 | Hatlestad et al. |
| 7,682,401 B2 | 3/2010 | Deal |
| 7,722,677 B2 | 5/2010 | Ward |
| 7,727,222 B2 | 6/2010 | Da Silva et al. |
| 7,736,354 B2 | 6/2010 | Gelfand et al. |
| 7,758,562 B2 | 7/2010 | Gelfand et al. |
| 7,758,563 B2 | 7/2010 | Gelfand et al. |
| 7,766,961 B2 | 8/2010 | Patel et al. |
| 7,837,667 B2 | 11/2010 | Gelfand et al. |
| 7,850,704 B2 | 12/2010 | Burnett et al. |
| 7,857,803 B1 | 12/2010 | Salinas et al. |
| 7,879,020 B1 | 2/2011 | Salinas et al. |
| 7,938,817 B2 | 5/2011 | Gelfand et al. |
| 7,972,292 B2 | 7/2011 | Behl et al. |
| 8,007,460 B2 | 8/2011 | Gelfand et al. |
| 8,021,307 B2 | 9/2011 | White et al. |
| 8,075,513 B2 | 12/2011 | Rudko et al. |
| 8,088,170 B2 | 1/2012 | Whitmore, III |
| 8,105,317 B2 | 1/2012 | Reever et al. |
| 8,152,786 B2 | 4/2012 | Shapland et al. |
| 8,157,785 B2 | 4/2012 | Salinas et al. |
| 8,177,741 B2 | 5/2012 | Hammack et al. |
| 8,252,065 B2 | 8/2012 | Ward |
| 8,328,877 B2 | 12/2012 | Gellman |
| 8,444,623 B2 | 5/2013 | Gelfand et al. |
| 8,486,010 B2 | 7/2013 | Nomura |
| 8,512,795 B2 | 8/2013 | Dias et al. |
| 8,568,387 B2 | 10/2013 | Paz |
| 8,585,675 B2 | 11/2013 | Salinas et al. |
| 8,597,260 B2 | 12/2013 | Tucker |
| 8,597,273 B2 | 12/2013 | Salinas et al. |
| 8,747,388 B2 | 6/2014 | Pandey et al. |
| 8,795,305 B2 | 8/2014 | Martin et al. |
| 8,827,924 B2 | 9/2014 | Paz et al. |
| 8,852,289 B2 | 10/2014 | Whitmore, III |
| 8,865,063 B2 | 10/2014 | Burnett |
| 8,932,320 B1 | 1/2015 | Janardhan et al. |
| 9,014,815 B2 | 4/2015 | Yang et al. |
| 9,060,888 B2 | 6/2015 | Gellman |
| 9,308,348 B2 | 4/2016 | Mulvihill et al. |
| 9,339,636 B1 | 5/2016 | Khan et al. |
| 9,682,220 B2 | 6/2017 | Schertiger et al. |
| 9,744,331 B2 | 8/2017 | Erbey, II et al. |
| 9,750,634 B2 | 9/2017 | Bar-Am |
| 9,788,928 B2 | 10/2017 | Forsell |
| 9,849,224 B2 | 12/2017 | Angwin et al. |
| 9,980,663 B2 | 5/2018 | Wabel et al. |
| 10,182,747 B2 | 1/2019 | Charlez et al. |
| 10,226,606 B2 | 3/2019 | Wan et al. |
| 10,307,564 B2 | 6/2019 | Erbey, II et al. |
| 10,307,566 B2 | 6/2019 | Bishawi |
| 10,449,329 B2 | 10/2019 | Foley et al. |
| 11,040,180 B2 | 6/2021 | Erbey, II et al. |
| 2001/0053936 A1 | 12/2001 | Whitmore, III |
| 2001/0056273 A1 | 12/2001 | Ewers |
| 2002/0052576 A1 | 5/2002 | Massengale |
| 2002/0062148 A1 | 5/2002 | Hart |
| 2002/0068093 A1 | 6/2002 | Trogolo et al. |
| 2002/0082547 A1 | 6/2002 | Deniega et al. |
| 2002/0085951 A1 | 7/2002 | Gelfand et al. |
| 2002/0143292 A1 | 10/2002 | Flinchbaugh |
| 2002/0143389 A1 | 10/2002 | St. Pierre |
| 2002/0177902 A1 | 11/2002 | Rioux et al. |
| 2002/0183852 A1 | 12/2002 | McWeeney |
| 2002/0183853 A1 | 12/2002 | Mitchell et al. |
| 2002/0188246 A1 | 12/2002 | Hayner et al. |
| 2002/0193667 A1 | 12/2002 | McNair |
| 2003/0009132 A1 | 1/2003 | Schwartz et al. |
| 2003/0018291 A1 | 1/2003 | Hill et al. |
| 2003/0060806 A1 | 3/2003 | Ikeguchi |
| 2003/0069534 A1 | 4/2003 | Work et al. |
| 2003/0074082 A1 | 4/2003 | Bottcher et al. |
| 2003/0109930 A1 | 6/2003 | Bluni et al. |
| 2003/0120261 A1 | 6/2003 | Gellman |
| 2003/0135147 A1 | 7/2003 | Rosenberg et al. |
| 2003/0135195 A1 | 7/2003 | Jimenez et al. |
| 2003/0144623 A1 | 7/2003 | Heath et al. |
| 2003/0153970 A1 | 8/2003 | Rao et al. |
| 2003/0171708 A1 | 9/2003 | Segura et al. |
| 2003/0176831 A1 | 9/2003 | Gellman et al. |
| 2003/0181842 A1 | 9/2003 | Gellman |
| 2003/0181887 A1 | 9/2003 | Castillo Deniega et al. |
| 2003/0191452 A1 | 10/2003 | Meglin et al. |
| 2003/0195456 A1 | 10/2003 | Robertson |
| 2003/0195537 A1 | 10/2003 | Dubrul et al. |
| 2003/0199805 A1 | 10/2003 | McWeeney |
| 2003/0216710 A1 | 11/2003 | Hurt |
| 2003/0224033 A1 | 12/2003 | Li et al. |
| 2004/0019358 A1 | 1/2004 | Kear |
| 2004/0054315 A1 | 3/2004 | Levin et al. |
| 2004/0054351 A1 | 3/2004 | Deniega et al. |
| 2004/0057037 A1 | 3/2004 | Ohishi et al. |
| 2004/0073194 A1 | 4/2004 | Olsen et al. |
| 2004/0097891 A1 | 5/2004 | Bolmsjo |
| 2004/0129616 A1 | 7/2004 | Mori et al. |
| 2004/0143209 A1 | 7/2004 | Liu et al. |
| 2004/0147871 A1 | 7/2004 | Burnett |
| 2004/0167415 A1 | 8/2004 | Gelfand et al. |
| 2004/0167634 A1 | 8/2004 | Atala et al. |
| 2004/0193098 A1 | 9/2004 | Wentling et al. |
| 2005/0042240 A1 | 2/2005 | Utterberg et al. |
| 2005/0049575 A1 | 3/2005 | Snell et al. |
| 2005/0049577 A1 | 3/2005 | Snell et al. |
| 2005/0101941 A1 | 5/2005 | Hakky et al. |
| 2005/0107736 A1 | 5/2005 | Landman et al. |
| 2005/0124969 A1 | 6/2005 | Fitzgerald et al. |
| 2005/0124978 A1 | 6/2005 | Kim |
| 2005/0177102 A1 | 8/2005 | Hart et al. |
| 2005/0187564 A1 | 8/2005 | Jayaraman |
| 2005/0240141 A1 | 10/2005 | Aliski et al. |
| 2005/0240280 A1 | 10/2005 | Aliski et al. |
| 2005/0256441 A1 | 11/2005 | Lotan et al. |
| 2005/0256447 A1 | 11/2005 | Richardson et al. |
| 2005/0288722 A1 | 12/2005 | Eigler et al. |
| 2006/0015015 A1 | 1/2006 | Kawamoto et al. |
| 2006/0015089 A1 | 1/2006 | Meglin et al. |
| 2006/0052879 A1 | 3/2006 | Kolb |
| 2006/0074388 A1 | 4/2006 | Dextradeur et al. |
| 2006/0074409 A1 | 4/2006 | Schuermann |
| 2006/0229553 A1 | 10/2006 | Hammack et al. |
| 2006/0229573 A1 | 10/2006 | Lamborne |
| 2006/0259151 A1 | 11/2006 | Ward |
| 2006/0271019 A1 | 11/2006 | Stoller et al. |
| 2007/0010797 A1 | 1/2007 | Nishtala et al. |
| 2007/0010798 A1 | 1/2007 | Stoller et al. |
| 2007/0055198 A1 | 3/2007 | OMahony et al. |
| 2007/0073271 A1 | 3/2007 | Brucker et al. |
| 2007/0088333 A1 | 4/2007 | Levin et al. |
| 2007/0112302 A1 | 5/2007 | Yu |
| 2007/0197957 A1 | 8/2007 | Hunter et al. |
| 2007/0208291 A1 | 9/2007 | Patel |
| 2007/0213665 A1 | 9/2007 | Curtin et al. |
| 2007/0219488 A1 | 9/2007 | Francescatti |
| 2007/0255230 A1 | 11/2007 | Gross et al. |
| 2008/0051678 A1 | 2/2008 | Lindahl |
| 2008/0051691 A1 | 2/2008 | Dragoon et al. |
| 2008/0058650 A1 | 3/2008 | Saadat et al. |
| 2008/0097463 A1 | 4/2008 | House |
| 2008/0119907 A1 | 5/2008 | Stahmann |
| 2008/0142023 A1 | 6/2008 | Schmid et al. |
| 2008/0183299 A1 | 7/2008 | Monga et al. |
| 2008/0215247 A1 | 9/2008 | Tonelli et al. |
| 2008/0243091 A1 | 10/2008 | Humphreys et al. |
| 2008/0255550 A1 | 10/2008 | Bell |
| 2008/0281291 A1 | 11/2008 | Tihon et al. |
| 2008/0288082 A1 | 11/2008 | Deal |
| 2008/0312550 A1 | 12/2008 | Nishtala et al. |

(56) References Cited

U.S. PATENT DOCUMENTS

| | | |
|---|---|---|
| 2009/0024091 A1 | 1/2009 | Li et al. |
| 2009/0030370 A1 | 1/2009 | Nishtala et al. |
| 2009/0030435 A1 | 1/2009 | Burnett et al. |
| 2009/0043229 A1 | 2/2009 | Dunn et al. |
| 2009/0088677 A1 | 4/2009 | Cohen |
| 2009/0093748 A1 | 4/2009 | Patterson et al. |
| 2009/0105719 A1 | 4/2009 | Honey et al. |
| 2009/0143713 A1 | 6/2009 | Van Dam et al. |
| 2009/0162530 A1 | 6/2009 | Nesbitt |
| 2009/0171137 A1 | 7/2009 | Farnan et al. |
| 2009/0171241 A1 | 7/2009 | Garcia et al. |
| 2009/0281507 A1 | 11/2009 | Humphreys |
| 2009/0318844 A1 | 12/2009 | Burnett |
| 2010/0057000 A1 | 3/2010 | Melsheimer et al. |
| 2010/0081148 A1 | 4/2010 | Singbartl et al. |
| 2010/0086580 A1 | 4/2010 | Nyman et al. |
| 2010/0121159 A1 | 5/2010 | Burnett et al. |
| 2010/0191183 A1 | 7/2010 | Tanghoej et al. |
| 2010/0204682 A1 | 8/2010 | Tanghoj et al. |
| 2010/0241240 A1 | 9/2010 | Willard et al. |
| 2010/0261985 A1 | 10/2010 | Cohen-Solal et al. |
| 2010/0298857 A1 | 11/2010 | Zook et al. |
| 2010/0312163 A1 | 12/2010 | Forsell |
| 2011/0009799 A1 | 1/2011 | Mullick et al. |
| 2011/0009831 A1 | 1/2011 | Burkholz et al. |
| 2011/0015558 A1 | 1/2011 | Kaye et al. |
| 2011/0077605 A1 | 3/2011 | Karpowicz et al. |
| 2011/0089111 A1 | 4/2011 | Mori et al. |
| 2011/0098683 A1 | 4/2011 | Wiita et al. |
| 2011/0118537 A1 | 5/2011 | Wampler |
| 2011/0132838 A1 | 6/2011 | Curtis et al. |
| 2011/0208319 A1 | 8/2011 | Laster |
| 2011/0230950 A1 | 9/2011 | Knapp |
| 2011/0238163 A1 | 9/2011 | Andrews et al. |
| 2011/0269167 A1 | 11/2011 | Bene |
| 2011/0276024 A1 | 11/2011 | Randolph et al. |
| 2011/0282264 A1 | 11/2011 | Hurt |
| 2011/0301553 A1 | 12/2011 | Goral et al. |
| 2011/0301662 A1 | 12/2011 | Bar-Yoseph et al. |
| 2011/0320008 A1 | 12/2011 | Teague et al. |
| 2012/0029937 A1 | 2/2012 | Neftel et al. |
| 2012/0042427 A1 | 2/2012 | Messier |
| 2012/0053700 A1 | 3/2012 | Rickner |
| 2012/0078226 A1 | 3/2012 | Latere Dwan'isa et al. |
| 2012/0083899 A1 | 4/2012 | Whitmore, III |
| 2012/0107420 A1 | 5/2012 | Breit et al. |
| 2012/0136343 A1 | 5/2012 | Burnett |
| 2012/0154264 A1 | 6/2012 | Wang et al. |
| 2012/0165641 A1 | 6/2012 | Burnett et al. |
| 2012/0179144 A1 | 7/2012 | Carleo |
| 2012/0179145 A1 | 7/2012 | Nishtala et al. |
| 2012/0220926 A1 | 8/2012 | Soykan et al. |
| 2012/0238802 A1 | 9/2012 | Knight et al. |
| 2012/0265020 A1 | 10/2012 | Pandey et al. |
| 2012/0277155 A1 | 11/2012 | VanAntwerp et al. |
| 2012/0316656 A1 | 12/2012 | Deal et al. |
| 2013/0030262 A1 | 1/2013 | Burnett et al. |
| 2013/0066166 A1 | 3/2013 | Burnett et al. |
| 2013/0085468 A1 | 4/2013 | Buydenok |
| 2013/0090648 A1 | 4/2013 | Nagale et al. |
| 2013/0131621 A1 | 5/2013 | Van Holten et al. |
| 2013/0138077 A1 | 5/2013 | ODay |
| 2013/0150828 A1 | 6/2013 | Conway |
| 2013/0172807 A1 | 7/2013 | Cruz |
| 2013/0172881 A1 | 7/2013 | Hill et al. |
| 2013/0184545 A1 | 7/2013 | Blomqvist et al. |
| 2013/0187563 A1 | 7/2013 | Sasai et al. |
| 2013/0197471 A1 | 8/2013 | Williams et al. |
| 2013/0199998 A1 | 8/2013 | Kelly et al. |
| 2013/0218135 A1 | 8/2013 | Dein |
| 2013/0231640 A1 | 9/2013 | Terry et al. |
| 2013/0231752 A1 | 9/2013 | Rosenbaum et al. |
| 2013/0253409 A1 | 9/2013 | Burnett |
| 2013/0267845 A1 | 10/2013 | Howle et al. |
| 2013/0274644 A1 | 10/2013 | Hertz |
| 2013/0274783 A1 | 10/2013 | Wynberg |
| 2013/0303865 A1 | 11/2013 | Rebec et al. |
| 2013/0303961 A1 | 11/2013 | Wolff et al. |
| 2013/0304082 A1 | 11/2013 | Aklog et al. |
| 2013/0317322 A1 | 11/2013 | Andrijauskas |
| 2013/0331824 A1 | 12/2013 | Kim |
| 2013/0338580 A1 | 12/2013 | Yamatani et al. |
| 2013/0345670 A1 | 12/2013 | Rajagopalan et al. |
| 2014/0031773 A1 | 1/2014 | Mikkaichi |
| 2014/0031787 A1 | 1/2014 | Burnes et al. |
| 2014/0039375 A1 | 2/2014 | Jimenez et al. |
| 2014/0058316 A1 | 2/2014 | Gupta et al. |
| 2014/0073926 A1 | 3/2014 | Rajendran et al. |
| 2014/0074144 A1 | 3/2014 | Shrivastava et al. |
| 2014/0135941 A1 | 5/2014 | Smouse et al. |
| 2014/0142539 A1 | 5/2014 | Salinas et al. |
| 2014/0148648 A1 | 5/2014 | Tycast et al. |
| 2014/0148754 A1 | 5/2014 | Soykan et al. |
| 2014/0155818 A1 | 6/2014 | Salinas et al. |
| 2014/0188248 A1 | 7/2014 | Gandhi |
| 2014/0188249 A1 | 7/2014 | Pendleton et al. |
| 2014/0214009 A1 | 7/2014 | Reyes |
| 2014/0228801 A1 | 8/2014 | Keeling |
| 2014/0275984 A1 | 9/2014 | Hermann et al. |
| 2014/0276341 A1 | 9/2014 | Ludin et al. |
| 2014/0276628 A1 | 9/2014 | Gandras et al. |
| 2014/0343515 A1 | 11/2014 | Sylvester et al. |
| 2014/0364820 A1 | 12/2014 | Solazzo et al. |
| 2015/0011855 A1 | 1/2015 | Burnett et al. |
| 2015/0011928 A1 | 1/2015 | Burnett |
| 2015/0017682 A1 | 1/2015 | Adam |
| 2015/0065783 A1 | 3/2015 | Buelna |
| 2015/0080844 A1 | 3/2015 | Donovan et al. |
| 2015/0094548 A1 | 4/2015 | Sabatini et al. |
| 2015/0094644 A1 | 4/2015 | Lenihan et al. |
| 2015/0094696 A1 | 4/2015 | Adams, Jr. et al. |
| 2015/0100009 A1 | 4/2015 | Bearss |
| 2015/0134073 A1 | 5/2015 | Tang et al. |
| 2015/0164370 A1 | 6/2015 | Wabel et al. |
| 2015/0194052 A1 | 7/2015 | Sagan et al. |
| 2015/0223953 A1 | 8/2015 | Pendleton et al. |
| 2015/0224241 A1 | 8/2015 | Fontanazzi et al. |
| 2015/0273120 A1 | 10/2015 | Zamarripa et al. |
| 2015/0283362 A1 | 10/2015 | Shelton et al. |
| 2015/0290411 A1 | 10/2015 | Warrington et al. |
| 2015/0306364 A1 | 10/2015 | Shevgoor |
| 2015/0328027 A1 | 11/2015 | Nishio et al. |
| 2015/0352339 A1 | 12/2015 | Wang |
| 2016/0051176 A1 | 2/2016 | Ramos et al. |
| 2016/0058489 A1 | 3/2016 | Fischell et al. |
| 2016/0183819 A1 | 6/2016 | Burnett et al. |
| 2016/0213881 A9 | 7/2016 | Adams, Jr. et al. |
| 2016/0303303 A1 | 10/2016 | Rovatti et al. |
| 2016/0310711 A1 | 10/2016 | Luxon et al. |
| 2016/0331294 A1 | 11/2016 | Imran et al. |
| 2016/0367747 A1 | 12/2016 | Loske |
| 2017/0020724 A1 | 1/2017 | Burnett et al. |
| 2017/0021128 A1 | 1/2017 | Erbey, II et al. |
| 2017/0095323 A1 | 4/2017 | Garcia |
| 2017/0095641 A1 | 4/2017 | Scarpine et al. |
| 2017/0113000 A1 | 4/2017 | Tobescu et al. |
| 2017/0119519 A1 | 5/2017 | Sambusseti et al. |
| 2017/0128639 A1 | 5/2017 | Erbey, II et al. |
| 2017/0128654 A1 | 5/2017 | Feld |
| 2017/0136222 A1 | 5/2017 | Hakim et al. |
| 2017/0196576 A1 | 7/2017 | Long et al. |
| 2017/0197028 A1 | 7/2017 | Goldsmith |
| 2017/0232153 A1 | 8/2017 | Babu et al. |
| 2017/0266414 A1 | 9/2017 | Rocha-Singh et al. |
| 2017/0325927 A1 | 11/2017 | Gobel |
| 2017/0348507 A1 | 12/2017 | Erbey, II et al. |
| 2017/0348512 A1 | 12/2017 | Orr et al. |
| 2017/0367636 A1 | 12/2017 | Mantinband et al. |
| 2018/0001055 A1 | 1/2018 | Utas et al. |
| 2018/0116751 A1 | 5/2018 | Schwartz et al. |
| 2018/0117288 A1 | 5/2018 | Lindsay et al. |
| 2018/0147330 A1 | 5/2018 | Pend et al. |
| 2018/0169313 A1 | 6/2018 | Schwammenthal et al. |
| 2018/0177458 A1 | 6/2018 | Burnett et al. |

(56) References Cited

U.S. PATENT DOCUMENTS

| | | |
|---|---|---|
| 2018/0193618 A1 | 7/2018 | Erbey, II et al. |
| 2018/0207412 A1 | 7/2018 | Malek et al. |
| 2018/0214288 A1* | 8/2018 | Smouse ............... A61F 2/95 |
| 2018/0289394 A1* | 10/2018 | Shah .............. A61B 17/320016 |
| 2018/0344250 A1 | 12/2018 | McKinney et al. |
| 2019/0030303 A1 | 1/2019 | Holman et al. |
| 2019/0091442 A1 | 3/2019 | Erbey, II et al. |
| 2019/0105465 A1 | 4/2019 | Erbey, II et al. |
| 2019/0201662 A1 | 7/2019 | Lad et al. |
| 2019/0240448 A1 | 8/2019 | Murdock |
| 2019/0247615 A1 | 8/2019 | Bishawi |
| 2020/0001045 A1 | 1/2020 | McIntyre |
| 2020/0094017 A1 | 3/2020 | Erbey, II et al. |
| 2021/0178133 A1 | 6/2021 | Walish et al. |

FOREIGN PATENT DOCUMENTS

| | | |
|---|---|---|
| CA | 236001 C | 9/2000 |
| CA | 2205473 C | 6/2006 |
| CA | 2992546 A1 | 1/2017 |
| CA | 2992322 C | 8/2019 |
| CN | 2175619 Y | 8/1994 |
| CN | 2562776 Y | 7/2003 |
| CN | 2588940 Y | 12/2003 |
| CN | 1479596 A | 3/2004 |
| CN | 2724715 Y | 9/2005 |
| CN | 2753382 Y | 1/2006 |
| CN | 2928043 Y | 8/2007 |
| CN | 101224148 A | 7/2008 |
| CN | 101426540 A | 5/2009 |
| CN | 201814968 U | 5/2011 |
| CN | 102176928 A | 9/2011 |
| CN | 202459720 U | 10/2012 |
| CN | 202526754 U | 11/2012 |
| CN | 202802478 U | 3/2013 |
| CN | 103096964 A | 5/2013 |
| CN | 103203062 A | 7/2013 |
| CN | 103841905 A | 6/2014 |
| CN | 203777060 U | 8/2014 |
| CN | 203842151 U | 9/2014 |
| CN | 204158867 U | 2/2015 |
| CN | 204246651 U | 4/2015 |
| CN | 204446944 U | 7/2015 |
| CN | 205126495 U | 4/2016 |
| CN | 106237417 A | 12/2016 |
| CN | 106473847 A | 3/2017 |
| CN | 106693092 A | 5/2017 |
| CN | 107261294 A | 10/2017 |
| DE | 29606509 U1 | 8/1996 |
| EP | 873760 A1 | 10/1998 |
| EP | 1011803 B1 | 9/2004 |
| EP | 1980292 A2 | 10/2008 |
| EP | 3325076 A2 | 5/2018 |
| EP | 3470107 A1 | 4/2019 |
| EP | 3488897 A1 | 5/2019 |
| EP | 3970775 A1 | 3/2022 |
| FR | 3052671 A1 | 12/2017 |
| JP | 59111748 A | 6/1984 |
| JP | 3222965 A | 10/1991 |
| JP | H42361 A | 1/1992 |
| JP | 7500513 A | 1/1995 |
| JP | H10504469 | 5/1998 |
| JP | 2002510536 A | 4/2002 |
| JP | 2002291879 A | 10/2002 |
| JP | 200253888 | 11/2002 |
| JP | 2002537893 A | 11/2002 |
| JP | 2003203163 A | 1/2003 |
| JP | 2003530165 A | 10/2003 |
| JP | 2004215787 A | 8/2004 |
| JP | 2006516214 A | 6/2006 |
| JP | 2006526464 A | 11/2006 |
| JP | 2009505802 A | 2/2009 |
| JP | 2009238520 A | 10/2009 |
| JP | 2009537256 A | 10/2009 |
| JP | 201005282 A | 1/2010 |
| JP | 2010508984 A | 3/2010 |
| JP | 2010119737 A | 6/2010 |
| JP | 2010230618 A | 10/2010 |
| JP | 2013149498 A | 1/2012 |
| JP | 2012505022 A | 3/2012 |
| JP | 2014136116 A | 7/2014 |
| JP | 2014176689 A | 9/2014 |
| JP | 2018196754 A | 12/2018 |
| RU | 2113245 C1 | 6/1998 |
| RU | 2300399 C1 | 6/2007 |
| RU | 149161 U1 | 12/2014 |
| TW | M540625 U | 5/2017 |
| WO | 9529716 A1 | 11/1995 |
| WO | 9716218 A1 | 5/1997 |
| WO | 9816171 A1 | 4/1998 |
| WO | 9850088 A1 | 11/1998 |
| WO | 0054701 A1 | 9/2000 |
| WO | 0160260 A1 | 8/2001 |
| WO | 6558350 A1 | 12/2001 |
| WO | 03017870 A1 | 3/2003 |
| WO | 2004064681 A1 | 8/2004 |
| WO | 2006017439 A2 | 2/2006 |
| WO | 2006023589 A2 | 3/2006 |
| WO | 2006044621 A2 | 4/2006 |
| WO | 2007001978 A2 | 1/2007 |
| WO | 2007027830 A1 | 3/2007 |
| WO | 2008066625 A1 | 6/2008 |
| WO | 2010082197 A2 | 7/2010 |
| WO | 2011109570 A2 | 9/2011 |
| WO | 2011139498 A1 | 11/2011 |
| WO | 197896 A1 | 12/2011 |
| WO | 2013022005 A1 | 2/2013 |
| WO | 2013029622 A1 | 3/2013 |
| WO | 2014025367 A1 | 2/2014 |
| WO | 2014043650 A2 | 3/2014 |
| WO | 2014062225 A1 | 4/2014 |
| WO | 2015105916 A1 | 7/2015 |
| WO | 2015157467 A1 | 10/2015 |
| WO | 2015198333 A1 | 12/2015 |
| WO | 2016049654 A1 | 3/2016 |
| WO | 2016103256 A1 | 6/2016 |
| WO | 2017015345 A2 | 1/2017 |
| WO | 2017015351 A2 | 1/2017 |
| WO | 2017019974 A1 | 2/2017 |
| WO | 2017087182 A1 | 5/2017 |
| WO | 2018136603 A1 | 7/2018 |
| WO | 2018186781 A1 | 10/2018 |
| WO | 2018200050 A1 | 11/2018 |
| WO | 2019038730 A1 | 2/2019 |
| WO | 2020236748 A1 | 11/2020 |

OTHER PUBLICATIONS

Bart et al.; "Ultrafiltration in Decompensated Heart Failure with Cardiorenal Syndrome"; N Engl J Med; 2012; p. 2296-2304; vol. 367.

Burr et al.; "Urinary catheter blockage depends on urine pH, calcium and rate of flow"; Spinal Cord; 1997; p. 521-525; vol. 35.

Clinical Practice Guidelines for Chronic Kidney Disease: Evaluation, Classification and Stratification; National Kidney Foundation; Am. J. Kidney Dis.; 2002; p. S1-S266; Suppl. 1.

"The Criteria Committee of the New York Heart Association", (1994), Nomenclature and Criteria for Diagnosis of Diseases of the Heart and Great Vessels, (9th ed.), Boston: Little, Brown Co. p. 253-256 (Abstract).

Harris et al., "Relationship between patients" outcomes and the changes in serum creatinine and urine output and Rifle classification in a large critical care cohort database, Kidney International, 2015, p. 369-377, vol. 88.

Jessup et al.; "The Cardiorenal Syndrome—Do We Need a Change of Strategy or a Change of Tactics"; Journal of the American College of Cardiology; 2009; p. 597-599; vol. 53:7.

Mardis et al., "Comparative Evaluation of Materials Used for Internal Ureteral Stents", Journal of Endourology, 1993, pp. 105-115, vol. 7:2.

(56) References Cited

OTHER PUBLICATIONS

Mullens et al.; "Importance of Venous Congestion for Worsening of Renal Function in Advanced Decompensated Heart Failure"; Journal of the American College of Cardiology; 2009; p. 589-596; vol. 53:7.
Peters et al.; "Short and Long-Term Effects of the Angiotensin II Receptor Blocker Irbesartan on Intradialytic Central Hemodynamics: A Randomized Double-Blind Placebo-Controlled One-Year Intervention Trial (the SAFIR Study)"; PLoS One; Jun. 1, 2015; p. 1-22.
"Standard Specification for Ureteral Stents", ASTM International, 2014, Designation F1828-97, p. 1-6.
Verbrugge et al.; "The kidney in congestive heart failure: are natriuresis, sodium, and diuretics really the good, the bad and the ugly"; European Journal of Heart Failure; 2014; p. 133-142; vol. 16.
Wolf, Jr. et al.; "Comparative Ureteral Microanatomy"; Journal of Endourology; 1996; p. 527-531; vol. 10:6.
Wolf, Jr. et al.; "Comparative Ureteral Microanatomy"; Journal of Endourology; 1996; p. 527-531; vol. 10:6.
Zelenko et al.; "Normal Ureter Size on Unenhanced Helical CT"; American Journal of Roentgenology; 2004; p. 1039-1041; vol. 182.
Damman et al., "Increased Central Venous Pressure Is Associated With Impaired Renal Function and Mortality in a Broad Spectrum of XPatients With Cardiovascular Disease", 2009, Journal of the American College of Cardiology, vol. 53:7, pp. 582-588.
Dixon et al., "The musculature of the human renal calices, pelvis and upper ureter", J, Anat., 1982, vol. 135, pp. 129-137.
Gregersen et al., "Regional Differences Exist in Elastic Wall Properties in the Ureter", Sjun, 1996, vol. 30, pp. 343-348.
Kiil, "Urinary Flow and Ureteral Peristalsis" in: Lutzeyer W., Melchior H. (Eds.) Urodynamics, 1973 Springer, Berlin, Heidelberg (pp. 57-70).
Lala et al., "Relief and Recurrence of Congestion During and After Hospitalization for Acute Heart Failure: Insights from DOSE-AHF and CARRESS-HF", Circ Heart Fail, 2015, vol. 8:4, pp. 741-748.
Legrand et al. "Association between systemic hemodynamics and septic acute kidney injury in critically ill patients: a retrospective observational study", Critical Care, 2013, vol. 17:R278, pp. 1-8.
Nohria et al., "Cardiorenal Interactions Insights from the ESCAPE Trial", Heart Failure, 2008, vol. 51:13, pp. 1268-1274.
Uthoff et al., "Central venous pressure and impaired renal function in patients with acute heart failure", European Journal of Heart Failure, 2011. vol. 13, pp. 432-439.
Walker, "Annals of Surgery" 1913, Lippincott Williams & Wilkins, p. 58, Figures 3 and 9.
Webb, "Percutaneous Renal Surgery: A Practical Clinical Handbook", 2016, Springer International Publishing, Switzerland, p. 92.
Woodburne et al., "The Uretal Lumen during Peristalsis", Am. J. Anat., 1972. vol. 133, pp. 255-258.
Johnson et al., "Clinical Practice Guidelines for Chronic Kidney Disease in Adults: Part I. Definition, Disease Stages, Evaluation, Treatment, and Risk Factors", American Family Physician, Sep. 1, 2004, p. 869-876, vol. 70 Issue 5.
Quadra-Coil | Olympus America | Medical, Ureteral Stents, https://www.medical.olympusamerica.com/products/quadra-coil (downloaded from the Internet Aug. 31, 2022) 2 pages.
Stents—Urology | Olympus America | Medical. Ureteral Stents, https://www.medical.olympusamerica.com/products/stents-Urology (downloaded from the Internet Aug. 31, 2022) 2 pages.
Ureteral stent—Quadra-Coil—Olympus Medical Europa, https://www.medicalexpo.com/prod/olympus-medical-europa/product-69587-661607.html (downloaded from the Internet Aug. 31, 2022) 5 pages.
U.S. Pat. No. 10,307,564 / U.S. Appl. No. 15/214,955, "Ureteral and Bladder Catheters and Methods of Inducing Negative Pressure to Increase Renal Perfusion", Jun. 4, 2019 / filed Jul. 20, 2016.
U.S. Pat. No. 9,744,331 / U.S. Appl. No. 15/215,081, "Ureteral and Bladder Catheters and Methods of Inducing Negative Pressure to Increase Renal Perfusion", Aug. 9, 2017 / filed Jul. 20, 2016.
U.S. Pat. No. 10,512,713 / U.S. Appl. No. 15/411,884, "Method of Removing Excess Fluid from a Patient with Hemodilution", Dec. 24, 2019 / filed Jan. 20, 2017.
U.S. Appl. No. 10/601,664 / U.S. Appl. No. 15/673,706, "Ureteral and Bladder Catheters and Methods of Inducing Negative Pressure to Increase Renal Perfusion", filed Apr. 7, 2020 / filed Aug. 10, 2017.
U.S. Pat. No. 10,765,834 / U.S. Appl. No. 15/687,064, "Ureteral and Bladder Catheters and Methods of Inducing Negative Pressure to Increase Renal Perfusion", Sep. 8, 2020 / filed Aug. 25, 2017.
U.S. Pat. No. 10,926,062 / U.S. Appl. No. 15/687,083, "Ureteral and Bladder Catheters and Methods of Inducing Negative Pressure to Increase Renal Perfusion", Feb. 23, 2021 / filed Aug. 25, 2017.
U.S. Pat. No. 11,040,172/U.S. Appl. No. 15/879,976, "Ureteral and Bladder Catheters and Methods of Inducing Negative Pressure to Increase Renal Perfusion", Jun. 22, 2021 / filed Jan. 25, 2018.
U.S. Pat. No. 10,918,827 / U.S. Appl. No. 15/879,869, "Catheter Device and Method for Inducing Negative Pressure in a Patient's Bladder", Feb. 16, 2021 / filed Jan. 25, 2018.
U.S. Appl. No. 15/745,823, "Catheter Device and Method for Inducing Negative Pressure in a Patient's Bladder", filed Jul. 20, 2016.
U.S. Pat. No. 11,040,180/U.S. Appl. No. 15/879,770, "Systems, Kits and Methods for Inducing Negative Pressure to Increase Renal Function", Jun. 22, 2021 / filed Jan. 25, 2018.
U.S. Pat. No. 10,918,825 / U.S. Appl. No. 16/012,233, "Ureteral and Bladder Catheters and Methods of Inducing Negative Pressure to Increase Renal Perfusion", Feb. 16, 2021 / filed Jun. 19, 2018.
U.S. Appl. No. 16/036,971 / U.S. Pat. No. 11,077,284, "Ureteral and Bladder Catheters and Methods of Inducing Negative Pressure to Increase Renal Perfusion", filed Jul. 17, 2018 / Aug. 3, 2021.
U.S. Appl. No. 16/206,207 / U.S. Pat. No. 11,229,284, "Percuatneous Ureteral Catheter", filed Nov. 30, 2018 / Jan. 5, 2022.
U.S. Appl. No. 16/206,389, "Coated Ureteral Catheter or Ureteral Stent and Method", filed Nov. 30, 2018.
U.S. Pat. No. 10,493,232 / U.S. Appl. No. 16/205,987, "Ureteral Catheters, Bladder Catheters, Systems, Kits and Methods for Inducing Negative Pressure to Increase Renal Function", Dec. 3, 2019 / filed Nov. 30, 2018.
U.S. Pat. No. 10,426,919 / U.S. Appl. No. 16/257,791, "Systems and Methods for Inducing Negative Pressure in a Portion of a Urinary Tract of a Patient", Oct. 1, 2019 / filed Jan. 25, 2019.
U.S. Appl. No. 16/390,154, "Ureteral and Bladder Catheters and Methods of Inducing Negative Pressure to Increase Renal Perfusion", filed Apr. 22, 2019.
U.S. Appl. No. 16/542,680, "Systems and Methods for Inducing Negative Pressure in a Portion of a Urinary Tract of a Patient", filed Aug. 16, 2019.
U.S. Appl. No. 16/670,249, "Method of Removing Excess Fluids from a Patient with Hemodilution", filed Oct. 31, 2019.
U.S. Pat. No. 10,799,668 / U.S. Appl. No. 16/662,536, "Ureteral Catheters, Bladder Catheters, Systems, Kits and Methods for Inducing Negative Pressure to Increase Renal Function", Oct. 13, 2020 / filed Oct. 24, 2019.
U.S. Appl. No. 16/662,212, "Catheter and Method for Inducing Negative Pressure in a Patient's Bladder", filed Oct. 24, 2019.
U.S. Appl. No. 16/696,026, "Coated and/or Impregnated Ureteral Catheter or Stent and Method", filed Nov. 26, 2019.
U.S. Appl. No. 16/850,052, "Method of Removing Excess Fluid from a Patient with Venous Congestion", filed Apr. 16, 2020.
U.S. Appl. No. 16/820,781, "Ureteral and Bladder Catheters and Methods of Inducing Negative Pressure to Increase Renal Perfusion", filed Mar. 17, 2020.
U.S. Appl. No. 16/640,210, "Indwelling Pump for Facilitating Removal of Urine from the Urinary Tract", filed Aug. 24, 2018.
U.S. Appl. No. 16/817,773, "Ureteral and Bladder Catheters and Methods of Inducing Negative Pressure to Increase Renal Perfusion", filed Mar. 13, 2020.
U.S. Appl. No. 16/826,347, "Ureteral and Bladder Catheters and Methods of Inducing Negative Pressure to Increase Renal Perfusion", filed Mar. 23, 2020.

(56) References Cited

OTHER PUBLICATIONS

U.S. Appl. No. 16/835,973, "Catheter Device and Method for Inducing Negative Pressure in a Patient's Bladder", filed Mar. 31, 2020.
U.S. Appl. No. 16/856,339, "Pump Assembly and System for Inducing Negative Pressure in a Portion of a Urinary Tract of a Patient", filed Apr. 23, 2020.
U.S. Appl. No. 16/872,965, "Ureteral and Bladder Catheters and Methods of Inducing Negative Pressure to Increase Renal Perfusion", filed May 12, 2020.
U.S. Appl. No. 17/077,793, "Ureteral and Bladder Catheters and Methods of Inducing Negative Pressure to Increase Renal Perfusion", filed Oct. 22, 2020.
U.S. Appl. No. 17/089,757, "Catheter Device and Method for Inducing Negative Pressure in a Patient's Bladder", filed Nov. 5, 2020.
U.S. Appl. No. 17/154,004, "Negative Pressure Therapy System", filed Jan. 20, 2021.
U.S. Appl. No. 17/152,636, "Systems, Kits and Methods for Inducing Negative Pressure to Increase Renal Function", filed Jan. 19, 2021.
U.S. Appl. No. 17/173,262, "Ureteral and Bladder Catheters and Methods of Inducing Negative Pressure to Increase Renal Perfusion", filed Feb. 11, 2021.
U.S. Appl. No. 17/238,454, "Method of Treatment Using Negative Pressure Renal Therapy and Medicament(s)", filed Apr. 23, 2021.
U.S. Appl. No. 17/340,858, "Ureteral and Bladder Catheters and Methods of Inducing Negative Pressure to Increase Renal Perfusion", filed Jun. 7, 2021.
U.S. Appl. No. 17/392,165, "Negative Pressure Therapy System", filed Aug. 2, 2021.

\* cited by examiner

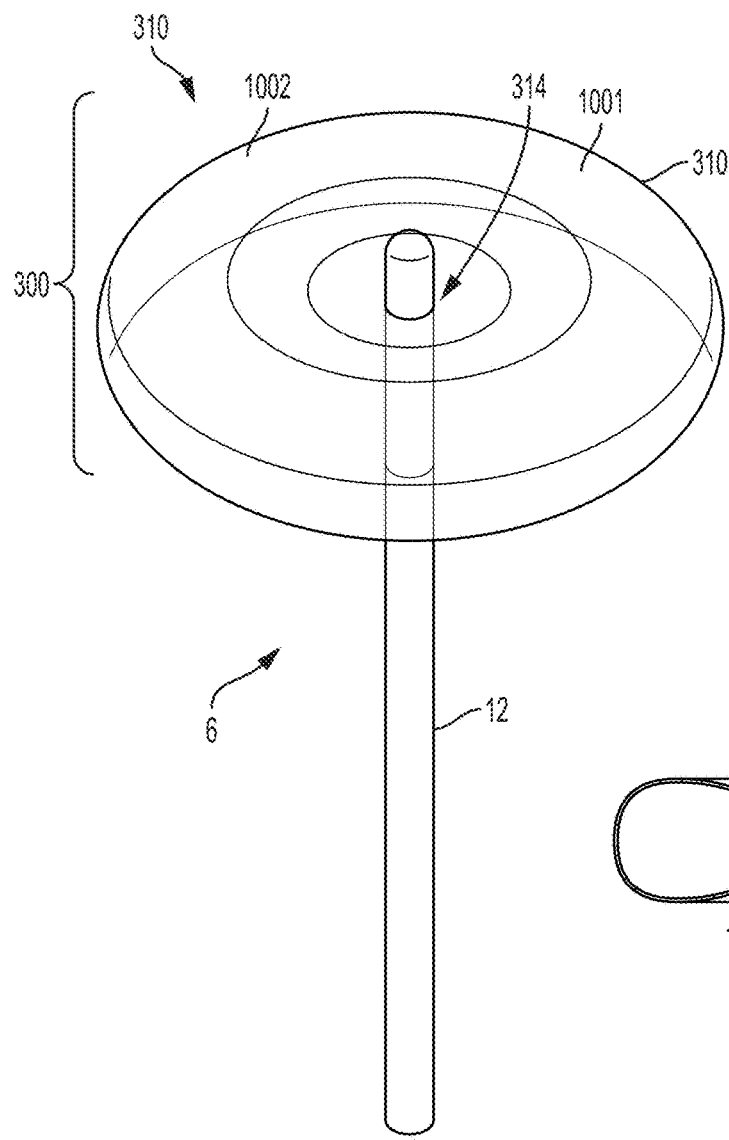
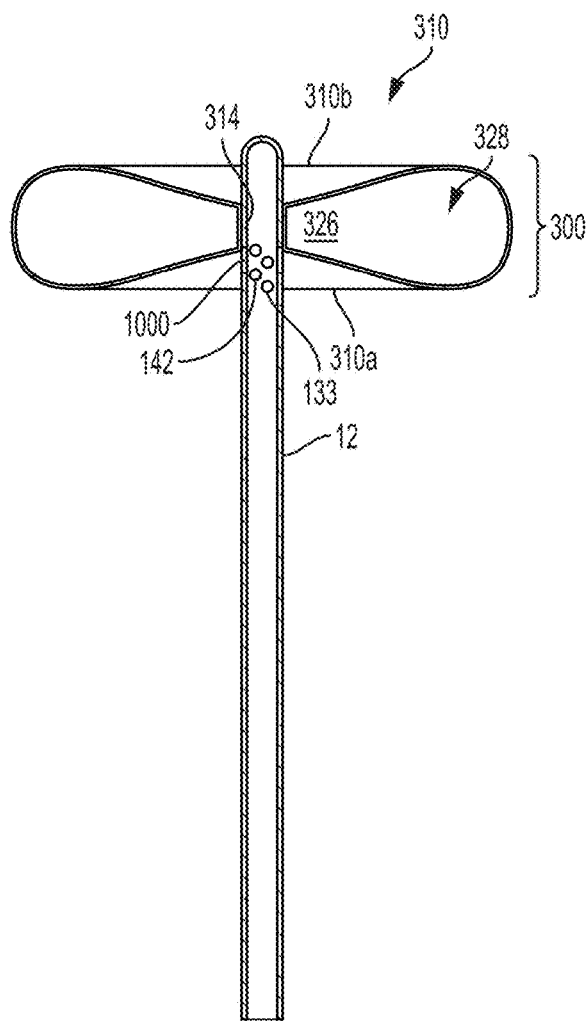
FIG. 1S
FIG. 1T

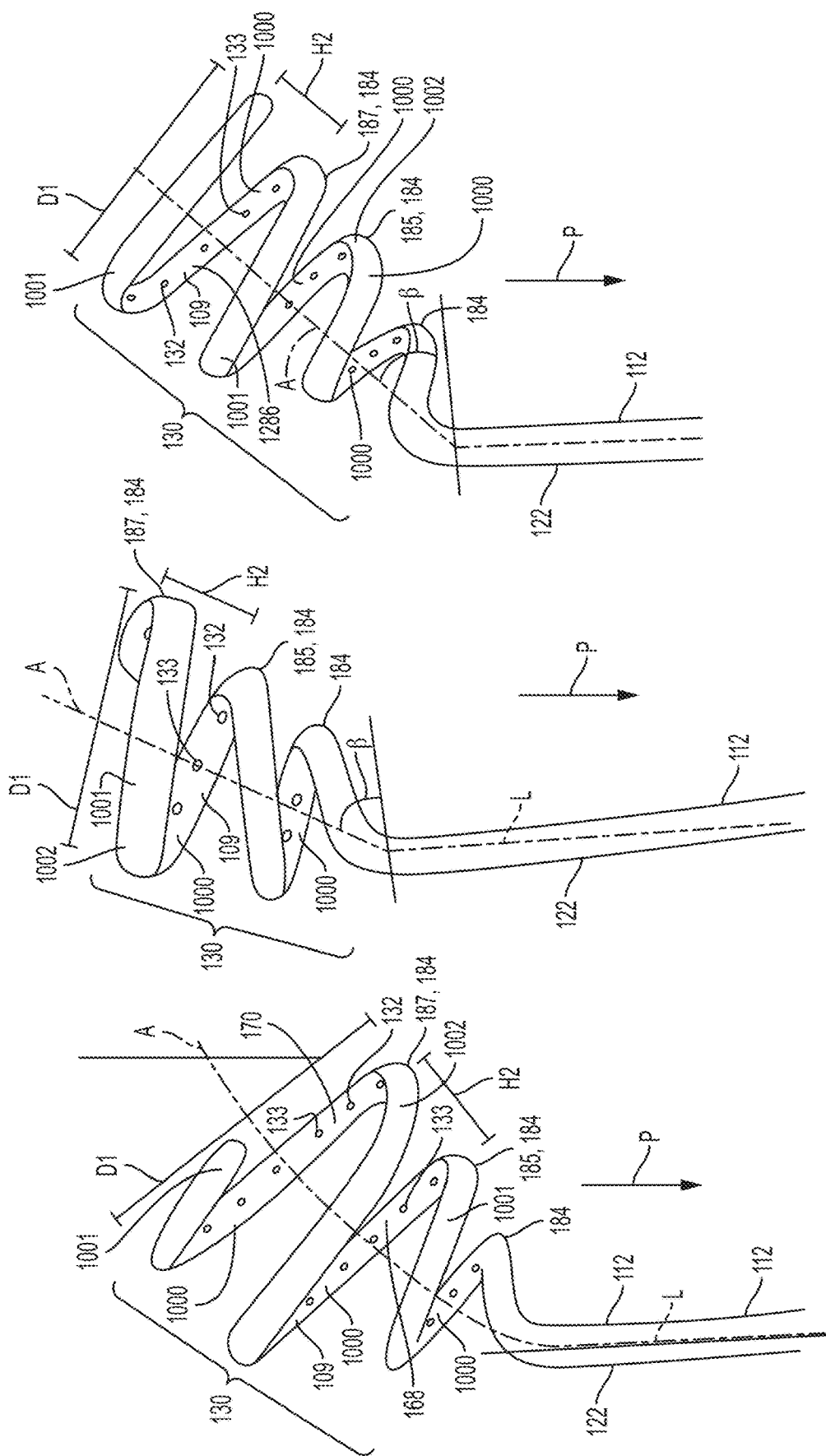

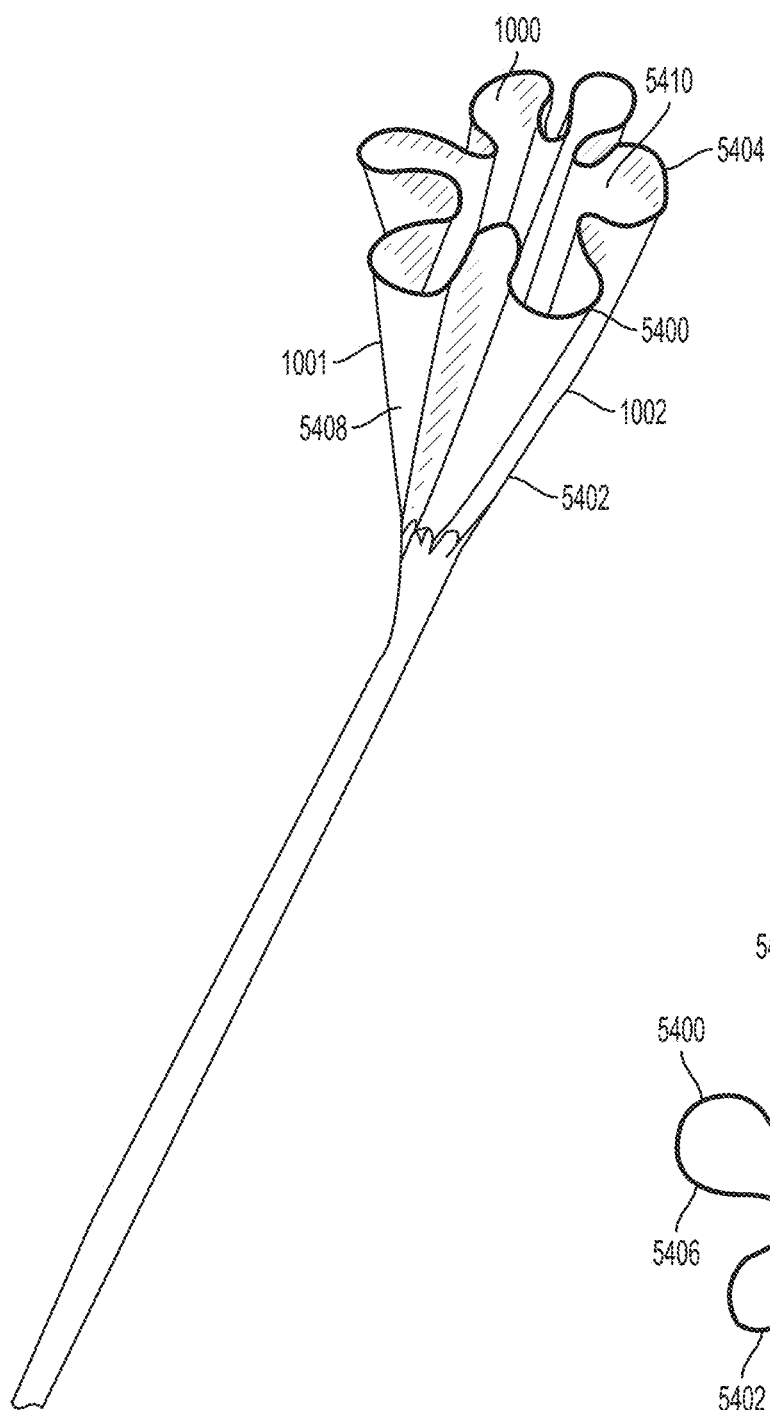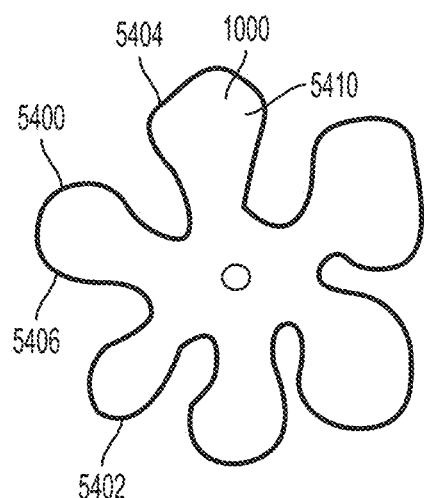
FIG. 30
FIG. 31

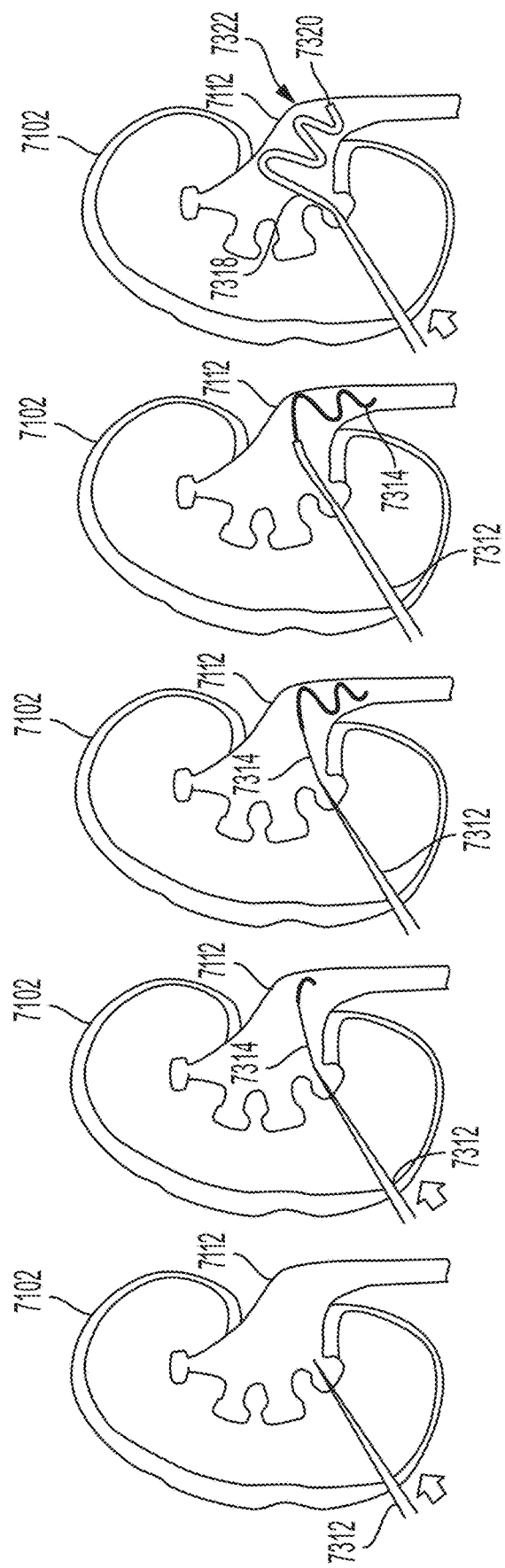

PERCUTANEOUS URINARY CATHETER

CROSS REFERENCE TO RELATED APPLICATIONS

This application is a continuation of U.S. patent application Ser. No. 16/206,207 filed Nov. 30, 2018, which is a continuation-in-part of U.S. patent application Ser. No. 15/879,770 filed Jan. 25, 2018, now issued as U.S. Pat. No. 11,040,180, which is a continuation-in-part of U.S. patent application Ser. No. 15/687,064 filed Aug. 25, 2017, now issued as U.S. Pat. No. 10,765,834, which is a continuation-in-part of U.S. patent application Ser. No. 15/411,884 filed Jan. 20, 2017, now issued as U.S. Pat. No. 10,512,713, which is a continuation-in-part of U.S. patent application Ser. No. 15/214,955 filed Jul. 20, 2016, now issued as U.S. Pat. No. 10,307,564, which claims the benefit of U.S. Provisional Application No. 62/300,025 filed Feb. 25, 2016, U.S. Provisional Application No. 62/278,721, filed Jan. 14, 2016, U.S. Provisional Application No. 62/260,966 filed Nov. 30, 2015, and U.S. Provisional Application No. 62/194,585, filed Jul. 20, 2015, each of which is incorporated by reference herein in their entireties.

Also, U.S. patent application Ser. No. 15/879,770 filed Jan. 25, 2018 is a continuation-in-part of U.S. patent application Ser. No. 15/687,083, filed Aug. 25, 2017, now issued as U.S. Pat. No. 10,926,062, which is a continuation-in-part of U.S. patent application Ser. No. 15/411,884 filed Jan. 20, 2017, now issued as U.S. Pat. No. 10,512,713, which is a continuation-in-part of U.S. patent application Ser. No. 15/214,955 filed Jul. 20, 2016, now issued as U.S. Pat. No. 10,307,564, which claims the benefit of U.S. Provisional Application No. 62/300,025 filed Feb. 25, 2016, U.S. Provisional Application No. 62/278,721, filed Jan. 14, 2016, U.S. Provisional Application No. 62/260,966 filed Nov. 30, 2015, and U.S. Provisional Application No. 62/194,585, filed Jul. 20, 2015, each of which is incorporated by reference herein in its entirety.

Also, U.S. patent application Ser. No. 15/879,770 filed Jan. 25, 2018 is a continuation-in-part of U.S. patent application Ser. No. 15/745,823 filed Jan. 18, 2018, which is the U.S. national phase of PCT/US2016/043101, filed Jul. 20, 2016, which claims the benefit of U.S. Provisional Application No. 62/300,025 filed Feb. 25, 2016, U.S. Provisional Application No. 62/278,721, filed Jan. 14, 2016, U.S. Provisional Application No. 62/260,966 filed Nov. 30, 2015, and U.S. Provisional Application No. 62/194,585, filed Jul. 20, 2015, each of which is incorporated by reference herein in its entirety.

Also, U.S. patent application Ser. No. 15/879,770 filed Jan. 25, 2018 claims the benefit of United States Provisional Application No. 62/489,789 filed Apr. 25, 2017 and U.S. Provisional Application No. 62/489,831 filed Apr. 25, 2017.

BACKGROUND

Technical Field

The present disclosure relates to devices and methods for treating impaired renal function across a variety of disease states and, in particular, to devices and methods for collection of urine and inducement of negative and/or positive pressure in portions of a patient's urinary tract through a percutaneously implanted catheter.

Background

The renal or urinary system includes a pair of kidneys, each kidney being connected by a ureter to the bladder, and a urethra for draining fluid or urine produced by the kidneys from the bladder. The kidneys perform several vital functions for the human body including, for example, filtering the blood to eliminate waste in the form of urine. The kidneys also regulate electrolytes (e.g., sodium, potassium and calcium) and metabolites, blood volume, blood pressure, blood pH, fluid volume, production of red blood cells, and bone metabolism. Adequate understanding of the anatomy and physiology of the kidneys is useful for understanding the impact that altered hemodynamics other fluid overload conditions have on their function.

In normal anatomy, the two kidneys are located retroperitoneally in the abdominal cavity. The kidneys are bean-shaped encapsulated organs. Urine is formed by nephrons, the functional unit of the kidney, and then flows through a system of converging tubules called collecting ducts. The collecting ducts join together to form minor calyces, then major calyces, which ultimately join near the concave portion of the kidney (renal pelvis). A major function of the renal pelvis is to direct urine flow to the ureter. Urine flows from the renal pelvis into the ureter, a tube-like structure that carries the urine from the kidneys into the bladder. The outer layer of the kidney is called the cortex, and is a rigid fibrous encapsulation. The interior of the kidney is called the medulla. The medulla structures are arranged in pyramids.

Each kidney is made up of approximately one million nephrons. Each nephron includes the glomerulus, Bowman's capsule, and tubules. The tubules include the proximal convoluted tubule, the loop of Henle, the distal convoluted tubule, and the collecting duct. The nephrons contained in the cortex layer of the kidney are distinct from the anatomy of those contained in the medulla. The principal difference is the length of the loop of Henle. Medullary nephrons contain a longer loop of Henle, which, under normal circumstances, allows greater regulation of water and sodium reabsorption than in the cortex nephrons.

The glomerulus is the beginning of the nephron, and is responsible for the initial filtration of blood. Afferent arterioles pass blood into the glomerular capillaries, where hydrostatic pressure pushes water and solutes into Bowman's capsule. Net filtration pressure is expressed as the hydrostatic pressure in the afferent arteriole minus the hydrostatic pressure in Bowman's space minus the osmotic pressure in the efferent arteriole.

$$\text{Net Filtration Pressure} = \text{Hydrostatic Pressure(Afferent Arteriole)} - \text{Hydrostatic Pressure(Bowman's Space)} - \text{Osmotic Pressure(Efferent Arteriole)} \quad \text{(Equation 1)}$$

The magnitude of this net filtration pressure defined by Equation 1 determines how much ultra-filtrate is formed in Bowman's space and delivered to the tubules. The remaining blood exits the glomerulus via the efferent arteriole. Normal glomerular filtration, or delivery of ultra-filtrate into the tubules, is about 90 ml/min/1.73 m$^2$.

The glomerulus has a three-layer filtration structure, which includes the vascular endothelium, a glomerular basement membrane, and podocytes. Normally, large proteins such as albumin and red blood cells, are not filtered into Bowman's space. However, elevated glomerular pressures and mesangial expansion create surface area changes on the basement membrane and larger fenestrations between the podocytes allowing larger proteins to pass into Bowman's space.

Ultra-filtrate collected in Bowman's space is delivered first to the proximal convoluted tubule. Re-absorption and secretion of water and solutes in the tubules is performed by a mix of active transport channels and passive pressure gradients. The proximal convoluted tubules normally reabsorb a majority of the sodium chloride and water, and nearly all glucose and amino acids that were filtered by the glomerulus. The loop of Henle has two components that are designed to concentrate wastes in the urine. The descending limb is highly water permeable and reabsorbs most of the remaining water. The ascending limb reabsorbs 25% of the remaining sodium chloride, creating a concentrated urine, for example, in terms of urea and creatinine. The distal convoluted tubule normally reabsorbs a small proportion of sodium chloride, and the osmotic gradient creates conditions for the water to follow.

Under normal conditions, there is a net filtration of approximately 14 mmHg. The impact of venous congestion can be a significant decrease in net filtration, down to approximately 4 mmHg. See Jessup M., The cardiorenal syndrome: Do we need a change of strategy or a change of tactics?, *JACC* 53(7):597-600, 2009 (hereinafter "Jessup"). The second filtration stage occurs at the proximal tubules. Most of the secretion and absorption from urine occurs in tubules in the medullary nephrons. Active transport of sodium from the tubule into the interstitial space initiates this process. However, the hydrostatic forces dominate the net exchange of solutes and water. Under normal circumstances, it is believed that 75% of the sodium is reabsorbed back into lymphatic or venous circulation. However, because the kidney is encapsulated, it is sensitive to changes in hydrostatic pressures from both venous and lymphatic congestion. During venous congestion the retention of sodium and water can exceed 85%, further perpetuating the renal congestion. See Verbrugge et al., The kidney in congestive heart failure: Are natriuresis, sodium, and diruetucs really the good, the bad and the ugly? *European Journal of Heart Failure* 2014:16, 133-42 (hereinafter "Verbrugge").

Venous congestion can lead to a prerenal form of acute kidney injury (AKI). Prerenal AKI is due to a loss of perfusion (or loss of blood flow) through the kidney. Many clinicians focus on the lack of flow into the kidney due to shock. However, there is also evidence that a lack of blood flow out of the organ due to venous congestion can be a clinically important sustaining injury. See Damman K, *Importance of venous congestion for worsening renal function in advanced decompensated heart failure*, JACC 17:589-96, 2009 (hereinafter "Damman").

Prerenal AKI occurs across a wide variety of diagnoses requiring critical care admissions. The most prominent admissions are for sepsis and Acute Decompensated Heart Failure (ADHF). Additional admissions include cardiovascular surgery, general surgery, cirrhosis, trauma, burns, and pancreatitis. While there is wide clinical variability in the presentation of these disease states, a common denominator is an elevated central venous pressure. In the case of ADHF, the elevated central venous pressure caused by heart failure leads to pulmonary edema, and, subsequently, dyspnea in turn precipitating the admission. In the case of sepsis, the elevated central venous pressure is largely a result of aggressive fluid resuscitation. Whether the primary insult was low perfusion due to hypovolemia or sodium and fluid retention, the sustaining injury is the venous congestion resulting in inadequate perfusion.

Hypertension is another widely recognized state that creates perturbations within the active and passive transport systems of the kidney(s). Hypertension directly impacts afferent arteriole pressure and results in a proportional increase in net filtration pressure within the glomerulus. The increased filtration fraction also elevates the peritubular capillary pressure, which stimulates sodium and water re-absorption. See Verbrugge.

Because the kidney is an encapsulated organ, it is sensitive to pressure changes in the medullary pyramids. The elevated renal venous pressure creates congestion that leads to a rise in the interstitial pressures. The elevated interstitial pressures exert forces upon both the glomerulus and tubules. See Verbrugge. In the glomerulus, the elevated interstitial pressures directly oppose filtration. The increased pressures increase the interstitial fluid, thereby increasing the hydrostatic pressures in the interstitial fluid and peritubular capillaries in the medulla of the kidney. In both instances, hypoxia can ensue leading to cellular injury and further loss of perfusion. The net result is a further exacerbation of the sodium and water re-absorption creating a negative feedback. See Verbrugge, 133-42. Fluid overload, particularly in the abdominal cavity is associated with many diseases and conditions, including elevated intra-abdominal pressure, abdominal compartment syndrome, and acute renal failure. Fluid overload can be addressed through renal replacement therapy. See Peters, C. D., *Short and Long-Term Effects of the Angiotensin II Receptor Blocker Irbesartanon Intradialytic Central Hemodynamics: A Randomized Double-Blind Placebo-Controlled One-Year Intervention Trial (the SAFIR Study)*, PLOS ONE (2015) 10(6): e0126882. doi:10.1371/journal.pone.0126882 (hereinafter "Peters"). However, such a clinical strategy provides no improvement in renal function for patients with the cardiorenal syndrome. See Bart B, *Ultrafiltration in decompensated heart failure with cardiorenal syndrome*, NEJM 2012; 367:2296-2304 (hereinafter "Bart").

In view of such problematic effects of fluid retention, systems and methods for improving removal of fluid such as urine from the patient and, specifically for increasing quantity and quality of fluid output from the kidneys, are needed.

SUMMARY

The present disclosure improves upon previous systems by providing a specialized catheter for percutaneous insertion and for deployment within a renal pelvis and/or kidney of a patient.

According to some examples, a catheter configured to be deployed in a urinary tract of a patient includes a proximal portion configured to pass through a percutaneous opening; and a distal portion including a retention portion configured to be deployed in a kidney, renal pelvis, and/or bladder of the patient. The retention portion includes one or more protected drainage holes, ports or perforations and is configured, when deployed, to establish an outer periphery or protective surface area that inhibits mucosal tissue from occluding the one or more protected drainage holes, ports, or perforations upon application of negative pressure through the catheter.

According to some other examples, a system for inducing negative pressure in a portion of a urinary tract of a patient includes a catheter configured to be deployed within a portion of the urinary tract of the patient. The catheter includes a proximal portion configured to pass through a percutaneous opening and a distal portion including a retention portion configured to be deployed in a kidney, renal pelvis, and/or bladder of the patient. The retention portion includes one or more protected drainage holes, ports or perforations and is configured, when deployed, to establish an outer periphery or protective surface area that inhibits mucosal tissue from occluding the one or more protected drainage holes, ports, or perforations upon application of negative pressure through the catheter. The system also includes a pump external to the patient's body for application of the negative pressure at the proximal portion of the catheter. The pump induces negative pressure to a portion of the urinary tract, which causes fluid from the urinary tract to be drawn into the catheter at least partially through the one or more protected drainage holes, ports, or perforations.

According to some other examples, a method for removing fluid from a urinary tract of a patient includes inserting a urinary catheter through a percutaneous opening and into a kidney, renal pelvis, and/or bladder of the patient and deploying a retention portion of the catheter within the kidney, renal pelvis, and/or bladder of the patient to maintain patency of fluid flow from the kidney of the patient through at least a portion of the catheter. The catheter includes a proximal portion configured to pass through the percutaneous opening and a distal portion including the retention portion configured to be deployed in the kidney, renal pelvis, and/or bladder of the patient. The retention portion includes one or more protected drainage holes, ports or perforations and is configured, when deployed, to establish an outer periphery or protective surface area that inhibits mucosal tissue from occluding the one or more protected drainage holes, ports, or perforations upon application of negative pressure through the catheter.

Non-limiting examples, aspects or embodiments of the present invention will now be described in the following numbered clauses:

Clause 1: A catheter configured to be deployed in a urinary tract of a patient, comprising: a proximal portion configured to pass through a percutaneous opening; and a distal portion comprising a retention portion configured to be deployed in a kidney, renal pelvis, and/or bladder of the patient, wherein the retention portion comprises one or more protected drainage holes, ports or perforations and is configured, when deployed, to establish an outer periphery or protective surface area that inhibits mucosal tissue from occluding the one or more protected drainage holes, ports, or perforations upon application of negative pressure through the catheter.

Clause 2: The catheter of clause 1, wherein the catheter is configured to transition between a contracted configuration, in which the catheter can pass through the percutaneous opening, and a deployed configuration, in which the retention portion is configured to retain at least the distal portion of the catheter within the kidneys, renal pelvis, and/or bladder of the patient.

Clause 3: The catheter of clause 1 or clause 2, wherein, when deployed, a maximum outer diameter of the retention portion is greater than a diameter of a drainage lumen of the catheter.

Clause 4: The catheter of any of clauses 1-3, wherein the retention portion comprises an expandable retention portion which, when deployed, defines a three-dimensional shape sized and positioned to maintain patency of fluid flow between a kidney and a proximal end of the catheter, such that at least a portion of the fluid flow flows through the expandable retention portion.

Clause 5: The catheter of clause 4, wherein an area of two-dimensional slices of the three-dimensional shape defined by the deployed expandable retention portion in a plane transverse to a central axis of the expandable retention portion decreases towards a distal end of the expandable retention portion.

Clause 6: The catheter of clause 4 or clause 5, wherein a maximum cross-sectional area of the three-dimensional shape defined by the deployed expandable retention portion in a plane transverse to a central axis of the expandable retention portion is less than or equal to about 500 mm2.

Clause 7: The catheter of any of clauses 1-6, wherein the retention portion comprises a proximal end sized to be positioned in a kidney and a distal end sized to be positioned in the renal pelvis.

Clause 8: The catheter of any of clauses 1-7, wherein the retention portion comprises a coiled retention portion comprising at least a first coil having a first diameter and at least a second coil having a second diameter, the first diameter being greater than the second diameter.

Clause 9: The catheter of clause 8, wherein the first coil is closer to the proximal portion of the catheter than is the second coil.

Clause 10: The catheter of any of clauses 1-8, wherein the retention portion comprises a coiled retention portion comprising a plurality of coils, and wherein a distal-most coil of the plurality of coils has a smaller diameter than other coils of the plurality of coils.

Clause 11: The catheter of clause 10, wherein the coiled retention portion comprises a straight portion extending through the retention portion, and wherein the plurality of coils are wrapped around the straight portion.

Clause 12: The catheter of any of clauses 1-11, wherein the retention portion is coextensive with other portions of the catheter.

Clause 13: The catheter of any of clauses 1-12, wherein an axial length of the retention portion from a proximal end to a distal end thereof is from about 5 mm to about 100 mm.

Clause 14: The ureteral catheter of any of clauses 1-13, wherein the one or more protected drainage holes, ports, or perforations have a diameter ranging from 0.0005 mm to about 2.0 mm.

Clause 15: The catheter of any of clauses 1-14, wherein the catheter comprises an elongated tube extending from a proximal end of the proximal portion to a distal end of the distal portion.

Clause 16: The catheter of clause 15, wherein the elongated tube is from about 30 cm to about 60 cm in length.

Clause 17: The catheter of clause 15 or clause 16, wherein the elongated tube has an outer diameter of from about 1.0 mm to about 10.0 mm, and/or an inner diameter of about 0.5 mm to about 9.5 mm.

Clause 18: The catheter of any of clauses 1-17, wherein a proximal end of the proximal portion of the catheter is configured to be connected to a pump for applying the negative pressure through the catheter.

Clause 19: The catheter of any of clauses 1-18, wherein the proximal portion is essentially free of or free of perforations and/or drainage ports.

Clause 20: A system for inducing negative pressure in a portion of a urinary tract of a patient, the system comprising: a catheter configured to be deployed within a portion of the urinary tract of the patient, comprising: a proximal portion configured to pass through a percutaneous opening; and a distal portion comprising a retention portion configured to be deployed in a kidney, renal pelvis, and/or bladder of the patient, wherein the retention portion comprises one or more protected drainage holes, ports or perforations and is configured, when deployed, to establish an outer periphery or protective surface area that inhibits mucosal tissue from occluding the one or more protected drainage holes, ports, or perforations upon application of negative pressure through the catheter; and a pump external to the patient's body for application of the negative pressure at the proximal portion of the catheter, wherein the pump induces negative pressure to a portion of the urinary tract, which causes fluid from the urinary tract to be drawn into the catheter at least partially through the one or more protected drainage holes, ports, or perforations.

Clause 21: The system of clause 20 further comprising a controller electrically connected to the pump configured to actuate the pump to control the application of the negative pressure to the proximal end of the catheter.

Clause 22: The system of clause 21, further comprising one or more physiological sensors associated with the patient, the physiological sensors being configured to provide information representative of at least one physical parameter to the controller, and wherein the controller is configured to actuate or cease operation of the pump based on the at least one physical parameter.

Clause 23: The system of any of clauses 20-22, wherein the negative pressure is provided within a range of about 2 mmHg to about 50 mmHg.

Clause 24: The system of any of clauses 20-23, wherein the pump provides a sensitivity of about 10 mmHg or less.

Clause 25: A method for removing fluid from a urinary tract of a patient, the method comprising: inserting a urinary catheter through a percutaneous opening and into a kidney, renal pelvis, and/or bladder of the patient; and deploying a retention portion of the catheter within the kidney, renal pelvis, and/or bladder of the patient to maintain patency of fluid flow from the kidney of the patient through at least a portion of the catheter, wherein the catheter comprises a proximal portion configured to pass through the percutaneous opening; and a distal portion comprising the retention portion configured to be deployed in the kidney, renal pelvis, and/or bladder of the patient, and wherein the retention portion comprises one or more protected drainage holes, ports or perforations and is configured, when deployed, to establish an outer periphery or protective surface area that inhibits mucosal tissue from occluding the one or more protected drainage holes, ports, or perforations upon application of negative pressure through the catheter.

Clause 26: The method of clause 25, wherein inserting the urinary catheter through the percutaneous opening comprises: inserting a needle of the ureteral catheter into a portion of the patient's body to create the percutaneous opening; inserting the needle into a kidney of the patient and advancing the needle through the kidney to the renal pelvis of the patient; and inserting an elongated tube of the ureteral catheter over the needle, such that a distal end of the elongated tube advances from the kidney into the renal pelvis.

Clause 27: The method of clause 26, wherein inserting the urinary catheter comprises inserting the needle of the urinary catheter into the abdominal region of the patient.

Clause 28: The method of any of clauses 25-27, further comprising attaching a proximal end of the urinary catheter directly or indirectly to a fluid pump and applying a negative pressure to a proximal end of the proximal portion of the urinary catheter by actuating the pump, thereby inducing the negative pressure in the kidney, renal pelvis, and/or bladder of the patient.

BRIEF DESCRIPTION OF THE DRAWINGS

These and other features and characteristics of the present disclosure, as well as the methods of operation and functions of the related elements of structures and the combination of parts and economics of manufacture, will become more apparent upon consideration of the following description and the appended clauses with reference to the accompanying drawings, all of which form a part of this specification, wherein like reference numerals designate corresponding parts in the various figures. It is to be expressly understood, however, that the drawings are for the purpose of illustration and description only and are not intended as a definition of the limit of the invention.

Further features and other examples and advantages will become apparent from the following detailed description made with reference to the drawings in which:

FIG. 1S is a perspective view of a retention portion of a bladder catheter, according to an example of the present invention;

FIG. 1T is a cross-sectional view of a portion of the retention portion of FIG. 1S, according to an example of the present invention;

FIG. 9C is a schematic drawing of another example of a retention portion for a catheter according to an example of the present invention;

FIG. 9D is a schematic drawing of another example of a retention portion for a catheter according to an example of the present invention;

FIG. 9E is a schematic drawing of another example of a retention portion for a catheter according to an example of the present invention;

FIG. 30 is a perspective view of a retention portion of another catheter according to an example of the present invention;

FIG. 31 is a top plan view of the retention portion of the catheter of FIG. 30;

FIG. 53 is a cross-sectional view of the catheter of FIG. 52A;

FIG. 54 is a schematic drawing showing a ureteral catheter inserted through a percutaneous access site and deployed in a renal pelvis of a patient;

FIG. 55 is a schematic drawing of a urinary tract of a patient showing a system for collecting fluid including the ureteral catheter of FIG. 54;

FIG. 56 is a flow chart of a method for deploying a ureteral catheter in the renal pelvis through a percutaneous access site;

FIGS. 57A-57E are schematic drawings showing steps for inserting a ureteral catheter to a renal pelvis of a patient;

FIG. 58A is a perspective view of another example of a catheter configured to be inserted to the renal pelvis through a percutaneous access site, according to an aspect of the disclosure; and FIG. 58B is a cross-sectional view of the catheter of FIG. 58A.

DETAILED DESCRIPTION OF THE INVENTION

Figure 1A:
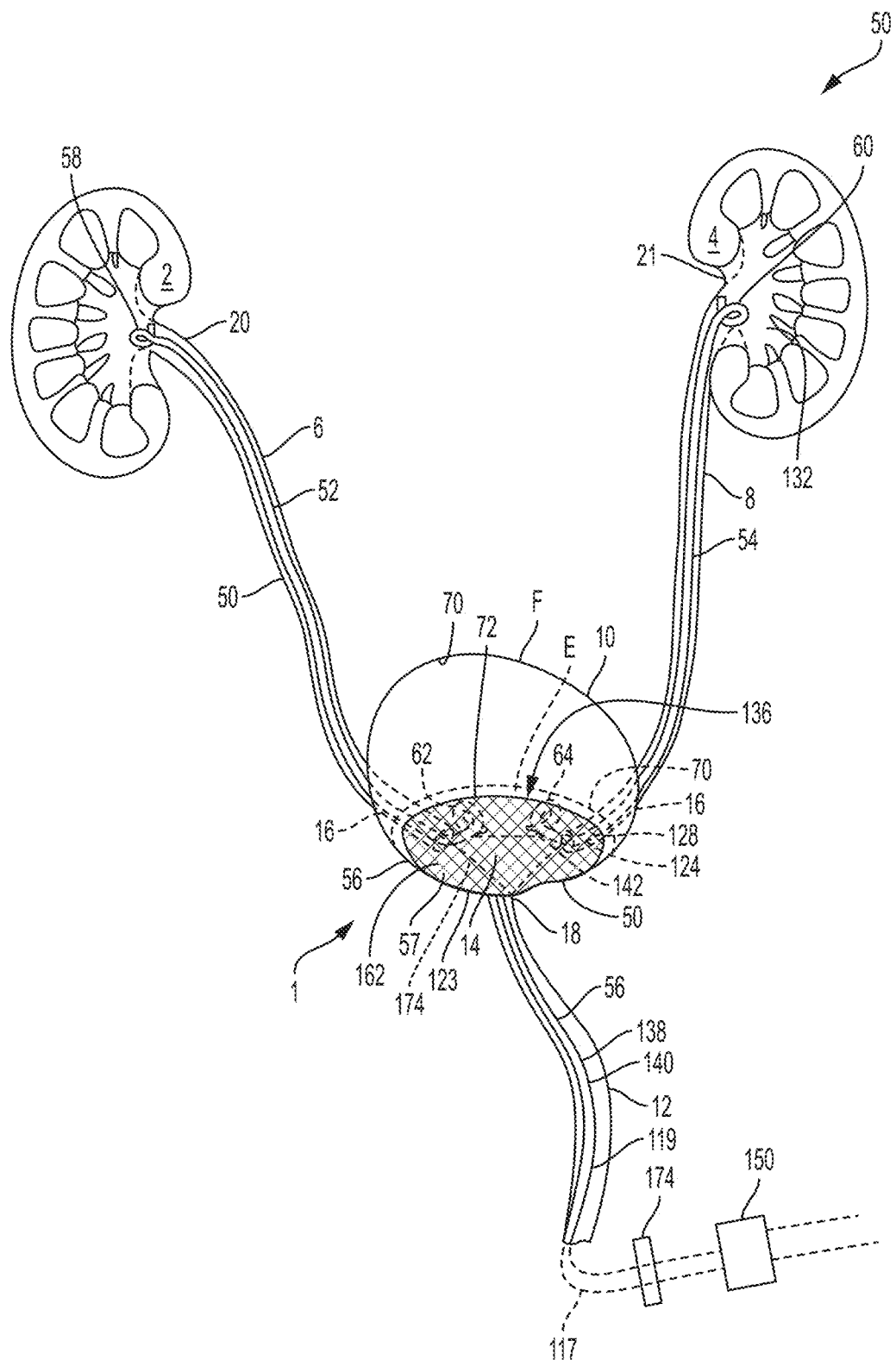
FIG. 1A is a schematic drawing of an indwelling portion of a system comprising a ureteral stent and a bladder catheter deployed in a urinary tract of a patient, according to an example of the present invention.

As used herein, the singular form of "a". "an", and "the" include plural referents unless the context clearly states otherwise.

As used herein, the terms "right", "left", "top", and derivatives thereof shall relate to the invention as it is oriented in the drawing figures. The term "proximal" refers to the portion of the catheter device that is manipulated or contacted by a user and/or to a portion of an indwelling catheter nearest to the urinary tract access site. The term "distal" refers to the opposite end of the catheter device that is configured to be inserted into a patient and/or to the portion of the device that is inserted farthest into the patient's urinary tract. However, it is to be understood that the invention can assume various alternative orientations and, accordingly, such terms are not to be considered as limiting. Also, it is to be understood that the invention can assume various alternative variations and stage sequences, except where expressly specified to the contrary. It is also to be understood that the specific devices and processes illustrated in the attached drawings, and described in the following specification, are examples. Hence, specific dimensions and other physical characteristics related to the embodiments disclosed herein are not to be considered as limiting.

For the purposes of this specification, unless otherwise indicated, all numbers expressing quantities of ingredients, reaction conditions, dimensions, physical characteristics, and so forth used in the specification and claims are to be understood as being modified in all instances by the term "about." Unless indicated to the contrary, the numerical parameters set forth in the following specification and attached claims are approximations that can vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

Also, it should be understood that any numerical range recited herein is intended to include all sub-ranges subsumed therein. For example, a range of "1 to 10" is intended to include any and all sub-ranges between and including the recited minimum value of 1 and the recited maximum value of 10, that is, all subranges beginning with a minimum value equal to or greater than 1 and ending with a maximum value equal to or less than 10, and all subranges in between, e.g., 1 to 6.3, or 5.5 to 10, or 2.7 to 6.1.

As used herein, the terms "communication" and "communicate" refer to the receipt or transfer of one or more signals, messages, commands, or other type of data. For one unit or component to be in communication with another unit or component means that the one unit or component is able to directly or indirectly receive data from and/or transmit data to the other unit or component. This can refer to a direct or indirect connection that can be wired and/or wireless in nature. Additionally, two units or components can be in communication with each other even though the data transmitted can be modified, processed, routed, and the like, between the first and second unit or component. For example, a first unit can be in communication with a second unit even though the first unit passively receives data, and does not actively transmit data to the second unit. As another example, a first unit can be in communication with a second unit if an intermediary unit processes data from one unit and transmits processed data to the second unit. It will be appreciated that numerous other arrangements are possible.

As used herein, "maintain patency of fluid flow between a kidney and a bladder of the patient" means establishing, increasing or maintaining flow of fluid, such as urine, from the kidneys through the ureter(s), ureteral stent(s) and/or ureteral catheter(s) to the bladder and outside of the body. In some examples, the fluid flow is facilitated or maintained by providing a protective surface area 1001 in the upper urinary tract and/or bladder to prevent the uroendothelium from contracting or collapsing into the fluid column or stream. As used herein, "fluid" means urine and any other fluid from the urinary tract.

As used herein, "negative pressure" means that the pressure applied to the proximal end of the bladder catheter or the proximal end of the ureteral catheter, respectively, is below the existing pressure at the proximal end of the bladder catheter or the proximal end of the ureteral catheter, respectively, prior to application of the negative pressure, e.g., there is a pressure differential between the proximal end of the bladder catheter or the proximal end of the ureteral catheter, respectively, and the existing pressure at the proximal end of the bladder catheter or the proximal end of the ureteral catheter, respectively, prior to application of the negative pressure. This pressure differential causes fluid from the kidney to be drawn into the ureteral catheter or bladder catheter, respectively, or through both the ureteral catheter and the bladder catheter, and then outside of the patient's body. For example, negative pressure applied to the proximal end of the bladder catheter or the proximal end of the ureteral catheter can be less than atmospheric pressure (less than about 760 mm Hg or about 1 atm), or less than the pressure measured at the proximal end of the bladder catheter or the proximal end of the ureteral catheter prior to the application of negative pressure, such that fluid is drawn from the kidney and/or bladder. In some examples, the negative pressure applied to the proximal end of the bladder catheter or the proximal end of the ureteral catheter can range from about 0.1 mmHg to about 150 mm Hg, or about 0.1 mm Hg to about 50 mm Hg, or about 0.1 mm Hg to about 10 mm Hg, or about 5 mm Hg to about 20 mm Hg, or about 45 mm Hg (gauge pressure at the pump 710 or at a gauge at the negative pressure source). In some examples, the negative pressure source comprises a pump external to the patient's body for application of negative pressure through both the bladder catheter and the ureteral catheter, which in turn causes fluid from the kidney to be drawn into the ureteral catheter, through both the ureteral catheter and the bladder catheter, and then outside of the patient's body. In some examples, the negative pressure source comprises a vacuum source external to the patient's body for application and regulation of negative pressure through both the bladder catheter and the ureteral catheter, which in turn causes fluid from the kidney to be drawn into the ureteral catheter, through both the ureteral catheter and the bladder catheter, and then outside of the patient's body. In some examples, the vacuum source is selected from the group consisting of a wall suction source, vacuum bottle, and manual vacuum source, or the vacuum source is provided by a pressure differential. In some examples, the negative pressure received from the negative pressure source can be controlled manually, automatically, or combinations thereof. In some examples, a controller is used to regulate negative pressure from the negative pressure source. Non-limiting examples of negative and positive pressure sources are discussed in detail below.

As used herein, "positive pressure" means that the pressure applied to the proximal end of the bladder catheter or the proximal end of the ureteral catheter, respectively, is above the existing pressure at the proximal end of the bladder catheter or the proximal end of the ureteral catheter, respectively, prior to application of the negative pressure, and causes fluid present in the ureteral catheter or bladder catheter, respectively, or through both the ureteral catheter and the bladder catheter, to flow back towards the bladder or kidney. In some examples, the positive pressure applied to the proximal end of the bladder catheter or the proximal end of the ureteral catheter can range from about 0.1 mmHg to about 150 mm Hg, or about 0.1 mm Hg to about 50 mm Hg, or about 0.1 mm Hg to about 10 mm Hg. or about 5 mm Hg to about 20 mm Hg, or about 45 mm Hg (gauge pressure at the pump 710 or at a gauge at the positive pressure source). The positive pressure source can be provided by a pump or wall pressure source, or pressurized bottle, for example, and can be controlled manually, automatically, or combinations thereof. In some examples, a controller is used to regulate positive pressure from the positive pressure source.

Fluid retention and venous congestion are central problems in the progression to advanced renal disease. Excess sodium ingestion coupled with relative decreases in excretion leads to isotonic volume expansion and secondary compartment involvement. In some examples, the present invention is generally directed to devices and methods for facilitating drainage of urine or waste from the bladder, ureter, and/or kidney(s) of a patient. In some examples, the present invention is generally directed to systems and methods for inducing a negative pressure in at least a portion of the bladder, ureter, and/or kidney(s), e.g., urinary system, of a patient. While not intending to be bound by any theory, it is believed that applying a negative pressure to at least a portion of the bladder, ureter, and/or kidney(s), e.g., urinary system, can offset the medullary nephron tubule re-absorption of sodium and water in some situations. Offsetting re-absorption of sodium and water can increase urine production, decrease total body sodium, and improve erythrocyte production. Since the intra-medullary pressures are driven by sodium and, therefore, volume overload, the targeted removal of excess sodium enables maintenance of volume loss. Removal of volume restores medullary hemostasis. Normal urine production is 1.48-1.96 L/day (or 1-1.4 ml/min).

Fluid retention and venous congestion are also central problems in the progression of prerenal Acute Kidney Injury (AKI). Specifically, AKI can be related to loss of perfusion or blood flow through the kidney(s). Accordingly, in some examples, the present invention facilitates improved renal hemodynamics and increases urine output for the purpose of relieving or reducing venous congestion. Further, it is anticipated that treatment and/or inhibition of AKI positively impacts and/or reduces the occurrence of other conditions, for example, reduction or inhibition of worsening renal function in patients with NYHA Class III and/or Class IV heart failure. Classification of different levels of heart failure are described in The Criteria Committee of the New York Heart Association, (1994), *Nomenclature and Criteria for Diagnosis of Diseases of the Heart and Great Vessels,* (9th ed.), Boston: Little, Brown & Co. pp. 253-256, the disclosure of which is incorporated by reference herein in its entirety. Reduction or inhibition of episodes of AKI and/or chronically decreased perfusion may also be a treatment for Stage 4 and/or Stage 5 chronic kidney disease. Chronic kidney disease progression is described in National Kidney Foundation, K/DOQI *Clinical Practice Guidelines for Chronic Kidney Disease: Evaluation, Classification and Stratification.* Am. J. Kidney Dis. 39:S1-S266, 2002 (Suppl. 1), the disclosure of which is incorporated by reference herein in its entirety.

Also, the ureteral catheters, ureteral stents and/or bladder catheters disclosed herein can be useful for preventing, delaying the onset of, and/or treating end-stage renal disease ("ESRD"). The average dialysis patient consumes about $90,000 per year in healthcare utilization for a total cost to the US government of $33.9 Billion. Today, ESRD patients comprise only 2.9% of Medicare's total beneficiaries, yet they account over 13% of total spending. While the incidence and costs per patient have stabilized in recent years, the volume of active patients continues to rise.

The five stages of advanced chronic kidney disease ("CKD") are based upon glomerular filtration rate (GFR). Stage 1 (GFR >90) patients have normal filtration, while stage 5 (GFR <15) have kidney failure. Like many chronic diseases, the diagnosis capture improves with increasing symptom and disease severity.

The CKD 3b/4 subgroup is a smaller subgroup that reflects important changes in disease progression, healthcare system engagement and transition to ESRD. Presentation to the emergency department rises with severity of CKD. Among the US Veteran's Administration population, nearly 86% of the incident dialysis patients had a hospital admission within the five years preceding the admission. Of those, 63% were hospitalized at initiation of dialysis. This suggests a tremendous opportunity to intervene prior to dialysis.

Despite being further down the arterial tree than other organs, the kidneys receive a disproportionate amount of cardiac output at rest. The glomerular membrane represents a path of least resistance of filtrate into the tubules. In healthy states, the nephron has multiple, intricate, redundant means of auto-regulating within normal ranges of arterial pressure.

Venous congestion has been implicated in reduced renal function and is associated with the systemic hypervolemia found in later stages of CKD. Since the kidney is covered with a semi-rigid capsule, small changes in venous pressure translate into direct changes in the intratubule pressures. This shift in intratubule pressure has been shown to upregulate reabsorption of sodium and water, perpetuating the vicious cycle.

Regardless of the initial insult and early progression, more advanced CKD is associated with decreased filtration (by definition) and greater azotemia. Regardless of whether the remaining nephrons are hyperabsorbing water or they are just unable to filtrate sufficiently, this nephron loss is associated with fluid retention and a progressive decline in renal function.

The kidney is sensitive to subtle shifts in volume. As pressure in either the tubule or capillary bed rises, the pressure in the other follows. As the capillary bed pressure rises, the production of filtrate and elimination of urine can decline dramatically. While not intending to be bound by any theory, it is believe that mild and regulated negative pressure delivered to the renal pelvis decreases the pressure among each of the functioning nephrons. In healthy anatomy, the renal pelvis is connected via a network of calyces and collecting ducts to approximately one million individual nephrons. Each of these nephrons are essentially fluid columns connecting Bowman's space to the renal pelvis. Pressure transmitted to the renal pelvis translates throughout. It is believed that, as negative pressure is applied to the renal pelvis, the glomerular capillary pressure forces more filtrate across the glomerular membrane, leading to increased urine output.

It is important to note that the tissues of the urinary tract are lined with urothelium, a type of transitional epithelium. The tissues lining the inside of the urinary tract are also referred to as uroendothelial or urothelial tissues, such as mucosal tissue 1003 of the ureter and/or kidney and bladder tissue 1004. Urothelium has a very high elasticity, enabling a remarkable range of collapsibility and distensibility. The urothelium lining the ureter lumen is surrounded first by the lamina propria, a thin layer of loose connective tissue, which together comprise the urothelial mucosa. This mucosa is then surrounded by a layer of longitudinal muscle fibers. These longitudinal muscle fibers surrounding the urothelial mucosa and the elasticity of the urothelial mucosa itself allow the ureter to relax into a collapsed stellate cross-section and then expand to full distention during diuresis. Histology of any normal ureteral cross-section reveals this star-shaped lumen in humans and other mammals generally used in translational medical research. Wolf et al., "Comparative Ureteral Microanatomy", JEU 10: 527-31 (1996).

The process of transporting urine from the kidney to the bladder is driven by contractions through the renal pelvis and peristalsis distally through the rest of the ureter. The renal pelvis is the widening of the proximal ureter into a funnel-shape where the ureter enters the kidney. The renal pelvis has actually been shown to be a continuation of the ureter, comprised of the same tissue but with one additional muscle layer that allows it to contract. Dixon and Gosling, "The Musculature of the Human Renal Calyces, Pelvis and Upper Ureter", J. Anat. 135: 129-37 (1982). These contractions push urine through the renal pelvis funnel to allow peristaltic waves to propagate the fluid through the ureter to the bladder.

Imaging studies have shown that the ureter of the dog can readily increase to up to 17× its resting cross-sectional area to accommodate large volumes of urine during diuresis. Woodburne and Lapides, "The Ureteral Lumen During Peristalsis", AJA 133: 255-8 (1972). Among swine, considered to be the closest animal model for the human upper urinary tract, the renal pelvis and most proximal ureter are actually shown to be the most compliant of all ureteral sections. Gregersen, et al., "Regional Differences Exist in Elastic Wall Properties in the Ureter". SJUN 30: 343-8 (1996). Wolf's comparative analysis of various research animals' ureteral microanatomy to that of humans revealed comparable thickness of lamina propria layer relative to whole ureter diameter in dogs (29.5% in humans and 34% in dogs) and comparable percentage of smooth muscle relative to total muscular cross sectional area in pigs (54% in humans and 45% in pigs). While there are certainly limitations to the comparisons between species, dogs and pigs have historically been strong foci in studying and understanding human ureter anatomy and physiology, and these reference values support this high level of translatability.

There is much more data available on structure and mechanics of pig and dog ureters and renal pelves than on human ureters. This is due partly to the invasiveness required for such detailed analyses as well as the inherent limitations of various imaging modalities (MRI, CT, ultrasound, etc.) to attempt to accurately identify size and composition of such small, flexible, and dynamic structures clinically. Nevertheless, this ability for the renal pelvis to distend or completely collapse in humans is a hurdle for nephrologists and urologists seeking to improve urine flow.

While not intending to be bound by any theory, the present inventors theorized that the application of negative pressure might help to facilitate fluid flow from the kidney, and that a very particular tool, designed to deploy a protective surface area in order to open or maintain the opening of the interior of the renal pelvis while inhibiting the surrounding tissues from contracting or collapsing into the fluid column under negative pressure, is needed to facilitate the application of negative pressure within the renal pelvis. The catheter designs of the present invention disclosed herein provide a protective surface area to inhibit surrounding urothelial tissues from contracting or collapsing into the fluid column under negative pressure. It is believed that the catheter designs of the present invention disclosed herein can successfully maintain the stellate longitudinal folding of the ureteral wall away from the central axis and protected holes of the catheter drainage lumen, and can inhibit natural sliding of the catheter down the stellate cross-sectional area of the ureteral lumen and/or downward migration by peristaltic waves.

Also, catheter designs of the present invention disclosed herein can avoid an unprotected open hole at the distal end of the drainage lumen which fails to protect surrounding tissues during suction. While it is convenient to think of the ureter as a straight tube, the true ureter and renal pelvis can enter the kidney at a variety of angles. Lippincott Williams & Wilkins, Annals of Surgery, 58, FIGS. 3 & 9 (1913). Therefore, it would be difficult to control the orientation of an unprotected open hole at the distal end of the drainage lumen when deploying such a catheter in the renal pelvis. This single hole may present a localized suction point that has no means of either reliable or consistent distancing from tissue walls, thereby permitting tissue to occlude the unprotected open hole and risking damage to the tissue. Also, catheter designs of the present invention disclosed herein can avoid placement of a balloon having an unprotected open hole at the distal end of the drainage lumen close to the kidney which may result in suction against and/or occlusion of the calyces. Placement of a balloon having an unprotected open hole at the distal end of the drainage lumen at the very base of the uretero—renal pelvis junction may result in suction against and occlusion by renal pelvis tissue. Also, a rounded balloon may present a risk of ureteral avulsion or other damage from incidental pulling forces on the balloon.

Delivering negative pressure into the kidney area of a patient has a number of anatomical challenges for at least three reasons. First, the urinary system is composed of highly pliable tissues that are easily deformed. Medical textbooks often depict the bladder as a thick muscular structure that can remain in a fixed shape regardless of the volume of urine contained within the bladder. However, in reality, the bladder is a soft deformable structure. The bladder shrinks to conform to the volume of urine contained in the bladder. An empty bladder more closely resembles a deflated latex balloon than a ball. In addition, the mucosal lining on the interior of the bladder is soft and susceptible to irritation and damage. It is desirable to avoid drawing the urinary system tissue into the orifices of the catheter to maintain adequate fluid flow therethrough and avoid injury to the surrounding tissue.

Second, the ureters are small tube-like structures that can expand and contract to transport urine from the renal pelvis to the bladder. This transport occurs in two ways: peristaltic activity and by a pressure gradient in an open system. In the peristaltic activity, a urine portion is pushed ahead of a contractile wave, which almost completely obliterates the lumen. The wave pattern initiates in the renal pelvis area, propagates along the ureter, and terminates in the bladder. Such a complete occlusion interrupts the fluid flow and can prevent negative pressure delivered in the bladder from reaching the renal pelvis without assistance. The second type of transport, by pressure gradient through a wide-open ureter, may be present during large urine flow. During such periods of high urine production, the pressure head in the renal pelvis would not need to be caused by contraction of the smooth muscles of the upper urinary tract, but rather is generated by the forward flow of urine, and therefore reflects arterial blood pressure. Kiil F., "Urinary Flow and Ureteral Peristalsis" in: Lutzeyer W., Melchior H. (Eds.) Urodynamics. Springer, Berlin, Heidelberg (pp. 57-70) (1973).

Third, the renal pelvis is at least as pliable as the bladder. The thin wall of the renal pelvis can expand to accommodate multiple times the normal volume, for example as occurs in patients having hydronephrosis.

More recently, the use of negative pressure in the renal pelvis to remove blood clots from the renal pelvis by the use of suction has been cautioned against because of the inevitable collapse of the renal pelvis, and as such discourages the use of negative pressure in the renal pelvis region. Webb, Percutaneous Renal Surgery: A Practical Clinical Handbook. p 92. Springer (2016).

While not intending to be bound by any theory, the tissues of the renal pelvis and bladder are flexible enough to be drawn inwardly during delivery of negative pressure to conform to the shape and volume of the tool being used to deliver negative pressure. Analogous to the vacuum sealing of a husked car of corn, the urothelial tissue will collapse around and conform to the source of negative pressure. To prevent the tissue from occluding the lumen and impeding the flow of urine, the present inventors theorized that a protective surface area sufficient to maintain the fluid column when mild negative pressure is applied would prevent or inhibit occlusion.

The present inventors determined that there are specific features that enable a catheter tool to be deployed successfully in and deliver negative pressure through the urological region that have not been previously described. These require a deep understanding of the anatomy and physiology of the treatment zone and adjacent tissues. The catheter must comprise a protective surface area within the renal pelvis by supporting the urothelium and inhibiting the urothelial tissue from occluding openings in the catheter during application of negative pressure through the catheter lumen. For example, establishing a three dimensional shape or void volume, that is free or essentially free from urothelial tissue, ensures the patency of the fluid column or flow from each of the million nephrons into the drainage lumen of the catheter.

Since the renal pelvis is comprised of longitudinally oriented smooth muscle cells, the protective surface area would ideally incorporate a multi-planar approach to establishing the protected surface area. Anatomy is often described in three planes, sagittal (vertical front to back that divides the body into right and left parts), coronal (vertical side to side dividing the body into dorsal and ventral parts) and transverse (horizontal or axial that divides the body into superior and inferior parts, and is perpendicular to the sagittal and coronal planes). The smooth muscle cells in the renal pelvis are oriented vertically. It is desirable for the catheter to also maintain a radial surface area across the many transverse planes between the kidney and the ureter. This enables a catheter to account for both longitudinal and horizontal portions of the renal pelvis in the establishment of a protective surface area 1001. In addition, given the flexibility of the tissues, the protection of these tissues from the openings or orifices that lead to the lumen of the catheter tool is desirable. The catheters discussed herein can be useful for delivering negative pressure, positive pressure, or can be used at ambient pressure, or any combination thereof.

In some examples, a deployable/retractable expansion mechanism is utilized that, when deployed, creates and/or maintains a patent fluid column or flow between the kidney and the catheter drainage lumen. This deployable/retractable mechanism, when deployed, creates the protective surface area 1001 within the renal pelvis by supporting the urothelium and inhibiting the urothelial tissue from occluding openings in the catheter during application of negative pressure through the catheter lumen. In some examples, the retention portion is configured to be extended into a deployed position in which a diameter of the retention portion is greater than a diameter of the drainage lumen portion.

With reference to FIGS. 1A-1C, 1F, 1P, 1U, 2A, 2B, 7A, 7B, 17, and 44, the urinary tract, indicated generally at 1, comprises a patient's right kidney 2 and left kidney 4. As discussed above, the kidneys 2, 4 are responsible for blood filtration and clearance of waste compounds from the body through urine. Urine produced by the right kidney 2 and the left kidney 4 is drained into a patient's bladder 10 through tubules, namely a right ureter 6 and a left ureter 8. For example, urine may be conducted through the ureters 6, 8 by peristalsis of the ureter walls, as well as by gravity. The ureters 6, 8 enter the bladder 10 through a ureter orifice or opening 16. The bladder 10 is a flexible and substantially hollow structure adapted to collect urine until the urine is excreted from the body. The bladder 10 is transitionable from an empty position (signified by reference line E) to a full position (signified by reference line F). When the bladder is in the empty position E, the bladder superior wall 70 can be positioned adjacent to and/or conform to the outer periphery 72, 1002 or protective surface area 1001 of the distal end 136 of the bladder catheter 56, 116, shown for example in FIGS. 1A and 1B as mesh 57, in FIGS. 1C, 1U and 7A as coil 1210, in FIG. 1F as a basket shaped structure or support cap 212 of a bladder superior wall support 210, in FIG. 1P as an annular balloon 310, and in FIG. 17 as funnel 116. Normally, when the bladder 10 reaches a substantially full state, urine is permitted to drain from the bladder 10 to a urethra 12 through a urethral sphincter or opening 18 located at a lower portion of the bladder 10. Contraction of the bladder 10 can be responsive to stresses and pressure exerted on a trigone region 14 of the bladder 10, which is the triangular region extending between the ureteral openings 16 and the urethral opening 18. The trigone region 14 is sensitive to stress and pressure, such that as the bladder 10 begins to fill, pressure on the trigone region 14 increases. When a threshold pressure on the trigone region 14 is exceeded, the bladder 10 begins to contract to expel collected urine through the urethra 12.

Similarly, as shown in FIGS. 1A, 1B, 1C, 1F, 1P. 1U, 2A and 2B, for example, the outer periphery 72, 1002 or protective surface area 1001 of the ureteral catheters 112, 114 of the present invention can support tissue 1003 of the ureter and/or kidney to maintain patency of fluid flow between the kidney and the bladder of the patient.

In some examples, methods and systems 50, 100, as shown for example in FIGS. 1A, 1B, 1C, 1F, 1P, 1U, 2A, 2B, 7, 17, and 44, are provided for removing fluid (such as urine) from a patient, the method comprising: deploying a ureteral stent 52, 54 (shown in FIG. 1A) or ureteral catheter 112, 114 (shown in FIGS. 1B, 1C, 1F, 1P, 1U, 2A, 2B, 7, 17, and 44) into a ureter 6, 8 of a patient to maintain patency of fluid flow between a kidney 2, 4 and a bladder 10 of the patient; and/or deploying a bladder catheter 56, 116 into the bladder 10 of the patient, wherein the bladder catheter 56, 116 comprises a distal end 136 configured to be positioned in a patient's bladder 10, a drainage lumen portion 140 having a proximal end 117, and a sidewall 119 extending therebetween; and applying negative pressure to the proximal end 117 of the bladder catheter 56, 116 and/or ureteral catheter(s) 112, 114 to induce negative pressure in a portion of the urinary tract of the patient to remove fluid from the patient. In some examples, the method further comprises deploying a second ureteral stent or second ureteral catheter into a second ureter or kidney of the patient to maintain patency of fluid flow between a second kidney and the bladder of the patient, as shown in FIGS. 1A, 1B, 1C, 1F, 1P. 1U, 2A, 2B, 7, 17, and 44. Specific characteristics of exemplary ureteral stents or ureteral catheters of the present invention are described in detail herein.

In some non-limiting examples, the ureteral or bladder catheter 56, 112, 114, 116, 312, 412, 512, 812, 1212, 5000, 5001 comprises (a) a proximal portion 117, 128, 1228, 5006, 5007, 5017 and (b) a distal portion 118, 318, 1218, 5004, 5005, the distal portion comprising a retention portion 130, 330, 410, 500, 1230, 1330, 2230, 3230, 4230, 5012, 5013 that comprises one or more protected drainage holes, ports or perforations 133, 533, 1233 and is configured to establish an outer periphery 1002 or protective surface area 1001 that inhibits urothelial tissue, such as mucosal tissue 1003 of the ureter and/or kidney and bladder tissue 1004, from occluding the one or more protected drainage holes, ports or perforations 133, 533, 1233 upon application of negative pressure through the catheter.

Exemplary Ureteral Catheters:

As shown in FIGS. 2A, 7, 17, and 44, examples of systems 100 including ureteral catheters 112, 114 configured to be positioned within the urinary tract of a patient are illustrated. For example, distal ends 120, 121, 1220, 5019, 5021 of the ureteral catheters 112, 114 can be configured to be deployed in at least one of the patient's ureters 2, 4; renal pelvis 20, 21 area of the kidneys 6, 8; or the kidneys 6, 8.

In some examples, suitable ureteral catheters are disclosed in U.S. Pat. No. 9,744,331, US Patent Application Publication No. US 2017/0021128 A1, US Patent Application No. 15/687,064, and U.S. patent application Ser. No. 15/687,083, each of which is incorporated by reference herein.

In some examples, the system 100 can comprise two separate ureteral catheters, such as a first catheter 112 disposed in or adjacent to the renal pelvis 20 of the right kidney 2 and a second catheter 114 disposed in or adjacent to the renal pelvis 21 of the left kidney 4. The catheters 112, 114 can be separate for their entire lengths, or can be held in proximity to one another by a clip, ring, clamp, or other type of connection mechanism (e.g., connector) to facilitate placement or removal of the catheters 112, 114. As shown in FIGS. 2A, 7, 17, 27, and 44, the proximal end 113, 115 of each catheter 112, 114 is positioned within the bladder 10, or at the proximal end of the ureter near the bladder 10, such that the fluid or urine drains into the bladder. In some examples, the proximal end 113, 115 of each catheter 112, 114 can be in fluid communication with the distal portion or end 136 of a bladder catheter 56, 116. In some examples, catheters 112, 114 can merge or be connected together within the bladder to form a single drainage lumen that drains into the bladder 10.

Figure 2A:
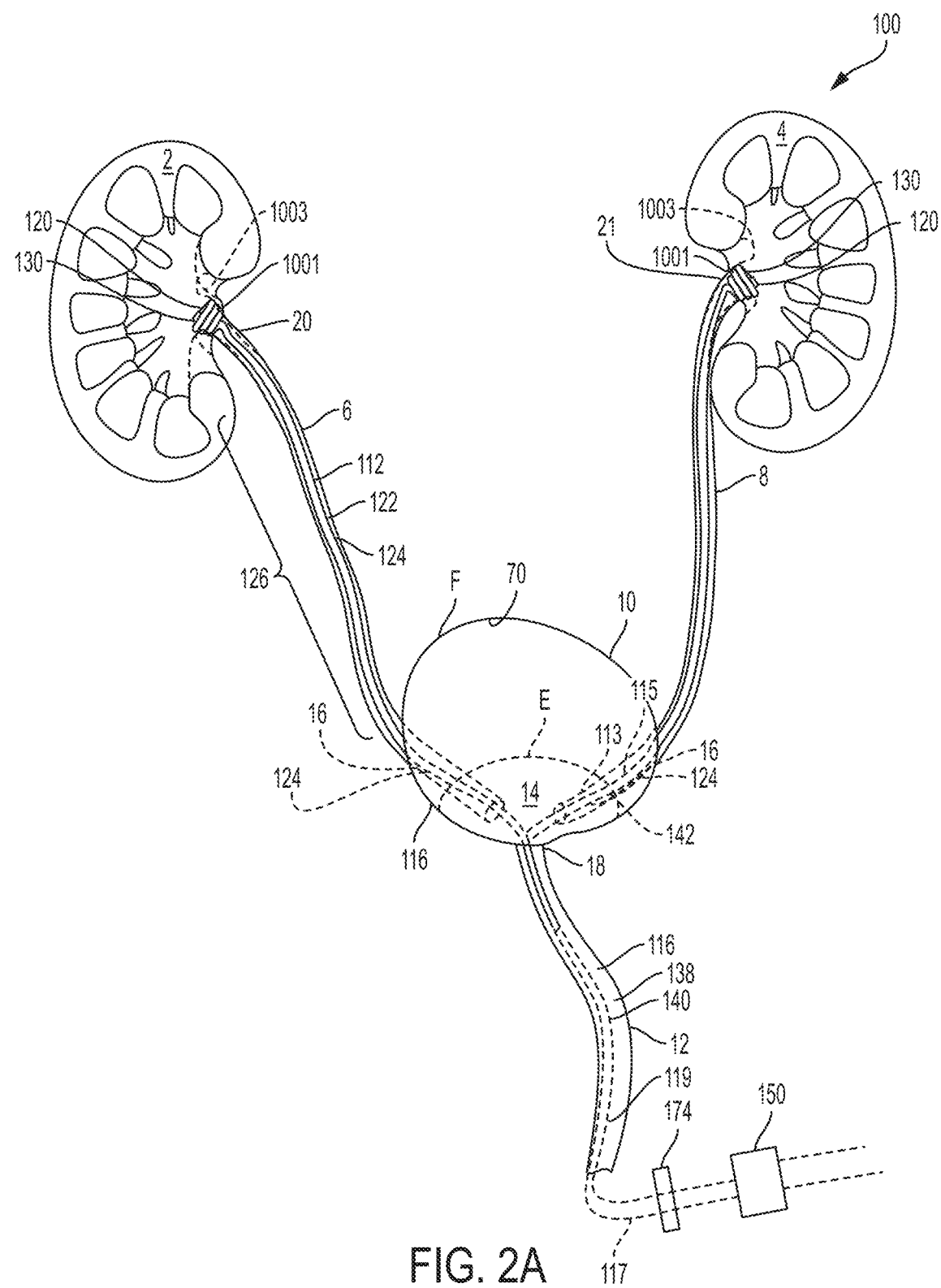
FIG. 2A is a schematic drawing of an indwelling portion of a system comprising a ureteral catheter deployed in a urinary tract of a patient, according to an example of the present invention.
Figure 2B:
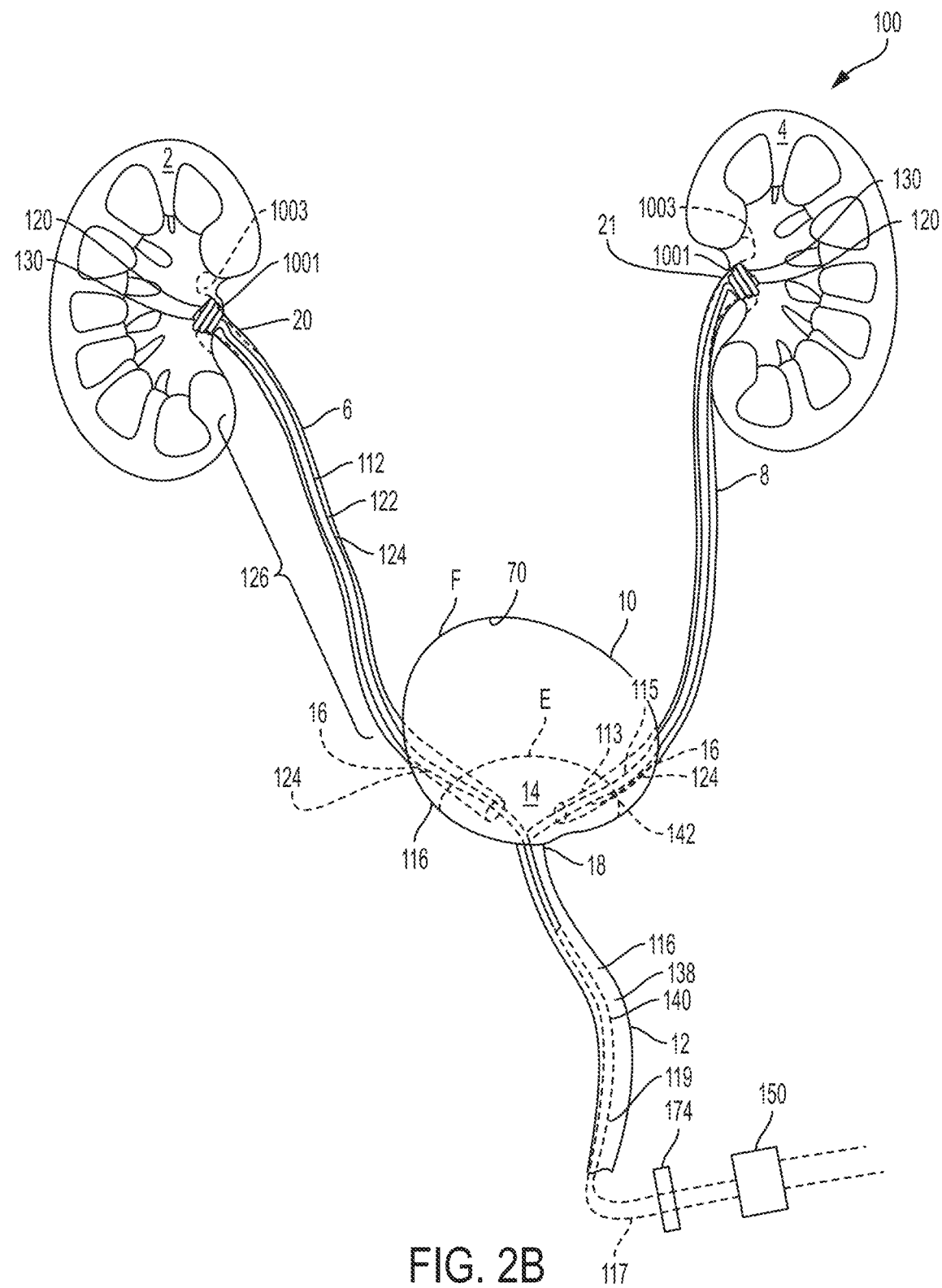
FIG. 2B is a schematic drawing of an indwelling portion of a system comprising a ureteral catheter deployed in a urinary tract of a patient, according to an example of the present invention.

As shown in FIG. 2A, in some examples, the proximal end 113, 115 of one or both of the catheters 112, 114 can be positioned within the urethra 12 and optionally connected to additional drainage tubing to drain fluid to the outside of the body of the patient. As shown in FIG. 2B, in some examples, the proximal end 113, 115 of one or both of the catheters 112, 114 can be positioned to extend from the urethra 12 outside of the body of the patient.

In other examples, the catheters 112, 114 can be inserted through or enclosed within another catheter, tube, or sheath along portions or segments thereof to facilitate insertion and retraction of the catheters 112, 114 from the patient's body. For example, a bladder catheter 116 can be inserted over and/or along the same guidewire as the ureteral catheters 112, 114, or within the same tubing used to insert the ureteral catheters 112, 114.

With reference to FIGS. 1B, 1C, 1F, 1P. 1U, 2A, 2B, 7, 8A, and 8B, an exemplary ureteral catheter 112, 1212, 5000 can comprise at least one elongated body or tube 122, 1222, 5009 the interior of which defines or comprises one or more drainage channel(s) or lumen(s), such as drainage lumen 124, 1224, 5002. The tube 122, 1222, 5009 size can range from about 1 Fr to about 9 Fr (French catheter scale). In some examples, the tube 122, 1222, 5009 can have an external diameter ranging from about 0.33 to about 3 mm, and an internal diameter ranging from about 0.165 to about 2.39 mm. In one example, the tube 122 is 6 Fr and has an outer diameter of 2.0±0.1 mm. The length of the tube 122, 1222, 5009 can range from about 30 cm to about 120 cm depending on the age (e.g., pediatric or adult) and gender of the patient.

Figure 7A:
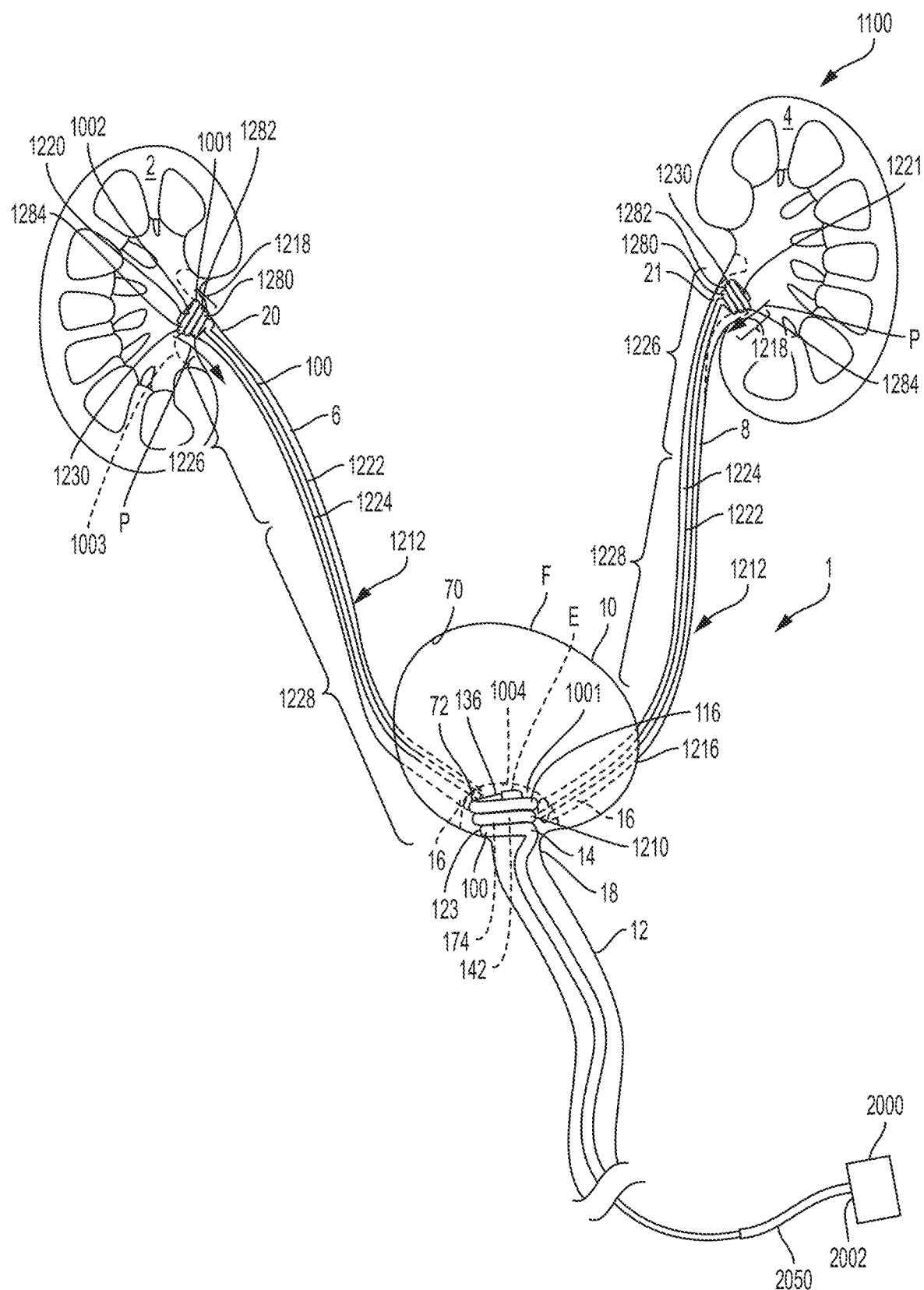
FIG. 7A is a schematic drawing of another example of an indwelling portion of a system comprising a ureteral catheter and a bladder catheter deployed in a urinary tract of a patient, according to an example of the present invention.
Figure 7B:
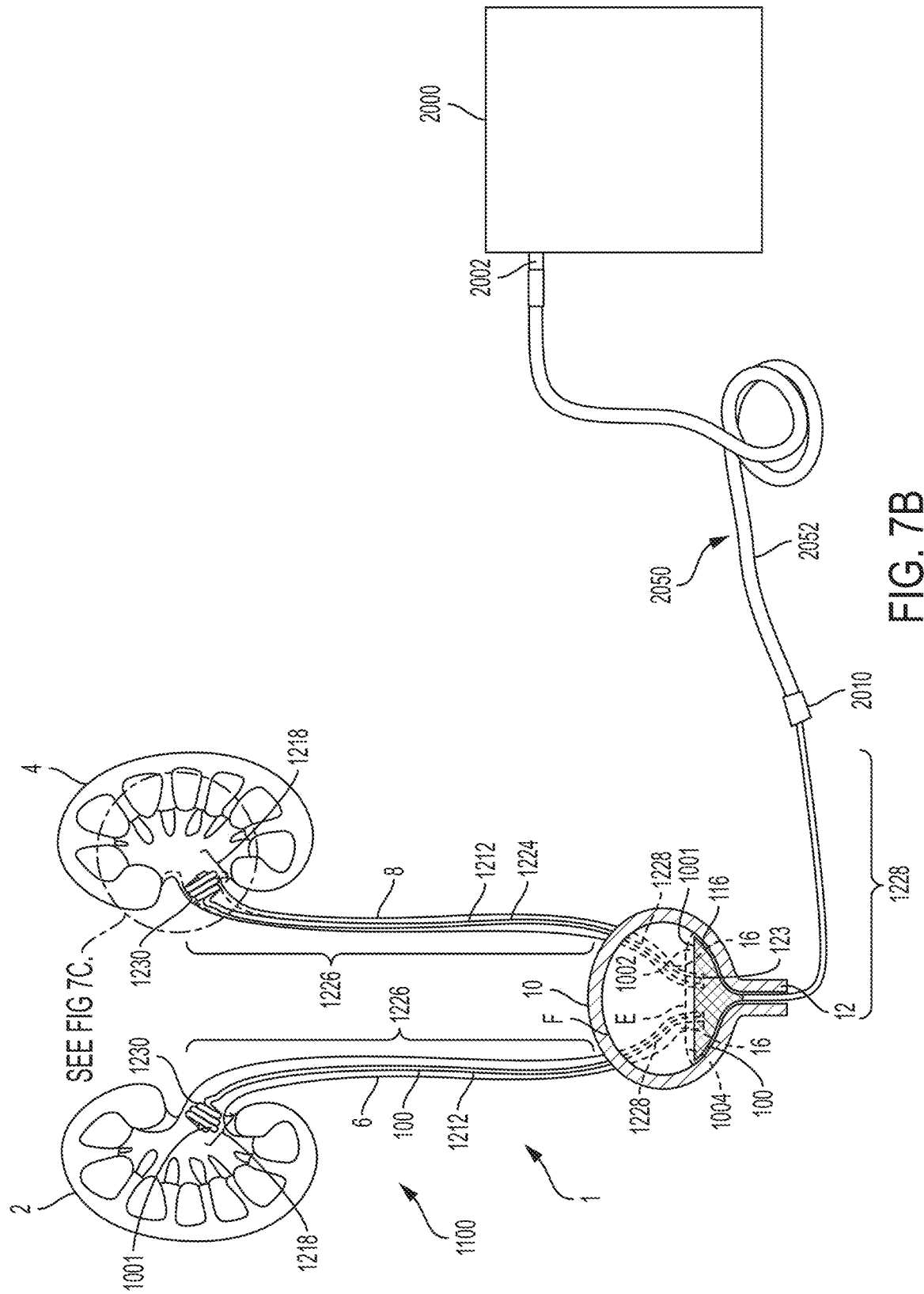
FIG. 7B is a schematic drawing of a system for inducing negative pressure to the urinary tract of a patient according to an example of the present invention.
Figure 7C:
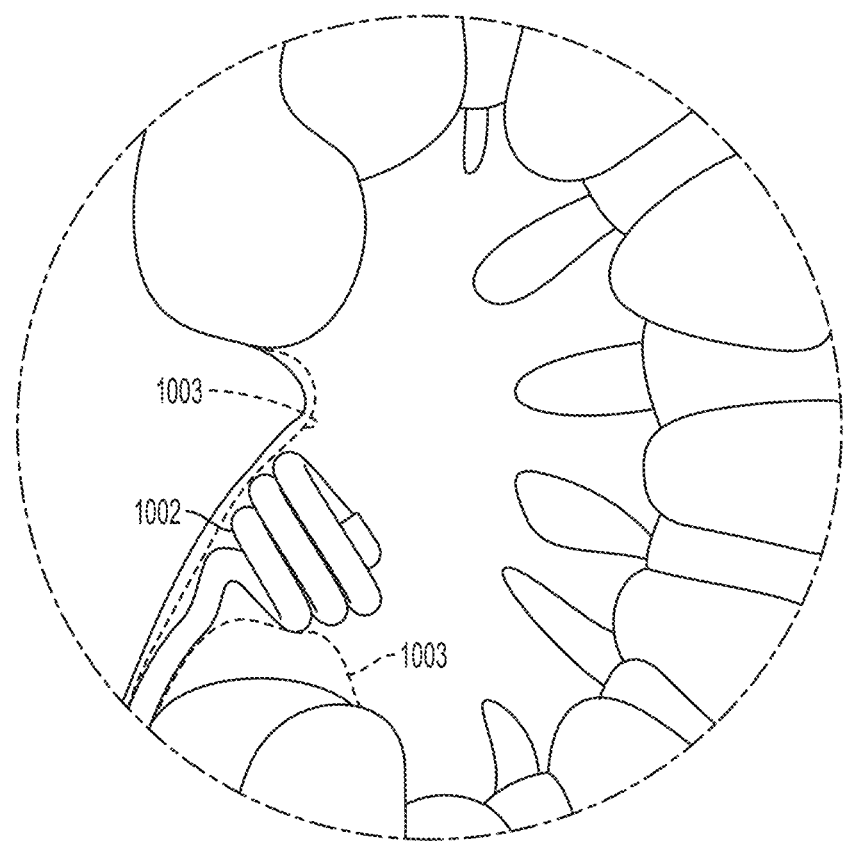
FIG. 7C is a an enlarged schematic drawing of a portion of a ureteral catheter according to the present invention positioned in the renal pelvis region of the kidney showing in phantom general changes believed to occur in the renal pelvis tissue in response to application of negative pressure through the ureteral catheter.

The tube 122, 1222, 5009 can be formed from a flexible and/or deformable material to facilitate advancing and/or positioning the tube 122, 1222, 5009 in the bladder 10 and ureters 6, 8 (shown in FIGS. 2 and 7). The catheter material should be flexible and soft enough to avoid or reduce irritation of the renal pelvis and ureter, but should be rigid enough that the tube 122, 1222, 5009 does not collapse when the renal pelvis or other portions of the urinary tract exert pressure on the exterior of the tube 122, 1222, 5009, or when the renal pelvis and/or ureter are drawn against the tube 122, 1222, 5009 during inducement of negative pressure. For example, the tube 122, 1222, 5009 or drainage lumen can be formed, at least in part, from one or more materials including copper, silver, gold, nickel-titanium alloy, stainless steel, titanium, and/or polymer such as biocompatible polymer(s), polyurethane, polyvinyl chloride, polytetrafluoroethylene (PTFE), latex, silicon coated latex, silicon, silicone, polyglycolide or poly(glycolic acid) (PGA), Polylactide (PLA), Poly(lactide-co-glycolide), Polyhydroxyalkanoates, Polycaprolactone and/or Poly(propylene fumarate). In one example, the tube 122, 1222, 5009 is formed from a thermoplastic polyurethane. The tube 122, 1222, 5009 can also include or be impregnated with one or more of copper, silver, gold, nickel-titanium alloy, stainless steel, and titanium. In some examples, the tube 122, 1222, 5009 is impregnated with or formed from a material viewable by fluoroscopic imaging. For example, the biocompatible polymer which forms the tube 122, 1222, 5009 can be impregnated with barium sulfate or a similar radiopaque material. As such, the structure and position of the tube 122, 1222, 5009 is visible to fluoroscopy.

At least a portion or all of the interior or exterior of the catheter 112, 1212, 5000, for example tube 122, 1222, 5009 can be coated with a hydrophilic coating to facilitate insertion and/or removal, and/or to enhance comfort. In some examples, the coating is a hydrophobic and/or lubricious coating. For example, suitable coatings can comprise ComfortCoat® hydrophilic coating which is available from Koninklijke DSM N. V. or hydrophilic coatings comprising polyelectrolyte(s) such as are disclosed in U.S. Pat. No. 8,512,795, which is incorporated herein by reference.

Figure 8A:
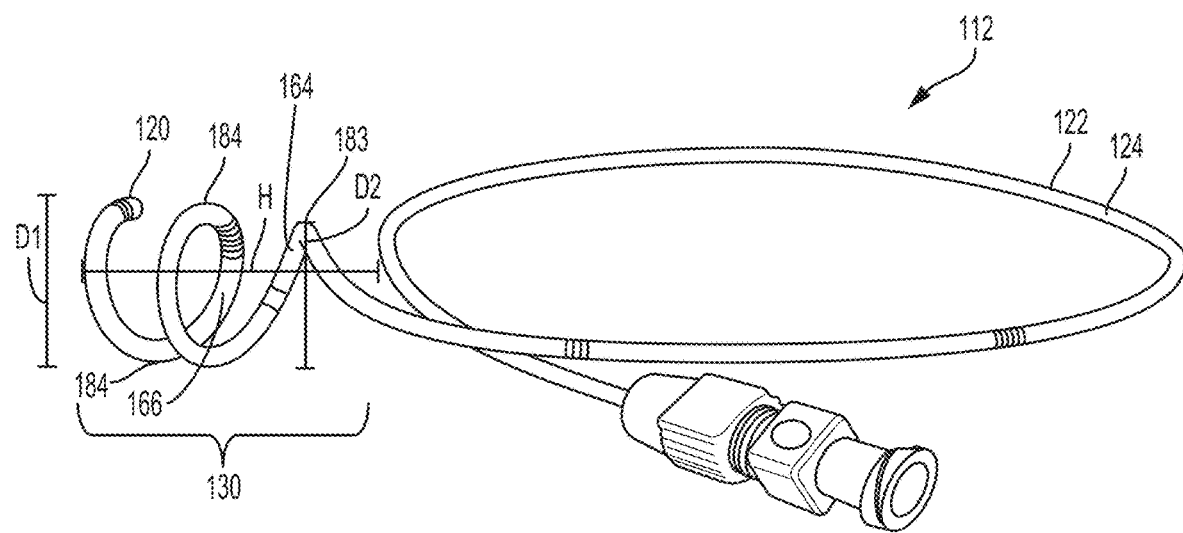
FIG. 8A is a perspective view of an exemplary catheter according to an example of the present invention.
Figure 8B:
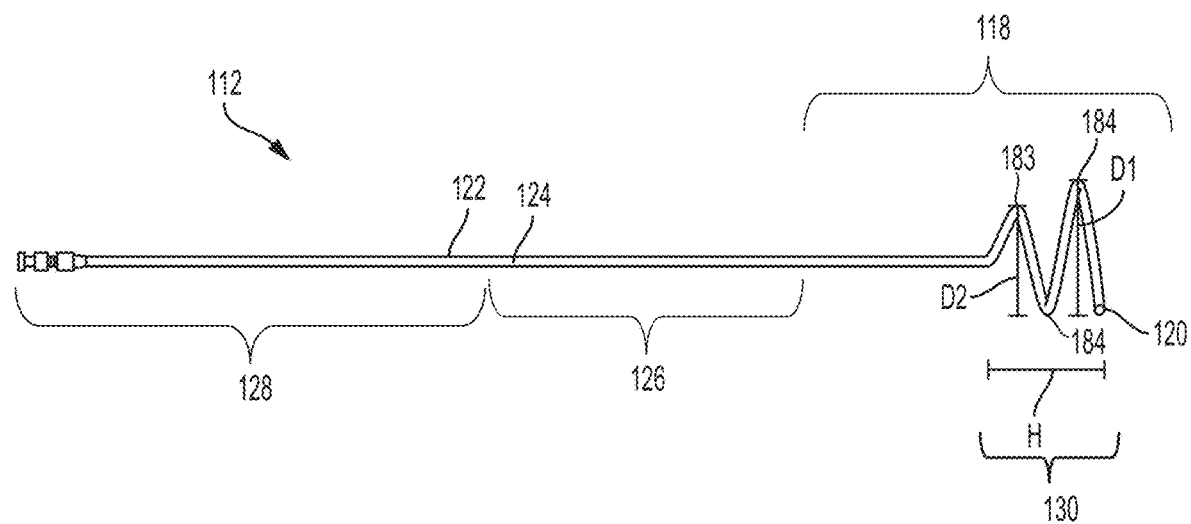
FIG. 8B is a front view of the catheter of FIG. 8A.

In some examples, as shown in FIG. 8B, for example, the tube 122 can comprise: a distal portion 118 (e.g., a portion of the tube 122 configured to be positioned in the ureter 6, 8 and renal pelvis 20, 21); a middle portion 126 (e.g., a portion of the tube 122 configured to extend from the distal portion 118 through the ureteral openings 16 into the patient's bladder 10 and urethra 12); and a proximal portion 128 (e.g., a portion of the tube 122 extending into the bladder 10, or urethra 12, or extending from the urethra 12 outside of the body of the patient). In one example, the combined length of the proximal portion 128 and the middle portion 126 of the tube 122 is about 54±2 cm. In some examples, the tube 122 terminates in the bladder 10. In that case, fluid drains from the proximal end of the ureteral catheter 112, 114 and is directed from the body through the additional indwelling bladder catheter. In other examples, the tube 122 terminates in the urethra 12, e.g., a bladder catheter is not required. In other examples, the tube extends from the urethra 12 outside of the body of the patient, e.g., a bladder catheter is not required.

Exemplary Ureteral Retention Portions:

Any of the retention portions disclosed herein can be formed from the same material as the drainage lumen discussed above, and can be unitary with or connected to the drainage lumen, or the retention portion can be formed from a different material, such as those that are discussed above for the drainage lumen, and connected thereto. For example, the retention portion can be formed from any of the aforementioned materials, for example a polymer such as polyurethane, flexible polyvinyl chloride, polytetrafluoroethylene (PTFE), latex, silicone, silicon, polyglycolide or poly (glycolic acid) (PGA), Polylactide (PLA), Poly(lactide-coglycolide), Polyhydroxyalkanoates. Polycaprolactone and/ or Poly(propylene fumarate).

Generally, and as shown for example in FIGS. 2A-C, 8A, and 8B, the distal portion 118 of the ureteral catheter 112 comprises a retention portion 130 for maintaining the distal end 120 of the catheter 112 at a desired fluid collection position proximate to or within the renal pelvis 20, 21 of the kidney 2, 4. In some examples, the retention portion 130 is configured to be flexible and bendable to permit positioning of the retention portion 130 in the ureter and/or renal pelvis. The retention portion 130 is desirably sufficiently bendable to absorb forces exerted on the catheter 112 and to prevent such forces from being translated to the ureters. For example, if the retention portion 130 is pulled in the proximal direction P (shown in FIG. 9A) toward the patient's bladder, the retention portion 130 can be sufficiently flexible to begin to unwind or be straightened so that it can be drawn through the ureter. Similarly, when the retention portion 130 can be reinserted into the renal pelvis or other suitable region within the ureter, it can be biased to return to its deployed configuration.

In some examples, the retention portion 130 is integral with the tube 122. In that case, the retention portion 130 can be formed by imparting a bend or curl to the catheter body 122 that is sized and shaped to retain the catheter at a desired fluid collection location. Suitable bends or coils can include a pigtail coil, corkscrew coil, and/or helical coil, such as are shown in FIGS. 1, 2A, 7A, and 8A-10G. For example, the retention portion 130 can comprise one or more radially and longitudinally extending helical coils configured to contact and passively retain the catheter 112 within the ureter 6, 8 proximate to or within the renal pelvis 20, 21, as shown for example in FIGS. 2A, 7A, and 8A-10G. In other examples, the retention portion 130 is formed from a radially flared or tapered portion of the catheter body 122. For example, the retention portion 130 can further comprise a fluid collecting portion, as shown in FIGS. 17-41C, such as a tapered or funnel-shaped inner surface 186. In other examples, the retention portion 130 can comprise a separate element connected to and extending from the catheter body or tube 122.

In some examples, the retention portion 130 can further comprise one or more perforated sections, such as drainage holes, perforations or ports 132, 1232 (shown, for example, in FIGS. 9A-9E, 10A, 10E, 11-14, 27, 32A, 32B, 33, 34, and 39-41A-C). A drainage port 132 can be located, for example, at the open distal end 120, 121 of the tube 122, as shown in FIG. 10D. In other examples, perforated sections and/or drainage ports 132, 1232 are disposed along the sidewall 109 of the distal portion 118 of the catheter tube 122, as shown in FIGS. 9A-9E, 10A, 10E, 11-14, 27, 32A, 32B, 33, 34, and 41A-C, or within the material of the retention portion, such as the sponge material of FIGS. 39 and 40. The drainage ports or holes 132, 1232 can be used for assisting in fluid collection by which fluid can flow into the drainage lumen for removal from the patient's body. In other examples, the retention portion 130 is solely a retention structure and fluid collection and/or imparting negative pressure is provided by structures at other locations on the catheter tube 122.

In some examples, such as are shown in FIGS. 9B-E, 10D-G, 18B, 18C-E, 20, 22A-35, 37B, 38A, 39B, 40A-41C, at least a portion of, most, or all of the drainage holes, ports or perforations 132, 1232 are positioned in the ureteral catheter 112, 114 or bladder catheter 116 in protected surface areas or inner surface areas 1000, such that tissue 1004, 1003 from the bladder or kidney does not directly contact or partially or fully occlude the protected drainage holes, ports or perforations 133. For example, as shown in FIGS. 2A-2C, 7A, 7B, 10F, 17, 18D, 24B, 29C, 39B, 40B, and 41B, when negative pressure is induced in the ureter and/or renal pelvis, a portion of the mucosal tissue 1003 of the ureter and/or kidney may be drawn against the outer periphery 72, 1002 or protective surface areas 1001 or outer regions of the retention portion 130 and may partially or fully occlude some drainage holes, ports or perforations 134 positioned on the outer periphery 72, 1002 or protective surface areas 1001 of the retention portion 130. Similarly, as shown in FIGS. 2A-2C, 7A, 7B, 10G, 17, 18E, 24C, 39C, 40C, and 41C, when negative pressure is induced in the bladder, a portion of the bladder tissue 1004, such as the transitional epithelial tissue lining, lamina propria connective tissue, muscularis propria and/or fatty connective tissue, may be drawn against the outer periphery 72, 1002 or protective surface areas 1001 or outer regions of the retention portion 130 and may partially or fully occlude some drainage holes, ports or perforations 134 positioned on the outer periphery 1002 or protective surface areas 1001 or outer regions of the retention portion 130.

At least a portion of protected drainage ports 133 located on the protected surface areas or inner surface areas 1000 of the retention portion 130 would not be partially or fully occluded when such tissues 1003, 1004 contact the outer periphery 72, 1002 or protective surface areas 1001 or outer regions of the retention portion 130. Further, risk of injury to the tissues 1003, 1004 from pinching or contact with the drainage ports 133 can be reduced or ameliorated. The configuration of the outer periphery 72, 1002 or protective surface areas 1001 or outer regions of the retention portion 130 depends upon the overall configuration of the retention portion 130. Generally, the outer periphery 72, 1002 or protective surface areas 1001 or outer regions of the retention portion 130 contacts and supports the bladder 1004 or kidney tissue 1003, and thereby inhibits occlusion or blockage of the protected drainage holes, ports or perforations 133.

Figure 10:
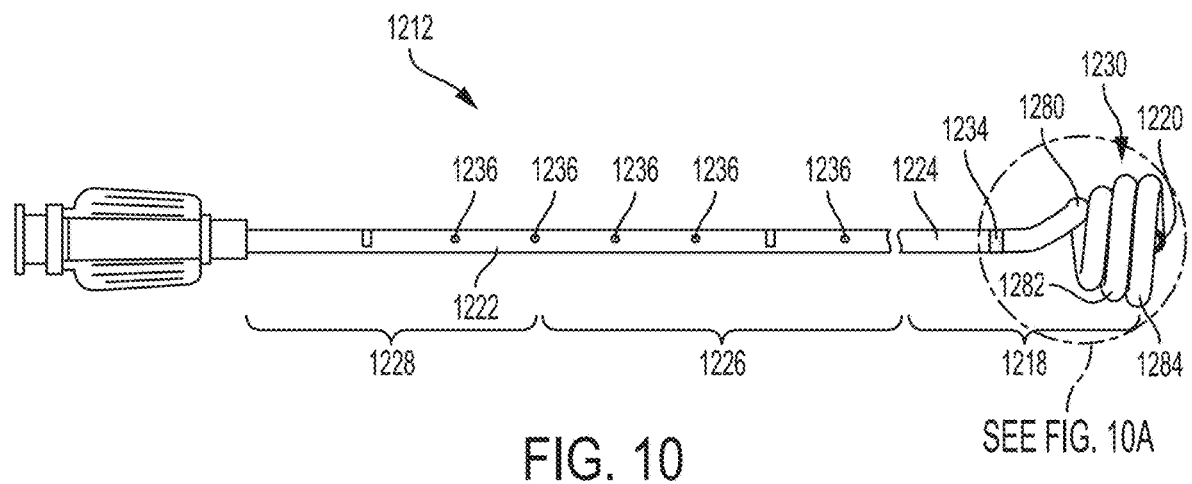
FIG. 10 is a front view of another example of a catheter according to an example of the present invention.
Figure 10A:
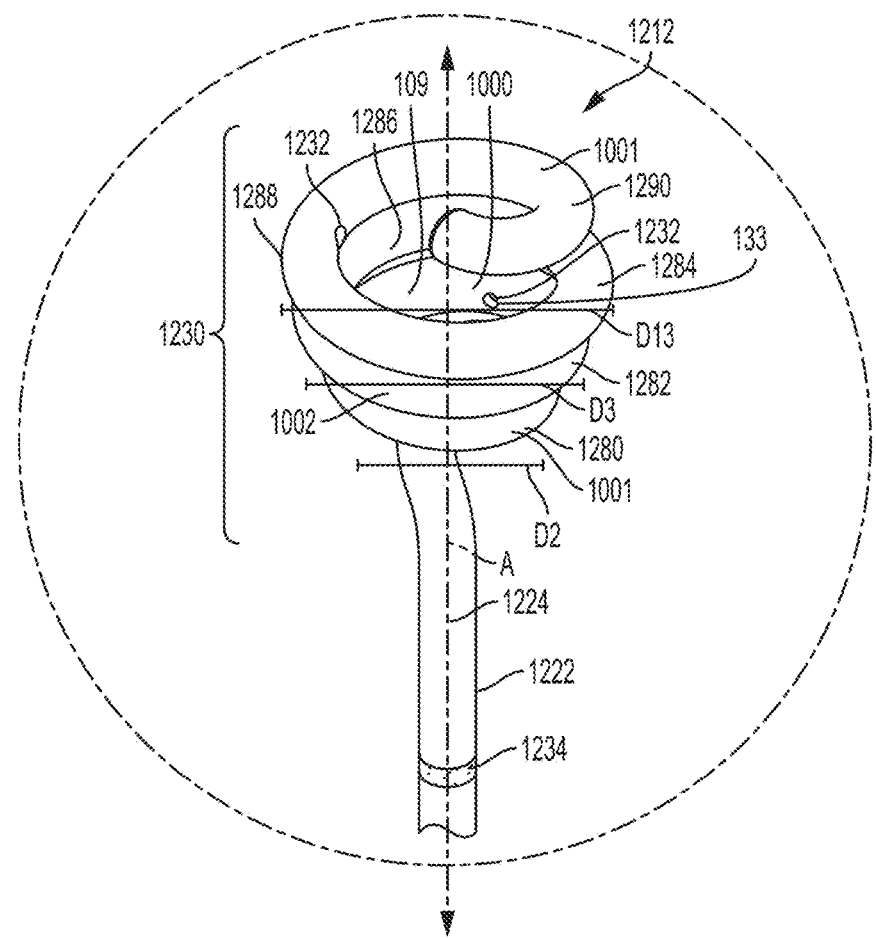
FIG. 10A is a perspective view of the retention portion of the catheter of FIG. 10 enclosed by circle 10A according to an example of the present invention.
Figure 10B:
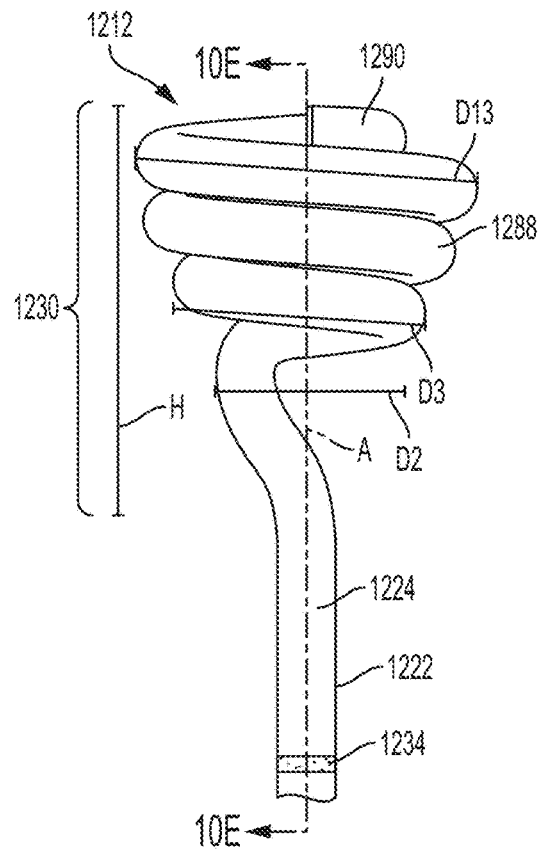
FIG. 10B is a front view of the retention portion of FIG. 10A according to an example of the present invention.
Figure 10C:
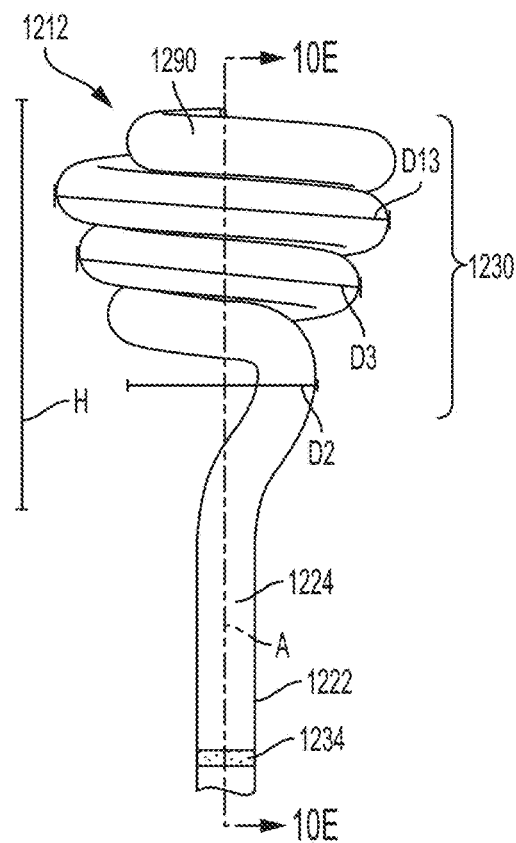
FIG. 10C is a rear view of the retention portion of FIG. 10A according to an example of the present invention.
Figure 10D:
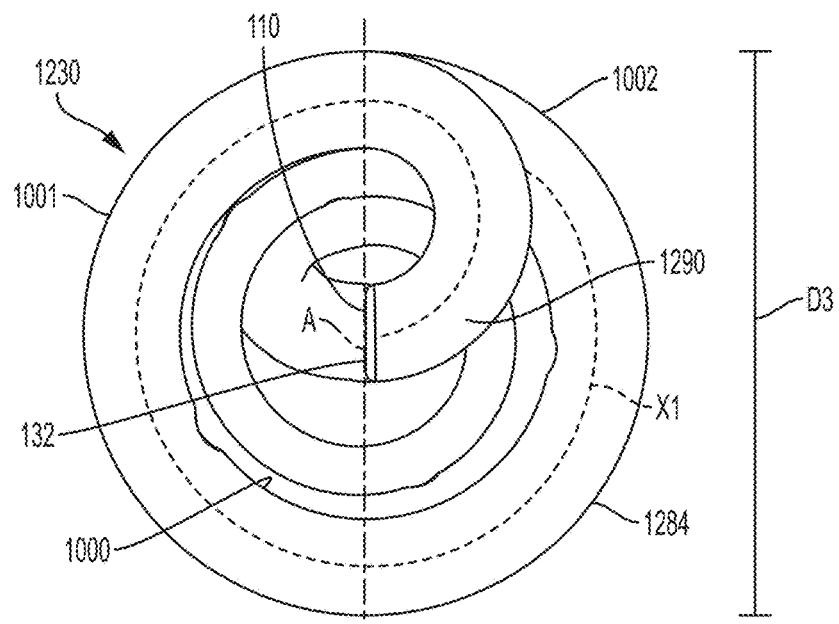
FIG. 10D is a top view of the retention portion of FIG. 10A according to an example of the present invention.
Figure 10E:
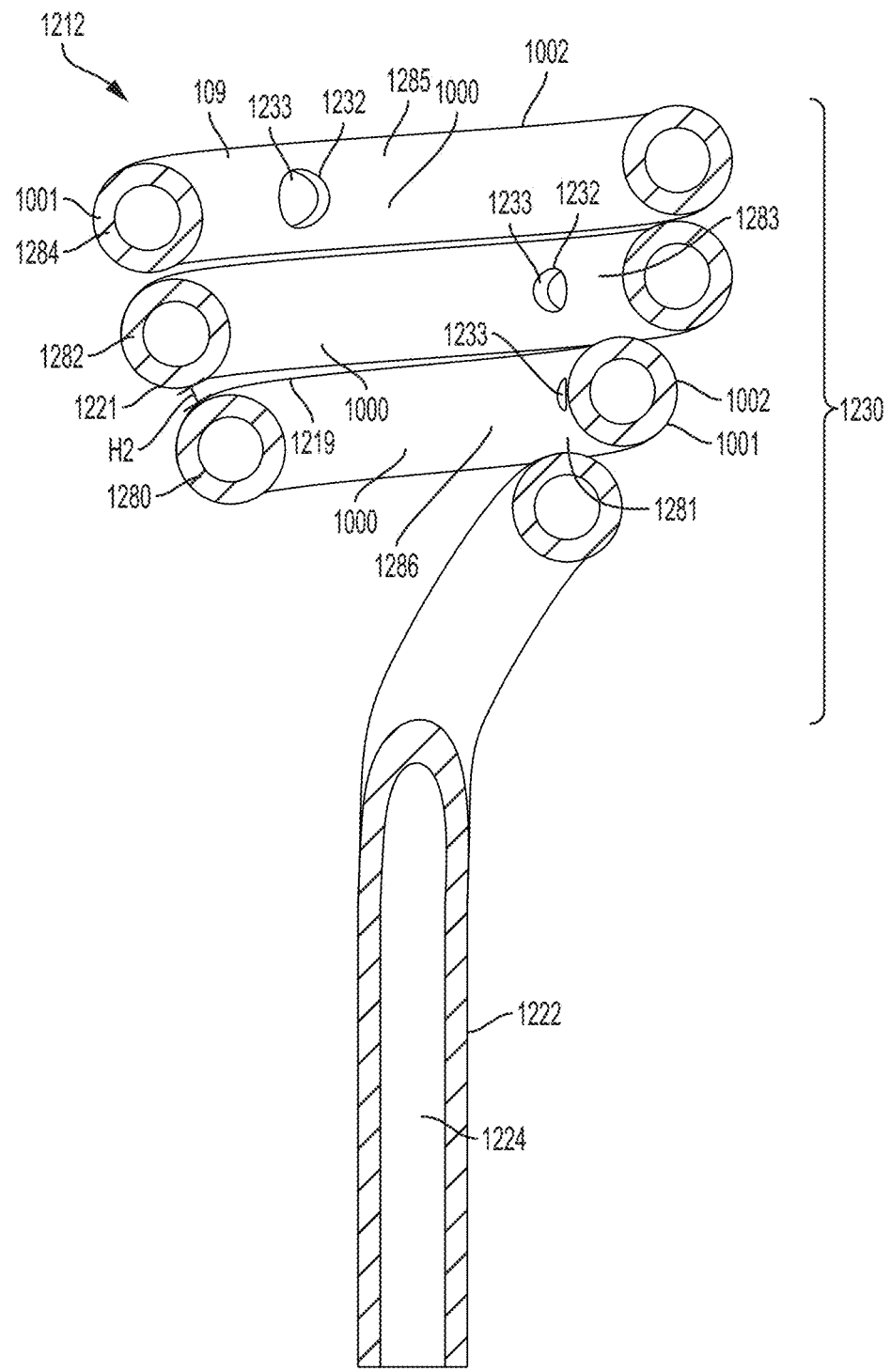
FIG. 10E is a cross sectional view of the retention portion of FIG. 10A taken along line 10E-10E according to an example of the present invention.
Figure 10F:
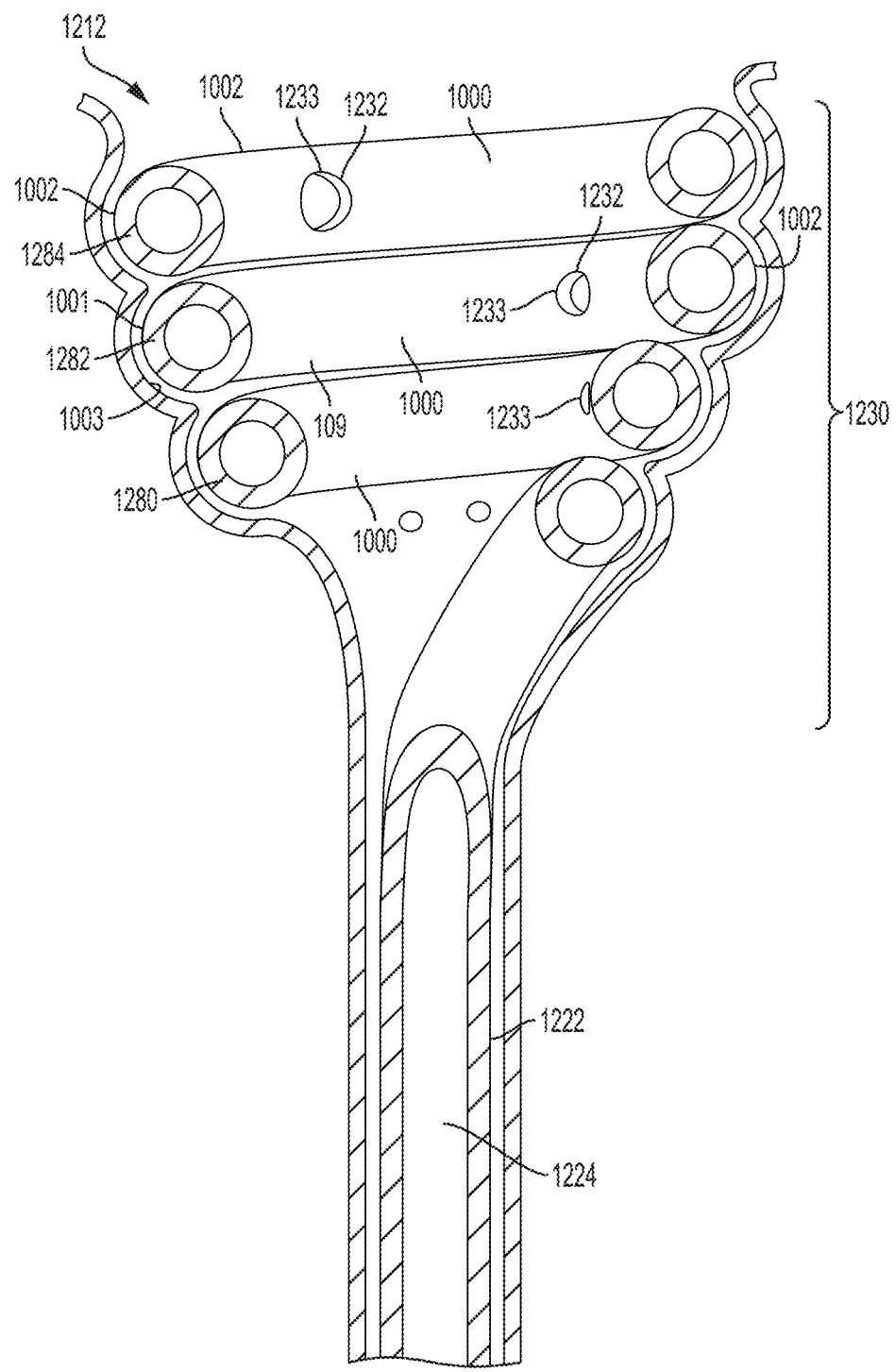
FIG. 10F is s a cross sectional view of the retention portion of FIG. 10A taken along line 10E-10E according to an example of the present invention positioned in the renal pelvis region of the kidney showing in general changes believed to occur in the renal pelvis tissue in response to application of negative pressure through the ureteral catheter.
Figure 10G:
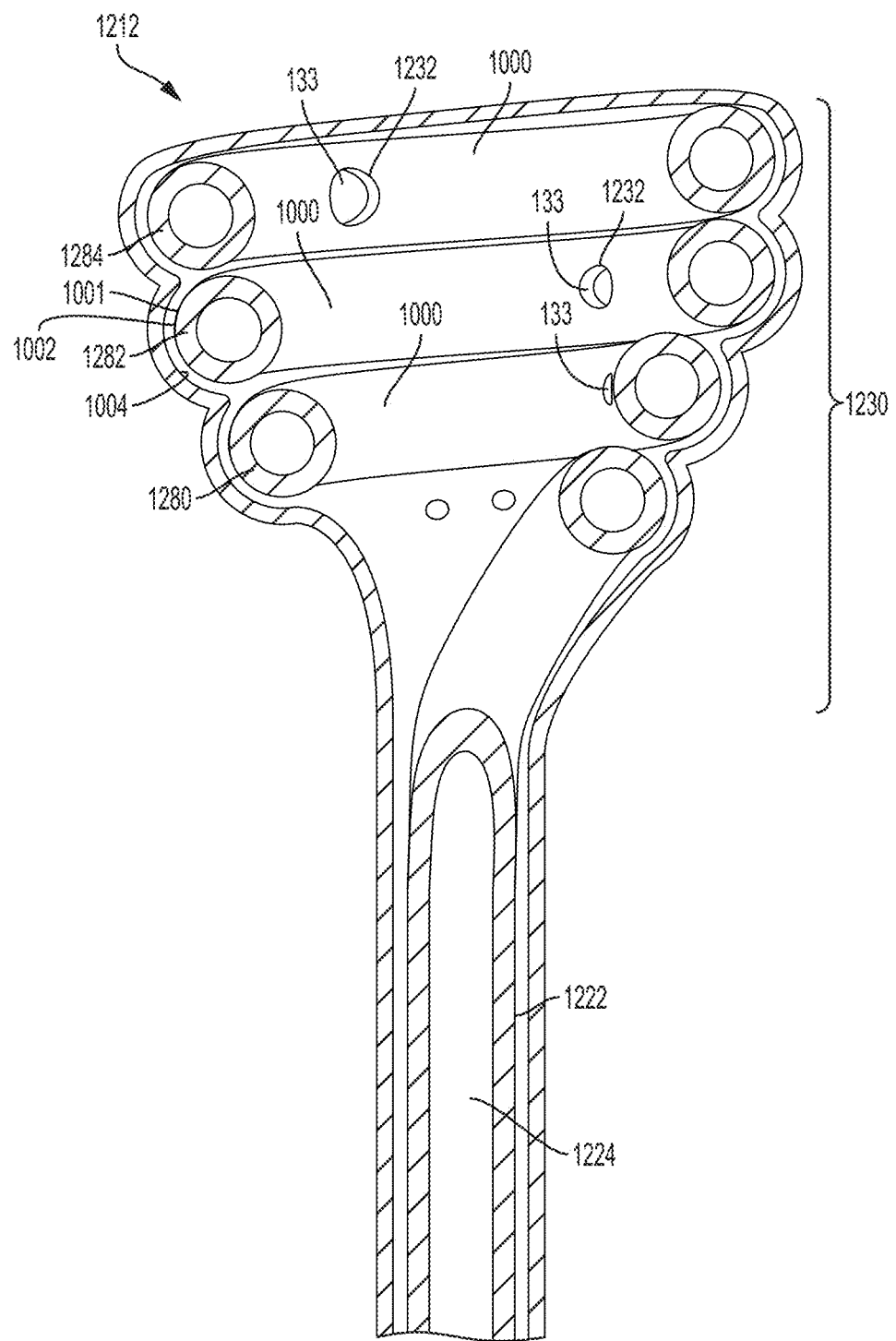
FIG. 10G is s a cross sectional view of the retention portion of FIG. 10A taken along line 10E-10E according to an example of the present invention positioned in the bladder showing in general changes believed to occur in the bladder tissue in response to application of negative pressure through the bladder catheter.

For example, as shown in FIG. 10E-G, there is shown an exemplary retention portion 1230 comprising a plurality of helical coils 1280, 1282, 1284. The outer periphery 1002 or protective surface areas 1001 or outer regions of the helical coils 1280, 1282, 1284 contact and support the bladder tissue 1004 or kidney tissue 1003 to inhibit occlusion or blockage of protected drainage holes, ports or perforations 1233 positioned in protected surface areas or inner surface areas 1000 of the helical coils 1280, 1282, 1284. The outer periphery 1002 or protective surface areas 1001 or outer regions of the helical coils 1280, 1282, 1284 provides protection for the protected drainage holes, ports or perforations 1233. In FIG. 10F, the kidney tissue 1003 is shown surrounding and contacting at least a portion of the outer periphery 1002 or protective surface areas 1001 or outer regions of the helical coils 1280, 1282, 1284, which inhibits contact of the kidney tissue 1003 with the protected surface areas or inner surface areas 1000 of the helical coils 1280, 1282, 1284, and thereby inhibits partial or full blockage of the protected drainage holes, ports or perforations 1233 by the kidney tissue 1003. In FIG. 10G, the bladder tissue 1004 is shown surrounding and contacting at least a portion of the outer periphery 1002 or protective surface areas 1001 or outer regions of the helical coils 1280, 1282, 1284, which inhibits contact of the bladder tissue 1004 with the protected surface areas or inner surface areas 1000 of the helical coils 1280, 1282, 1284, and thereby inhibits partial or full blockage of the protected drainage holes, ports or perforations 1233 by the bladder tissue 1004.

Similarly, other examples of configurations of bladder and/or ureteral retention portions shown in FIGS. 1, 2A, 7A, 17, 18A, 18B, 18C, 19, 20, 21, 22A, 22B, 23A, 23B, 24, 25, 26, 27, 28A, 28B, 29A, 29B, 30, 31, 32A, 32B, 33, 34, 35A, 35B, 36, 37A, 37B, 38A, 38B, 39, 40, and 41 provide an outer periphery 1002 or protective surface areas 1001 or outer regions which can contact and support the bladder tissue 1004 or kidney tissue 1003 to inhibit occlusion or blockage of protected drainage holes, ports or perforations 133, 1233 positioned in protected surface areas or inner surface areas 1000 of the retention portions. Each of these examples will be discussed further below.

Referring now to FIGS. 8A, 8B, and 9A-9E, exemplary retention portions 130 for ureteral catheters or bladder catheters comprising a plurality of helical coils, such as one or more full coils 184 and one or more half or partial coils 183, are illustrated. The retention portion 130 is capable of moving between a contracted position and the deployed position with the plurality of helical coils. For example, a substantially straight guidewire can be inserted through the retention portion 130 to maintain the retention portion 130 in a substantially straight contracted position. When the guidewire is removed, the retention portion 130 can transition to its coiled configuration. In some examples, the coils 183, 184 extend radially and longitudinally from the distal portion 118 of the tube 122. With specific reference to FIGS. 8A and 8B, in an exemplary embodiment, the retention portion 130 comprises two full coils 184 and one half coil 183. For example, as shown in FIGS. 8A and 8B, the outer diameter of the full coils 184, shown by line D1, is about 18±2 mm, the half coil 183 diameter D2 can be about 14 mm+2 mm, and the coiled retention portion 130 can have a height H of about 16±2 mm.

The retention portion 130 can further comprise the one or more drainage holes 132, 1232 (shown in FIGS. 9A-9E, 10A and 10E, for example) configured to draw fluid into an interior of the catheter tube 122. In some examples, the retention portion 130 can comprise two, three, four, five, six, seven, eight or more drainage holes 132, 1232, plus an additional hole 110 at the distal tip or end 120 of the retention portion. In some examples, the diameter of each of the drainage holes 132, 1232 (shown in FIGS. 9A-9E, 10A and 10E, for example) can range from about 0.7 mm to 0.9 mm and, preferably, is about 0.83±0.01 mm. In some examples, the diameter of the additional hole 110 at the distal tip or end of the retention portion 130 (shown in FIGS. 9A-9E, 10A and 10E, for example) can range from about 0.165 mm to about 2.39 mm, or about 0.7 to about 0.97 mm. The distance between adjacent drainage holes 132, specifically the linear distance between the closest outer edges of adjacent drainage holes 132, 1232 when the coils are straightened, can be about 15 mm+2.5 mm, or about 22.5±2.5 mm or more.

Figure 9A:
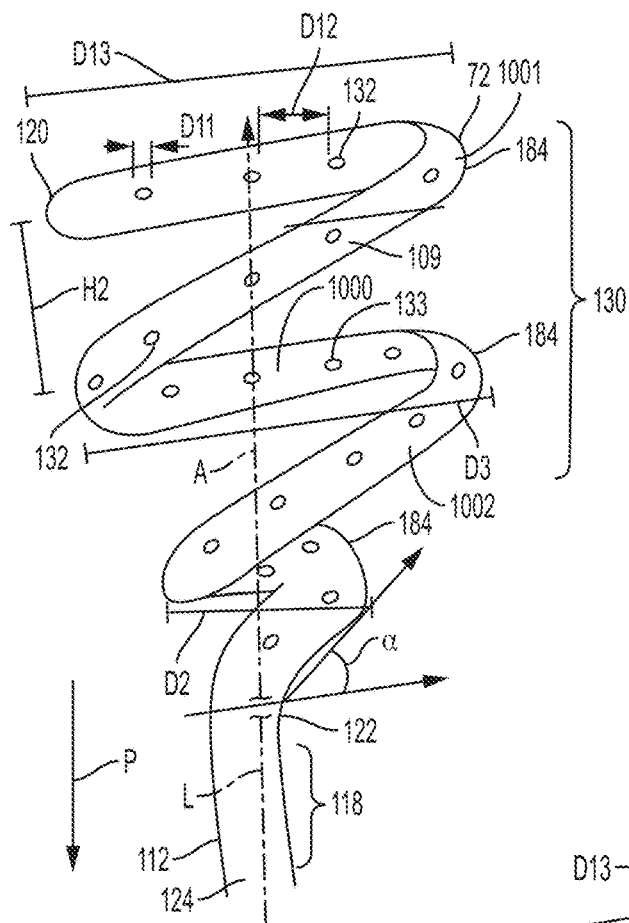
FIG. 9A is a schematic drawing of an example of a retention portion for a catheter according to an example of the present invention.
Figure 9B:
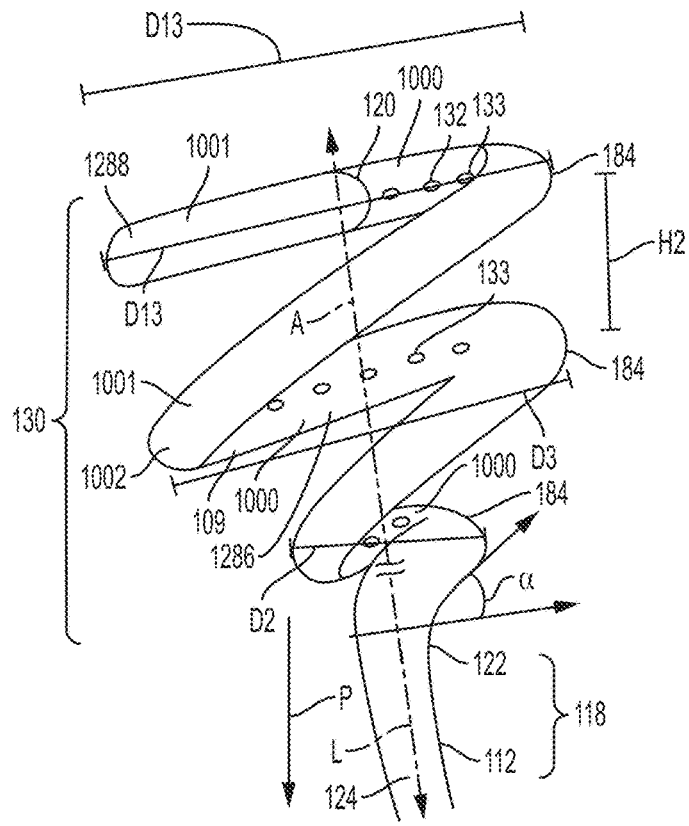
FIG. 9B is a schematic drawing of another example of a retention portion for a catheter according to an example of the present invention.

As shown in FIGS. 9A-9E, in another exemplary embodiment, the distal portion 118 of the drainage lumen 124 proximal to the retention portion 130 defines a straight or curvilinear central axis L. In some examples, at least a half or first coil 183 and a full or second coil 184 of the retention portion 130 extend about an axis A of the retention portion 130. The first coil 183 initiates or begins at a point where the tube 122 is bent at an angle α ranging from about 15 degrees to about 75 degrees from the central axis L, as indicated by angle α, and preferably about 45 degrees. As shown in FIGS. 9A and 9B, prior to insertion in the body, the axis A can be coextensive with the longitudinal central axis L. In other examples, as shown in FIGS. 9C-9E, prior to insertion in the body, the axis A extends from and is curved or angled, for example at angle β, relative to the central longitudinal axis L.

In some examples, multiple coils 184 can have the same or different inner and/or outer diameter D and height H2 between adjacent coils 184. In that case, the outer diameter D1 of each of the coils 184 may range from about 10 mm to about 30 mm. The height H2 between each of the adjacent coils 184 may range from about 3 mm to about 10 mm.

In other examples, the retention portion 130 is configured to be inserted in the tapered portion of the renal pelvis. For example, the outer diameter D1 of the coils 184 can increase toward the distal end 120 of the tube 122, resulting in a helical structure having a tapered or partially tapered configuration. For example, the distal or maximum outer diameter D of the tapered helical portion ranges from about 10 mm to about 30 mm, which corresponds to the dimensions of the renal pelvis, and the outer diameter D1 of each adjacent coil can decrease closer to the proximal end 128 of the retention portion 130. The overall height H of the retention portion 130 can range from about 10 mm to about 30 mm.

In some examples, the outer diameter D1 of each coil 184 and/or height H2 between each of the coils 184 can vary in a regular or irregular fashion. For example, the outer diameter D1 of coils or height H2 between adjacent coils can increase or decrease by a regular amount (e.g., about 10% to about 25% between adjacent coils 184). For example, for a retention portion 130 having three coils (as shown, for example, in FIGS. 9A and 9B) an outer diameter D2 of a proximal-most coil or first coil 183 can be about 6 mm to 18 mm, an outer diameter D3 of a middle coil or second coil 185 can be about 8 mm to about 24 mm, and an outer diameter D13 of a distal-most or third coil 187 can be between about 10 mm and about 30 mm.

The retention portion 130 can further comprise the drainage perforations, holes or ports 132 disposed on or through the sidewall 109 of the catheter tube 122 on, or adjacent to, the retention portion 130 to permit urine waste to flow from the outside of the catheter tube 122 to the inside drainage lumen 124 of the catheter tube 122. The position and size of the drainage ports 132 can vary depending upon the desired flow rate and configuration of the retention portion 130. The diameter D11 of each of the drainage ports 132 can range independently from about 0.005 mm to about 1.0 mm. The spacing D12 between the closest edge of each of the drainage ports 132 can range independently from about 1.5 mm to about 5 mm. The drainage ports 132 can be spaced in any arrangement, for example, random, linear or offset. In some examples, the drainage ports 132 can be non-circular, and can have a surface area of about 0.00002 to 0.79 mm$^2$.

In some examples, as shown in FIG. 9A, the drainage ports 132 are located around the entire outer periphery 72, 1002 or protective surface area 1001 of the sidewall 109 of the catheter tube 122 to increase an amount of fluid that can be drawn into the drainage lumen 124 (shown in FIGS. 2, 9A, and 9B). In other examples, as shown in FIGS. 9B-9E and 10-10E, the drainage holes, ports or perforations 132 can be disposed essentially only or only on the protected surface areas or inner surface areas 1000 or radially inwardly facing side 1286 of the coils 184 to prevent occlusion or blockage of the drainage ports 132, 1232 and the outwardly facing side 1288 of the coils may be essentially free of drainage ports 132, 1232 or free of drainage ports 132, 1232. The outer periphery 72, 189, 1002 or protective surface area 1001 or outer regions 192 of the helical coils 183, 184, 1280, 1282, 1284 can contact and support the bladder tissue 1004 or kidney tissue 1003 to inhibit occlusion or blockage of protected drainage holes, ports or perforations 133, 1233 positioned in protected surface areas or inner surface areas 1000 of the helical coils 183, 184, 1280, 1282, 1284. For example, when negative pressure is induced in the ureter and/or renal pelvis, mucosal tissue of the ureter and/or kidney may be drawn against the retention portion 130 and may occlude some drainage ports 134 on the outer periphery 72, 189, 1002 of the retention portion 130. Drainage ports 133, 1233 located on the radially inward side 1286 or protected surface areas or inner surface areas 1000 of the retention structure would not be appreciably occluded when such tissues 1003, 1004 contact the outer periphery 72, 189, 1002 or protective surface area 1001 or outer regions of the retention portion 130. Further, risk of injury to the tissues from pinching or contact with the drainage ports 132, 133, 1233, or protected drainage holes, ports or perforations 133, 1233 can be reduced or ameliorated.

With reference to FIGS. 9C and 9D, other examples of ureteral catheters 112 having a retention portion 130 comprising a plurality of coils 184 are illustrated. As shown in FIG. 9C, the retention portion 130 comprises three coils 184 extending about the axis A. The axis A is a curved arc extending from the central longitudinal axis L of the portion of the drainage lumen 181 proximal to the retention portion 130. The curvature imparted to the retention portion 130 can be selected to correspond to the curvature of the renal pelvis, which comprises a cornucopia-shaped cavity.

As shown in FIG. 9D, in another exemplary embodiment, the retention portion 130 can comprise two coils 184 extending about an angled axis A. The angled axis A extends at an angle from a central longitudinal axis L, and is angled, as shown by angle β, relative to an axis generally perpendicular to the central axis L of the portion of the drainage lumen. The angle ß can range from about 15 to about 75 degrees (e.g., about 105 to about 165 degrees relative to the central longitudinal axis L of the drainage lumen portion of the catheter 112).

FIG. 9E shows another example of a ureteral catheter 112. The retention portion comprises three helical coils 184 extending about an axis A. The axis A is angled, as shown by angle β, relative to the horizontal. As in the previously-described examples, the angle ß can range from about 15 to about 75 degrees (e.g., about 105 to about 165 degrees relative to the central longitudinal axis L of the drainage lumen portion of the catheter 112).

In some examples shown in FIGS. 10-10E, the retention portion 1230 is integral with the tube 1222. In other examples, the retention portion 1230 can comprise a separate tubular member connected to and extending from the tube or drainage lumen 1224.

In some examples, the retention portion comprises a plurality of radially extending coils 184. The coils 184 are configured in the shape of a funnel, and thereby form a funnel support. Some examples of coil funnel supports are shown in FIGS. 2A-C, 7A, 7B, 8A, and 8A-10E.

In some examples, the at least one sidewall 119 of the funnel support comprises at least a first coil 183 having a first diameter and a second coil 184 having a second diameter, the first diameter being less than the second diameter, wherein the maximum distance between a portion of a sidewall of the first coil and a portion of an adjacent sidewall of the second coil ranges from about 0 mm to about 10 mm. In some examples, the first diameter of the first coil 183 ranges from about 1 mm to about 10 mm and the second diameter of the second coil 184 ranges from about 5 mm to about 25 mm. In some examples, the diameter of the coils increases toward a distal end of the drainage lumen, resulting in a helical structure having a tapered or partially tapered configuration. In some embodiments, the second coil 184 is closer to an end of the distal portion 118 of the drainage lumen 124 than is the first coil 183. In some examples, the second coil 184 is closer to an end of the proximal portion 128 of the drainage lumen 124 than is the first coil 183.

In some examples, the at least one sidewall 119 of the funnel support comprises an inwardly facing side 1286 and an outwardly facing side 1288, the inwardly facing side 1286 comprising at least one opening 133, 1233 for permitting fluid flow into the drainage lumen, the outwardly facing side 1288 being essentially free of or free of openings, as discussed below. In some examples, the at least one opening 133, 1233 has an area ranging from about 0.002 mm$^2$ to about 100 mm$^2$.

In some examples, the first coil 1280 comprises a sidewall 119 comprising a radially inwardly facing side 1286 and a radially outwardly facing side 1288, the radially inwardly facing side 1286 of the first coil 1280 comprising at least one opening 1233 for permitting fluid flow into the drainage lumen.

In some examples, the first coil 1280 comprises a sidewall 119 comprising a radially inwardly facing side 1286 and a radially outwardly facing side 1288, the radially inwardly facing side 1286 of the first coil 1280 comprising at least two openings 1233 for permitting fluid flow into the drainage lumen 1224.

In some examples, the first coil 1280 comprises a sidewall 119 comprising a radially inwardly facing side 1286 and a radially outwardly facing side 1288, the radially outwardly facing side 1288 of the first coil 1280 being essentially free of or free of one or more openings 1232.

In some examples, the first coil 1280 comprises a sidewall 119 comprising a radially inwardly facing side 1286 and a radially outwardly facing side 1288, the radially inwardly facing side 1286 of the first coil 1280 comprising at least one opening 1233 for permitting fluid flow into the drainage lumen 1224 and the radially outwardly facing side 1288 being essentially free of or free of one or more openings 1232.

Referring now to FIGS. 10-10E, in some examples, the distal portion 1218 comprises an open distal end 1220 for drawing fluid into the drainage lumen 1224. The distal portion 1218 of the ureteral catheter 1212 further comprises a retention portion 1230 for maintaining the distal portion 1218 of the drainage lumen or tube 1222 in the ureter and/or kidney. In some examples, the retention portion 1230 comprises a plurality of radially extending coils 1280, 1282, 1284. The retention portion 1230 can be flexible and bendable to permit positioning of the retention portion 1230 in the ureter, renal pelvis, and/or kidney. For example, the retention portion 1230 is desirably sufficiently bendable to absorb forces exerted on the catheter 1212 and to prevent such forces from being translated to the ureters. Further, if the retention portion 1230 is pulled in the proximal direction P (shown in FIGS. 9A-9E) toward the patient's bladder 10, the retention portion 1230 can be sufficiently flexible to begin to unwind or be straightened so that it can be drawn through the ureter 6, 8. In some examples, the retention portion 1230 is integral with the tube 1222. In other examples, the retention portion 1230 can comprise a separate tubular member connected to and extending from the tube or drainage lumen 1224. In some examples, the catheter 1212 comprises a radiopaque band 1234 (shown in FIG. 29) positioned on the tube 1222 at a proximal end of the retention portion 1230. The radiopaque band 1234 is visible by fluoroscopic imaging during deployment of the catheter 1212. In particular, a user can monitor advancement of the band 1234 through the urinary tract by fluoroscopy to determine when the retention portion 1230 is in the renal pelvis and ready for deployment.

In some examples, the retention portion 1230 comprises perforations, drainage ports, or openings 1232 in a sidewall of the tube 1222. As described herein, a position and size of the openings 1232 can vary depending upon a desired volumetric flow rate for each opening and size constraints of the retention portion 1230. In some examples, a diameter D11 of each of the openings 1232 can range independently from about 0.05 mm to about 2.5 mm and have an area of about 0.002 mm$^2$ to about 5 mm$^2$. Openings 1232 can be positioned extending along on a sidewall 119 of the tube 1222 in any direction desired, such as longitudinal and/or axial. In some examples, spacing between the closest adjacent edge of each of the openings 1232 can range from about 1.5 mm to about 15 mm. Fluid passes through one or more of the perforations, drainage ports, or openings 1232 and into the drainage lumen 1234. Desirably, the openings 1232 are positioned so that they are not occluded by tissues 1003 of the ureters 6, 8 or kidney when negative pressure is applied to the drainage lumen 1224. For example, as described herein, openings 1233 can be positioned on interior portions or protected surfaces areas 1000 of coils or other structures of the retention portion 1230 to avoid occlusion of the openings 1232, 1233. In some examples, the middle portion 1226 and proximal portion 1228 of the tube 1222 can be essentially free of or free from perforations, ports, openings or openings to avoid occlusion of openings along those portions of the tube 1222. In some examples, a portion 1226, 1228 which is essentially free from perforations or openings includes substantially fewer openings 1232 than other portions such as distal portion 1218 of the tube 1222. For example, a total area of openings 1232 of the distal portion 1218 may be greater than or substantially greater than a total area of openings of the middle portion 1226 and/or the proximal portion 1228 of the tube 1222.

In some examples, the openings 1232 are sized and spaced to improve fluid flow through the retention portion 1230. In particular, the present inventors have discovered that when a negative pressure is applied to the drainage lumen 1224 of the catheter 1212 a majority of fluid is drawn into the drainage lumen 1224 through proximal-most perforations or openings 1232. In order to improve flow dynamics so that fluid is also received through more distal openings and/or through the open distal end 1220 of the tube 1222, larger size or a greater number of openings 1232 can be provided towards the distal end 1220 of the retention portion 1230. For example, a total area of openings 1232 on a length of tube 1222 near a proximal end 1228 of the retention portion 1230 may be less than a total area of openings 1232 of a similar sized length of the tube 1222 located near the open distal end 1220 of the tube 1222. In particular, it may be desirable to produce a flow distribution through the drainage lumen 1224 in which less than 90%, preferably less than 70%, and, more preferably, less than 55% of fluid flow is drawn into the drainage lumen 1224 through a single opening 1232 or a small number of openings 1232 positioned near the proximal end 1228 of the retention portion 1230.

In many examples, the openings 1232 are generally a circular shape, although triangular, elliptical, square-shaped, diamond shaped, and any other opening shapes may also be used. Further, as will be appreciated by one of ordinary skill in the art, a shape of the openings 1232 may change as the tube 1222 transitions between an uncoiled or elongated position and a coiled or deployed position. It is noted that while the shape of the openings 1232 may change (e.g., the orifices may be circular in one position and slightly elongated in the other position), the area of the openings 1232 is substantially similar in the elongated or uncoiled position compared to the deployed or coiled position.

In some examples, the drainage lumen 1224 defined by tube 1222 comprises: a distal portion 1218 (e.g., a portion of the tube 1222 configured to be positioned in the ureter 6, 8 and renal pelvis 20, 21 (shown for example in FIGS. 7A and 10)); a middle portion 1226 (e.g., a portion of the tube 1222 configured to extend from the distal portion through ureteral openings 16 into the patient's bladder 10 and urethra 12 (shown in FIGS. 7A and 10)); and a proximal portion 1228 (e.g., a portion of the tube 1222 extending from the urethra 12 to an external fluid collection container and/or pump 2000). In one example, the combined length of the proximal portion 1228 and the middle portion 1226 of the tube 1222 is about 54±2 cm. In some examples, the middle portion 1226 and proximal portion 1228 of the tube 1222 includes distance markings 1236 (shown in FIG. 10) on a sidewall of the tube 1222 which can be used, during deployment of the catheter 1212, to determine how far the tube 1222 is inserted into the urinary tract of the patient.

As shown in FIGS. 7A and 10-14, an exemplary ureteral catheter 1212 comprises at least one elongated body or tube 1222, the interior of which defines or comprises one or more drainage channel(s) or lumen(s), such as drainage lumen 1224. The tube 1222 size can range from about 1 Fr to about 9 Fr (French catheter scale). In some examples, the tube 1222 can have an external diameter ranging from about 0.33 to about 3.0 mm, and an internal diameter ranging from about 0.165 to about 2.39 mm. In one example, the tube 1222 is 6 Fr and has an outer or external diameter of 2.0±0.1 mm. The overall length of the tube 1222 can range from about 30 cm to about 120 cm depending on the age (e.g., pediatric or adult) and gender of the patient.

The tube 1222 can be formed from a flexible and/or deformable material to facilitate advancing and/or positioning the tube 1222 in the bladder 10 and ureters 6, 8 (shown in FIG. 7), such as any of the materials discussed above. For example, the tube 1222 can be formed from one or more materials such as biocompatible polymers, polyvinyl chloride, polytetrafluoroethylene (PTFE) such as Teflon®, silicon coated latex, or silicon. In one example, the tube 1222 is formed from a thermoplastic polyurethane.

Helical Coil Retention Portion

Referring now to FIGS. 10A-10E, an exemplary retention portion 1230 comprises helical coils 1280, 1282, 1284. In some examples, the retention portion 1230 comprises a first or half coil 1280 and two full coils, such as a second coil 1282 and a third coil 1284. As shown in FIGS. 10A-10D, in some examples, the first coil 1280 comprises a half coil extending from 0 degrees to 180 degrees around a curvilinear central axis A of the retention portion 1230. In some examples, as shown the curvilinear central axis A is substantially straight and co-extensive with a curvilinear central axis of the tube 1222. In other examples, the curvilinear central axis A of the retention portion 1230 can be curved giving the retention portion 1230, for example, a cornucopia shape. The first coil 1280 can have a diameter D1 of about 1 mm to 20 mm and preferably about 8 mm to 10 mm. The second coil 1282 can be a full coil extending from 180 degrees to 540 degrees along the retention portion 1230 having a diameter D2 of about 5 mm to 50 mm, preferably about 10 mm to 20 mm, and more preferably about 14 mm+2 mm. The third coil 1284 can be a full coil extending between 540 degrees and 900 degrees and having a diameter D3 of between 5 mm and 60 mm, preferably about 10 mm to 30 mm, and more preferably about 18 mm±2 mm. In other examples, multiple coils 1282, 1284 can have the same inner and/or outer diameter. For example, an outer diameter of the full coils 1282, 1284, can each be about 18±2 mm.

In some examples, an overall height H of the retention portion 1230 ranges from about 10 mm to about 30 mm and, preferably about 18±2 mm. A height H2 of a gap between adjacent coils 1284, namely between the sidewall 1219 of the tube 1222 of the first coil 1280 and the adjacent sidewall 1221 of the tube 122 of the second coil 1282 is less than 3.0 mm, preferably between about 0.25 mm and 2.5 mm, and more preferably between about 0.5 mm and 2.0 mm.

The retention portion 1230 can further comprise a distal-most curved portion 1290. For example, the distal most portion 1290 of the retention portion 1230, which includes the open distal end 1220 of the tube 1222, can be bent inwardly relative to a curvature of the third coil 1284. For example, a curvilinear central axis X1 (shown in FIG. 10D) of the distal-most portion 1290 can extend from the distal end 1220 of the tube 1222 towards the curvilinear central axis A of the retention portion 1230.

The retention portion 1230 is capable of moving between a contracted position, in which the retention portion 1230 is straight for insertion into the patient's urinary tract, and the deployed position, in which the retention portion 1230 comprises the helical coils 1280, 1282, 1284. Generally, the tube 1222 is naturally biased toward the coiled configuration. For example, an uncoiled or substantially straight guidewire can be inserted through the retention portion 1230 to maintain the retention portion 1230 in its straight contracted position, as shown for example in FIGS. 11-14. When the guidewire is removed, the retention portion 1230 naturally transitions to its coiled position.

In some examples, the openings 1232, 1233 are disposed essentially only or only on a radially inwardly facing side 1286 or protected surface area or inner surface area 1000 of the coils 1280, 1282, 1284 to prevent occlusion or blockage of the openings 1232, 1233. A radially outwardly facing side 1288 of the coils 1280, 1282, 1284 may be essentially free of the openings 1232. In similar examples, a total area of openings 1232, 1233 on the inwardly facing side 1286 of the retention portion 1230 can be substantially greater than a total area of openings 1232 on the radially outwardly facing side 1288 of the retention portion 1230. Accordingly, when negative pressure is induced in the ureter and/or renal pelvis, mucosal tissue of the ureter and/or kidney may be drawn against the retention portion 1230 and may occlude some openings 1232 on the outer periphery 1002 or protective surface area 1001 of the retention portion 1230. However, openings 1232 located on the radially inward side 1286 or protected surface area or inner surface area 1000 of the retention portion 1230 are not appreciably occluded when such tissues contacts the outer periphery 1002 or protective surface area 1001 of the retention portion 1230. Therefore, risk of injury to the tissues from pinching or contact with the drainage openings 1232 can be reduced or eliminated.

Hole or Opening Distribution Examples

In some examples, the first coil 1280 can be free or essentially free from openings 1232. For example, a total area of openings 1232 on the first coil 1280 can be less than or substantially less than a total area of openings 1232 of the full coils 1282, 1284. Examples of various arrangements of openings or openings 1232, which could be used for a coiled retention portion (such as coiled retention portion 1230 shown in FIGS. 10A-10E), are illustrated in FIGS. 11-14. As shown in FIGS. 11-14, a retention portion 1330 is depicted in its uncoiled or straight position, as occurs when a guidewire is inserted through the drainage lumen.

Figure 11:
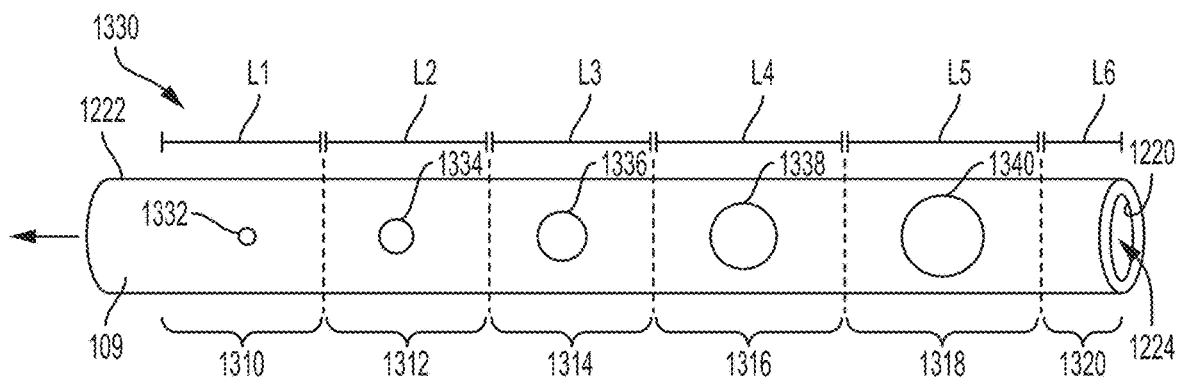
FIG. 11 is a schematic drawing of a retention portion of a catheter in a constrained or linear position according to an example of the present invention.

An exemplary retention portion 1330 is illustrated in FIG. 11. In order to more clearly describe positioning of openings of the retention portion 1330, the retention portion 1330 is referred to herein as being divided into a plurality of sections or perforated sections, such as a proximal-most or first section 1310, a second section 1312, a third section 1314, a fourth section 1316, a fifth section 1318, and a distal-most or sixth section 1320. One of ordinary skill in the art would understand that fewer or additional sections can be included, if desired. As used herein, "section" refers to a discrete length of the tube 1322 within the retention portion 1330. In some examples, sections are equal in length. In other examples, some sections can have the same length, and other sections can have a different length. In other examples, each section has a different length. For example, each of sections 1310, 1312, 1314, 1316, 1318 and 1320 can have a length L1-L6, respectively, ranging from about 5 mm to about 35 mm, and preferably from about 5 mm to 15 mm.

In some examples, each section 1310, 1312, 1314, 1316, 1318 and 1320 comprises one or more openings 1332. In some examples, each section each comprises a single opening 1332. In other examples, the first section 1310 includes a single opening 1332 and other sections comprise multiple openings 1332. In other examples, different sections comprise one or more openings 1332, each of the opening(s) having a different shape or different total area.

In some examples, such as the retention portion 1230 shown in FIGS. 10A-10E, the first or half coil 1280, which extends from 0 to about 180 degrees of the retention portion 1230 can be free from or essentially free from openings. The second coil 1282 can include the first section 1310 extending between about 180 and 360 degrees. The second coil 1282 can also include the second and third sections 1312, 1314 positioned between about 360 degrees and 540 degrees of the retention portion 1230. The third coil 1284 can include the fourth and fifth sections 1316, 1318 positioned between about 540 degrees and 900 degrees of the retention portion 1230.

In some examples, the openings 1332 can be sized such that a total area of openings of the first section 1310 is less than a total area of openings of the adjacent second section 1312. In a similar manner, if the retention portion 1330 further comprises a third section 1314, then openings of a third section 1314 can have a total area that is greater than the total area of the openings of the first section 1310 or the second section 1312. Openings of the forth 1316, fifth 1318, and sixth 1320 sections may also have a gradually increasing total area and/or number of openings to improve fluid flow through the tube 1222.

As shown in FIG. 11, the retention portion 1230 of the tube includes five sections 1310, 1312, 1314, 1316, 1318, each of which includes a single opening 1332, 1334, 1336, 1338, 1340. The retention portion 1330 also includes a sixth section 1320 which includes the open distal end 1220 of the tube 1222. In this example, the opening 1332 of the first section 1310 has the smallest total area. For example, a total area of the opening 1332 of the first section can range from about 0.002 $mm^2$ and about 2.5 $mm^2$, or about 0.01 $mm^2$ and 1.0 $mm^2$, or about 0.1 $mm^2$ and 0.5 $mm^2$. In one example, the opening 1332 is about 55 mm from the distal end 1220 of the catheter, has a diameter of 0.48 mm, and an area of 0.18 $mm^2$. In this example, a total area of openings 1334 of the second section 1312 is greater than the total area of openings 1232 of the first section 1310 and can range in size from about 0.01 $mm^2$ to about 1.0 $mm^2$. The third 1336, fourth 1338, and fifth 1350 openings can also range in size from about 0.01 $mm^2$ to about 1.0 $mm^2$. In one example, the second opening 1334 is about 45 mm from the distal end of the catheter 1220, has a diameter of about 0.58 mm, and an area of about 0.27 mm². The third opening 1336 can be about 35 mm from the distal end of the catheter 1220 and have a diameter of about 0.66 mm. The fourth opening 1338 can be about 25 mm from the distal end 1220 and have a diameter of about 0.76 mm. The fifth opening 1340 can be about 15 mm from the distal end 1220 of the catheter and have a diameter of about 0.889 mm. In some examples, the open distal end 1220 of the tube 1222 has the largest opening having an area ranging from about 0.5 mm² to about 5.0 mm² or more. In one example, the open distal end 1220 has a diameter of about 0.97 mm and an area of about 0.74 mm².

As described herein, openings 1332 1334, 1336, 1338, 1340 can be positioned and sized so that a volumetric flow rate of fluid passing through the first opening 1332 more closely corresponds to a volumetric flow rate of openings of more distal sections, when negative pressure is applied to the drainage lumen 1224 of the catheter 1212, for example from the proximal portion 1228 of the drainage lumen 1224. As described above, if each opening were the same area, then, when negative pressure is applied to the drainage lumen 1224, the volumetric flow rate of fluid passing through the proximal-most of first opening 1332 would be substantially greater than a volumetric flow rate of fluid passing through openings 1334 closer to the distal end 1220 of the retention portion 1330. While not intending to be bound by any theory, it is believed that when negative pressure is applied, the pressure differential between the interior of the drainage lumen 1224 and external to the drainage lumen 1224 is greater in the region of the proximal-most opening and decreases at each opening moving towards the distal end of the tube. For example, sizes and positions of the openings 1332 1334, 1336, 1338, 1340 can be selected so that a volumetric flow rate for fluid which flows into openings 1334 of the second section 1312 is at least about 30% of a volumetric flow rate of fluid which flows into the opening(s) 1332 of the first section 1310. In other examples, a volumetric flow rate for fluid flowing into the proximal-most or first section 1310 is less than about 60% of a total volumetric flow rate for fluid flowing through the proximal portion of the drainage lumen 1224. In other examples, a volumetric flow rate for fluid flowing into openings 1332, 1334 of the two proximal-most sections (e.g., the first section 1310 and the second section 1312) can be less than about 90% of a volumetric flow rate of fluid flowing through the proximal portion of the drainage lumen 1224 when a negative pressure, for example a negative pressure of about −45 mmHg, is applied to the proximal end of the drainage lumen.

As will be appreciated by one of ordinary skill in the art, volumetric flow rate and distribution for a catheter or tube comprising a plurality of openings or perforations can be directly measured or calculated in a variety of different ways. As used herein, "volumetric flow rate" means actual measurement of the volumetric flow rate downstream and adjacent to each opening or using a method for "Calculated Volumetric Flow Rate" described below.

For example, actual measurement of the dispersed fluid volume over time can be used to determine the volumetric flow rate through each opening 1332, 1334, 1336, 1338, 1340. In one exemplary experimental arrangement, a multi-chamber vessel comprising individual chambers sized to receive sections 1310, 1312, 1314, 1316, 1318, 1320 of the retention portion 1330 could be sealed around and enclose the retention portion 1330. Each opening 1332, 1334, 1336, 1338, 1340 could be sealed in one of the chambers. An amount of fluid volume drawn from the respective chamber into the tube 3222 through each opening 1332, 1334, 1336, 1338, 1340 could be measured to determine an amount of fluid volume drawn into each opening over time when a negative pressure is applied. The cumulative amount of fluid volume collected in the tube 3222 by a negative pressure pump system would be equivalent to the sum of fluid drawn into each opening 1332, 1334, 1336, 1338, 1340.

Alternatively, volumetric fluid flow rate through different openings 1332, 1334, 1336, 1338, 1340 can be calculated mathematically using equations for modeling fluid flow through a tubular body. For example, volumetric flow rate of fluid passing through openings 1332 1334, 1336, 1338, 1340 and into the drainage lumen 1224 can be calculated based on a mass transfer shell balance evaluation, as described in detail below in connection with the Mathematical Examples and FIGS. 15A-15C. Steps for deriving mass balance equations and for calculating a flow distribution between or volumetric flow rates for the openings 1332 1334, 1336, 1338, 1340 are also described in detail below in connection with FIGS. 15A-15C.

Figure 12:
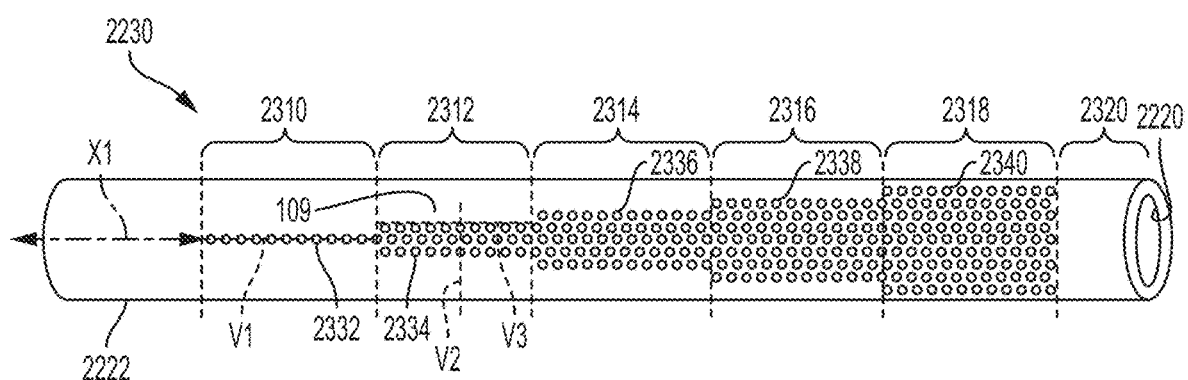
FIG. 12 is a schematic drawing of another example of a retention portion of a catheter in a constrained or linear position according to an example of the present invention.

Another exemplary retention portion 2230 with openings 2332, 2334, 2336, 2338, 2340 is illustrated in FIG. 12. As shown in FIG. 12, the retention portion 2230 comprises numerous smaller perforations or openings 2332, 2334, 2336, 2338, 2340. Each of the openings 2332, 2334, 2336, 2338, 2340 can have a substantially identical cross-sectional area or one or more openings 2332, 2334, 2336, 2338, 2340 can have different cross-sectional areas. As shown in FIG. 12, the retention portion 2330 comprises six sections 2310, 2312, 2314, 2316, 2318, 2320, such as are described above, wherein each section comprises a plurality of the openings 2332, 2334, 2336, 2338, 2340. In the example shown in FIG. 12, a number of openings 2332, 2334, 2336, 2338, 2340 per section increases towards the distal end 2220 of the tube 2222, such that a total area of openings 1332 in each section increases compared to a proximally adjacent section.

As shown in FIG. 12, openings 2332 of the first section 2310 are arranged along a first virtual line V1, which is substantially parallel to a central axis X1 of the retention portion 2230. Openings 2334, 2336, 2338, 2340 of the second 2312, third 2314, fourth 2316, and fifth 2318 sections, respectively, are positioned on the sidewall of the tube 2222 in a gradually increasing number of rows, such that openings 2334, 2336, 2338, 2340 of these sections also line up around a circumference of the tube 2222. For example, some of the openings 2334 of the second section 2312 are positioned such that a second virtual line V2 extending around a circumference of the sidewall of the tube 2222 contacts at least a portion of multiple openings 2334. For example, the second section 2312 can comprise two or more rows of perforations or openings 2334, in which each opening 2334 has an equal or different cross-sectional area. Further, in some examples, at least one of the rows of the second section 2312 can be aligned along a third virtual line V3, which is parallel with the central axis X1 of the tube 2222, but is not co-extensive with the first virtual line V1. In a similar manner, the third section 2314 can comprise five rows of perforations or openings 2336, in which each opening 2336 has an equal or different cross-sectional area; the fourth section 2316 can comprise seven rows of perforations or openings 2338; and the fifth section 2318 can comprise nine rows of perforations or openings 2340. As in previous examples, the sixth section 2320 comprises a single opening, namely the open distal end 2220 of the tube 2222. In the example of FIG. 12, each of the openings has the same area, although the area of one or more openings can be different if desired.

Figure 13:
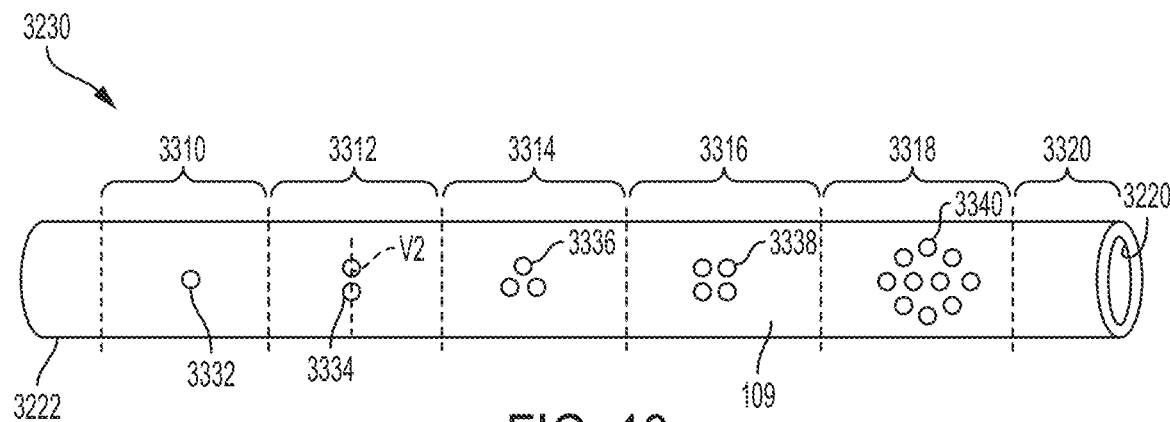
FIG. 13 is a schematic drawing of another example of a retention portion of a ureteral catheter in a constrained or linear position according to an example of the present invention.

Another exemplary retention portion 3230 with openings 3332, 3334, 3336, 3338, 3340 is illustrated in FIG. 13. The retention portion 3230 of FIG. 13 includes a plurality of similarly sized perforations or openings 3332, 3334, 3336, 3338, 3340. As in previous examples, the retention portion 3230 can be divided into six sections 3310, 3312, 3314, 3316, 3318, 3320, each of which comprises at least one opening. The proximal-most or first section 3310 includes one opening 3332. The second section 3312 includes two openings 3334 aligned along the virtual line V2 extending around a circumference of the sidewall of the tube 3222. The third section 3314 comprises a grouping of three openings 3336, positioned at vertices of a virtual triangle. The fourth section 3316 comprises a grouping of four openings 3338 positioned at corners of a virtual square. The fifth section 3318 comprises ten openings 3340 positioned to form a diamond shape on the sidewall of the tube 3222. As in previous examples, the sixth section 3320 comprises a single opening, namely the open distal end 3220 of the tube 3222. The area of each opening can range from about 0.001 mm$^2$ and about 2.5 mm$^2$. In the example of FIG. 13, each of the openings has the same area, although the area of one or more openings can be different if desired.

Figure 14:
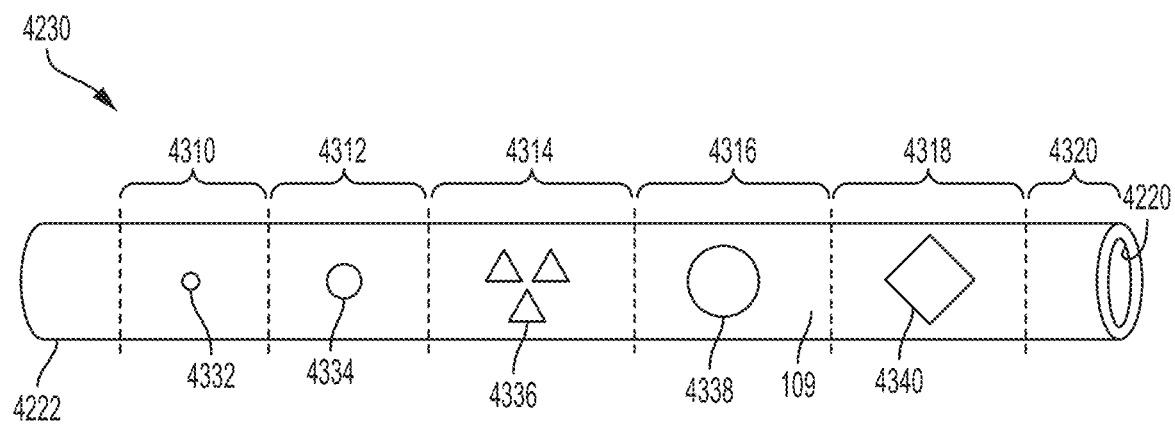
FIG. 14 is a schematic drawing of another example of a retention portion of a catheter in a constrained or linear position according to an example of the present invention.

Another exemplary retention portion 4230 with openings 4332, 4334, 4336, 4338, 4340 is illustrated in FIG. 14. The openings 4332, 4334, 4336, 4338, 4340 of the retention portion 4330 have different shapes and sizes. For example, the first section 4310 includes a single circular opening 4332. The second section 4312 has a circular opening 4334 with a larger cross sectional area than the opening 4332 of the first section 4310. The third section 4314 comprises three triangular shaped openings 4336. The fourth section 4316 comprises a large circular opening 4338. The fifth section 4318 comprises a diamond shaped opening 4340. As in previous examples, the sixth section 4320 comprises the open distal end 4220 of the tube 4222. FIG. 14 illustrates one example of an arrangement of different shapes of openings in cach section. It is understood that the shape of each opening in each section can be independently selected, for example the first section 4310 can have one or more diamond-shaped openings or other shapes. The area of each opening can be the same or different and can range from about 0.001 mm$^2$ and about 2.5 mm$^2$.

EXAMPLES

Calculation of Volumetric Flow Rate and Percentage of Flow Distribution

Figure 16:
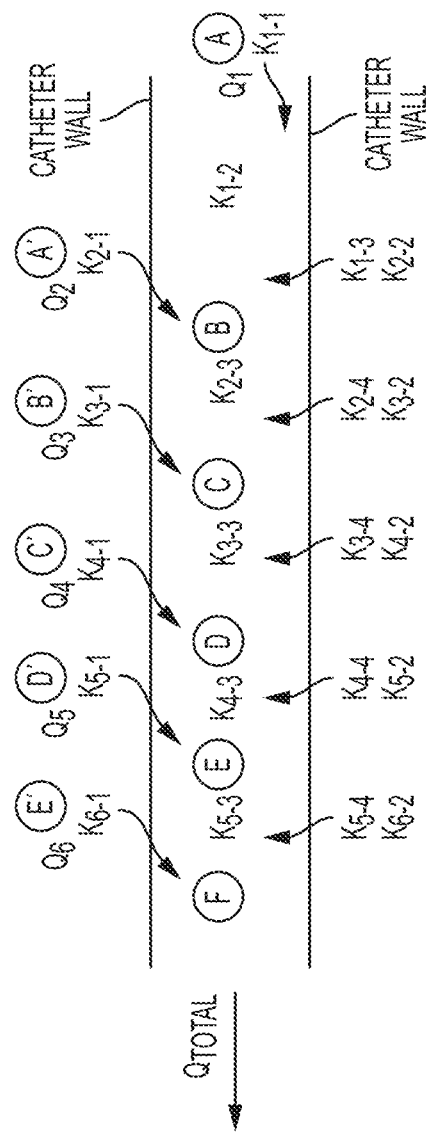
FIG. 16 is a schematic drawing of a retention portion of a catheter showing stations for calculating fluid flow coefficients for a mass transfer balance evaluation according to an example of the present invention.

Having described various arrangements of openings for retention portions of the ureteral catheter 1212, a method for determining the Calculated Percentage of Flow Distribution and Calculated Volumetric Flow Rate through the catheter will now be described in detail. A schematic drawing of an exemplary catheter with sidewall openings showing a position of portions of the tube or drainage lumen used in the following calculations is shown in FIG. 16. Calculated Percentage of Flow Distribution refers to a percentage of total fluid flowing through proximal portions of the drainage lumen which entered the drainage lumen through different openings or sections of the retention portion. Calculated Volumetric Flow rate refers to fluid flow per unit time through different portions of the drainage lumen or openings of the retention portion. For example, a volumetric flow rate for a proximal portion of the drainage lumen describes a rate of flow for a total amount of fluid passing through the catheter. A volumetric flow rate for an opening refers to a volume of fluid which passes through the opening and into the drainage lumen per unit time. In Tables 3-5 below flow is described as a percentage of total fluid flow or of a total volumetric flow rate for a proximal portion of the drainage lumen. For example, an opening having a flow distribution of 100% means that all fluid entering the drainage lumen passed through the opening. An opening having a distribution of 0% would indicate that none of the fluid in the drainage lumen entered the drainage lumen through that opening.

These volumetric flow rate calculations were used to determine and model fluid flow through the retention portion 1230 of the ureter catheter 1212 shown in FIGS. 7A and 10-10E. Further, these calculations show that adjusting the area of openings and linear distribution of openings along the retention portion effects a distribution of fluid flow through different openings. For example, reducing the area of the proximal-most opening decreases the proportion of fluid drawn into the catheter through the proximal most opening and increases the proportion of fluid drawn into more distal openings of the retention portion.

For the following calculations, a tube length of 86 cm having an inner diameter of 0.97 mm and an end hole inner diameter of 0.97 mm was used. Density of urine was 1.03 g/mL and had a coefficient of friction μ of 8.02×10-3 Pa·S (8.02×10-3 kg/s·m) at 37° C. The urine volumetric flow rate passing through the catheter was 2.7 ml per minute ($Q_{Total}$) as determined by experimental measurement.

Calculated Volumetric Flow Rate is determined by a volumetric mass balance equation in which a sum total of volumetric flow through all perforations or openings 1232 of the five sections of the retention portion (referred to herein as volumetric flow $Q_2$ to $Q_6$) and through the open distal end 1220 (referred to herein as volumetric flow $Q_1$) equals the total volumetric flow ($Q_{Total}$) exiting the proximal end of the tube 1222 at a distance of 10 cm to 60 cm away from the last proximal opening, as shown in Equation 2.

$$Q_{Total} = Q_1 + Q_2 + Q_3 + Q_4 + Q_5 + Q_6 \quad \text{(Equation 2)}$$

A Modified Loss Coefficient (K') for each of the sections is based on three types of loss coefficients within the catheter model, namely: an Inlet Loss Coefficient taking into account a pressure loss resulting at a pipe inlet (e.g., the openings and open distal end of the tube 1222); a Friction Loss Coefficient which takes into account pressure loss resulting from friction between the fluid and pipe wall; and a Flow Junction Loss Coefficient taking into account pressure loss resulting from the interaction of two flows coming together.

The Inlet Loss Coefficient is dependent on a shape of the orifice or opening. For example, a tapered or nozzle shaped orifice would increase flow rate into the drainage lumen 1224. In a similar manner, a sharp-edged orifice would have different flow properties than an orifice with less defined edges. For purposes of the following calculations, it is assumed that the openings 1232 are side orifice openings and the open distal end 1220 of the tube 1222 is a sharp-edged opening. The cross sectional area of each opening is considered constant through the tube sidewall.

The Friction Loss Coefficient approximates pressure loss resulting from friction between the fluid and the adjacent inner wall of the tube 1222. Friction loss is defined according to the following equations:

$$Re = \frac{\rho UD}{\mu} \quad \text{(Equation 3.1)}$$

$$f = \frac{C_f}{Re} \quad \text{(Equation 3.2)}$$

$$K_{1-2} = K_{2-3} = K_{3-3} = K_{4-3} = K_{5-3} = K_f = f\frac{L}{D} \quad \text{(Equation 3.3)}$$

The Flow Junction Loss Coefficients are derived from loss coefficients for combining flow at a branch angle of 90 degrees. Values for the loss coefficients were obtained from Charts 13.10 and 13.11 of Miller D S, *Internal Flow Systems*, 1990, incorporated by reference herein. The charts use the ratio of the inlet orifice area (referred to as A1 in the charts) to the pipe cross-sectional area (referred to as A3 in the charts) and the ratio of the inlet orifice volumetric flow rate (Q1 in the charts) to the resulting combined pipe volumetric flow rate (Q3 in the charts). For example, for an area ratio of 0.6 between an area of the opening and an area of the drainage lumen, the following Flow Junction Loss Coefficients ($K_{13}$ and $K_{23}$) would be used.

| | Flow Ratio ($Q_1/Q_3$) | | | | | | | | | |
|---|---|---|---|---|---|---|---|---|---|---|
| | 0.1 | 0.2 | 0.3 | 0.4 | 0.5 | 0.6 | 0.7 | 0.8 | 0.9 | 1.0 |
| $K_{13}$ | −0.58 | −0.04 | 0.11 | 0.45 | 0.75 | 1.13 | 1.48 | 1.81 | 2.16 | 2.56 |
| $K_{23}$ | 0.15 | 0.27 | 0.39 | 0.48 | 0.56 | 0.63 | 0.69 | 0.72 | 0.74 | 0.76 |

To calculate the Total Manifold Loss Coefficient (K), it is necessary to separate the model into so-called "reference stations" and progressively work through and balance the pressure and flow distributions of the two paths (e.g., flow through the opening and flow through the drainage lumen of the tube) to reach each station starting from the distal tip to the most proximal "Station". A graphical representation of the different stations used for this calculation is shown in FIG. 16. For example, a most-distal "Station" A is the distal open end 1220 of the tube 122. A second Station A' is the distal most opening on the sidewall of the tube 122 (e.g., the opening(s) of the fifth section 1318 in FIGS. 11-14). The next station B is for flow through the drainage lumen 1224 just proximal to the A' opening.

To calculate loss between Station A (the distal opening) and Station B for fluid entering through the open distal end of the tube 1222 (Path 1), the modified loss coefficient (K') is equal to:

$$K' = \text{Inlet Loss} + \text{Friction Loss} + \text{Flow Junction Loss} \quad \text{(Equation 4.1)}$$

$$K'_B = K_{1-1} \times \left(\frac{A_{Pipe}}{A_1} \times Q_1\right)^2 + K_{1-2} \times Q_1^2 + K_{1-3} \times (Q_1 + Q_2)^2 \quad \text{(Equation 4.2)}$$

In a similar manner, a second path to Station B is through the opening(s) 1334 of the fifth section 1318 (shown in FIGS. 11-14) of the retention portion 1330. A modified loss calculation for Path 2 is calculated as follows:

$$K' = \text{Inlet Loss} + \text{Flow Junction Loss} \quad \text{(Equation 5.1)}$$

$$K'_B = K_{2-1} \times \left(\frac{A_{Pipe}}{A_2} \times Q_2\right)^2 + K_{2-2} \times (Q_1 + Q_2)^2 \quad \text{(Equation 5.2)}$$

The modified loss coefficients of both Path 1 and Path 2 must equate to ensure the volumetric flow rates ($Q_1$ and $Q_2$) reflect the balanced distribution within the manifold at Station B. The volumetric flow rates are adjusted until equal modified loss coefficients for both paths is achieved. The volumetric flow rates can be adjusted because they represent a fractional portion of a total volumetric flow rate ($Q'_{Total}$), which is assumed to be unity for the purpose of this step-by-step solution. Upon equating the two modified loss coefficients, one can then proceed to equating the two paths to reach station C (the fourth section 1316 in FIGS. 11-14).

Loss coefficients between Station B (flow through drainage lumen in the fifth section 1318) and Station C (flow through lumen in the fourth section 1316) are calculated in a similar manner as shown by Equations 5.1 and 5.2). For example, for Path 1 (Station B to Station C), the modified loss coefficient (K') for the opening(s) of the fourth section 1316 is defined as:

$$K' = \text{Loss to Station } B + \text{Friction Loss} + \text{Flow Junction Loss} \quad \text{(Equation 6.1)}$$

$$K'_C = K_B' + K_{2-3} \times (Q_1 + Q_2)^2 + K_{2-4} \times (Q_1 + Q_2 + Q_3)^2 \quad \text{(Equation 6.2)}$$

For Path 2 (Station B to C), the modified loss coefficient (K') based on the flow area of the opening(s) of the fourth section 1316 are defined as:

$$K' = \text{Inlet Loss} + \text{Flow Junction Loss} \quad \text{(Equation 7.1)}$$

$$K'_C = K_{3-1} \times \left(\frac{A_{Pipe}}{A_3} \times Q_3\right)^2 + K_{3-2} \times (Q_1 + Q_2 + Q_3)^2 \quad \text{(Equation 7.2)}$$

As with the previous stations, the modified loss coefficients of both Path 1 and Path 2 must equate to ensure the volumetric flow rates ($Q_1$, $Q_2$, and $Q_3$) reflect the balanced distribution within the manifold up to Station C. Upon equating the two modified loss coefficients, one can then proceed to equating the two paths to reach Station D, Station E and Station F. The step-by-step solution process proceeds through each station as demonstrated until calculating the modified loss coefficient for the final station, Station F in this case. The Total Loss Coefficient (K) for the manifold can then be calculated using an actual $Q_{Total}$ (volumetric flow rate through a proximal portion of the drainage lumen) determined through experimental measurement.

$$K = \frac{K'_F}{Q_{Total}} \quad \text{(Equation 8)}$$

The fractional volumetric flow rates calculated through the step-by-step exercise can then be multiplied by the actual total volumetric flow rate ($Q_{Total}$) to determine the flow through each opening 1232 (shown in FIGS. 10-10E) and open distal end 1220.

EXAMPLES

Figure 15A:
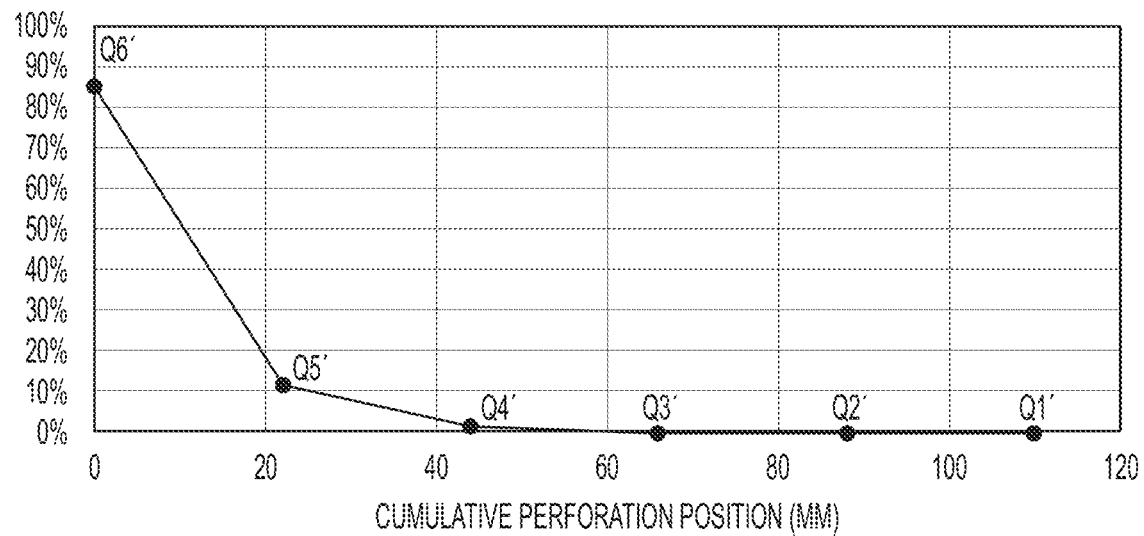
FIG. 15A is a graph showing a percentage of fluid flow through openings of an exemplary catheter as a function of position according to an example of the present invention.
Figure 15B:
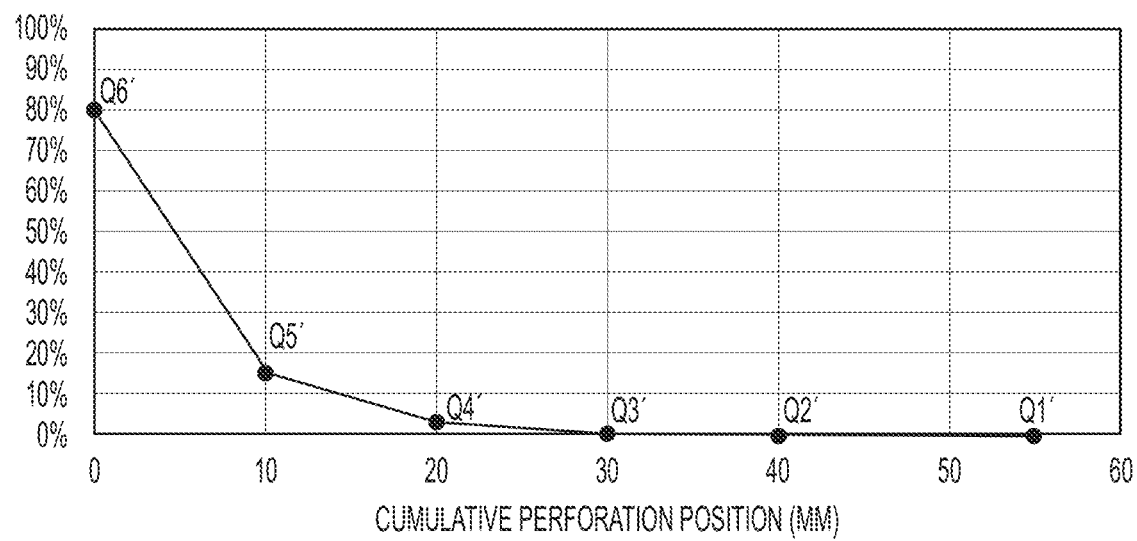
FIG. 15B is a graph showing a percentage of fluid flow through openings of another exemplary catheter as a function of position according to an example of the present invention.
Figure 15C:
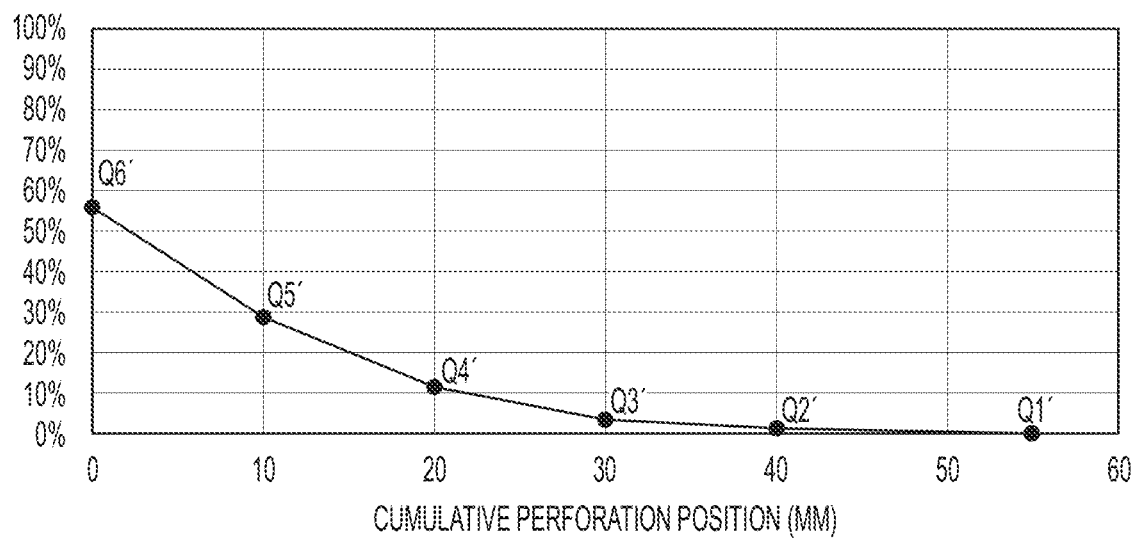
FIG. 15C is a graph showing a percentage of fluid flow through openings of another exemplary catheter as a function of position according to an example of the present invention.

Examples are provided below and shown in Tables 3-5 and FIGS. 15A-15C for the calculated volumetric flow rates.

Example 1

Example 1 illustrates a distribution of fluid flow for a retention member tube with different sized openings, which corresponds to the embodiment of the retention member 1330 shown in FIG. 11. As shown in Table 3, the proximal most opening ($Q_6$) had a diameter of 0.48 mm, the distal-most opening ($Q_5$) on the sidewall of the tube had a diameter of 0.88 mm, and the open distal end ($Q_6$) of the tube had a diameter of 0.97 mm. Each of the openings was circular.

The Percentage of Flow Distribution and Calculated Volumetric Flow Rate were determined as follows.

Path to Station B Through Distal End of Tube (Path 1)

| | | |
|---|---|---|
| f | 8.4= | Cf/Re (Cf = 64 for circular cross-section) |
| $K_{INLET}$ | 0.16 | (Contraction coefficient. for sharp edged orifice entering pipe) |
| $K_{ORIFICE}$ | 2.8 | (Contraction coefficient. for sharp edged orifice w/ no outlet pipe) |
| $K_{FRICTION}=$ | f*(L/D) | (Dependent on the length between orifices) |
| Part 1-1= | | Inlet loss coef × $(A_T/A_1 \times Q'_1)^2$ |
| Part 1-2= | | Catheter friction loss × $Q'_1{}^2$ |
| Part 1-3= | | Through flow junction loss to station 2 × $(Q'_1 + Q'_2)^2$ |
| $A_2/A_T=$ | 0.82 | |
| $Q'_2/(Q'_1 + Q'_2)=$ | 0.83 | |
| $K_{1-3}=$ | 0.61 | (From Miller, see table above) |
| Part 1-1= | 0.0000 | |
| Part 1-2= | 0.0376 | |
| Part 1-3= | 0.0065 | |
| K'= | 0.0442 | |

Path to Station B Through Sidewall Opening (Path 2)

| | | |
|---|---|---|
| Part 2-1= | | Orfice loss coef × $(A_T/A_2 \times Q'_2)^2$ |
| Part 2-2= | | Branch flow junction loss to station 2 × $(Q'_1 + Q'_2)^2$ |
| $A_2/A_T=$ | 0.82 | |
| $Q'_2/(Q'_1 + Q'_2)=$ | 0.83 | |
| $K_{2-2}=$ | 1.3 | (From Chart 13.10 of Miller) |
| Part 2-1= | 0.0306 | |
| Part 2-2= | 0.0138 | |
| K'= | 0.0444 | |

Path to Station C from Station B (Path 1+Path 2)

| | | |
|---|---|---|
| Part 2-3= | | Catheter friction loss × $(Q'_1 + Q'_2)^2$ |
| Part 2-4= | | Through flow junction loss to station 3 × $(Q'_1 + Q'_2 + Q'_3)^2$ |
| $A_3/A_T=$ | 0.61 | |
| $Q'_3/(Q'_1 + Q'_2 + Q'_3)=$ | 0.76 | |
| $K_{2-4}=$ | 0.71 | (From Chart 13.11 of Miller) |
| Loss coefficient to | | |
| Station 2= | 0.044 | |
| Part 2-3= | 0.921 | |
| Part 2-4= | 0.130 | |
| K'= | 1.095 | |

Path to Station C Through Sidewall Opening (Path 3)

| | | |
|---|---|---|
| Part 3-1= | | Orifice loss coef × $(A_T/A_3 \times Q'_3)^2$ |
| Part 3-2= | | Branch flow junction loss to station 3 × $(Q'_1 + Q'_2 + Q'_3)^2$ |
| $A_3/A_T=$ | 0.61 | |
| $Q'_3/(Q'_1 + Q'_2 + Q'_3)=$ | 0.76 | |
| $K_{3-2}=$ | 1.7 | (From Chart 13.10 Miller) |
| Part 3-1= | 0.785 | |
| Part 3-2= | 0.311 | |
| K'= | 1.096 | |

Path to Station D from Station C (Path 1+Path 2+Path 3)

| | | |
|---|---|---|
| Part 3-3= | | Catheter friction loss × $(Q'_1 + Q'_2 + Q'_3)^2$ |
| Part 3-4= | | Through flow junction loss to station 4 × $(Q'_1 + Q'_2 + Q'_3 + Q'_4)^2$ |
| $A_4/A_T=$ | 0.46 | |
| $Q'_4/(Q'_1 + Q'_2 + Q'_3 + Q'_4)=$ | 0.70 | |
| $K_{3-4}=$ | 0.77 | (From Chart 13.11 of Miller) |

-continued

| | | |
|---|---|---|
| Loss coefficient to | | |
| Station 3= | 1.10 | |
| Part 3-3= | 15.90 | |
| Part 3-4= | 1.62 | |
| K'= | 18.62 | |

Path to Station D Through Sidewall Opening (Path 4)

| | | |
|---|---|---|
| Part 4-1= | | Orifice loss coef × $(A_T/A_4 \times Q'_4)^2$ |
| Part 4-2= | | Branch flow junction loss to station 4 × $(Q'_1 + Q'_2 + Q'_3 + Q'_4)^2$ |
| $A_4/A_T=$ | 0.46 | |
| $Q'_4/(Q'_1 + Q'_2 + Q'_3 + Q'_4)=$ | 0.70 | |
| $K_{4-2}=$ | 2.4 | (From Chart 13.10 of Miller) |
| Part 4-1= | 13.59 | |
| Part 4-2= | 5.04 | |
| K'= | 18.62 | |

Path to Station E from Station D (Path 1+Path 2+Path 3+Path 4)

| | | |
|---|---|---|
| Part 4-3= | | Catheter friction loss × $(Q'_1 + Q'_2 + Q'_3 + Q'_4)^2$ |
| Part 4-4= | | Through flow junction loss to station 5 × $(Q'_1 + Q'_2 + Q'_3 + Q'_4 + Q'_5)^2$ |
| $A_5/A_T=$ | 0.36 | |
| $Q'_5/(Q'_1 + Q'_2 + Q'_3 + Q'_4 + Q'_5)=$ | 0.65 | |
| $K_{3-4}=$ | 0.78 | (From Chart 13.11 of Miller) |
| Loss of coefficient to | | |
| Station 4= | 18.6 | |
| Part 4-3= | 182.3 | |
| Part 4-4= | 13.3 | |
| K'= | 214.2 | |

Path to Station E Through Sidewall Opening (Path 5)

| | | |
|---|---|---|
| Part 5-1= | | Orifice loss coef × $(A_T/A_5 \times Q'_5)^2$ |
| Part 5-2= | | Branch flow junction loss to station 5 × $(Q'_1 + Q'_2 + Q'_3 + Q'_4 + Q'_5)^2$ |
| $A_5/A_T=$ | 0.36 | |
| $Q'_5/$ | 0.62 | |

-continued

| | | |
|---|---|---|
| $(Q'_1 + Q'_2 + Q'_3 + Q'_4 + Q'_5)=$ | | |
| $K_{4-2}=$ | 3.3 | (From Chart 13.10 of Miller) |
| Part 5-1= | 157.8 | |
| Part 5-2= | 56.4 | |
| K'= | 214.2 | |

Path to Station F from Station E (Through Paths 1-5)

| | | |
|---|---|---|
| Part 5-3= | Catheter friction loss × $(Q'_1 + Q'_2 + Q'_3 + Q'_4 + Q'_5)^2$ | |
| Part 5-4= | Through flow junction loss to station $6 \times (Q'_1 + Q'_2 + Q'_3 + Q'_4 + Q'_5 + Q'_6)^2$ | |
| $A_6/A_T=$ | 0.24 | |
| $Q'_6/$ $(Q'_1 + Q'_2 + Q'_3 + Q'_4 + Q'_5 + Q'_6)=$ | 0.56 | |
| $K_{3-4}=$ Loss coefficient to | 0.77 | (From Chart 13.11 of Miller) |
| Station 5= | 214.2 | |
| Part 5-3= | 1482.9 | |
| Part 5-4= | 68.3 | |
| K'= | 1765.4 | |

Path to Station F Through Sidewall Opening (Path 6)

| | | |
|---|---|---|
| Part 6-1= | Orifice loss coef × $(A_T/A_6 \times Q'_6)^2$ | |
| Part 6-2= | Branch flow junction loss to station $6 \times (Q'_1 + Q'_2 + Q'_3 + Q'_4 + Q'_5 + Q'_6)^2$ | |
| $A_6/A_T=$ | 0.24 | |
| $Q'_6/$ $(Q'_1 + Q'_2 + Q'_3 + Q'_4 + Q'_5 + Q'_6)=$ | 0.56 | |
| $K_{4-2}=$ | 5.2 | (From Chart 13.10 of Miller) |
| Part 6-1= | 1304.3 | |
| Part 6-2= | 461.2 | |
| K'= | 1765.5 | |

In order to calculate flow distribution for each "Station" or opening, the calculated K' values were multiplied by actual total volumetric flow rate ($Q_{Total}$) to determine the flow through each perforation and distal end hole. Alternatively, calculated results could be presented as a percentage of total flow or a flow distribution as shown in Table 3. As shown in Table 3 and in FIG. 15C, the Percentage of Flow Distribution (% Flow Distribution) through the proximal most opening (Q6) was 56.1%. Flow through the two proximal-most openings (Q6 and Q5) was 84.6%.

TABLE 3

| Position | % Flow Distribution | Diameter (mm) | Length (mm) | Cumulative Length (mm) |
|---|---|---|---|---|
| $Q_6'$ (proximal) | 56.1% | 0.48 | 0 | 0 |
| $Q_5'$ | 28.5% | 0.58 | 10 | 10 |
| $Q_4'$ | 10.8% | 0.66 | 10 | 20 |
| $Q_3'$ | 3.5% | 0.76 | 10 | 30 |
| $Q_2'$ | 0.9% | 0.88 | 10 | 40 |
| $Q_1'$ (distal) | 0.2% | 0.97 | 15 | 55 |
| $Q_{TOTAL}$ | 100% | | | |

As demonstrated in Example 1, the increasing diameters of perforations going from the proximal to distal regions of the retention portion of the tube results in more evenly distributed flow across the entire retention portion.

Example 2

In Example 2, each opening has the same diameter and area. As shown in Table 4 and FIG. 15A, in that case, flow distribution through the proximal-most opening is 86.2% of total flow through the tube. Flow distribution through the second opening is 11.9%. Therefore, in this example, it was calculated that 98.1% of fluid passing through the drainage lumen entered the lumen through the two proximal-most openings. Compared to Example 1, Example 2 has increased flow through the proximal end of the tube. Therefore, Example 1 provides a wider flow distribution in which a greater percentage of fluid enters the drainage lumen through openings other than the proximal-most opening. As such, fluid can be more efficiently collected through multiple openings reducing fluid backup and improving distribution of negative pressure through the renal pelvis and/or kidneys.

TABLE 4

| Position | % Flow Distribution | Diameter (mm) | Length (mm) | Cumulative Length (mm) |
|---|---|---|---|---|
| $Q_6'$ (proximal) | 86.2% | 0.88 | 0 | 0 |
| $Q_5'$ | 11.9% | 0.88 | 22 | 22 |
| $Q_4'$ | 1.6% | 0.88 | 22 | 44 |
| $Q_3'$ | 0.2% | 0.88 | 22 | 66 |
| $Q_2'$ | 0.03% | 0.88 | 22 | 88 |
| $Q_1'$ (distal) | 0.01% | 0.97 | 22 | 110 |
| $Q_{TOTAL}$ | 100% | | | |

Example 3

Example 2 also illustrates flow distribution for openings having the same diameter. However, as shown in Table 5, the openings are closer together (10 mm vs. 22 mm). As shown in Table 5 and FIG. 15B, 80.9% of fluid passing through the drainage lumen entered the drainage lumen through the proximal most opening (Q6). 96.3% of fluid in the drainage lumen entered the drainage lumen through the two proximal-most openings (Q5 and Q6).

TABLE 5

| Position | % Flow Distribution | Diameter (mm) | Length (mm) | Cumulative Length (mm) |
|---|---|---|---|---|
| $Q_6'$ (proximal) | 80.9% | 0.88 | 0 | 0 |
| $Q_5'$ | 15.4% | 0.88 | 10 | 10 |
| $Q_4'$ | 2.9% | 0.88 | 10 | 20 |
| $Q_3'$ | 0.6% | 0.88 | 10 | 30 |
| $Q_2'$ | 0.1% | 0.88 | 10 | 40 |
| $Q_1'$ (distal) | 0.02% | 0.97 | 15 | 55 |
| $Q_{TOTAL}$ | 100% | | | |

Figure 17:
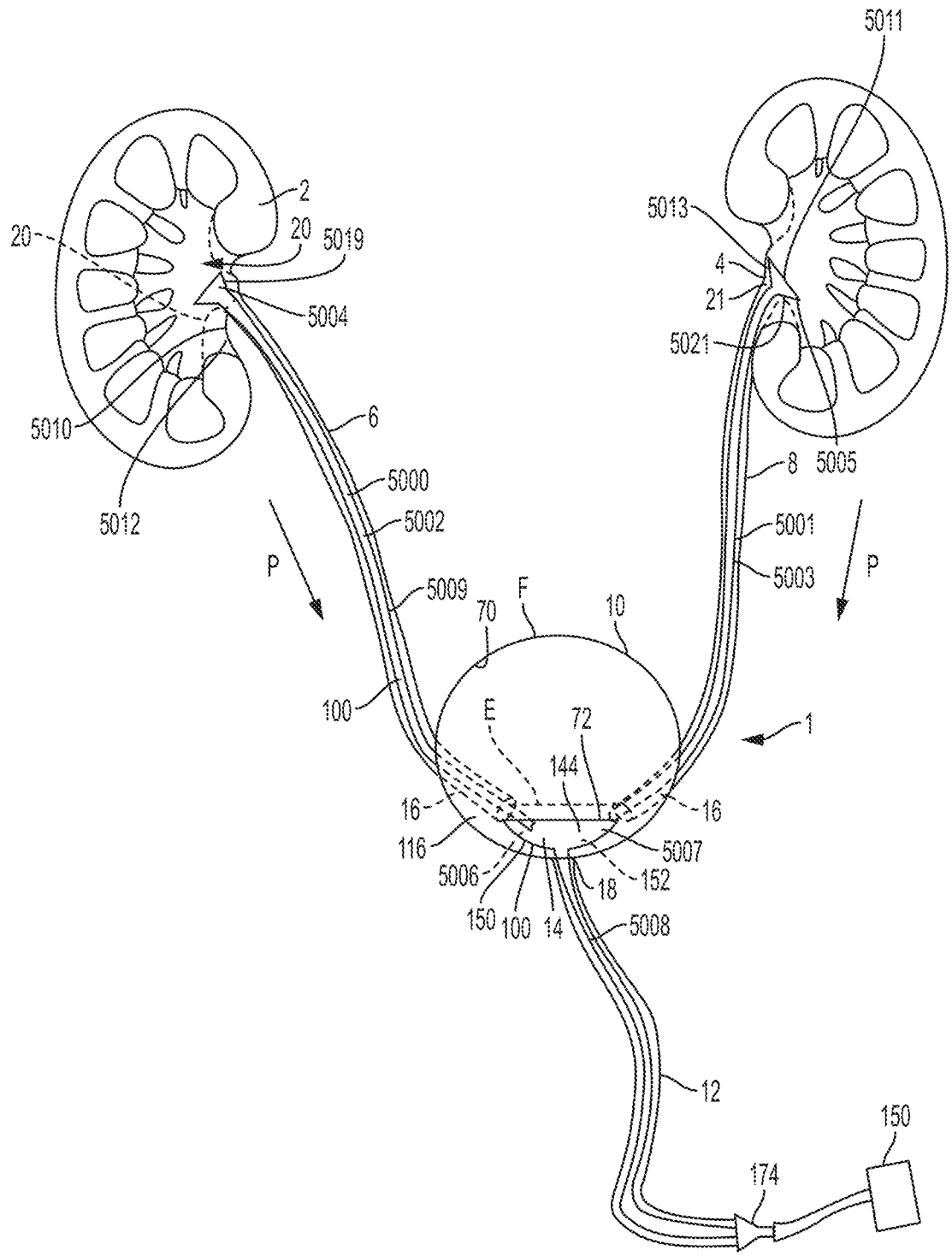
FIG. 17 is a schematic drawing of an indwelling portion of a system comprising a ureteral catheter and a bladder catheter deployed in a urinary tract of a patient, according to another example of the present invention.

Referring generally now to FIGS. 17-41C, and more specifically to FIG. 17, there are shown two exemplary ureteral catheters 5000, 5001 positioned within the urinary tract of a patient, and a bladder catheter 116. The ureteral catheter 5000, 5001 comprises: a drainage lumen 5002, 5003 for draining fluid such as urine from at least one of a patient's kidney 2, 4, renal pelvis 20, 21 or in the ureter 6, 8 adjacent to the renal pelvis 20, 21. The drainage lumen 5002, 5003 comprises a distal portion 5004, 5005 configured to be positioned in a patient's kidney 2, 4, renal pelvis 20, 21 and/or in the ureter 6, 8 adjacent to the renal pelvis 20, 21 and a proximal portion 5006, 5007 through which fluid 5008 is drained to the bladder 10 or outside of the body of the patient, as shown in FIGS. 2B and 2C.

In some examples, the distal portion 5004, 5005 comprises an open distal end 5010, 5011 for drawing fluid into the drainage lumen 5002, 5003. The distal portion 5004, 5005 of the ureteral catheter 5000, 5001 further comprises a retention portion 5012, 5013 for maintaining the distal portion 5004, 5005 of the drainage lumen or tube 5002, 5003 in the ureter and/or kidney. The retention portion 5012, 5013 can be flexible and/or bendable to permit positioning of the retention portion 5012, 5013 in the ureter, renal pelvis, and/or kidney. For example, the retention portion 5012, 5013 is desirably sufficiently bendable to absorb forces exerted on the catheter 5000, 5001 and to prevent such forces from being translated to the ureters. Further, if the retention portion 5012, 5013 is pulled in the proximal direction P (shown in FIG. 17) toward the patient's bladder 10, the retention portion 5012, 5013 can be sufficiently flexible to begin to unwind, straightened or collapsed so that it can be drawn through the ureter 6, 8.

In some examples, the retention portion comprises a funnel support. Non-limiting examples of different shapes of funnel supports are shown in FIGS. 7A, 7B, 17, and 18A-41C, which are discussed in detail below. Generally, the funnel support comprises at least one sidewall. The at least one sidewall of the funnel support comprises a first diameter and a second diameter, the first diameter being less than the second diameter. The second diameter of the funnel support is closer to an end of the distal portion of the drainage lumen than the first diameter.

The proximal portion of the drainage lumen or drainage tube is essentially free of or free of openings. While not intending to be bound by any theory, it is believed that when negative pressure is applied at the proximal end of the proximal portion of the drainage lumen, that openings in the proximal portion of the drainage lumen or drainage tube may be undesirable as such openings may diminish the negative pressure at the distal portion of the ureteral catheter and thereby diminish the draw or flow of fluid or urine from the kidney and renal pelvis of the kidney. It is desirable that the flow of fluid from the ureter and/or kidney is not prevented by occlusion of the ureter and/or kidney by the catheter. Also, while not intending to be bound by any theory, it is believed that when negative pressure is applied at the proximal end of the proximal portion of the drainage lumen, ureter tissue may be drawn against or into openings along the proximal portion of the drainage lumen, which may irritate the tissues.

Some examples of ureteral catheters comprising a retention portion comprising a funnel support according to the present invention are shown in FIGS. 7A, 7B, 17, and 18A-41C. In FIGS. 7A-10E, the funnel support is formed by a coil of tubing. In FIGS. 17-41C, other examples of the funnel support are shown. Each of these funnel supports according to the present invention will be discussed in detail below.

Figure 18A:
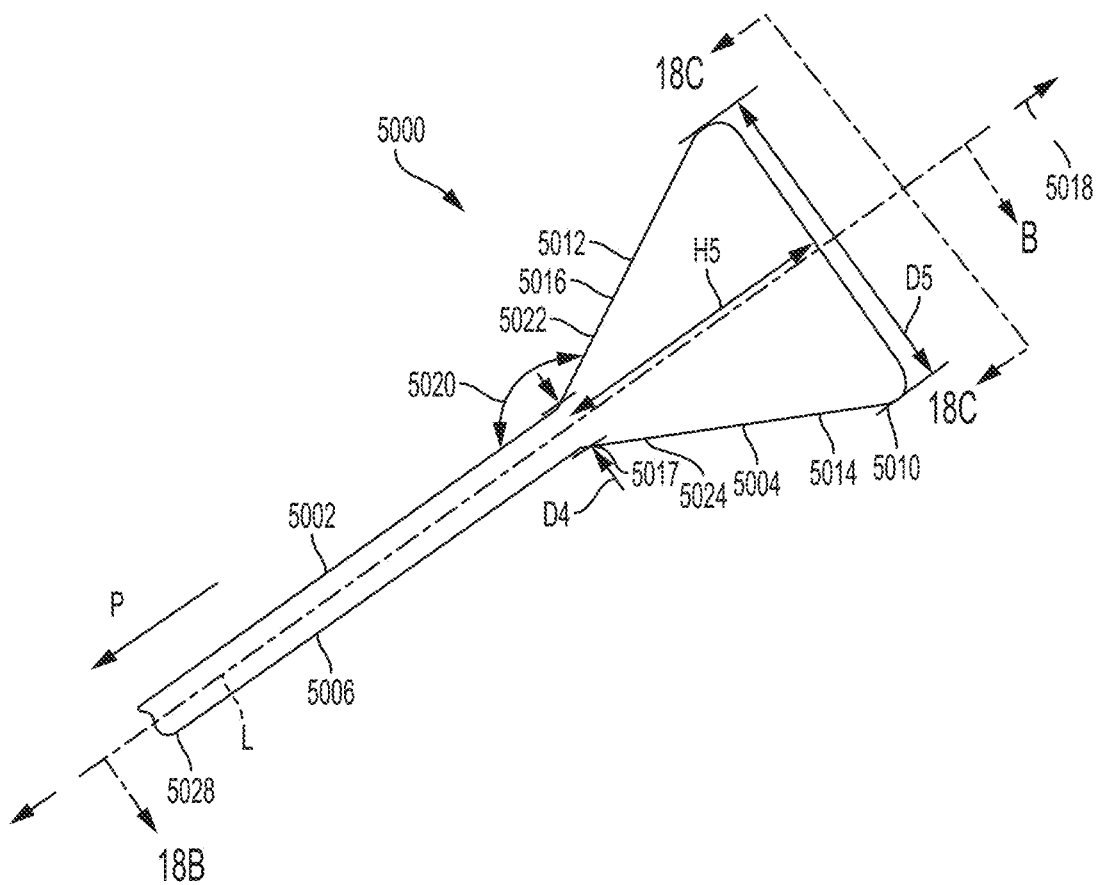
FIG. 18A is side elevational view of a retention portion of a catheter according to an example of the present invention.
Figure 18B:
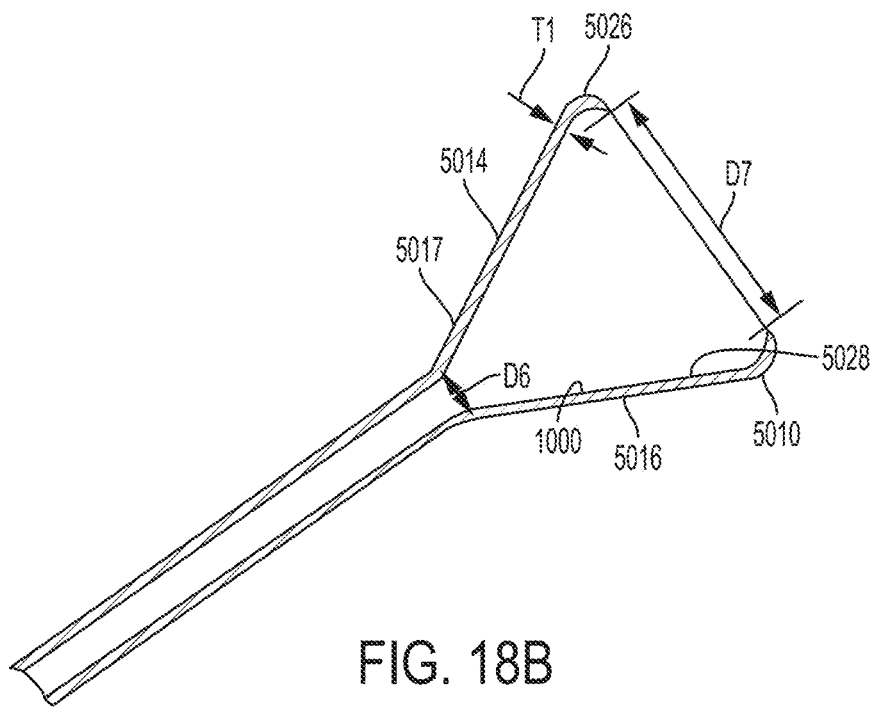
FIG. 18B is cross-sectional view of the retention portion of the catheter of FIG. 18A taken along lines B-B of FIG. 18A.
Figure 18C:
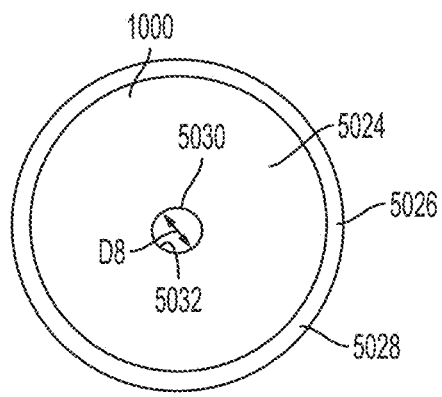
FIG. 18C is a top plan view of the retention portion of the catheter of FIG. 18A taken along lines C-C of FIG. 18A.
Figure 18D:
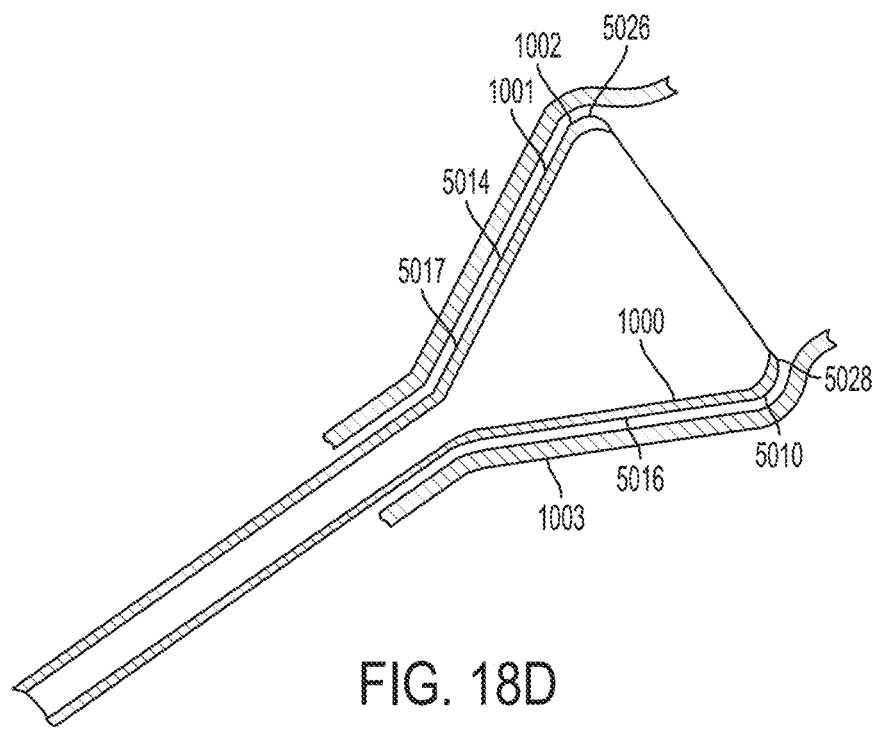
FIG. 18D is cross sectional view of a retention portion of a ureteral catheter according to an example of the present invention positioned in the renal pelvis region of the kidney showing in general changes believed to occur in the renal pelvis tissue in response to application of negative pressure through the ureteral catheter.
Figure 18E:
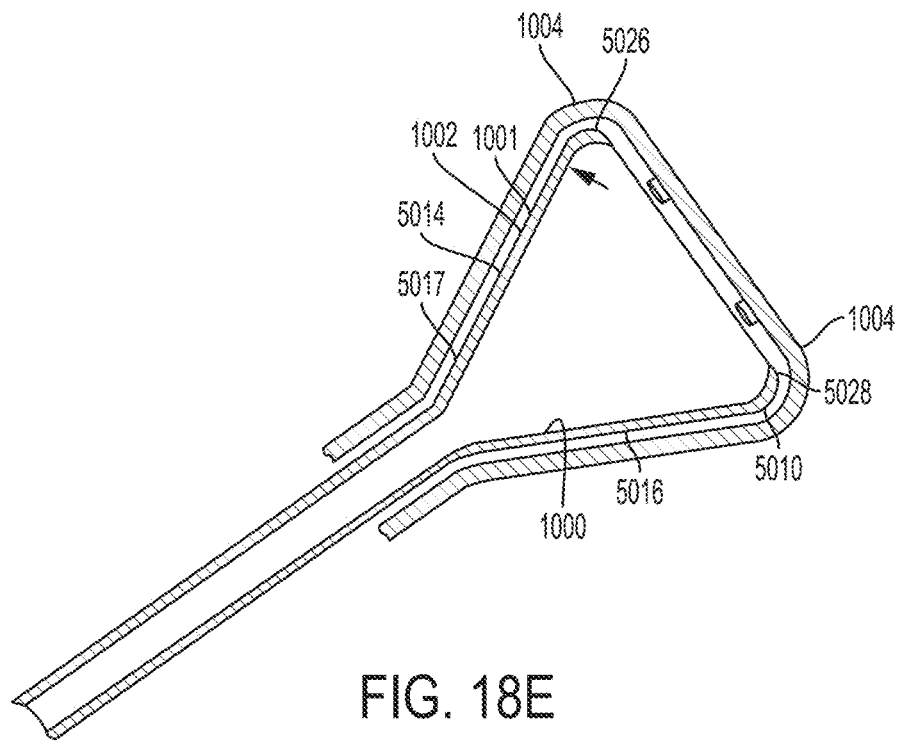
FIG. 18E is cross sectional view of a retention portion of a bladder catheter according to an example of the present invention positioned in the bladder showing in general changes believed to occur in the bladder tissue in response to application of negative pressure through the bladder catheter.

Referring now to FIGS. 18A-D, in some examples, there is shown a distal portion 5004 of the ureteral catheter, indicated generally as 5000. The distal portion 5004 comprises a retention portion 5012 comprising a funnel-shaped support 5014. The funnel-shaped support 5014 comprises at least one sidewall 5016. As shown in FIGS. 18C and 18D, the outer periphery 1002 or protective surface area 1001 comprises the outer surface or outer wall 5022 of the funnel-shaped support 5014. The one or more drainage holes, ports or perforations, or interior opening 5030, are disposed on the protected surface areas or inner surface areas 1000 of the funnel-shaped support 5014. As shown in FIGS. 18C and 18D, there is a single drainage hole 5030 at the base portion 5024 of the funnel-shaped support, although multiple holes can be present.

The at least one sidewall 5016 of the funnel support 5014 comprises a first (outer) diameter D4 and a second (outer) diameter D5, the first outer diameter D4 being less than the second outer diameter D5. The second outer diameter D5 of the funnel support 5014 is closer to the distal end 5010 of the distal portion 5004 of the drainage lumen 5002 than is the first outer diameter D4. In some examples the first outer diameter D4 can range from about 0.33 mm to 4 mm (about 1 Fr to about 12 Fr (French catheter scale)), or about 2.0±0.1 mm. In some examples, the second outer diameter D5 is greater than first outer diameter D4 and can range from about 1 mm to about 60 mm, or about 10 mm to 30 mm, or about 18 mm+2 mm.

In some examples, the at least one sidewall 5016 of the funnel support 5014 can further comprise a third diameter D7 (shown in FIG. 18B), the third diameter D7 being less than the second outer diameter D5. The third diameter D7 of the funnel support 5014 is closer to the distal end 5010 of the distal portion 5004 of the drainage lumen 5002 than is the second diameter D5. The third diameter D7 is discussed in greater detail below regarding the lip. In some examples, the third diameter D7 can range from about 0.99 mm to about 59 mm, or about 5 mm to about 25 mm.

The at least one sidewall 5016 of the funnel support 5014 comprises a first (inner) diameter D6. The first inner diameter D6 is closer to the proximal end 5017 of the funnel support 5014 than is the third diameter D7. The first inner diameter D6 is less than the third diameter D7. In some examples the first inner diameter D6 can range from about 0.05 mm to 3.9 mm, or about 1.25±0.75 mm.

In some examples, an overall height H5 of the sidewall 5016 along a central axis 5018 of the retention portion 5012 can range from about 1 mm to about 25 mm. In some examples, the height H5 of the sidewall can vary at different portions of the sidewall, for example if the sidewall has an undulating edge or rounded edges such as is shown in FIG. 24. In some examples, the undulation can range from about 0.01 mm to about 5 mm or more, if desired.

In some examples, as shown in FIGS. 7A-10E, and 17-41C, the funnel support 5014 can have a generally conical shape. In some examples, the angle 5020 between the outer wall 5022 near the proximal end 5017 of the funnel support 5014 and the drainage lumen 5002 adjacent to the base portion 5024 of the funnel support 5014 can range from about 100 degrees to about 180 degrees, or about 100 degrees to about 160 degrees, or about 120 degrees to about 130 degrees. The angle 5020 may vary at different positions about the circumference of the funnel support 5014, such as is shown in FIG. 22A, in which the angle 5020 ranges from about 140 degrees to about 180 degrees.

Figure 22A:
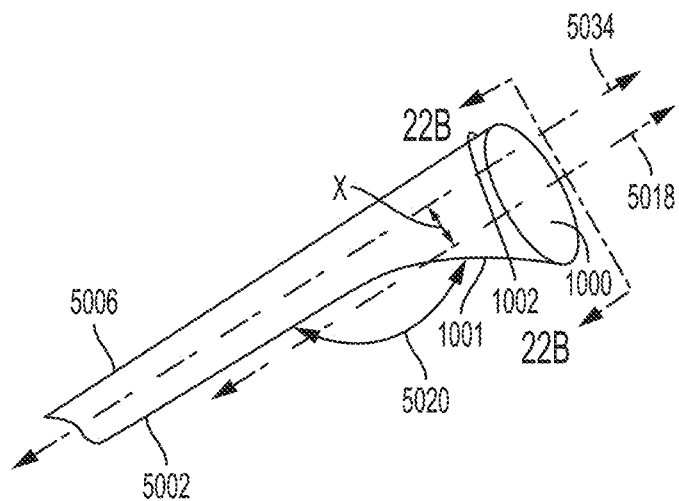
FIG. 22A is a perspective view of a retention portion of another ureteral catheter according to an example of the present invention.
Figure 22B:
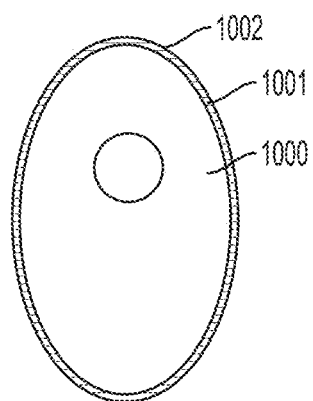
FIG. 22B is a top plan view of the retention portion of the catheter of FIG. 22A taken along lines 22B-22B of FIG. 22A.
Figure 23A:
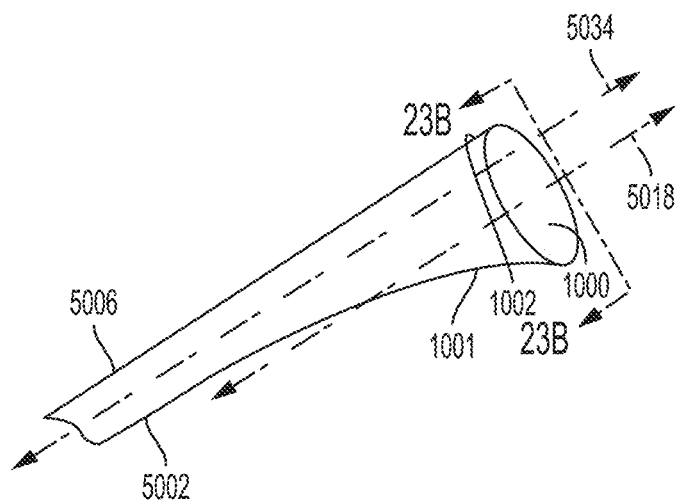
FIG. 23A is a perspective view of a retention portion of another catheter according to an example of the present invention.
Figure 23B:
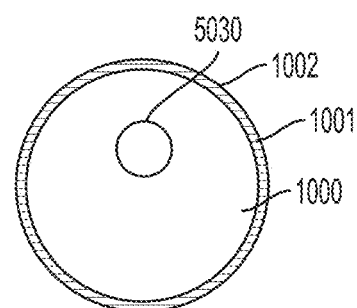
FIG. 23B is a top plan view of the retention portion of the catheter of FIG. 23A taken along lines 23B-23B of FIG. 23A.
Figures 28A, 28B:
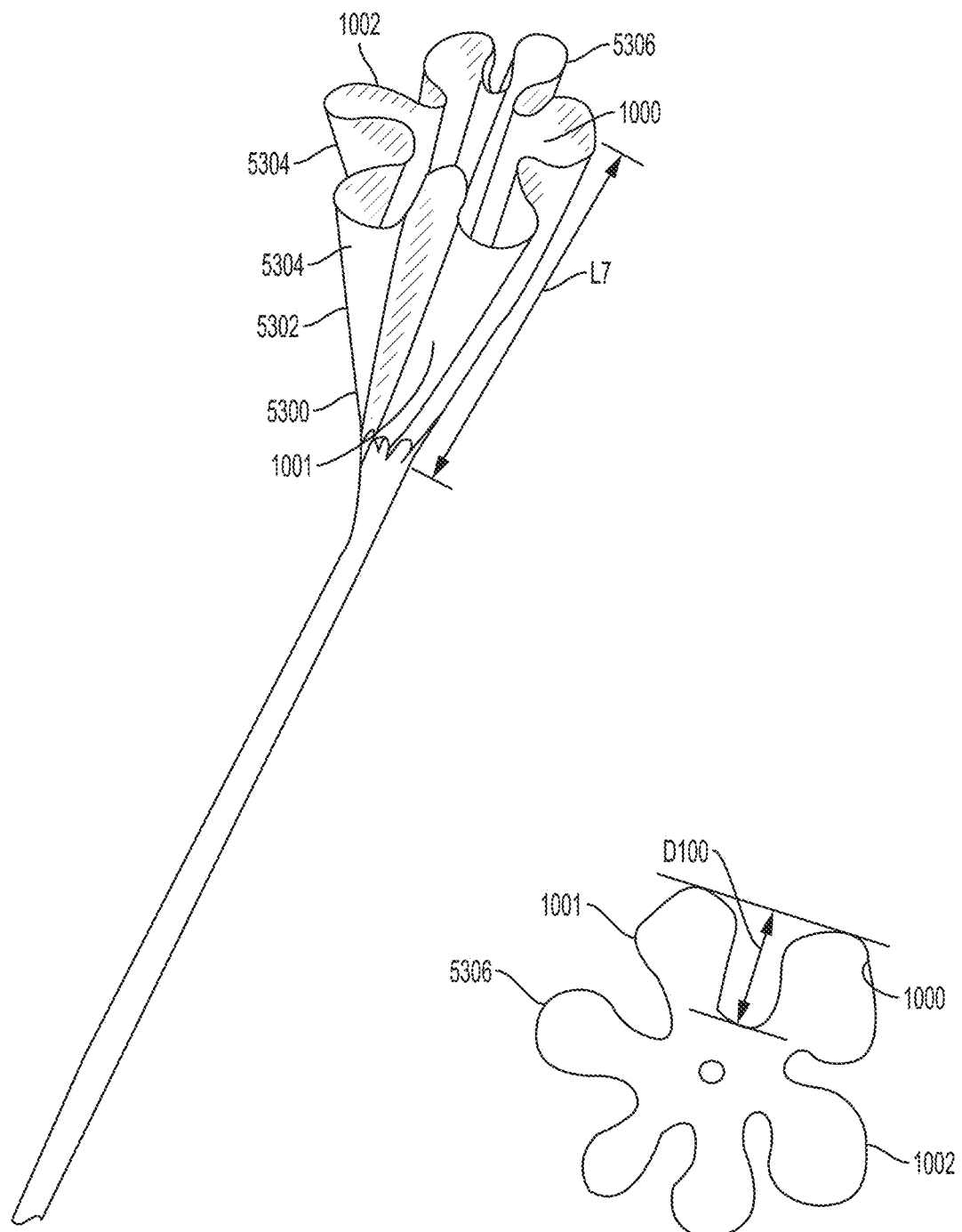
FIG. 28A is a perspective view of a retention portion of another catheter according to an example of the present invention.
FIG. 28B is a top plan view of the retention portion of the catheter of FIG. 28A.

In some examples, the edge or lip 5026 of the distal end 5010 of the at least one sidewall 5016 can be rounded, square, or any shape desired. The shape defined by the edge 5026 can be, for example, circular (as shown in FIGS. 18C and 23B), elliptical (as shown in FIG. 22B), lobes (as shown in FIGS. 28B, 29B and 31), square, rectangular, or any shape desired.

Referring now to FIGS. 28A-31, there is shown a funnel support 5300 wherein the at least one sidewall 5302 comprises a plurality of lobe-shaped longitudinal folds 5304 along the length L7 of the sidewall 5302. The outer periphery 1002 or protective surface area 1001 comprises the outer surface or outer wall 5032 of the funnel-shaped support 5300. The one or more drainage holes, ports or perforations, or interior opening, are disposed on the protected surface areas or inner surface areas 1000 of the funnel-shaped support 5300. As shown in FIG. 28B, there is a single drainage hole at the base portion of the funnel-shaped support, although multiple holes can be present.

The number of folds 5304 can range from 2 to about 20, or about 6, as shown. In this example, the folds 5304 can be formed from one or more flexible materials, such as silicone, polymer, solid material, fabric, or a permeable mesh to provide the desired lobe shape. The folds 5304 can have a generally rounded shape as shown in cross-sectional view 51B. The depth D100 of each fold 5304 at the distal end 5306 of the funnel support 5300 can be the same or vary, and can range from about 0.5 mm to about 5 mm.

Figures 29A, 29B:
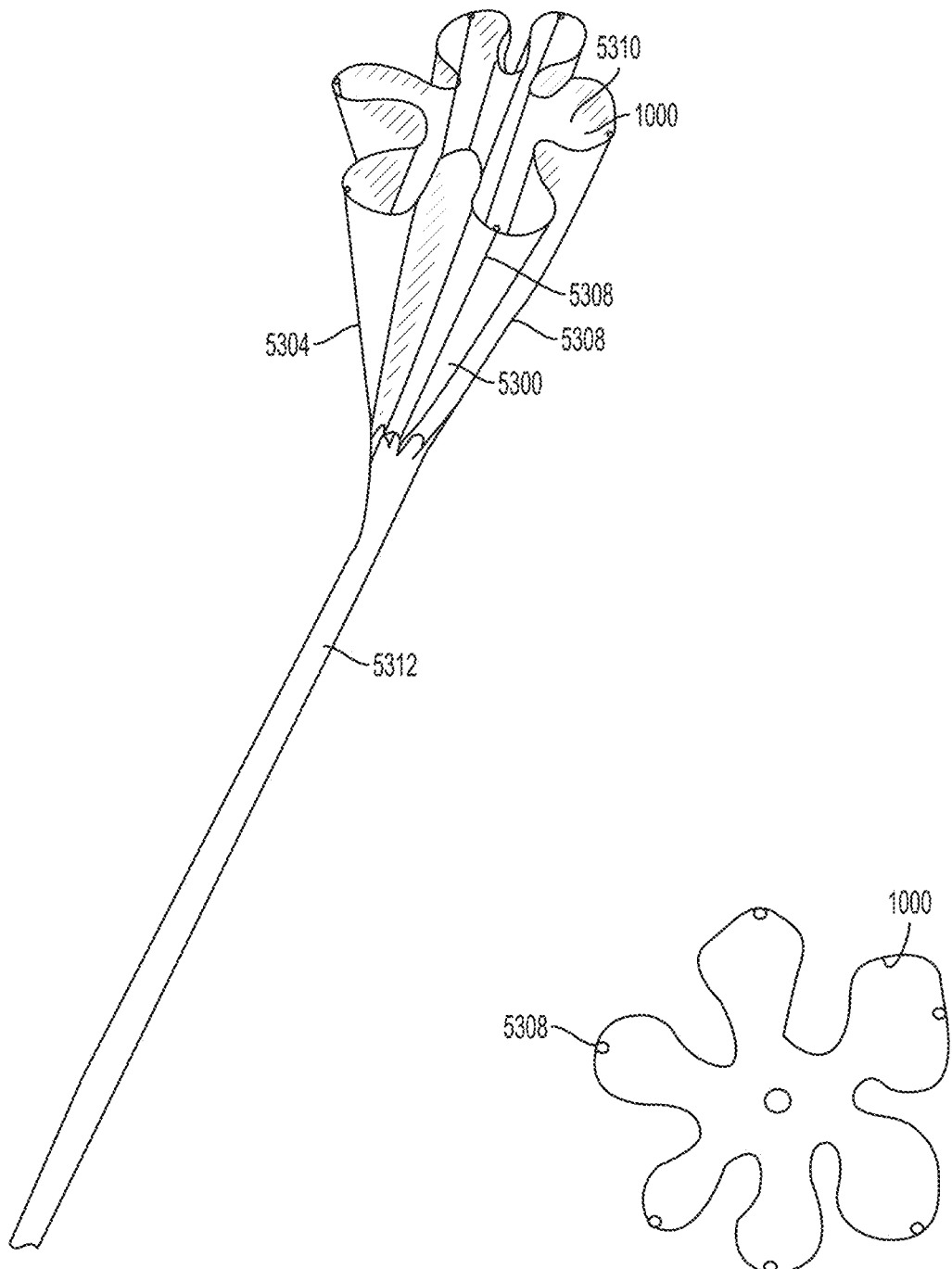
FIG. 29A is a perspective view of a retention portion of another catheter according to an example of the present invention.
FIG. 29B is a top plan view of the retention portion of the catheter of FIG. 29A.
Figure 29C:
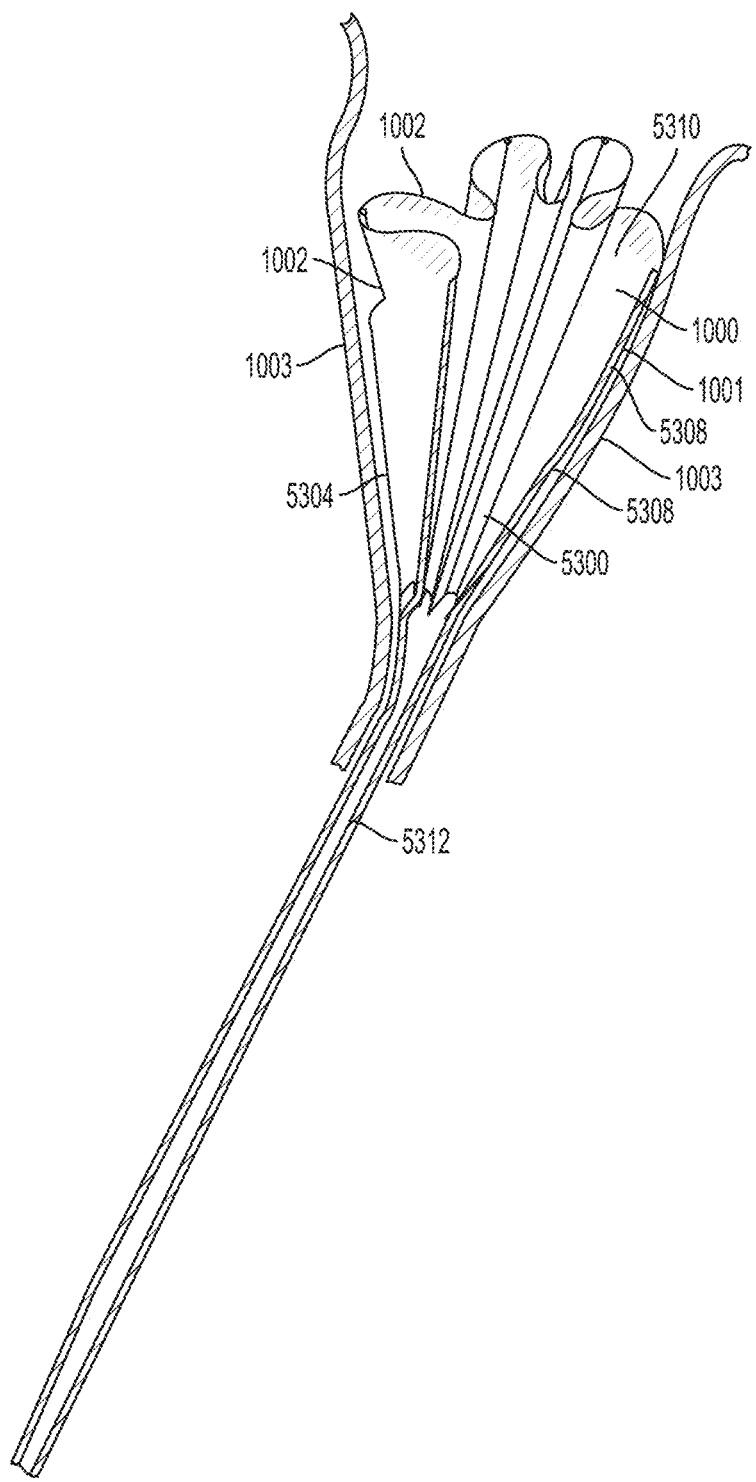
FIG. 29C is a cross sectional view of a retention portion of a ureteral catheter according to an example of the present invention positioned in the renal pelvis region of the kidney showing in general changes believed to occur in the renal pelvis tissue in response to application of negative pressure through the ureteral catheter.

Referring now to FIGS. 29A and 29B, one or more folds 5304 can comprise at least one longitudinal support member 5308. The longitudinal support member(s) 5308 can span the entire length L7 or a portion of the length L7 of the funnel support 5300. The longitudinal support members 5308 can be formed from a flexible yet partially rigid material, such as a temperature sensitive shape memory material, for example nitinol. The thickness of the longitudinal support members 5308 can range from about 0.01 mm to about 1 mm, as desired. In some examples, the nitinol frame can be covered with a suitable waterproof material such as silicon to form a tapered portion or funnel. In that case, fluid is permitted to flow down the inner surface 5310 of the funnel support 5300 and into the drainage lumen 5312. In other examples, the folds 5304 are formed from various rigid or partially rigid sheets or materials bended or molded to form a funnel-shaped retention portion.

Referring now to FIGS. 30 and 31, the distal end or edge 5400 of the folds 5402 can comprise at least one edge support member 5404. The edge support member(s) 5404 can span the entire circumference 5406 or one or more portions of the circumference 5406 of the distal edge 5400 of the funnel support 5408. The edge support member(s) 5404 can be formed from a flexible yet partially rigid material, such as a temperature sensitive shape memory material, for example nitinol. The thickness of the edge support member(s) 5404 can range from about 0.01 mm to about 1 mm, as desired.

In some examples, such as are shown in FIGS. 18A-C, the distal end 5010 of the drainage lumen 5002 (or funnel support 5014) can have an inwardly facing lip 5026 oriented towards the center of the funnel support 5014, for example of about 0.01 mm to about 1 mm, to inhibit irritating the kidney tissue. Thus, the funnel support 5014 can comprise a third diameter D7 less than the second diameter D5, the third diameter D7 being closer to an end 5010 of the distal portion 5004 of the drainage lumen 5002 than the second diameter D5. The outer surface 5028 of the lip 5026 can be rounded, a square edge, or any shape desired. The lip 5026 may assist in providing additional support to the renal pelvis and internal kidney tissues.

Figure 24A:
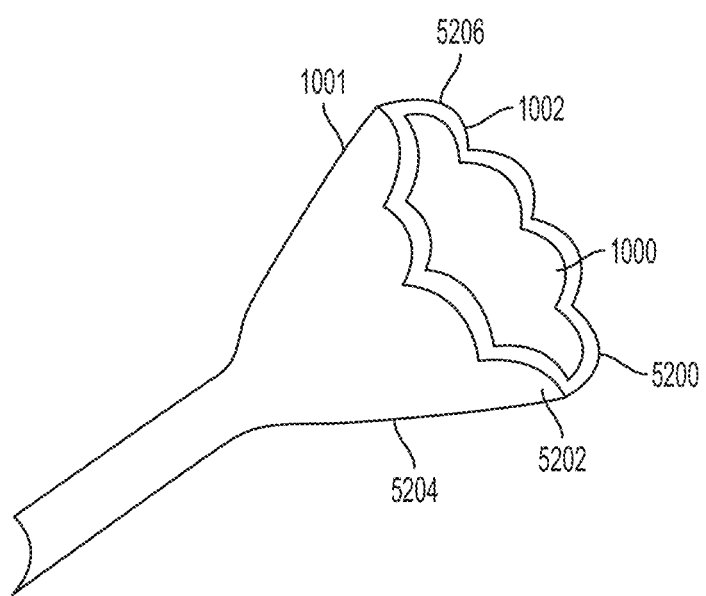
FIG. 24A is a perspective view of a retention portion of another catheter according to an example of the present invention.
Figure 24B:
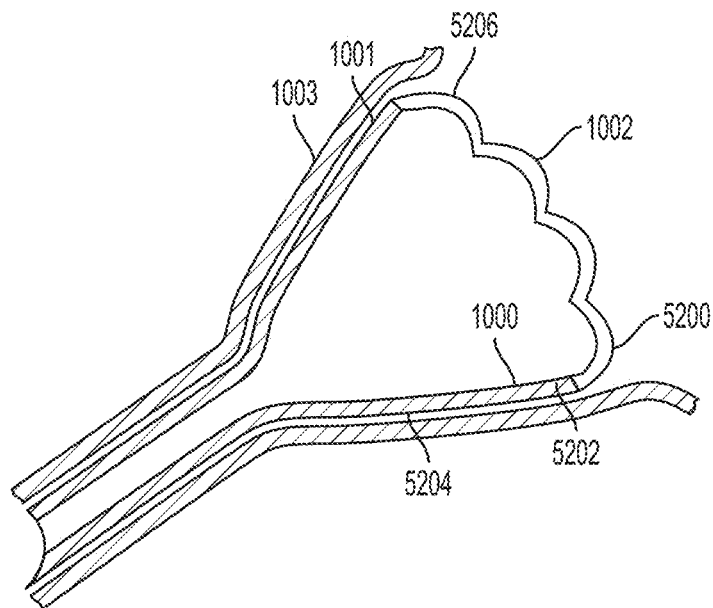
FIG. 24B is a cross sectional view of a retention portion of a ureteral catheter according to an example of the present invention positioned in the renal pelvis region of the kidney showing in general changes believed to occur in the renal pelvis tissue in response to application of negative pressure through the ureteral catheter.
Figure 24C:
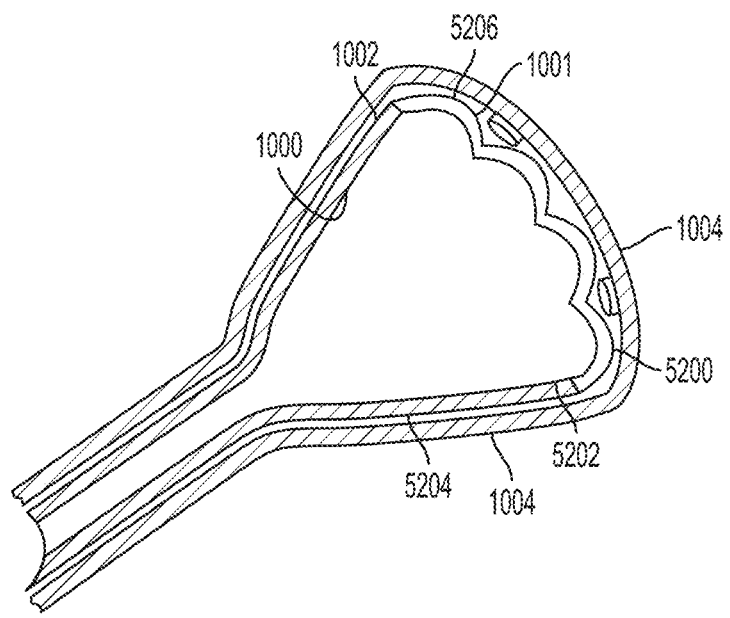
FIG. 24C is a cross sectional view of a retention portion of a bladder catheter according to an example of the present invention positioned in the bladder showing in general changes believed to occur in the bladder tissue in response to application of negative pressure through the bladder catheter.

Referring now to FIGS. 24A-C, in some examples, the edge 5200 of the distal end 5202 of the at least one sidewall 5204 can be shaped. For example, the edge 5200 can comprise a plurality of generally rounded edges 5206 or scallops, for example about 4 to about 20 or more rounded edges. The rounded edges 5206 can provide more surface area than a straight edge to help support the tissue of the renal pelvis or kidney and inhibit occlusion. The edge 5200 can have any shape desired, but preferably is essentially free of or free of sharp edges to avoid injuring tissue.

In some examples, such as are shown in FIGS. 18A-C and 22A-23B, the funnel support 5014 comprises a base portion 5024 adjacent to the distal portion 5004 of the drainage lumen 5002. The base portion 5024 comprises at least one interior opening 5030 aligned with an interior lumen 5032 of the drainage lumen 5002 of the proximal portion 5006 of the drainage lumen 5002 for permitting fluid flow into the interior lumen 5032 of the proximal portion 5006 of the drainage lumen 5002. In some examples, the cross-section of the opening 5030 is circular, although the shape may vary, such as ellipsoid, triangular, square, etc.

In some examples, such as is shown in FIGS. 22A-23B, a central axis 5018 of the funnel support 5014 is offset with respect to a central axis 5034 of the proximal portion 5006 of the drainage lumen 5002. The offset distance X from the central axis 5018 of the funnel support 5014 with respect to the central axis 5034 of the proximal portion 5006 can range from about 0.1 mm to about 5 mm.

The at least one interior opening 5030 of the base portion 5024 has a diameter D8 (shown, for example, in FIGS. 18C and 23B) ranging from about 0.05 mm to about 4 mm. In some examples, the diameter D8 of the interior opening 5030 of the base portion 5024 is about equal to the first inner diameter D6 of the adjacent proximal portion 5006 of the drainage lumen.

In some examples, the ratio of the height H5 of the at least one sidewall 5016 funnel support 5014 to the second outer diameter D5 of the at least one sidewall 5016 of the funnel support 5014 ranges from about 1:25 to about 5:1.

In some examples, the at least one interior opening 5030 of the base portion 5024 has a diameter D8 ranging from about 0.05 mm to about 4 mm, the height H5 of the at least one sidewall 5016 of the funnel support 5014 ranges from about 1 mm to about 25 mm, and the second outer diameter D5 of the funnel support 5014 ranges from about 5 mm to about 25 mm.

In some embodiments, the thickness T1 (shown in FIG. 18B, for example) of the at least one sidewall 5016 of the funnel support 5014 can range from about 0.01 mm to about 1.9 mm, or about 0.5 mm to about 1 mm. The thickness T1 can be generally uniform throughout the at least one sidewall 5016, or it may vary as desired. For example, the thickness T1 of the at least one sidewall 5016 can be less or greater near the distal end 5010 of the distal portion 5004 of the drainage lumen 5002 than at the base portion 5024 of the funnel support 5014.

Figure 19:
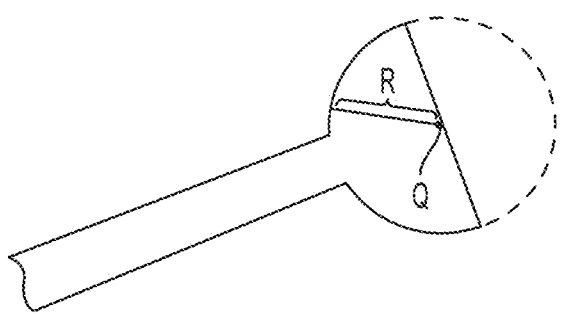
FIG. 19 is a side elevational view of a retention portion of another catheter according to an example of the present invention.
Figure 20:
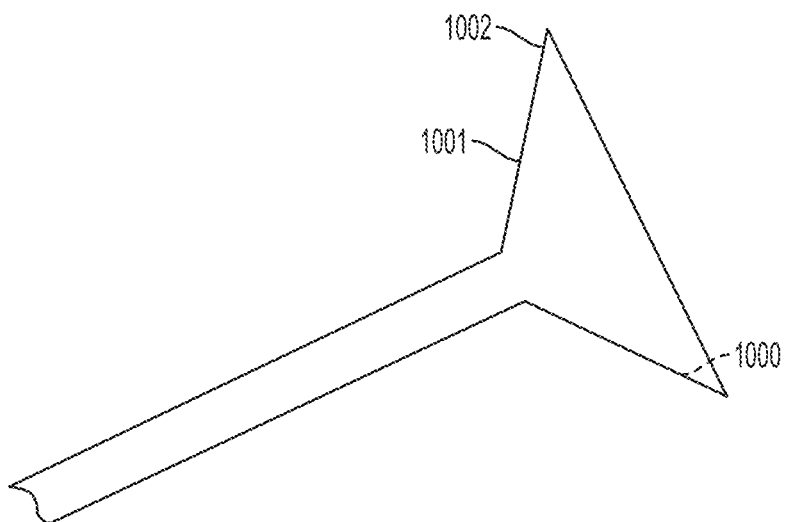
FIG. 20 is a side elevational view of a retention portion of another catheter according to an example of the present invention.
Figure 21:
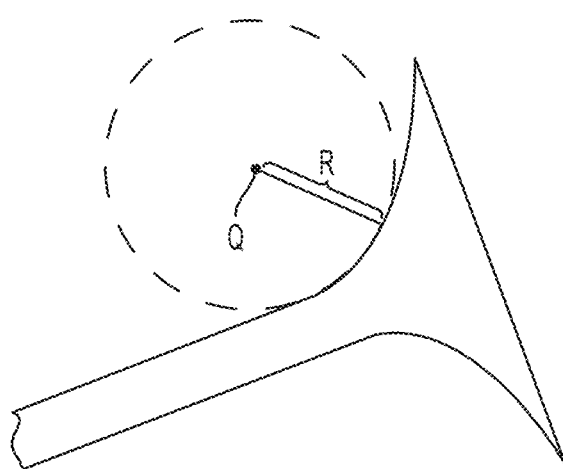
FIG. 21 is a side elevational view of a retention portion of another catheter according to an example of the present invention.

Referring now to FIGS. 18A-21, along the length of the at least one sidewall 5016, the sidewall 5016 can be straight (as shown in FIGS. 18A and 20), convex (as shown in FIG. 19), concave (as shown in FIG. 21), or any combination thereof. As shown in FIGS. 19 and 21, the curvature of the sidewall 5016 can be approximated from the radius of curvature R from the point Q such that a circle centered at Q meets the curve and has the same slope and curvature as the curve. In some examples, the radius of curvature ranges from about 2 mm to about 12 mm. In some examples, the funnel support 5014 has a generally hemispherical shape, as shown in FIG. 19.

Figure 35A:
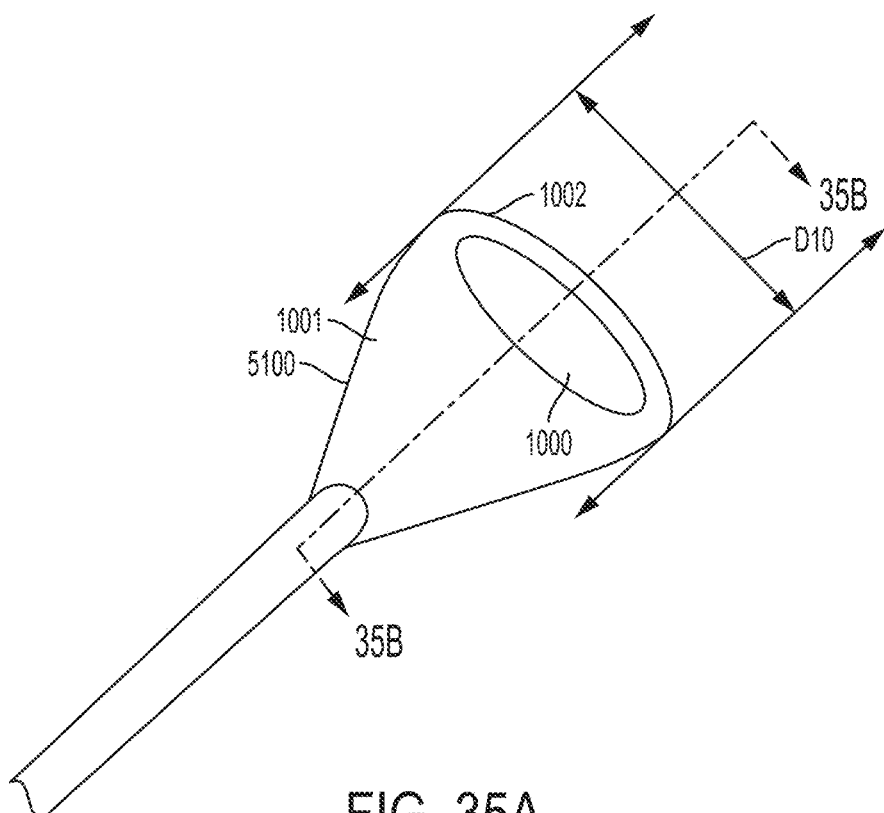
FIG. 35A is a perspective view of a retention portion of another catheter according to an example of the present invention.
Figure 35B:
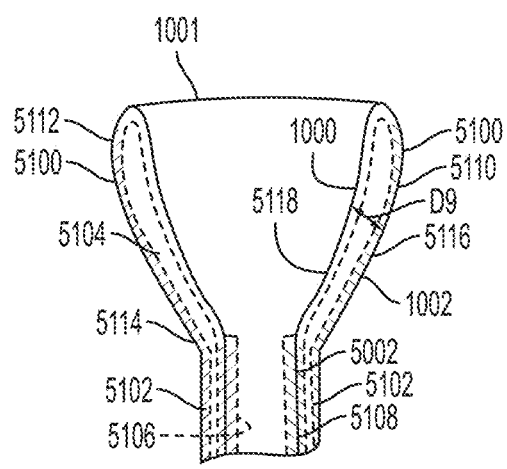
FIG. 35B is a cross-sectional side elevational view of the retention portion of the catheter of FIG. 35A taken along lines B-B of FIG. 35A.
Figure 36:
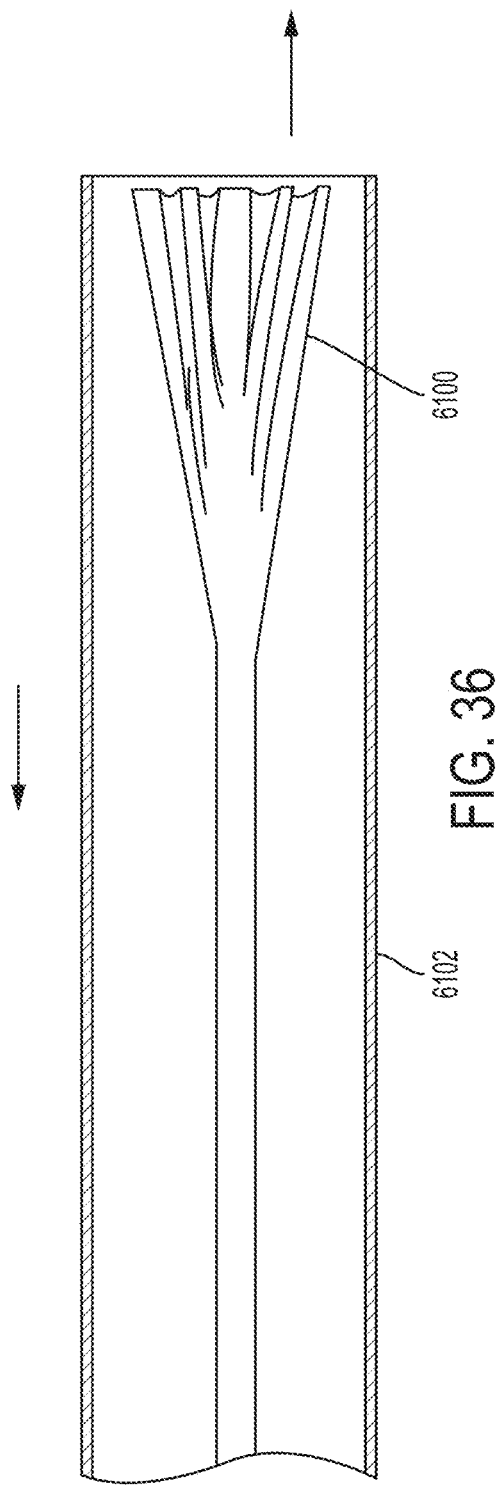
FIG. 36 is a side elevational view showing a cut away cross-sectional view of the sheath surrounding a catheter according to an example of the present invention in a contracted configuration for insertion into a patient's ureter.

In some examples, the at least one sidewall 5016 of the funnel support 5014 is formed from a balloon 5100, for example as shown in FIGS. 35A, 35 B, 38A and 38B. The balloon 5100 can have any shape that provides a funnel support to inhibit occlusion of the ureter, renal pelvis, and/or the rest of the kidney. As shown in FIGS. 35A and 35B, the balloon 5100 has the shape of a funnel. The balloon can be inflated after insertion or deflated before removal by adding or removing gas or air through the gas port(s) 5102. The gas port(s) 5102 can simply be contiguous with the interior 5104 of the balloon 5100, e.g., the balloon 5100 can be adjacent to the interior 5106 or encase the exterior 5108 of an adjacent portion of the proximal portion 5006 of the drainage lumen 5002. The diameter D9 of the sidewall 5110 of the balloon 5100 can range from about 1 mm to about 3 mm, and can vary along its length such that the sidewall has a uniform diameter, tapers toward the distal end 5112 or tapers toward the proximal end 5114 of the funnel support 5116. The outer diameter D10 of the distal end 5112 of the funnel support 5116 can range from about 5 mm to about 25 mm.

In some examples, the at least one sidewall 5016 of the funnel support 5014 is continuous along the height H5 of the at least one sidewall 5016, for example as shown in FIGS. 18A, 19, 20, and 21. In some examples, the at least one sidewall 5016 of the funnel support 5014 comprises a solid wall, for example the sidewall 5016 is not permeable through the sidewall after 24 hours of contact with a fluid such as urine on one side.

In some examples, the at least one sidewall of the funnel support is discontinuous along the height or the body of the at least one sidewall. As used herein, "discontinuous" means that the at least one sidewall comprises at least one opening for permitting the flow of fluid or urine therethrough into the drainage lumen, for example by gravity or negative pressure. In some examples, the opening can be a conventional opening through the sidewall, or openings within a mesh material, or openings within a permeable fabric. The cross-sectional shape of the opening can be circular or non-circular, such as rectangular, square, triangular, polygonal, ellipsoid, as desired. In some examples, an "opening" is a gap between adjacent coils in a retention portion of a catheter comprising a coiled tube or conduit.

As used herein, "opening" or "hole" means a continuous void space or channel through the sidewall from the outside to the inside of the sidewall, or vice versa. In some examples, each of the at least one opening(s) can have an area which can be the same or different and can range from about 0.002 mm$^2$ to about 100 mm$^2$, or about 0.002 mm$^2$ to about 10 mm$^2$. As used herein, the "area" or "surface area" or "cross-sectional area" of an opening means the smallest or minimum planar area defined by a perimeter of the opening. For example, if the opening is circular and has a diameter of about 0.36 mm (area of 0.1 mm$^2$) at the outside of the sidewall, but a diameter of only 0.05 mm (area of 0.002 mm$^2$) at some point within the sidewall or on the opposite side of the sidewall, then the "area" would be 0.002 mm$^2$ since that is the minimum or smallest planar area for flow through the opening in the sidewall. If the opening is square or rectangular, the "area" would be the length times the width of the planar area. For any other shapes, the "area" can be determined by conventional mathematical calculations well known to those skilled in the art. For example, the "area" of an irregular shaped opening is found by fitting shapes to fill the planar area of the opening, calculating the area of each shape and adding together the area of each shape.

In some examples, at least a portion of the sidewall comprises at least one (one or more) openings. Generally, the central axis of the opening(s) can be generally perpendicular to the planar outer surface of the sidewall, or the opening(s) can be angled with respect to the planar outer surface of the sidewalls. The dimensions of the bore of the opening may be uniform throughout its depth, or the width may vary along the depth, either increasing, decreasing, or alternating in width through the opening from the exterior surface of the sidewall to the interior surface of the sidewall.

Referring now to FIGS. 9A-9E, 10A, 10E, 11-14, 27, 32A, 32B, 33 and 34, in some examples at least a portion of the sidewall comprises at least one (one or more) openings. The opening(s) can be positioned anywhere along the sidewall. For example, the openings can be uniformly positioned throughout the sidewall, or positioned in specified regions of the sidewall, such as closer to the distal end of the sidewall or closer to the proximal end of the sidewall, or in vertical or horizontal or random groupings along the length or circumference of the sidewall. While not intending to be bound by any theory, it is believed that, when negative pressure is applied at the proximal end of the proximal portion of the drainage lumen, openings in the proximal portion of the funnel support that are directly adjacent to the ureter, renal pelvis and/or other kidney tissue may be undesirable as such openings may diminish the negative pressure at the distal portion of the ureteral catheter and thereby diminish the draw or flow of fluid or urine from the kidney and renal pelvis of the kidney, as well as perhaps irritate the tissue.

The number of openings can vary from 1 to 1000 or more, as desired. For example, in FIG. 27, six openings (three on each side) are shown. As discussed above, in some examples, each of the at least one opening(s) can have an area which can be the same or different and can range from about 0.002 mm$^2$ to about 50 mm$^2$, or about 0.002 mm$^2$ to about 10 mm$^2$.

Figure 27:
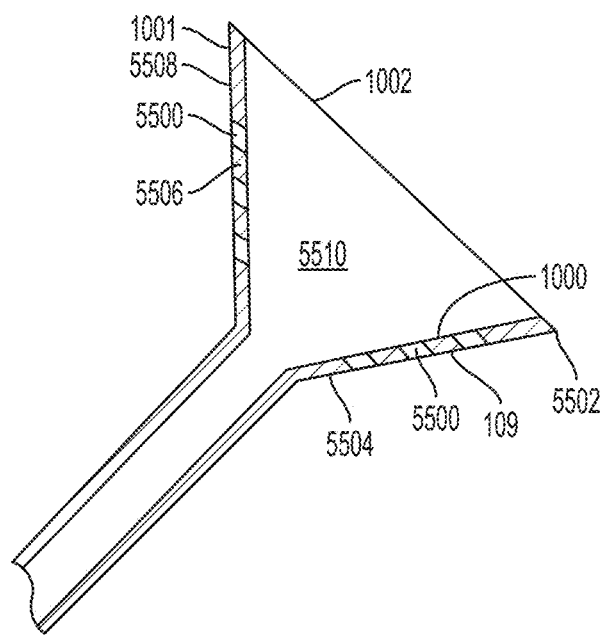
FIG. 27 is a cross-sectional side view of a retention portion of another catheter according to an example of the present invention.

In some examples, as shown in FIG. 27, the openings 5500 can be positioned closer the distal end 5502 of the sidewall 5504. In some examples, the opening(s) are positioned in the distal half 5506 of the sidewall towards the distal end 5502. In some examples, the openings 5500 are evenly distributed around the circumference of the distal half 5506 or even closer to the distal end 5502 of the sidewall 5504.

Figure 32A:
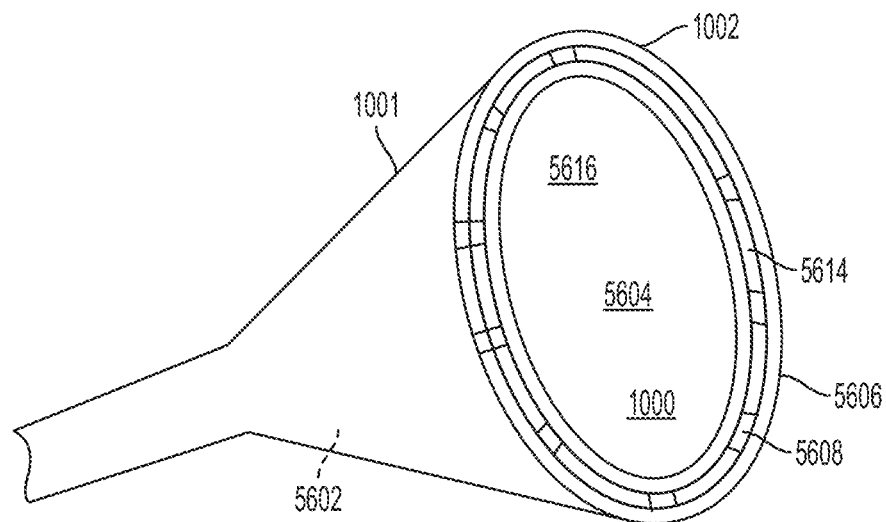
FIG. 32A is a perspective view of a retention portion of another catheter according to an example of the present invention.
Figure 32B:
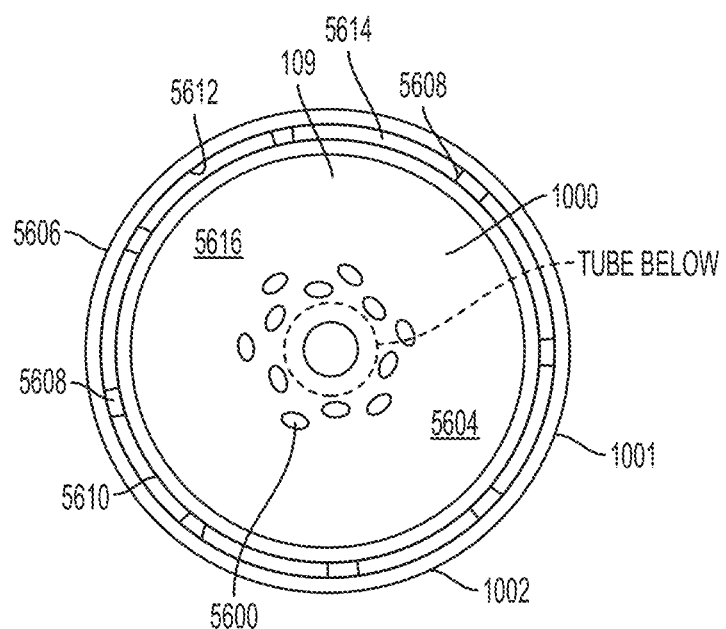
FIG. 32B is a top plan view of the retention portion of the catheter of FIG. 32A.
Figure 33:
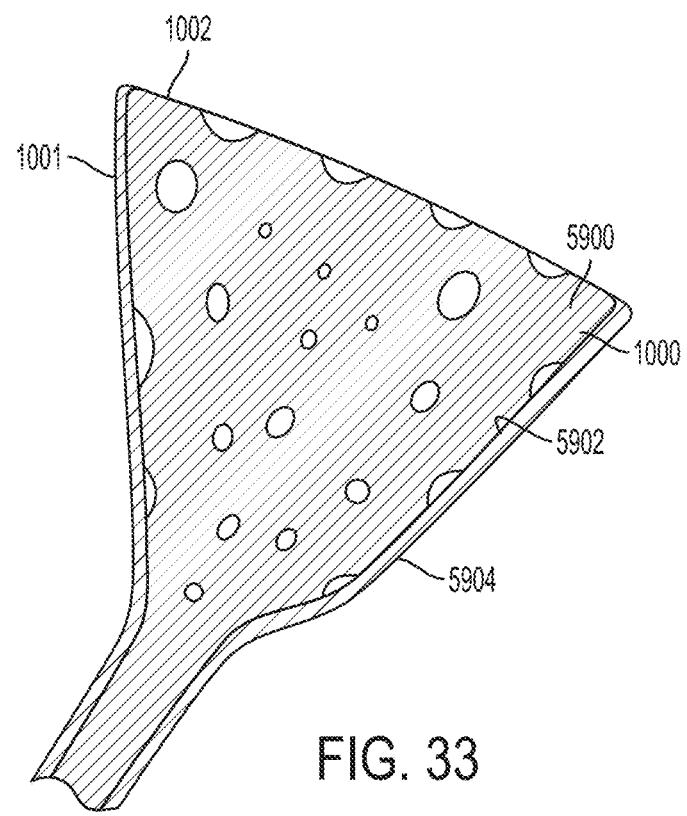
FIG. 33 is a cross-sectional side elevational view of a retention portion of another catheter according to an example of the present invention.
Figure 34:
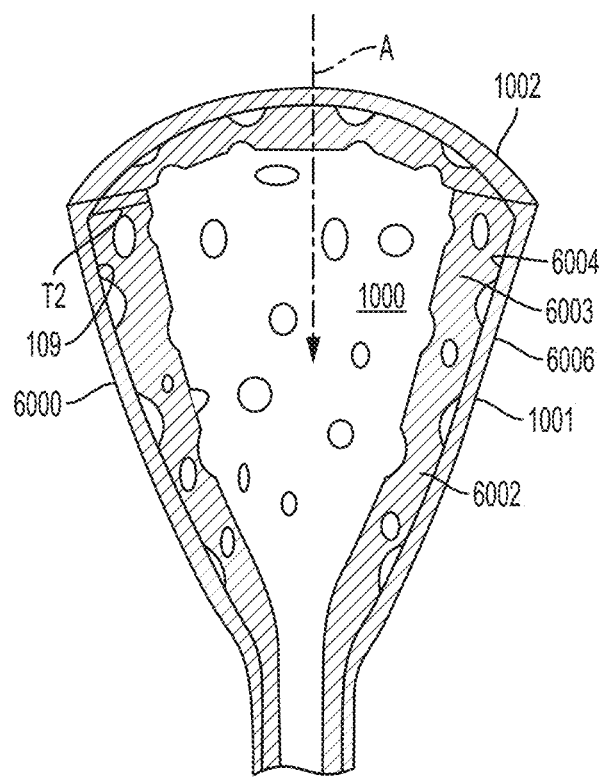
FIG. 34 is a cross-sectional side elevational view of a retention portion of another catheter according to an example of the present invention.

In contrast, in FIG. 32B, the openings 5600 are positioned near the proximal end 5602 of an inner sidewall 5604, and do not directly contact the tissue since there is an outer sidewall 5606 between the opening 5600 and the tissue. Alternatively or additionally, one or more opening(s) 5600 can be positioned near the distal end of the inner sidewall, as desired. The inner sidewall 5604 and outer sidewall 5606 can be connected by one or more supports 5608 or ridges connecting the outside 5610 of the inner sidewall 5604 to the inside 5612 of the outer sidewall 5606.

In some non-limiting examples, such as are shown in FIGS. 9A-9E, 10A, 10D-10G, 18B, 18D, 18E, 20, 22A, 22B, 23A, 23B, 24A-24C, 25, 26, 27, 28A, 28B, 29A-29C, 30, 31, 32A, 32B, 33, 34, 35A, 35B, 37B, 38A, 39B, 39C, 40A-40C, and 41A-41C, a protected surface area(s) or inner surface area(s) 1000 can be established by a variety of different shapes or materials. Non-limiting examples of protected surface areas or inner surface areas 1000 can comprise, for example, the interior portions 152, 5028, 5118, 5310, 5410, 5510, 5616, 5710, 5814, 6004 of a funnel 150, 5014, 5116, 5300, 5408, 5508, 5614, 5702, 5802, 6000, the interior portions 164, 166, 168, 170, 338, 1281, 1283, 1285 of a coil 183, 184, 185, 187, 334, 1280, 1282, 1284, the interior portions 5902, 6003 of a porous material 5900, 6002, the interior portions 162, 5710, 5814 of a mesh 57, 5704, 5804, or the interior portions 536 of a cage 530 with protected drainage holes 533.

In some non-limiting examples, one or more protected drainage holes, ports or perforations 133, 1233 are disposed on the protected surface area 1000. Upon application of negative pressure therapy through the catheter, the urothelial or mucosal tissue 1003, 1004 conforms or collapses onto the outer periphery 189, 1002 or protective surface area 1001 of the retention portion 130, 330, 410, 500, 1230, 1330, 2230, 3230, 4230, 5012, 5013 of the catheter and is thereby prevented or inhibited from occluding one or more of the protected drainage holes, ports or perforations 133, 1233 disposed on the protected surface area or inner surface area 1000, and thereby a patent fluid column or flow is established, maintained, or enhanced between the renal pelvis and calyces and the drainage lumen 124, 324, 424, 524, 1224, 5002, 5003, 5312, 5708, 5808.

In some examples, the retention portion 130, 330, 410, 500, 1230, 1330, 2230, 3230, 4230, 5012, 5013 comprises one or more helical coils having outwardly facing sides 1288 and inwardly facing sides 1286, and wherein the outer periphery 1002 or protective surface area 1001 comprises the outwardly facing sides 1288 of the one or more helical coils, and the one or more protected drainage holes, ports or perforations 133, 1233 are disposed on the inwardly facing sides 1286 (protected surface area or inner surface area 1000) of the one or more helical coils.

Figure 25:
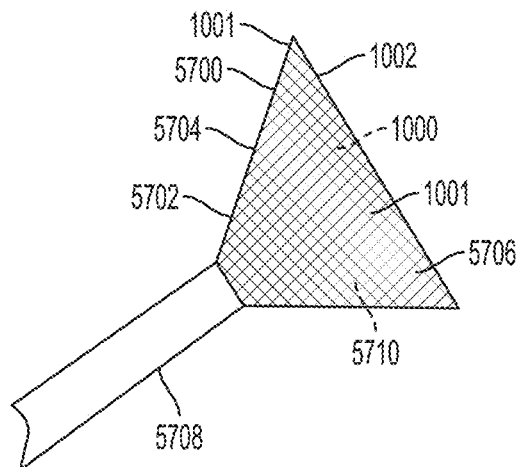
FIG. 25 is a side elevational view of a retention portion of another catheter according to an example of the present invention.

For example, a funnel shape, as shown in FIG. 25, can create a sidewall 5700 that conforms to the natural anatomical shape of the renal pelvis preventing the urothelium from constricting the fluid column. The interior 5710 of the funnel support 5702 provides a protected surface area 1000 having openings 5706 therethrough which provide a passageway through which a fluid column can flow from the calyces into the drainage lumen 5708. Similarly, the mesh form of FIG. 26 can also create a protected surface area 1000, such as interior 5814 of the mesh 5804, between the calyces and the drainage lumen 5808 of the catheter. The mesh 5704, 5804 comprises a plurality of openings 5706, 5806 therethrough for permitting fluid flow into the drainage lumen 5708, 5808. In some examples, the maximum area of an opening can be less than about 100 mm$^2$, or less than about 1 mm$^2$, or about 0.002 mm$^2$ to about 1 mm$^2$, or about 0.002 mm$^2$ to about 0.05 mm$^2$. The mesh 5704, 5804 can be formed from any suitable metallic or polymeric material such as are discussed above.

Figure 26:
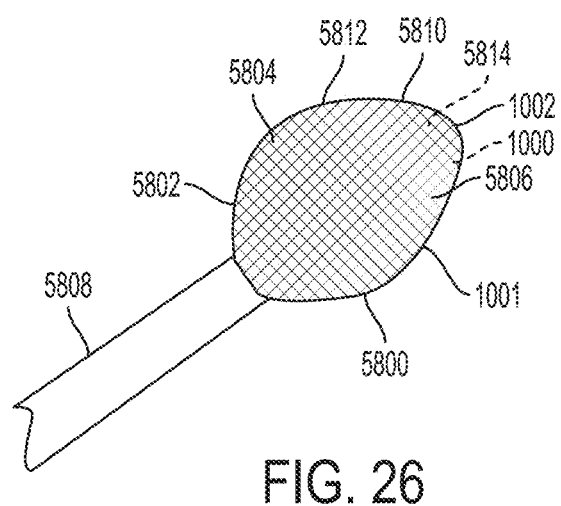
FIG. 26 is a side elevational view of a retention portion of another catheter according to an example of the present invention.

In some examples, the funnel support further comprises a cover portion over the distal end of the funnel support. This cover portion can be formed as an integral part of the funnel support or connected to the distal end of the funnel support. For example, as shown in FIG. 26, the funnel support 5802 comprises a cover portion 5810 across the distal end 5812 of the funnel support 5802 and projecting from the distal end 5812 of the funnel support 5802. The cover portion 5810 can have any shape desired, such as flat, convex, concave, undulating, and combinations thereof. The cover portion 5810 can be formed from mesh or any polymeric solid material as discussed above. The cover portion 5810 can provide an outer periphery 1002 or protective surface area 1001 to assist in supporting the pliant tissue in the kidney region to facilitate urine production.

Figure 39A:
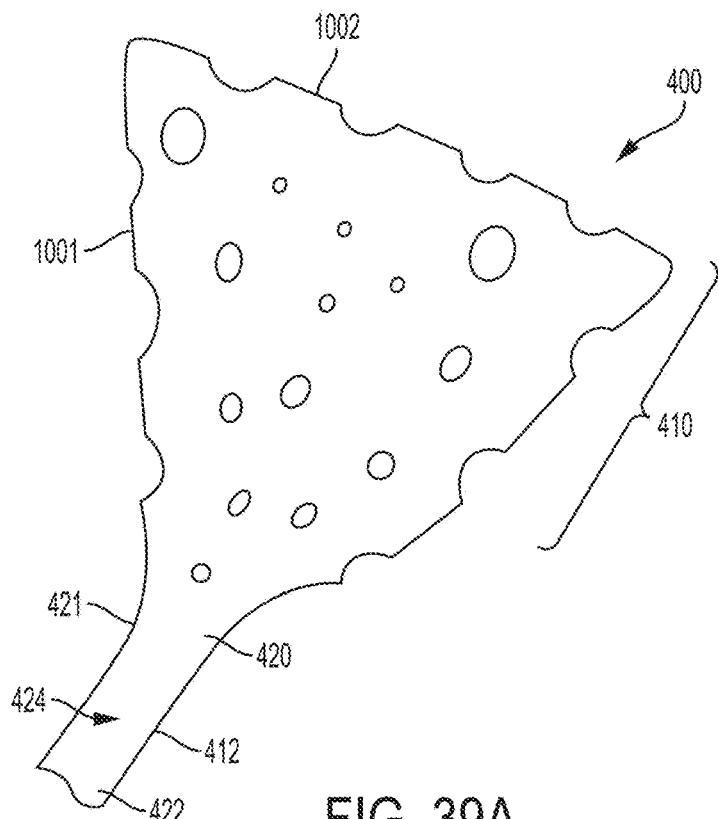
FIG. 39A is a schematic drawing of another example of a retention portion for a catheter according to an example of the present invention.
Figure 39B:
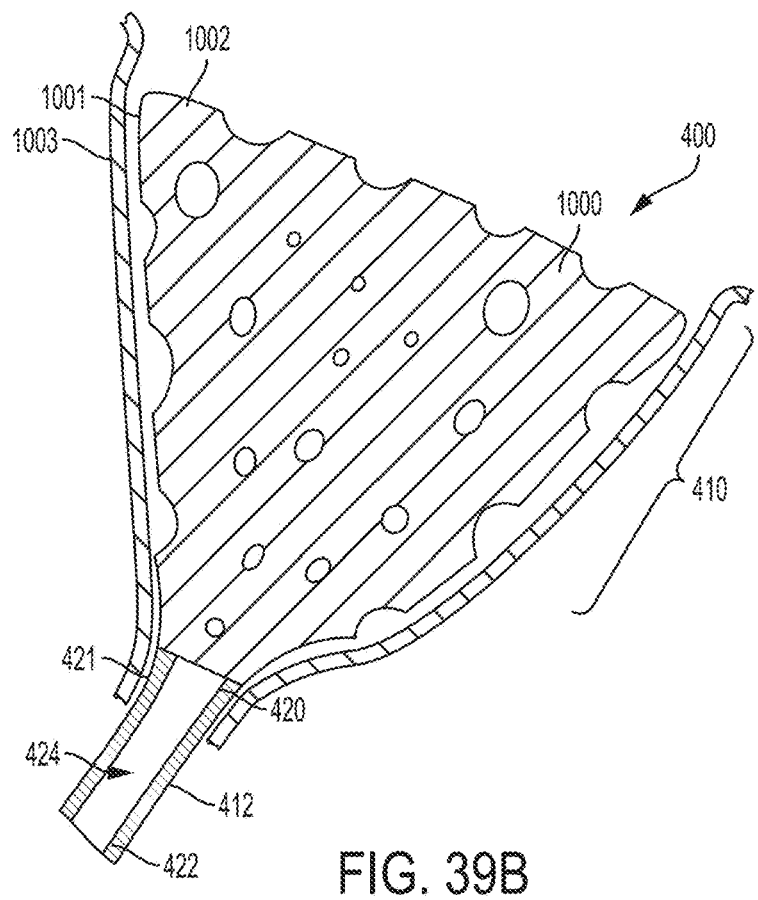
FIG. 39B is a schematic drawing of a cross section of another example of a retention portion for a ureteral catheter according to an example of the present invention positioned in the renal pelvis region of the kidney showing in general changes believed to occur in the renal pelvis tissue in response to application of negative pressure through the ureteral catheter.
Figure 39C:
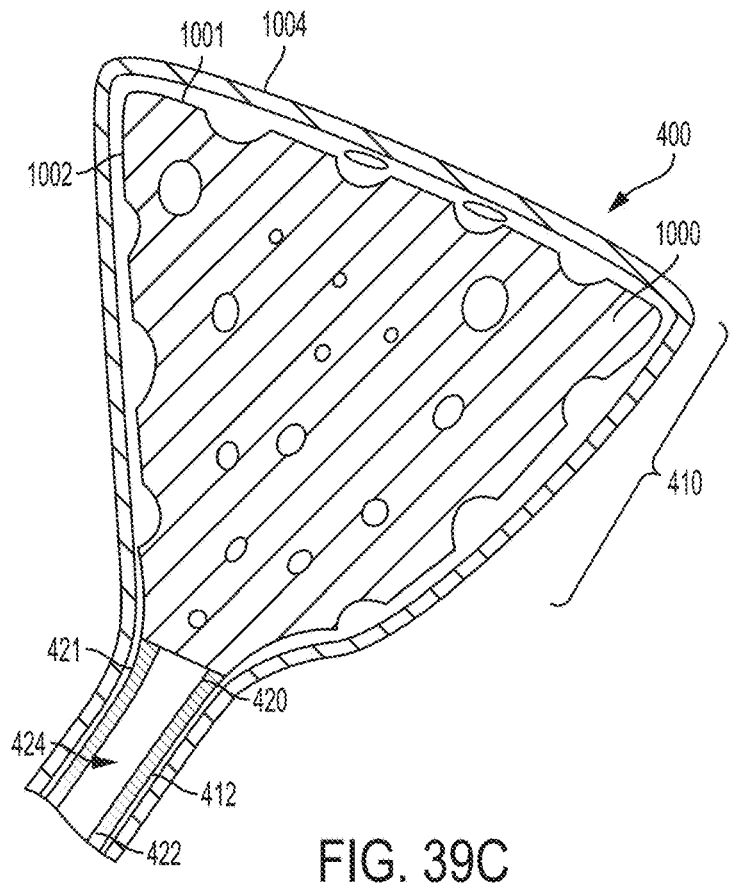
FIG. 39C is a schematic drawing of a cross section of another example of a retention portion for a bladder catheter according to an example of the present invention positioned in the bladder showing in general changes believed to occur in the bladder tissue in response to application of negative pressure through the bladder catheter.
Figure 40A:
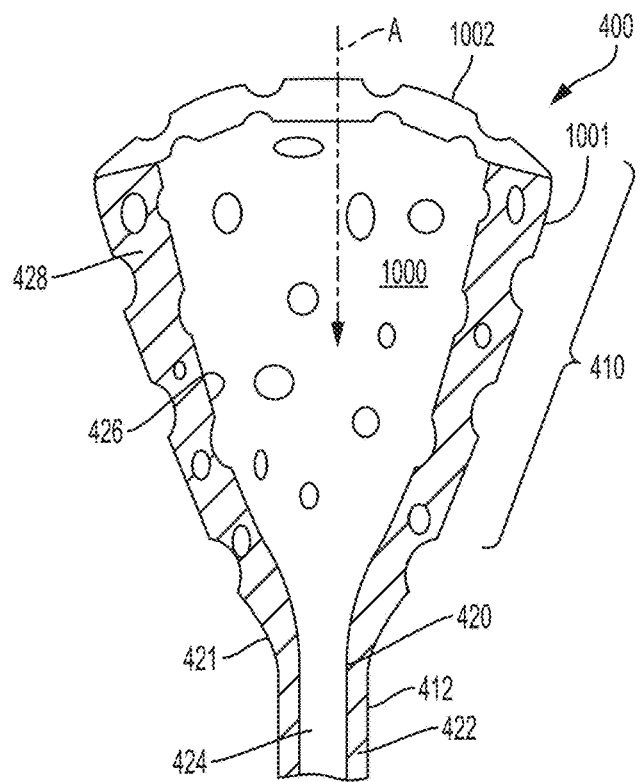
FIG. 40A is a schematic drawing of a cross section of another example of a retention portion for a catheter according to an example of the present invention.
Figure 40B:
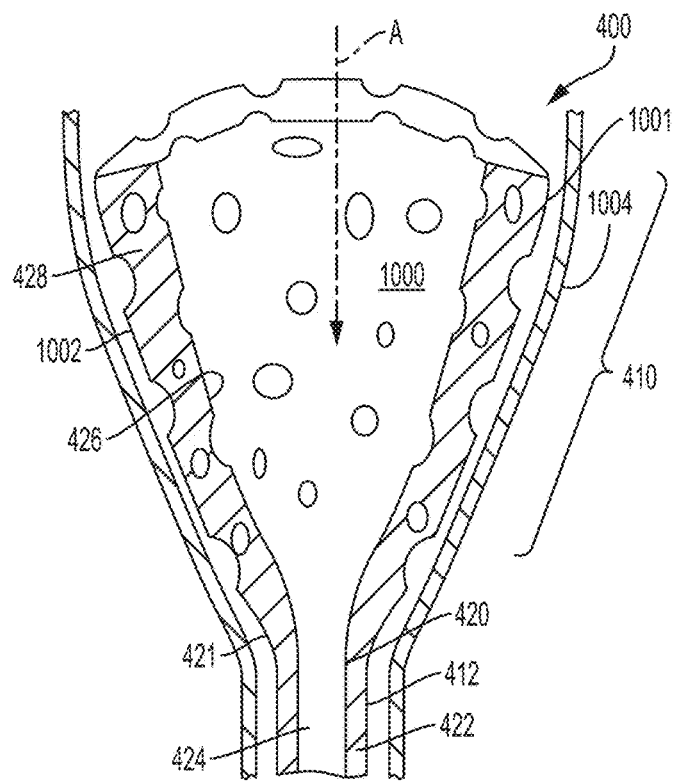
FIG. 40B is a schematic drawing of a cross section of another example of a retention portion for a ureteral catheter according to an example of the present invention positioned in the renal pelvis region of the kidney showing in general changes believed to occur in the renal pelvis tissue in response to application of negative pressure through the ureteral catheter.
Figure 40C:
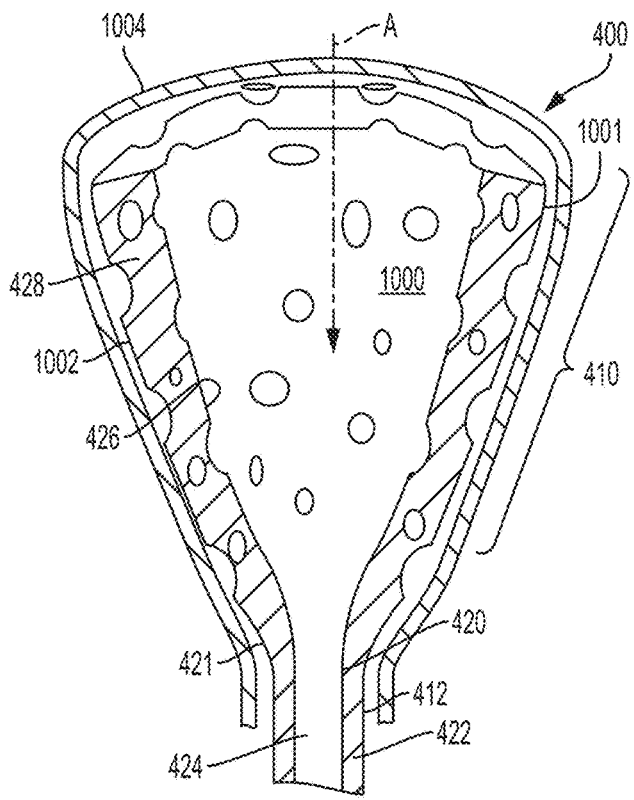
FIG. 40C is a schematic drawing of a cross section of another example of a retention portion for a bladder catheter according to an example of the present invention positioned in the bladder showing in general changes believed to occur in the bladder tissue in response to application of negative pressure through the bladder catheter.
Figure 41A:
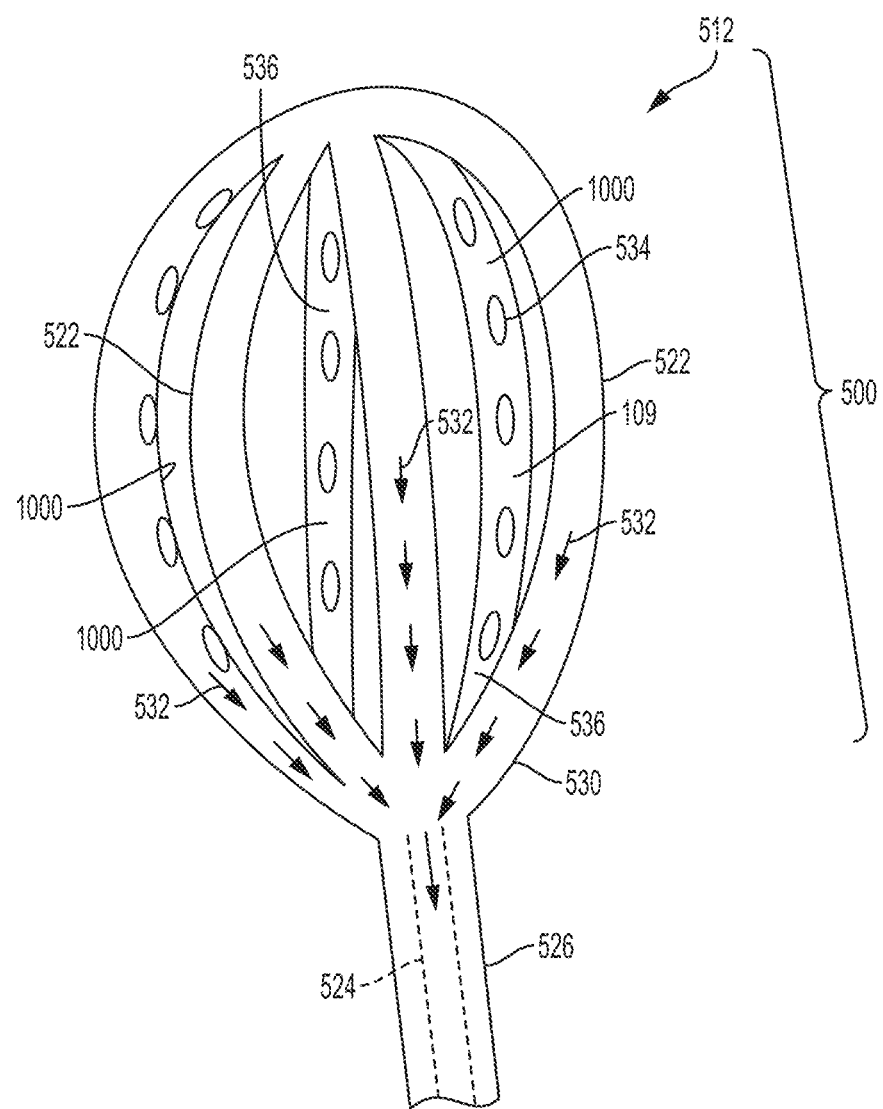
FIG. 41A is a schematic drawing of another example of a retention portion for a catheter according to an example of the present invention.
Figure 41B:
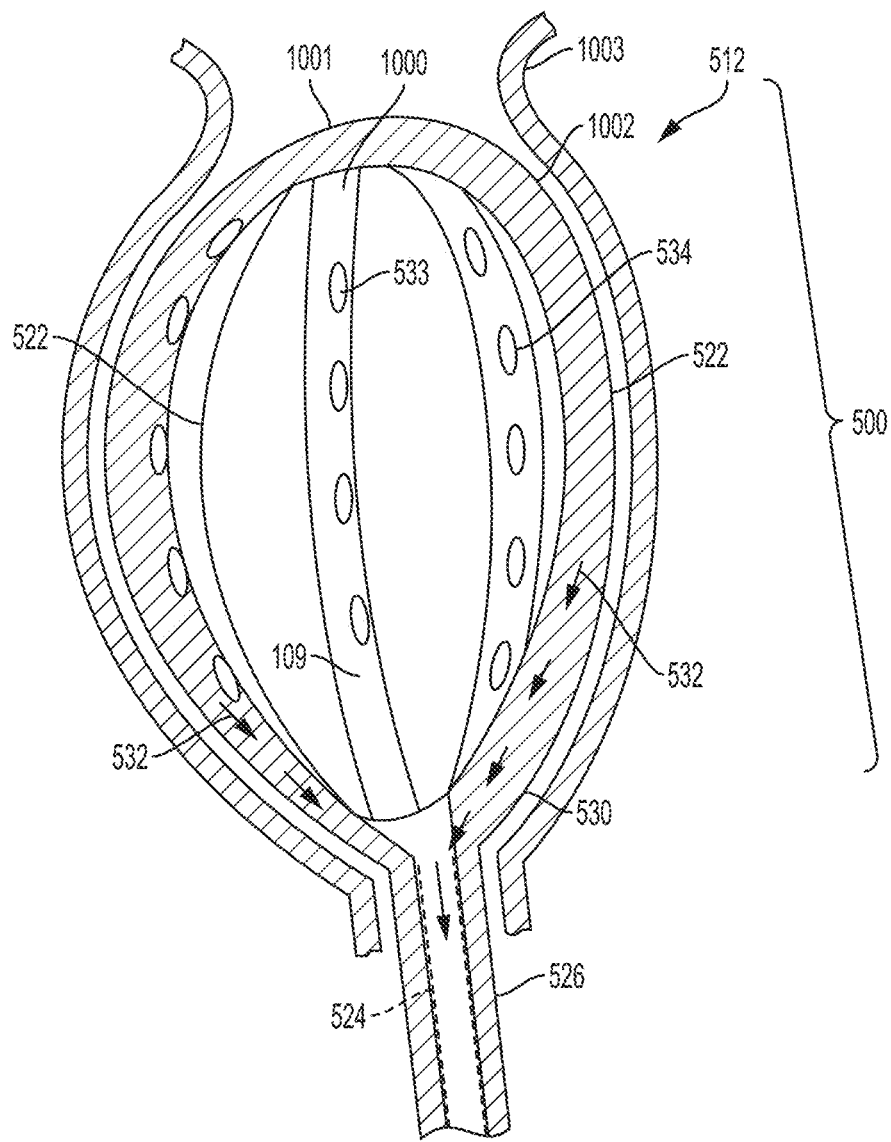
FIG. 41B is a schematic drawing of a cross section of another example of a retention portion for a ureteral catheter according to an example of the present invention positioned in the renal pelvis region of the kidney showing in general changes believed to occur in the renal pelvis tissue in response to application of negative pressure through the ureteral catheter.
Figure 41C:
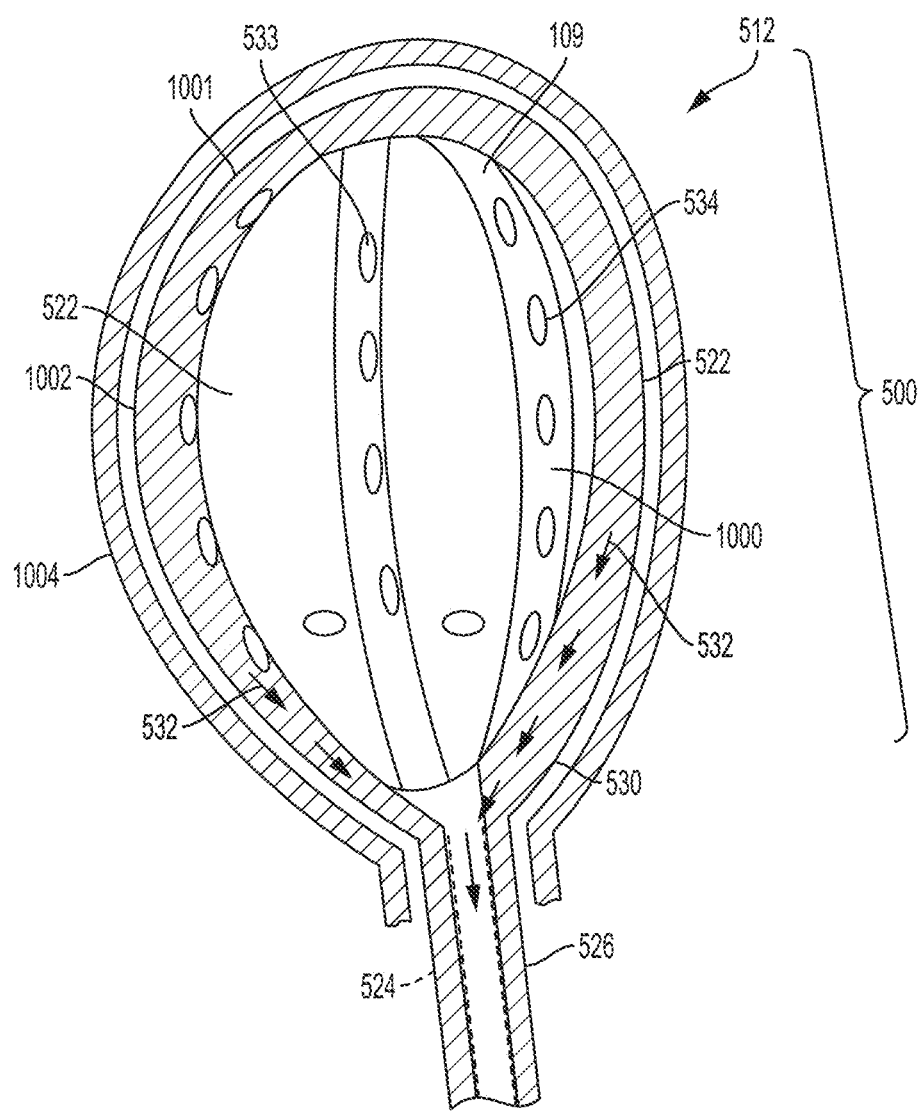
FIG. 41C is a schematic drawing of a cross section of another example of a retention portion for a bladder catheter according to an example of the present invention positioned in the bladder showing in general changes believed to occur in the bladder tissue in response to application of negative pressure through the bladder catheter.

In some examples, the funnel support comprises a porous material, for example as shown in FIGS. 39A-40C. FIGS. 39A-40C and suitable porous materials are discussed in detail below. Briefly, in FIGS. 39 and 40, the porous material itself is the funnel support. In FIG. 39, the funnel support is a wedge of porous material. In FIG. 40, the porous material is in the shape of a funnel. In some examples, such as FIG. 33, the porous material 5900 is positioned within the interior 5902 of the sidewall 5904. In some examples, such as FIG. 34, the funnel support 6000 comprises a porous liner 6002 positioned adjacent to the interior 6004 of the sidewall 6006. The thickness T2 of the porous liner 6002 can range from about 0.5 mm to about 12.5 mm, for example. The area of the openings within the porous material can be about 0.002 mm$^2$ to about 100 mm$^2$, or less.

Figure 37A:
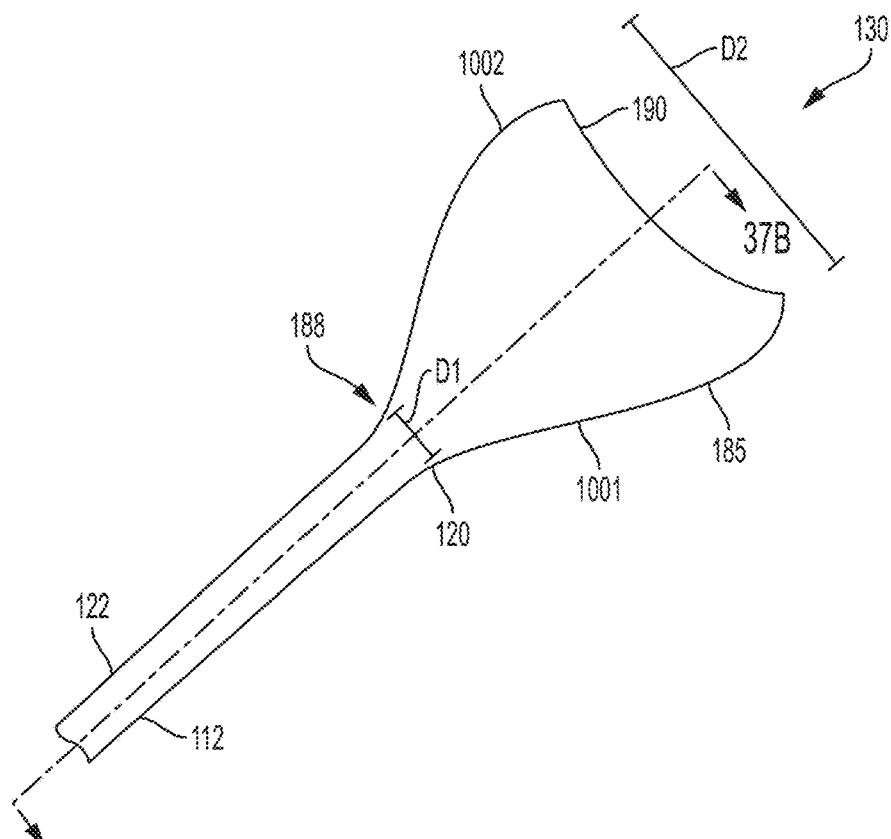
FIG. 37A is a schematic drawing of another example of a retention portion for a catheter according to an example of the present invention.
Figure 37B:
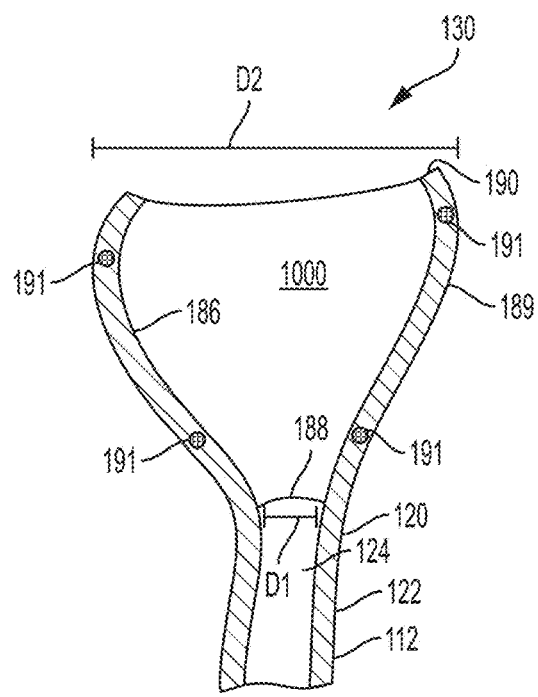
FIG. 37B is a schematic drawing of a cross-sectional view of a portion of the retention portion of FIG. 37A, taken along lines B-B of FIG. 37A.

Referring now to FIGS. 37A and 37B, for example, a retention portion 130 of a ureteral catheter 112 comprises a catheter tube 122 having a widened and/or tapered distal end portion which, in some examples, is configured to be positioned in the patient's renal pelvis and/or kidney. For example, the retention portion 130 can be a funnel-shaped structure comprising an outer surface 185 configured to be positioned against the ureter and/or kidney wall and comprising an inner surface 186 configured to direct fluid toward a drainage lumen 124 of the catheter 112. The retention portion can be configured into a funnel-shaped support having an outer surface 185 and an inner surface 186, and wherein the outer periphery 189 or protective surface area 1001 comprises the outer surface 185 of the funnel-shaped support, and the one or more drainage holes, ports or perforations 133, 1233 are disposed on the inner surface 186 at the base of the funnel-shaped support. In another example shown in FIGS. 32A and 32B, the retention portion can be configured into a funnel-shaped support 5614 having an outer surface and an inner surface 5616, and wherein the outer periphery 1002 or protective surface area 1001 comprises the outer surface of the outer sidewall 5606. The protected surface area 1000 can comprise the inner sidewall 5604 of the inner funnel and the one or more drainage holes, ports or perforations 5600 can be disposed on the inner sidewall 5604 of the funnel-shaped support.

Referring to FIGS. 37A and 37B, the retention portion 130 can comprise a proximal end 188 adjacent to the distal end of the drainage lumen 124 and having a first diameter D1 and a distal end 190 having a second diameter D2 that is greater than the first diameter D1 when the retention portion 130 is in its deployed position. In some examples, the retention portion 130 is transitionable from a collapsed or compressed position to the deployed position. For example, the retention portion 130 can be biased radially outward such that when the retention portion 130 is advanced to its fluid collecting position, the retention portion 130 (e.g., the funnel portion) expands radially outward to the deployed state.

The retention portion 130 of the ureteral catheter 112 can be made from a variety of suitable materials that are capable of transitioning from the collapsed state to the deployed state. In one example, the retention portion 130 comprises a framework of tines or elongated members formed from a temperature sensitive shape memory material, such as nitinol. In some examples, the nitinol frame can be covered with a suitable waterproof material such as silicon to form a tapered portion or funnel. In that case, fluid is permitted to flow down the inner surface 186 of the retention portion 130 and into the drainage lumen 124. In other examples, the retention portion 130 is formed from various rigid or partially rigid sheets or materials bended or molded to form a funnel-shaped retention portion as illustrated in FIGS. 37A and 37B.

In some examples, the retention portion of the ureteral catheter 112 can include one or more mechanical stimulation devices 191 for providing stimulation to nerves and muscle fibers in adjacent tissues of the ureter(s) and renal pelvis. For example, the mechanical stimulation devices 191 can include linear or annular actuators embedded in or mounted adjacent to portions of the sidewall of the catheter tube 122 and configured to emit low levels of vibration. In some examples, mechanical stimulation can be provided to portions of the ureters and/or renal pelvis to supplement or modify therapeutic effects obtained by application of negative pressure. While not intending to be bound by theory, it is believed that such stimulation affects adjacent tissues by, for example, stimulating nerves and/or actuating peristaltic muscles associated with the ureter(s) and/or renal pelvis. Stimulation of nerves and activation of muscles may produce changes in pressure gradients or pressure levels in surrounding tissues and organs which may contribute to or, in some cases, enhance therapeutic benefits of negative pressure therapy.

Figure 38A:
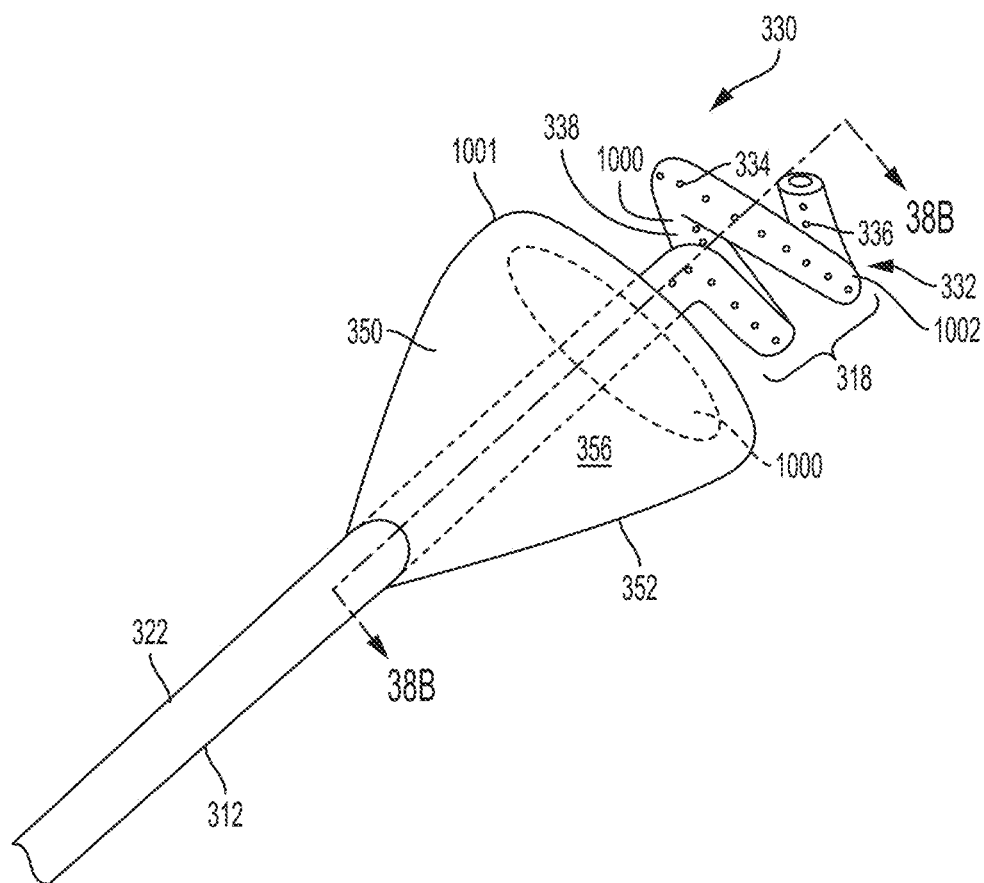
FIG. 38A is a schematic drawing of another example of a retention portion for a catheter according to an example of the present invention.
Figure 38B:
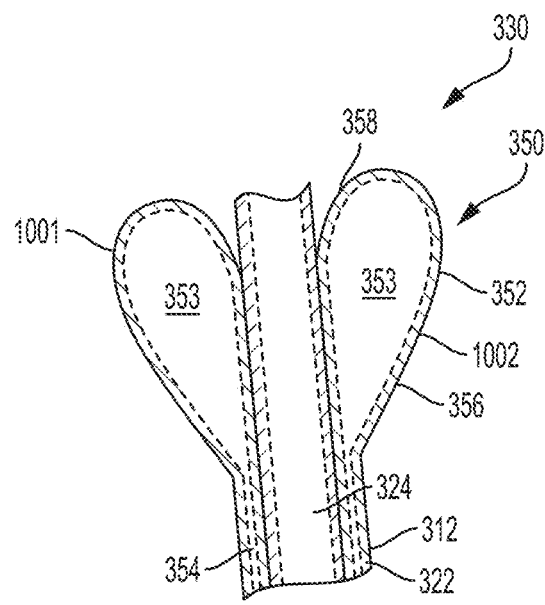
FIG. 38B is a schematic drawing of a portion of a cross-sectional view of the retention portion of FIG. 5A, taken along lines B-B of FIG. 38A.

With reference to FIGS. 38A and 38B, according to another example, a retention portion 330 of a ureteral catheter 312 comprises a catheter tube 322 having a distal portion 318 formed in a helical structure 332 and an inflatable element or balloon 350 positioned proximal to the helical structure 332 to provide an additional degree of retention in the renal pelvis and/or fluid collection location. A balloon 350 can be inflated to pressure sufficient to retain the balloon in the renal pelvis or ureter, but low enough to avoid distending or damaging these structures. Suitable inflation pressures are known to those skilled in the art and are readily discernible by trial and error. As in previously-described examples, the helical structure 332 can be imparted by bending the catheter tube 322 to form one or more coils 334. The coils 334 can have a constant or variable diameter and height as described above. The catheter tube 322 further comprises a plurality of drainage ports 336 disposed on the sidewall of the catheter tube 322 to allow urine to be drawn into the drainage lumen 324 of the catheter tube 322 and to be directed from the body through the drainage lumen 324, for example on the inwardly facing and/or outwardly facing sides of the coil 334.

As shown in FIG. 38B, the inflatable element or balloon 350 can comprise an annular balloon-like structure having, for example, a generally heart-shaped cross section and comprising a surface or cover 352 defining a cavity 353. The cavity 353 is in fluid communication with an inflation lumen 354 extending parallel to the drainage lumen 324 defined by the catheter tube 322. The balloon 350 can be configured to be inserted in the tapered portion of the renal pelvis and inflated such that an outer surface 356 thereof contacts and rests against an inner surface of the ureter and/or renal pelvis. The inflatable element or balloon 350 can comprise a tapered inner surface 358 extending longitudinally and radially inward towards the catheter tube 322. The inner surface 358 can be configured to direct urine toward the catheter tube 322 to be drawn into the drainage lumen 324. The inner surface 358 can also be positioned to prevent fluid from pooling in the ureter, such as around the periphery of the inflatable element or balloon 350. The inflatable retention portion or balloon 350 is desirably sized to fit within the renal pelvis and can have a diameter ranging from about 10 mm to about 30 mm.

With reference to FIGS. 39A-40C, in some examples, an assembly 400 including a ureteral catheter 412 comprising a retention portion 410 is illustrated. The retention portion 410 is formed from a porous and/or sponge-like material that is attached to a distal end 421 of a catheter tube 422. The porous material can be configured to channel and/or absorb urine and direct the urine toward a drainage lumen 424 of the catheter tube 422. The retention portion 410 can be configured into a funnel-shaped support having an outer surface and an inner surface, and wherein the outer periphery 1002 or protective surface area 1001 comprises the outer surface of the funnel-shaped support, and the one or more drainage holes, ports or perforations in the porous material can be disposed within the porous material or on the inner surface 426 of the funnel-shaped support.

As shown in FIG. 40, the retention portion 410 can be a porous wedge shaped-structure configured for insertion and retention in the patient's renal pelvis. The porous material comprises a plurality of holes and/or channels. Fluid can be drawn through the channels and holes, for example, by gravity or upon inducement of negative pressure through the catheter 412. For example, fluid can enter the wedge-shaped retention portion 410 through the holes and/or channels and is drawn toward a distal opening 420 of the drainage lumen 424, for example, by capillary action, peristalsis, or as a result of the inducement of negative pressure in the holes and/or channels. In other examples, as shown in FIG. 40, the retention portion 410 comprises a hollow, funnel structure formed from the porous sponge-like material. As shown by arrow A, fluid is directed down an inner surface 426 of the funnel structure into the drainage lumen 424 defined by the catheter tube 422. Also, fluid can enter the funnel structure of the retention portion 410 through holes and channels in the porous sponge-like material of a sidewall 428. For example, suitable porous materials can include open-celled polyurethane foams, such as polyurethane ether. Suitable porous materials can also include laminates of woven or non-woven layers comprising, for example, polyurethane, silicone, polyvinyl alcohol, cotton, or polyester, with or without antimicrobial additives such as silver, and with or without additives for modifying material properties such as hydrogels, hydrocolloids, acrylic, or silicone.

With reference to FIG. 41, according to another example, a retention portion 500 of a ureteral catheter 512 comprises an expandable cage 530. The expandable cage 530 comprises one or more longitudinally and radially extending hollow tubes 522. For example, the tubes 522 can be formed from an elastic, shape memory material such as nitinol. The cage 530 is configured to transition from a contracted state, for insertion through the patient's urinary tract, to a deployed state for positioning in the patient's ureters and/or kidney. The hollow tubes 522 comprise a plurality of drainage ports 534 which can be positioned on the tubes, for example, on radially inward facing sides thereof. The ports 534 are configured to permit fluid to flow or be drawn through the ports 534 and into the respective tubes 522. The fluid drains through the hollow tubes 522 into a drainage lumen 524 defined by a catheter body 526 of the ureteral catheter 512. For example, fluid can flow along the path indicated by the arrows 532 in FIG. 41. In some examples, when negative pressure is induced in the renal pelvis, kidneys, and/or ureters, portions of the ureter wall and/or renal pelvis may be drawn against the outward facing surfaces of the hollow tubes 522. The drainage ports 534 are positioned and configured so as not to be appreciably occluded by ureteral structures upon application of negative pressure to the ureters and/or kidney.

In some examples, the ureteral catheter comprising a funnel support can be deployed into a patient's urinary tract, and more specifically in the renal pelvis region/kidney using a conduit through the urethra and into the bladder. The funnel support 6100 is in a collapsed state (shown in FIG. 36) and sheathed in a ureteral sheath 6102. To deploy the ureteral catheter, the medical professional would insert a cystoscope into the urethra to provide a channel for tools to enter the bladder. The ureteral orifice would be visualized and guide wire would be inserted through the cystoscope and ureter until the tip of the guide wire reaches the renal pelvis. The cystoscope likely would be removed, and a "pusher tube" would be fed over the guide wire up to the renal pelvis. The guidewire would be removed while the "pusher tube" stays in place to act as deployment sheath. The ureteral catheter would be inserted through the pusher tube/sheath and the catheter tip would be actuated once it extends beyond the end of the pusher tube/sheath. The funnel support would expand radially to assume the deployed position.

Exemplary Ureteral Stents:

Referring now to FIG. 1A, in some examples, the ureteral stent 52, 54 comprises an elongated body comprising a proximal end 62, a distal end 58, a longitudinal axis, and at least one drainage channel that extends along the longitudinal axis from the proximal end to the distal end to maintain patency of fluid flow between a kidney and a bladder of the patient. In some examples, the ureteral stent further comprises a pigtail coil or loop(s) on at least one of the proximal end or the distal end. In some examples, the body of the ureteral stent further comprises at least one perforation on a sidewall thereof. In other examples, the body of the ureteral stent is essentially free of or free of perforation(s) on a sidewall thereof.

Some examples of ureteral stents 52, 54 that can be useful in the present systems and methods include CONTOUR™ ureteral stents, CONTOUR VL™ ureteral stents, POLARIS™ Loop ureteral stents, POLARIS™ Ultra ureteral stents, PERCUFLEX™ ureteral stents, PERCUFLEX™ Plus ureteral stents, STRETCH™ VL Flexima ureteral stents, each of which are commercially available from Boston Scientific Corporation of Natick, Massachusetts. See "Ureteral Stent Portfolio", a publication of Boston Scientific Corp., (July 2010), hereby incorporated by reference herein. The CONTOUR™ and CONTOUR VL™ ureteral stents are constructed with soft Percuflex™ Material that becomes soft at body temperature and is designed for a 365-day indwelling time. Variable length coils on distal and proximal ends allow for one stent to fit various ureteral lengths. The fixed length stent can be 6F-8F with lengths ranging from 20 cm-30 cm, and the variable length stent can be 4.8F-7F with lengths of 22-30 cm. Other examples of suitable ureteral stents include INLAY® ureteral stents, INLAY® OPTIMA® ureteral stents, BARDEX®double pigtail ureteral stents, and FLUORO-4™ silicone ureteral stent, each of which are commercially available from C. R. Bard, Inc. of Murray Hill, NJ. See "Ureteral Stents", http://www.bardmedical.com/products/kidney-stone-management/ureteral-stents/ (Jan. 21, 2018), hereby incorporated by reference herein.

The stents 52, 54 can be deployed in one or both of the patient's kidneys or kidney area (renal pelvis or ureters adjacent to the renal pelvis), as desired. Typically, these stents are deployed by inserting a stent having a nitinol wire therethrough through the urethra and bladder up to the kidney, then withdrawing the nitinol wire from the stent, which permits the stent to assume a deployed configuration. Many of the above stents have a planar loop 58, 60 on the distal end (to be deployed in the kidney), and some also have a planar loop 62, 64 on the proximal end of the stent which is deployed in the bladder. When the nitinol wire is removed, the stent assumes the pre-stressed planar loop shape at the distal and/or proximal ends. To remove the stent, a nitinol wire is inserted to straighten the stent and the stent is withdrawn from the ureter and urethra.

Other examples of suitable ureteral stents 52, 54 are disclosed in PCT Patent Application Publication WO 2017/019974, which is incorporated by reference herein. In some examples, as shown, for example, in FIGS. 1-7 of WO 2017/019974) and in FIG. 3 herein (same as FIG. 1 of WO 2017/019974), the ureteral stent 100 can comprise: an elongated body 101 comprising a proximal end 102, a distal end 104, a longitudinal axis 106, an outer surface 108, and an inner surface 110, wherein the inner surface 110 defines a transformable bore 111 that extends along the longitudinal axis 106 from the proximal end 102 to the distal end 104; and at least two fins 112 projecting radially away from the outer surface 108 of the body 101; wherein the transformable bore 111 comprises: (a) a default orientation 113A (shown on the left in FIG. 59) comprising an open bore 114 defining a longitudinally open channel 116; and (b) a second orientation 113B (shown on the right in FIG. 59) comprising an at least essentially closed bore 118 or closed bore defining a longitudinally essentially closed drainage channel 120 along the longitudinal axis 106 of the elongated body 101, wherein the transformable bore 111 is moveable from the default orientation 113A to the second orientation 113B upon radial compression forces 122 being applied to at least a portion of the outer surface 108 of the body 101.

Figure 3:
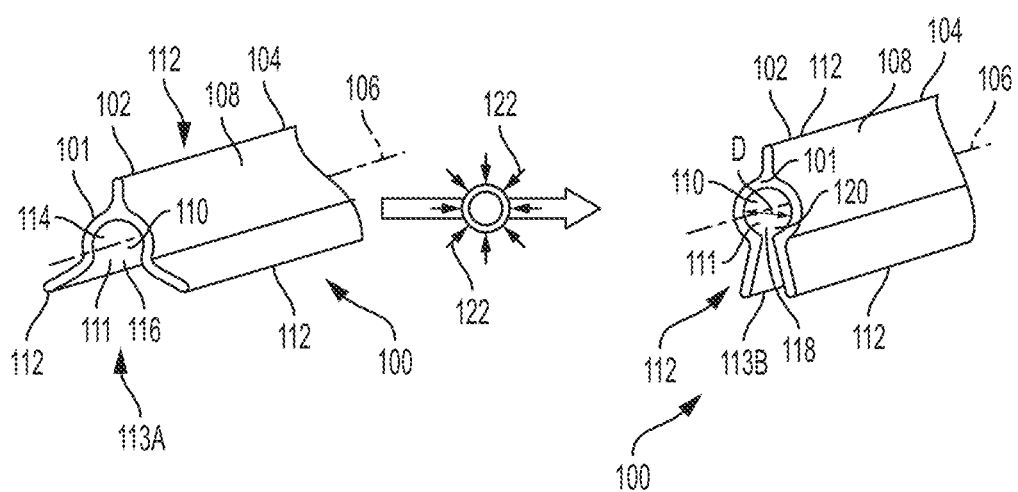
FIG. 3 is a diametric view of an example of a prior art transformable ureteral stent according to FIG. 1 of PCT Patent Application Publication WO 2017/019974, wherein the image on the left represents the uncompressed state of the stent and the image on the right represents the compressed state of the stent.
Figure 4:
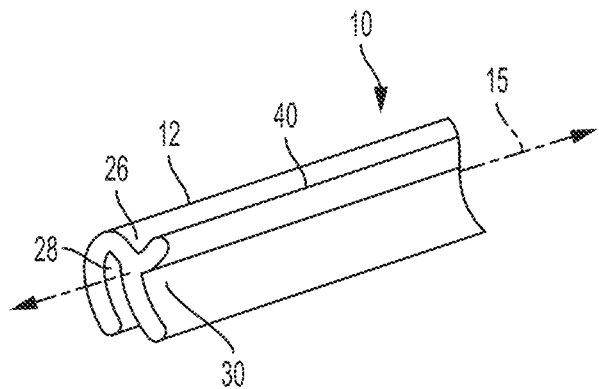
FIG. 4 is a perspective view of an example of a prior art ureteral stent according to FIG. 4 of US Patent Application Publication No. 2002/0183853 A1.
Figure 5:
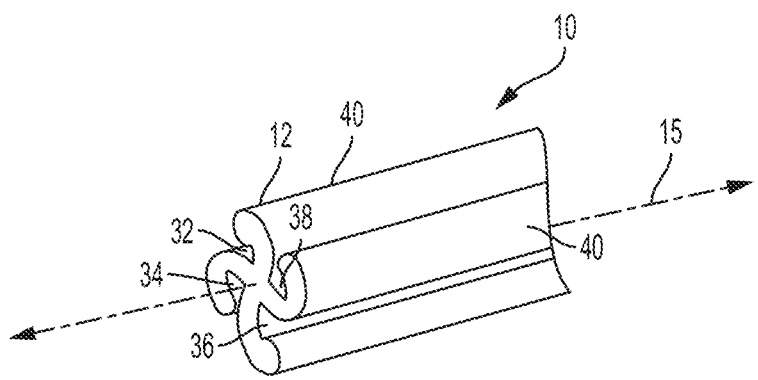
FIG. 5 is a perspective view of an example of a prior art ureteral stent according to FIG. 5 of US Patent Application Publication No. 2002/0183853 A1.

In some examples, as shown in FIG. 3, the drainage channel 120 of the ureteral stent 100 has a diameter D which is reduced upon the transformable bore 111 moving from the default orientation 113A to the second orientation 113B, wherein the diameter is reducible up to the point above where urine flow through the transformable bore 111 would be reduced. In some examples, the diameter D is reduced by up to about 40% upon the transformable bore 111 moving from the default orientation 113A to the second orientation 113B. In some examples, the diameter D in the default orientation 113A can range from about 0.75 to about 5.5 mm, or about 1.3 mm or about 1.4 mm. In some examples, the diameter D in the second orientation 113B can range from about 0.4 to about 4 mm, or about 0.9 mm.

In some examples, one or more fins 112 comprise a flexible material that is soft to medium soft based on the Shore hardness scale. In some examples, the body 101 comprises a flexible material that is medium hard to hard based on the Shore hardness scale. In some examples, one or more fins have a durometer between about 15 A to about 40 A. In some examples, the body 101 has a durometer between about 80 A to about 90 A. In some examples, one or more fins 112 and the body 101 comprise a flexible material that is medium soft to medium hard based on the Shore hardness scale, for example having a durometer between about 40 A to about 70 A.

In some examples, one or more fins 112 and the body 101 comprise a flexible material that is medium hard to hard based on the Shore hardness scale, for example having a durometer between about 85 A to about 90 A.

In some examples, the default orientation 113A and the second orientation 113B support fluid or urine flow around the outer surface 108 of the stent 100 in addition to through the transformable bore 111.

In some examples, one or more fins 112 extend longitudinally from the proximal end 102 to the distal end 104. In some examples, the stent has two, three or four fins.

In some examples, the outer surface 108 of the body has an outer diameter in the default orientation 113A ranging from about 0.8 mm to about 6 mm, or about 3 mm. In some examples, the outer surface 108 of the body has an outer diameter in the second orientation 113B ranging from about 0.5 mm to about 4.5 mm, or about 1 mm. In some examples, one or more fins have a width or tip ranging from about 0.25 mm to about 1.5 mm, or about 1 mm, projecting from the outer surface 108 of the body in a direction generally perpendicular to the longitudinal axis.

In some examples, the radial compression forces are provided by at least one of normal ureter physiology, abnormal ureter physiology, or application of any external force. In some examples, the ureteral stent 100 purposefully adapts to a dynamic ureteral environment, the ureteral stent 100 comprising: an elongated body 101 comprising a proximal end 102, a distal end 104, a longitudinal axis 106, an outer surface 108, and an inner surface 110, wherein the inner surface 110 defines a transformable bore 111 that extends along the longitudinal axis 106 from the proximal end 102 to the distal end 104; wherein the transformable bore 111 comprises: (a) a default orientation 113A comprising an open bore 114 defining a longitudinally open channel 116; and (b) a second orientation 113B comprising an at least essentially closed bore 118 defining a longitudinally essentially closed channel 120, wherein the transformable bore is moveable from the default orientation 113A to the second orientation 113B upon radial compression forces 122 being applied to at least a portion of the outer surface 108 of the body 101, wherein the inner surface 110 of the body 101 has a diameter D which is reduced upon the transformable bore 111 moving from the default orientation 113A to the second orientation 113B, wherein the diameter is reducible up to the point above where fluid flow through the transformable bore 111 would be reduced. In some examples, the diameter D is reduced by up to about 40% upon the transformable bore 111 moving from the default orientation 113A to the second orientation 113B.

Other examples of suitable ureteral stents are disclosed in US Patent Application Publication US 2002/0183853 A1, which is incorporated by reference herein. In some examples, as shown, for example, in FIGS. 4, 5 and 7 of US 2002/0183853 A1 and in FIGS. 4-6 herein (same as FIGS. 1 of 4, 5 and 7 of US 2002/0183853 A1), the ureteral stent comprises an elongated, body 10 comprising a proximal end 12, a distal end 14 (not shown), a longitudinal axis 15, and at least one drainage channel (for example, 26, 28, 30 in FIGS. 4; 32, 34, 36 and 38 in FIG. 5; and 48 in FIG. 6) that extends along the longitudinal axis 15 from the proximal end 12 to the distal end 14 to maintain patency of fluid flow between a kidney and a bladder of the patient. In some examples, the at least one drainage channel is partially open along at least a longitudinal portion thereof. In some examples, the at least one drainage channel is closed along at least a longitudinal portion thereof. In some examples, the at least one drainage channel is closed along the longitudinal length thereof. In some examples, the ureteral stent is radially compressible. In some examples, the ureteral stent is radially compressible to narrow the at least one drainage channel. In some examples, the elongated body 10 comprises at least one external fin 40 along the longitudinal axis 15 of the elongated body 10. In some examples, the elongated body comprises one to four drainage channels. The diameter of the drainage channel can be the same as described above.

Systems for Inducing Negative Pressure

In some examples, a system for inducing negative pressure in a portion of a urinary tract of a patient or for removing fluid from the urinary tract of a patient is provided, comprising: a ureteral stent or ureteral catheter for maintaining patency of fluid flow between at least one of a kidney and a bladder of the patient; a bladder catheter comprising a drainage lumen for draining fluid from the bladder of the patient; and a pump in fluid communication with a distal end of the drainage lumen, the pump comprising a controller configured to actuate the pump to apply negative pressure to the proximal end of the catheter to induce negative pressure in a portion of the urinary tract of the patient to remove fluid from the urinary tract of the patient.

In some examples, a system for inducing negative pressure in a portion of a urinary tract of a patient is provided, the system comprising: (a) a ureteral catheter comprising a distal portion for insertion within the patient's kidney and a proximal portion; (b) a bladder catheter comprising a distal portion for insertion within the patient's bladder and a proximal portion for application of negative pressure, the proximal portion extending outside of the patient's body; and (c) a pump external to the patient's body for application of negative pressure through both the bladder catheter and the ureteral catheter, which in turn causes fluid from the kidney to be drawn into the ureteral catheter, through both the ureteral catheter and the bladder catheter, and then outside the patient's body.

In some examples, a system for inducing negative pressure in a portion of a urinary tract of a patient is provided, the system comprising: (a) at least one ureteral catheter, the at least one ureteral catheter comprising a distal portion for insertion within the patient's kidney and a proximal portion; (b) a bladder catheter comprising a distal portion for insertion within the patient's bladder and a proximal portion for receiving negative pressure from a negative pressure source, wherein at least one of the at least one ureteral catheter(s) or the bladder catheter comprises (a) a proximal portion; and (b) a distal portion, the distal portion comprising a retention portion that comprises one or more protected drainage holes, ports or perforations and is configured to establish an outer periphery or protective surface area that inhibits mucosal tissue from occluding the one or more protected drainage holes, ports or perforations upon application of negative pressure through the catheter; and (c) a negative pressure source for application of negative pressure through both the bladder catheter and the ureteral catheter(s), which in turn causes fluid from the kidney to be drawn into the ureteral catheter(s), through both the ureteral catheter(s) and the bladder catheter, and then outside of the patient's body.

In some examples, a system for inducing negative pressure in a portion of a urinary tract of a patient, the system comprising: (a) at least one ureteral catheter, the at least one ureteral catheter comprising a distal portion for insertion within the patient's kidney and a proximal portion; (b) a bladder catheter comprising a distal portion for insertion within the patient's bladder and a proximal portion for receiving a pressure differential, wherein the pressure differential causes fluid from the kidney to be drawn into the ureteral catheter(s), through both the ureteral catheter(s) and the bladder catheter, and then outside of the patient's body, the pressure differential being applied to increase, decrease and/or maintain fluid flow therethrough, wherein at least one of the at least one ureteral catheter(s) or the bladder catheter comprises (a) a proximal portion; and (b) a distal portion, the distal portion comprising a retention portion that comprises one or more protected drainage holes, ports or perforations and is configured to establish an outer periphery or protective surface area that inhibits mucosal tissue from occluding the one or more protected drainage holes, ports or perforations upon application of differential pressure through the catheter.

With reference to FIGS. 1A, 1B, 1C, 1F, 1P, 1U, 2A, 2B, 7A and 7B, an exemplary system 1100 for inducing negative pressure in a urinary tract of a patient for increasing renal perfusion is illustrated. The system 1100 comprises one or two ureteral catheters 1212 (or alternatively ureteral stents shown in FIG. 1A) connected to a fluid pump 2000 for generating the negative pressure. More specifically, the patient's urinary tract comprises the patient's right kidney 2 and left kidney 4. The kidneys 2, 4 are responsible for blood filtration and clearance of waste compounds from the body through urine. Urine or fluid produced by the right kidney 2 and the left kidney 4 is drained into a patient's bladder 10 through tubules, namely a right ureter 6 and a left ureter 8, which are connected to the kidneys at the renal pelvis 20, 21. Urine may be conducted through the ureters 6, 8 by peristalsis of the ureter walls, as well as by gravity. The ureters 6, 8 enter the bladder 10 through a ureter orifice or opening 16. The bladder 10 is a flexible and substantially hollow structure adapted to collect urine until the urine is excreted from the body. The bladder 10 is transitionable from an empty position (signified by reference line E) to a full position (signified by reference line F). Normally, when the bladder 10 reaches a substantially full state, fluid or urine is permitted to drain from the bladder 10 to a urethra 12 through a urethral sphincter or opening 18 located at a lower portion of the bladder 10. Contraction of the bladder 10 can be responsive to stresses and pressure exerted on a trigone region 14 of the bladder 10, which is the triangular region extending between the ureteral openings 16 and the urethral opening 18. The trigone region 14 is sensitive to stress and pressure, such that as the bladder 10 begins to fill, pressure on the trigone region 14 increases. When a threshold pressure on the trigone region 14 is exceeded, the bladder 10 begins to contract to expel collected urine through the urethra 12.

As shown in FIGS. 1, 2A, 7A and 7B, distal portions of the ureteral catheter(s) are deployed in the renal pelvis 20, 21 near the kidneys 2, 4. Proximal portions of the one or more of the catheter(s) 1212 empty into the bladder, into the urethra or outside of the body. In some examples, the proximal portion 1216 of the ureteral catheter 1212 is in fluid communication with the distal portion or end 136 of the bladder catheter 56, 116. A proximal portion 1216 of the bladder catheter 56, 116 is connected to a source of negative pressure, such as a fluid pump 2000. The shape and size of the connector can be selected based on the type of pump 2000 being used. In some examples, the connector can be manufactured with a distinctive configuration so that it can only be connected to a particular pump type, which is deemed to be safe for inducing negative pressure in a patient's bladder, ureter, or kidneys. In other examples, as described herein, the connector can be a more generic configuration adapted for attachment to a variety of different types of fluid pumps. System 1100 is but one example of a negative pressure system for inducing negative pressure that can be used with the bladder catheters disclosed herein.

Referring now to FIGS. 1A, 1B, 1C, 1F, 1P. 1U, 2A, 2B 7A, 7B, 17, in some examples the system 50, 100 comprises a bladder catheter 116. The distal ends 120, 121 of the ureteral catheters 112, 114 can drain directly into the bladder, and the fluid can drain through the bladder catheter 116, and optionally along the sides of the bladder catheter tube.

Exemplary Bladder Catheters

Any of the ureteral catheters disclosed herein can be used as bladder catheters useful in the present methods and systems. In some examples, the bladder catheter 116 comprises a retention portion 123 or deployable seal and/or anchor 136 for anchoring, retaining, and/or providing passive fixation for indwelling portions of the urine collection assembly 100 and, in some examples, to prevent premature and/or untended removal of assembly components during use. The retention portion 123 or anchor 136 is configured to be located adjacent to the lower wall of the patient's bladder 10 (shown in FIGS. 1A, 1B, 1C, 1F, 1P, 1U, 2A, 2B, 7A, 7B, 17) to prevent patient motion and/or forces applied to indwelling catheters 112, 114, 116 from translating to the ureters. The bladder catheter 116 comprises an interior of which defines a drainage lumen 140 configured to conduct urine from the bladder 10 to an external urine collection container 712 (shown in FIG. 44). In some examples, the bladder catheter 116 tube size can range from about 8 Fr to about 24 Fr. In some examples, the bladder catheter 116 can have an external tube diameter ranging from about 2.7 to about 8 mm. In some examples, the bladder catheter 116 can have an internal diameter ranging from about 2.16 to about 10 mm. The bladder catheter 116 can be available in different lengths to accommodate anatomical differences for gender and/or patient size. For example, the average female urethra length is only a few inches, so the length of a tube 138 can be rather short. The average urethra length for males is longer due to the penis and can be variable. It is possible that woman can use bladder catheters 116 with longer length tubes 138 provided that the excess tubing does not increase difficulty in manipulating and/or preventing contamination of sterile portions of the catheter 116. In some examples, a sterile and indwelling portion of the bladder catheter 116 can range from about 1 inch to 3 inches (for women) to about 20 inches for men. The total length of the bladder catheter 116 including sterile and non-sterile portions can be from one to several feet.

In some examples, such as are shown in FIGS. 1A, 1B, 1C, 1F, 1P. 1U, 2A, 2B, 7A and 7B, the distal portion 136 of the bladder catheter 56, 116 comprises a retention portion 123 that includes one or more drainage holes, ports or perforations 142 and is configured to establish an outer periphery 1002 or protective surface area 1001 that inhibits mucosal tissue from occluding the one or more drainage holes, ports or perforations 142 upon the application of negative pressure by the pump 710, 2000.

In some examples in which the retention portion 123 comprises a tube 138, the tube 138 can comprise one or more drainage holes, ports or perforations 142 configured to be positioned in the bladder 10 for drawing urine into the drainage lumen 140. For example, fluid or urine that flows into the patient's bladder 10 from the ureteral catheters 112, 114 is expelled from the bladder 10 through the ports 142 and drainage lumen 140. The drainage lumen 140 may be pressurized to a negative pressure to assist in fluid collection.

In some examples, such as are shown in FIGS. 1A, 1B, 1C, 1F, 1P, 1U, 2A, 2B, 7A and 7B, the one or more drainage holes, ports or perforations 142, 172 of the bladder catheter 56, 116, like the ureteral catheters discussed above, are disposed on a protected surface area or inner surface area 1000 of the retention portion 123, and wherein, upon application of negative pressure, the mucosal tissue 1003, 1004 conforms or collapses onto the outer periphery 1002 or protective surface area 1001 of the retention portion 173 of the bladder catheter 56, 116 and is thereby prevented or inhibited from occluding the one or more of the protected drainage holes, ports or perforations 172 of the bladder catheter 56, 116

With specific reference to FIGS. 1A, 1B, 1C, 1F, 1P, 1U, 2A, 2B, 7A and 7B, the retention portion 123 or deployable seal and/or anchor 136 is disposed at or adjacent to a distal end 148 of the bladder catheter 116. The retention portion 123 or deployable anchor 136 is configured to transition between a contracted state for insertion into the bladder 10 through the urethra 12 and urethral opening 18 and a deployed state. The retention portion 123 or deployable anchor 136 is configured to be deployed in and seated adjacent to a lower portion of the bladder 10 and/or against the urethral opening 18. For example, the retention portion 123 or deployable anchor 136 can be positioned adjacent to the urethral opening 18 to enhance suction of a negative pressure applied to the bladder 10 or to partially, substantially, or entirely seal the bladder 10 to ensure that urine in the bladder 10 is directed through the drainage lumen 140 and to prevent leakage to the urethra 12. For a bladder catheter 116 including an 8 Fr to 24 Fr elongated tube 138, the retention portion 123 or deployable anchor 136 can have a diameter of about 10 mm to about 100 mm) in the deployed state.

Exemplary Bladder Anchor Structures

Figure 1B:
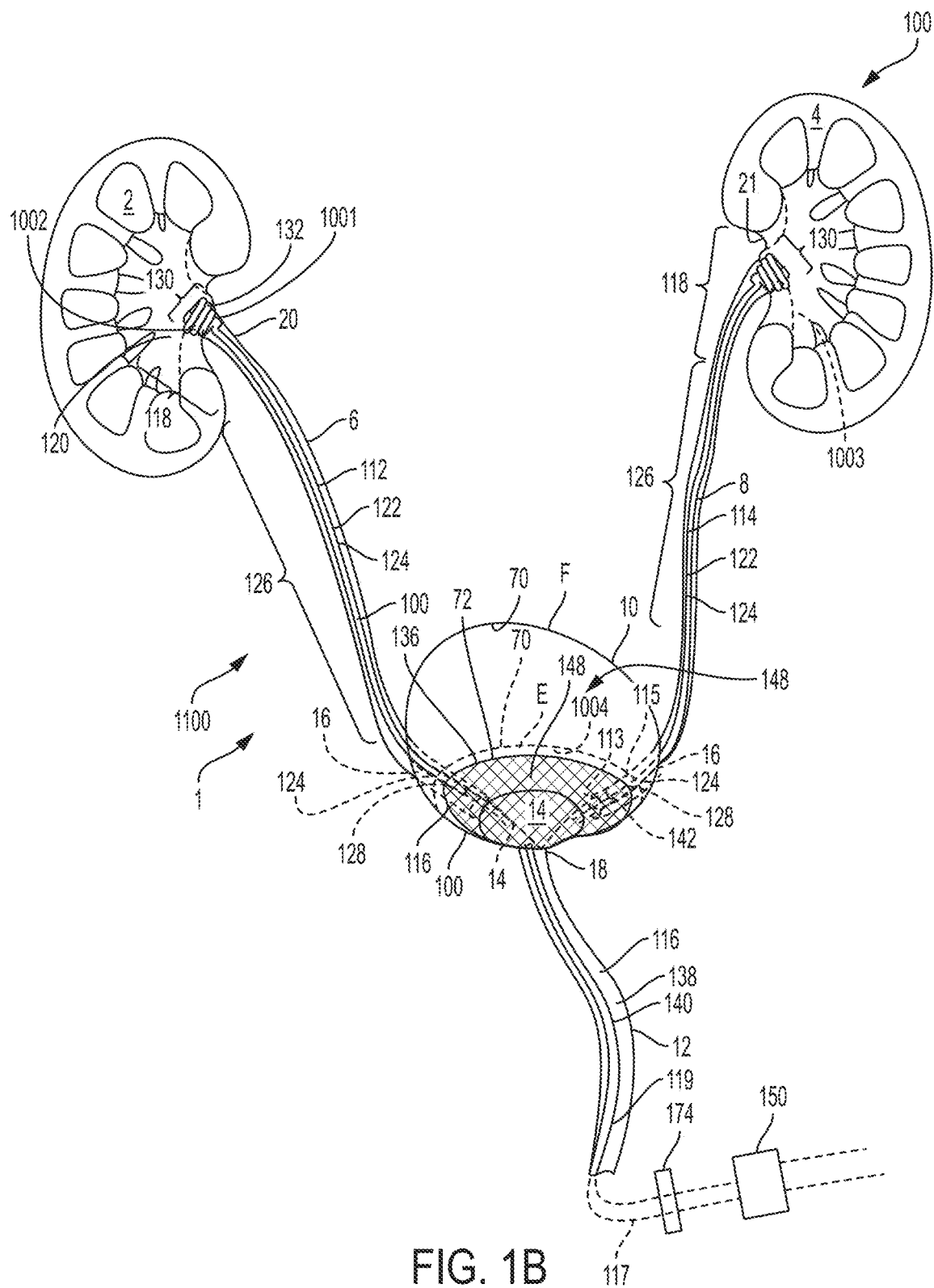
FIG. 1B is a schematic drawing of an indwelling portion of a system comprising a ureteral catheter and a bladder catheter deployed in a urinary tract of a patient, according to an example of the present invention.
Figure 1C:
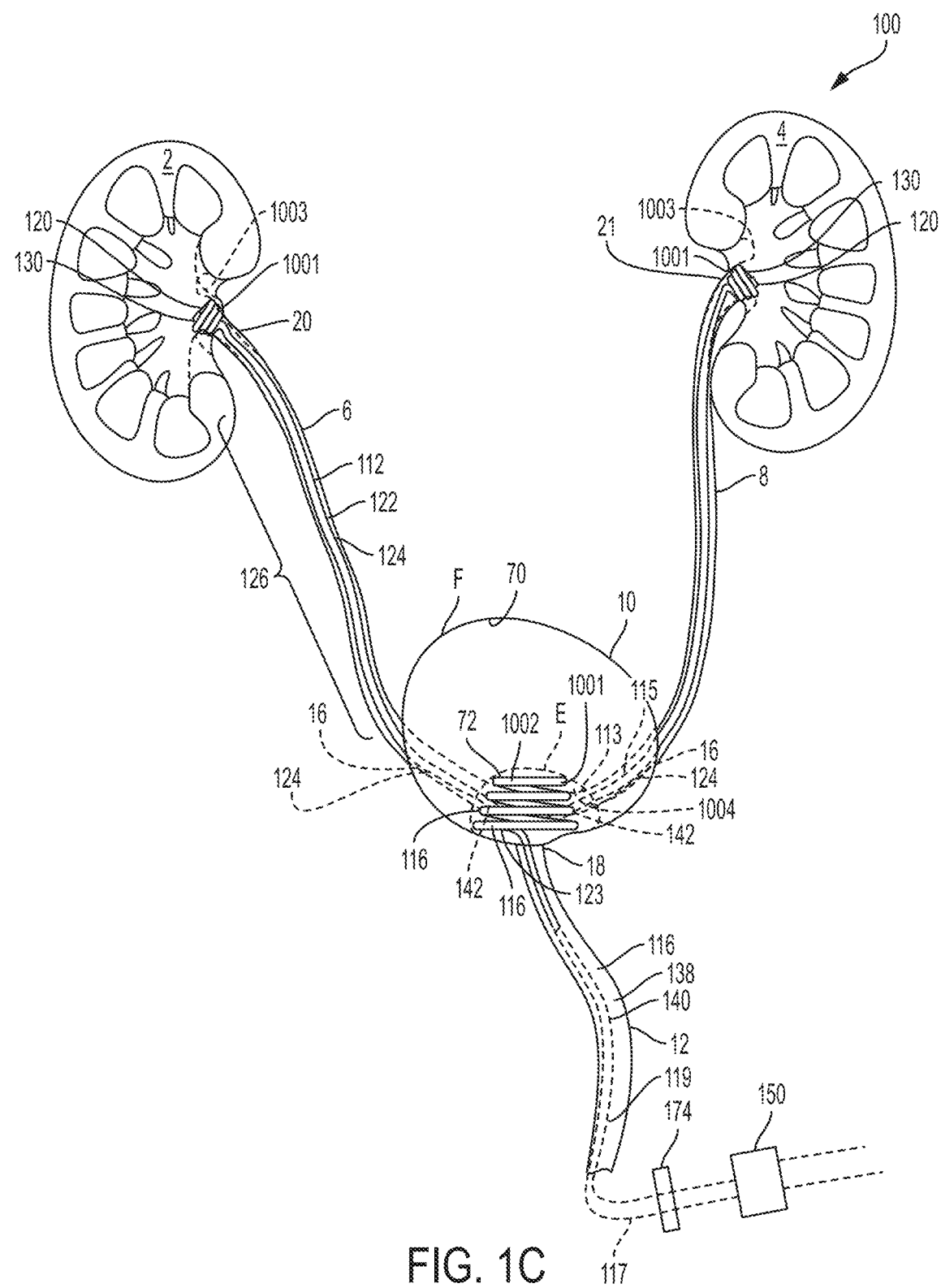
FIG. 1C is a schematic drawing of an indwelling portion of a system comprising a ureteral catheter and a bladder catheter deployed in a urinary tract of a patient, according to an example of the present invention.
Figure 1D:
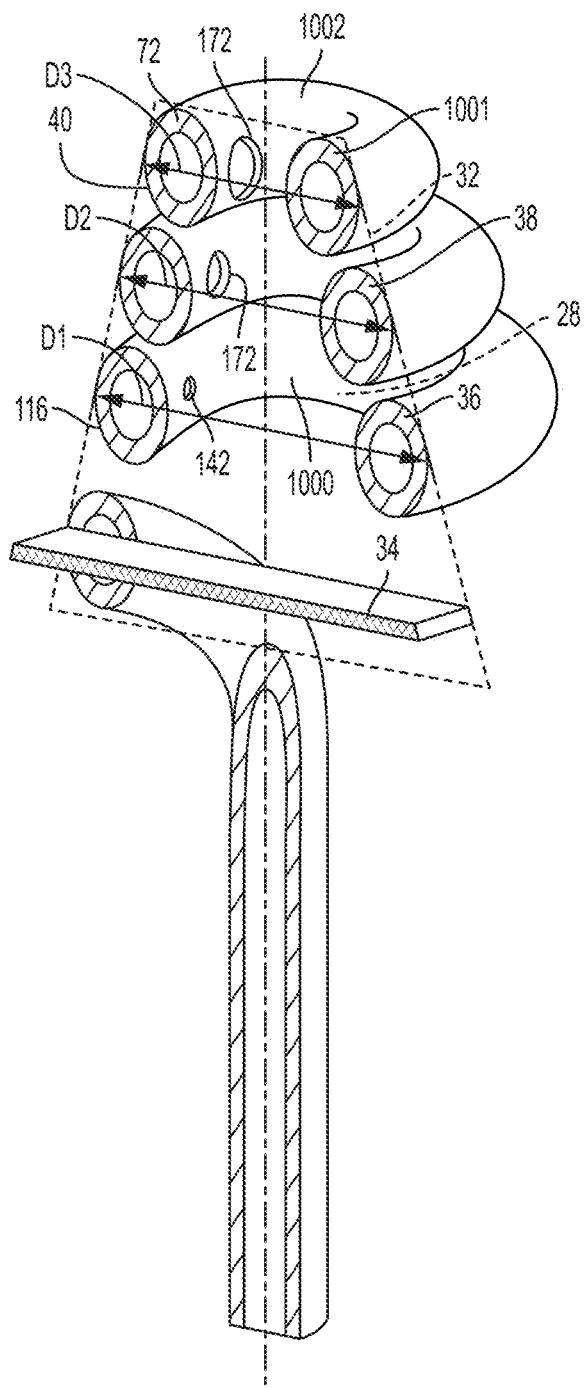
FIG. 1D is a perspective view of a retention portion of a bladder catheter, according to an example of the present invention.
Figure 1E:
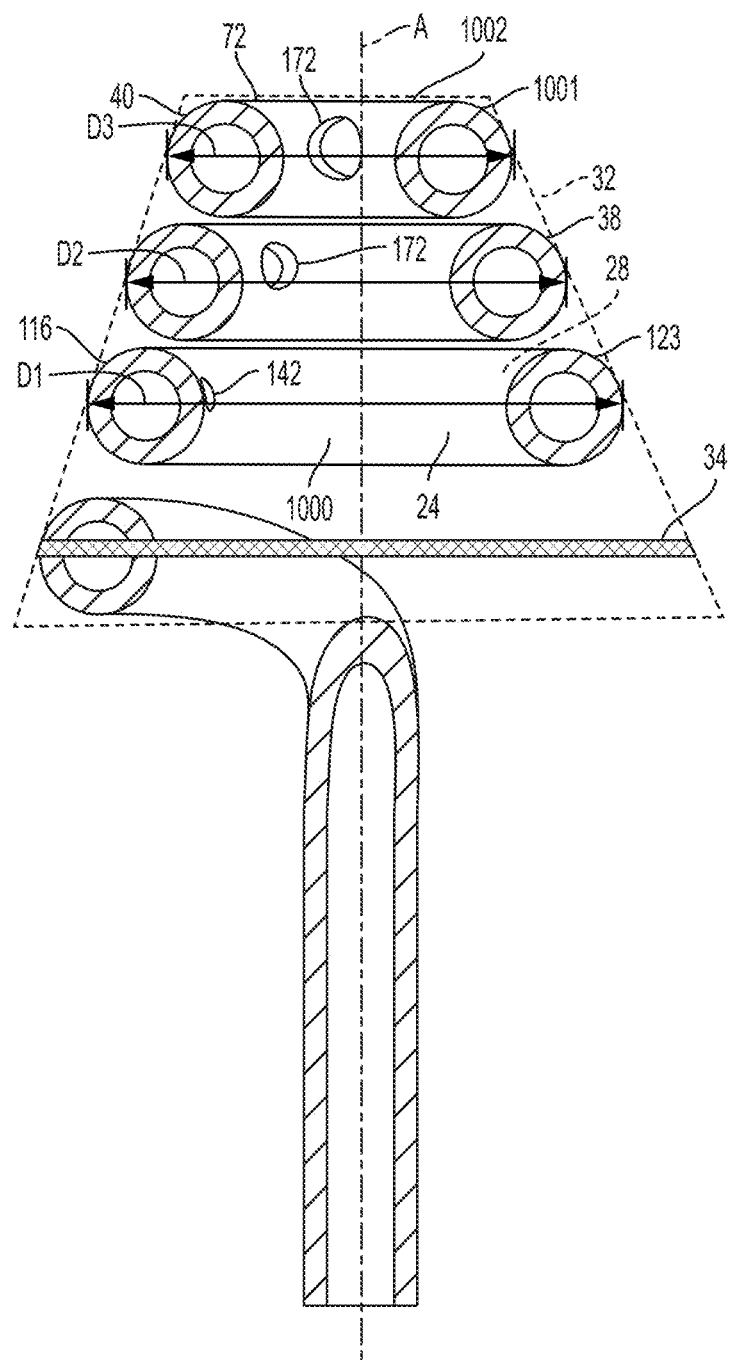
FIG. 1E is a cross sectional view of the retention portion of FIG. 1D, taken along line 1E-1E of FIG. 1D, according to an example of the present invention.
Figure 1F:
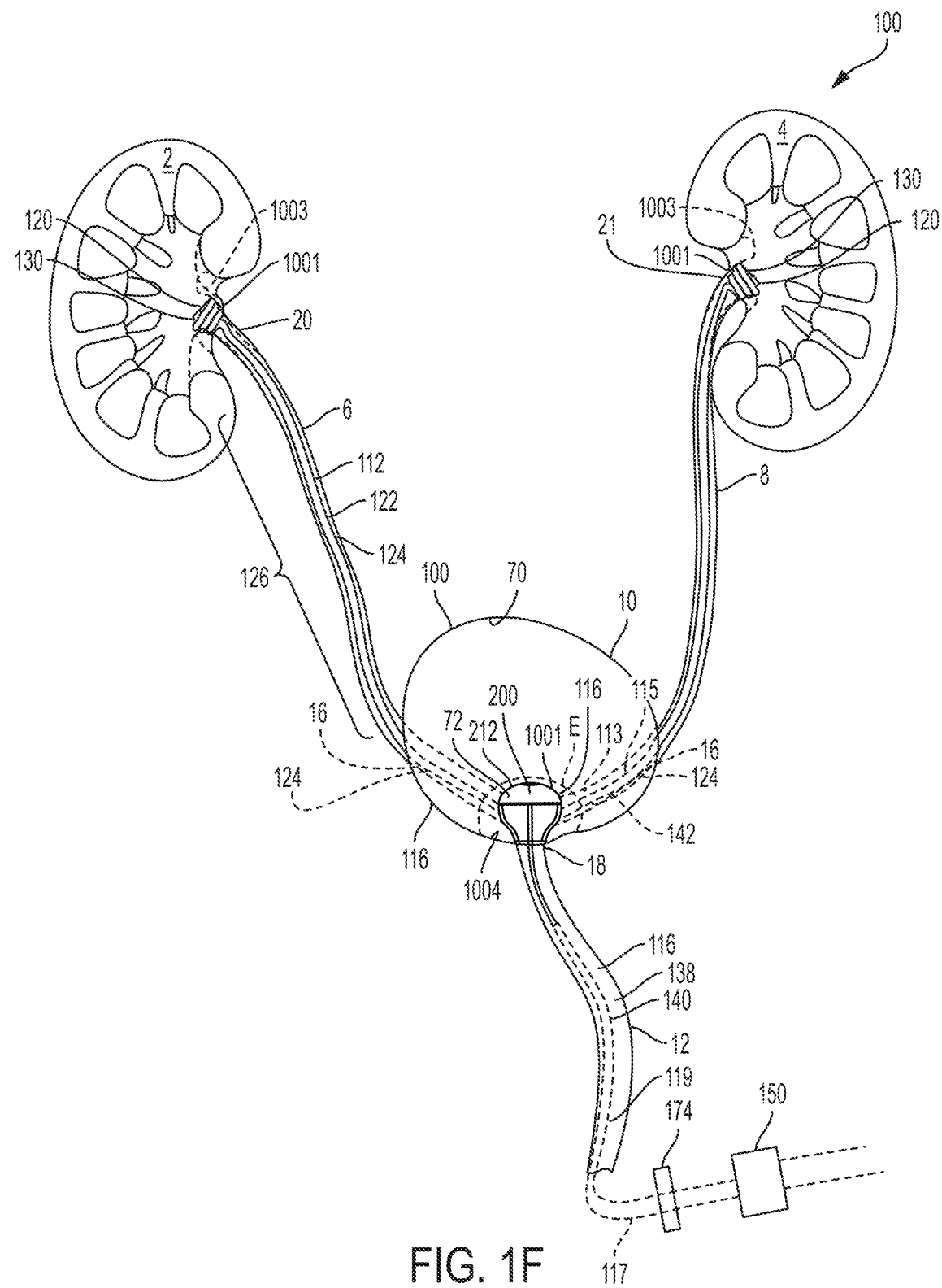
FIG. 1F is a schematic drawing of an indwelling portion of a system comprising a ureteral catheter and a bladder catheter deployed in a urinary tract of a patient, according to an example of the present invention.
Figure 1G:
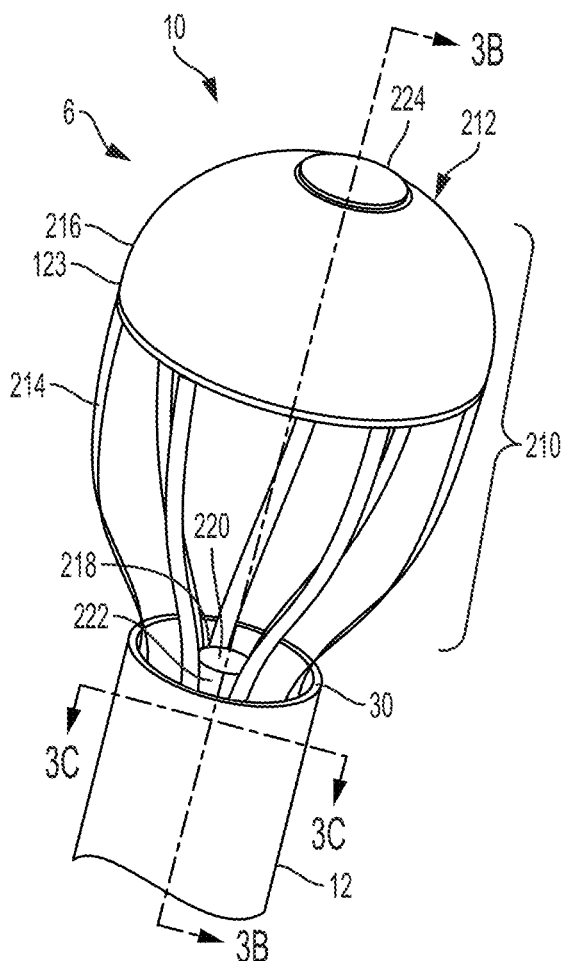
FIG. 1G is a perspective view of a retention portion of a bladder catheter, according to an example of the present invention.
Figure 1H:
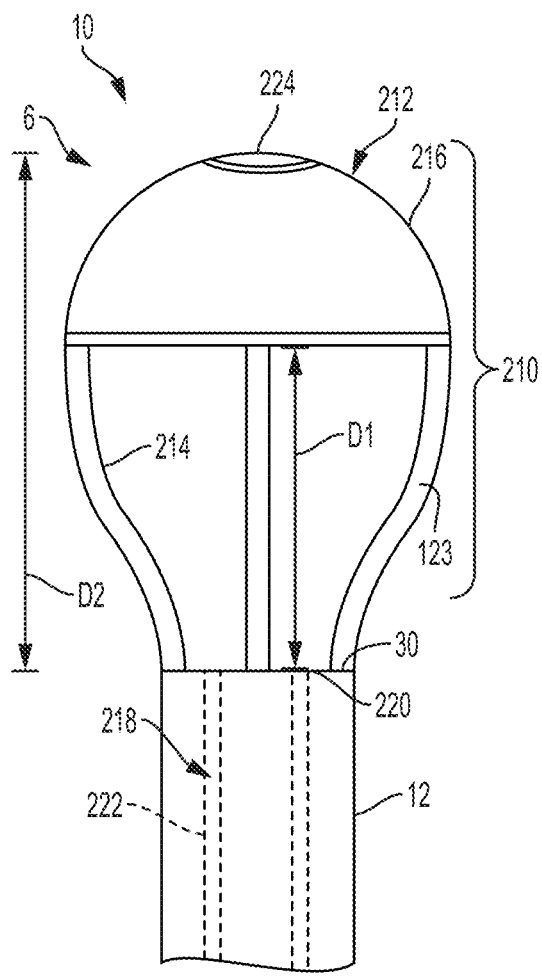
FIG. 1H is a side elevational view of the retention portion of FIG. 1G, according to an example of the present invention.
Figure 1I:
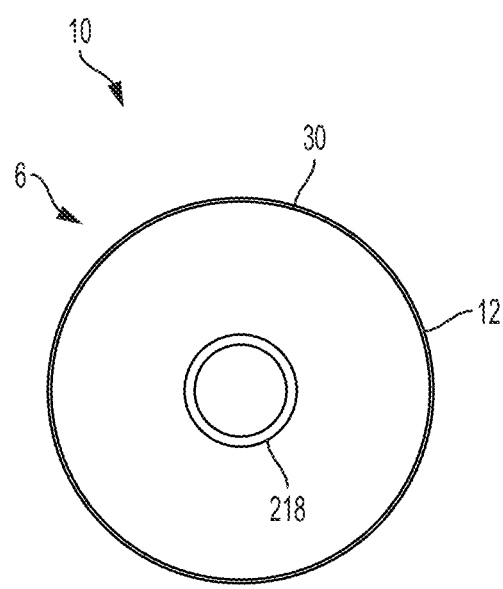
FIG. 1I is a top plan view of the retention portion of FIG. 1G, according to an example of the present invention.
Figure 1J:
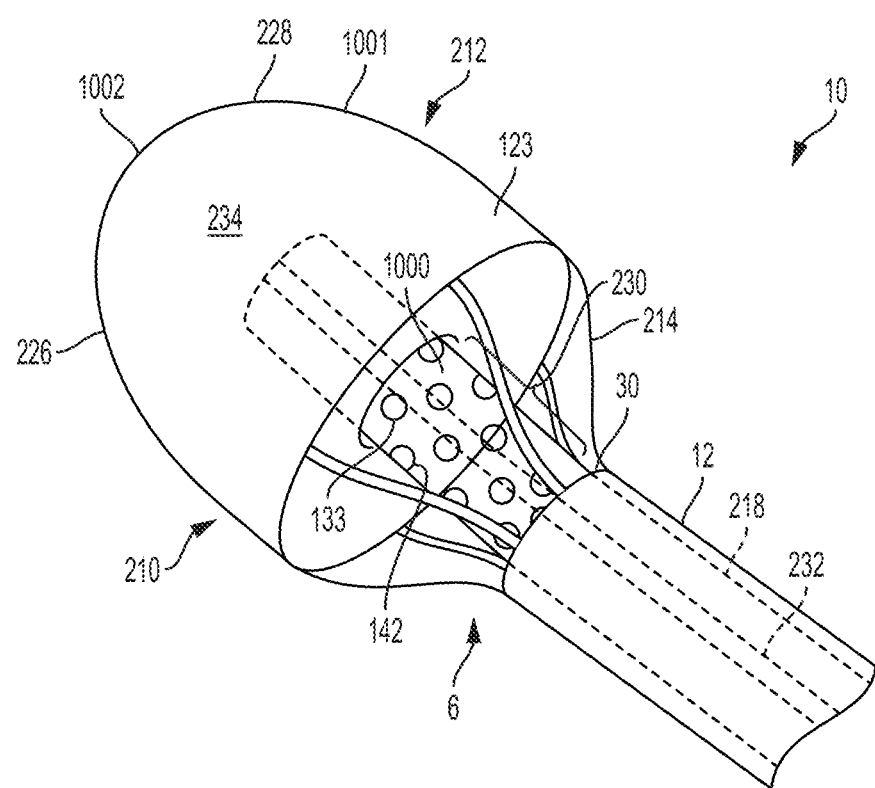
FIG. 1J is a perspective view of a retention portion of a bladder catheter, according to an example of the present invention.
Figure 1K:
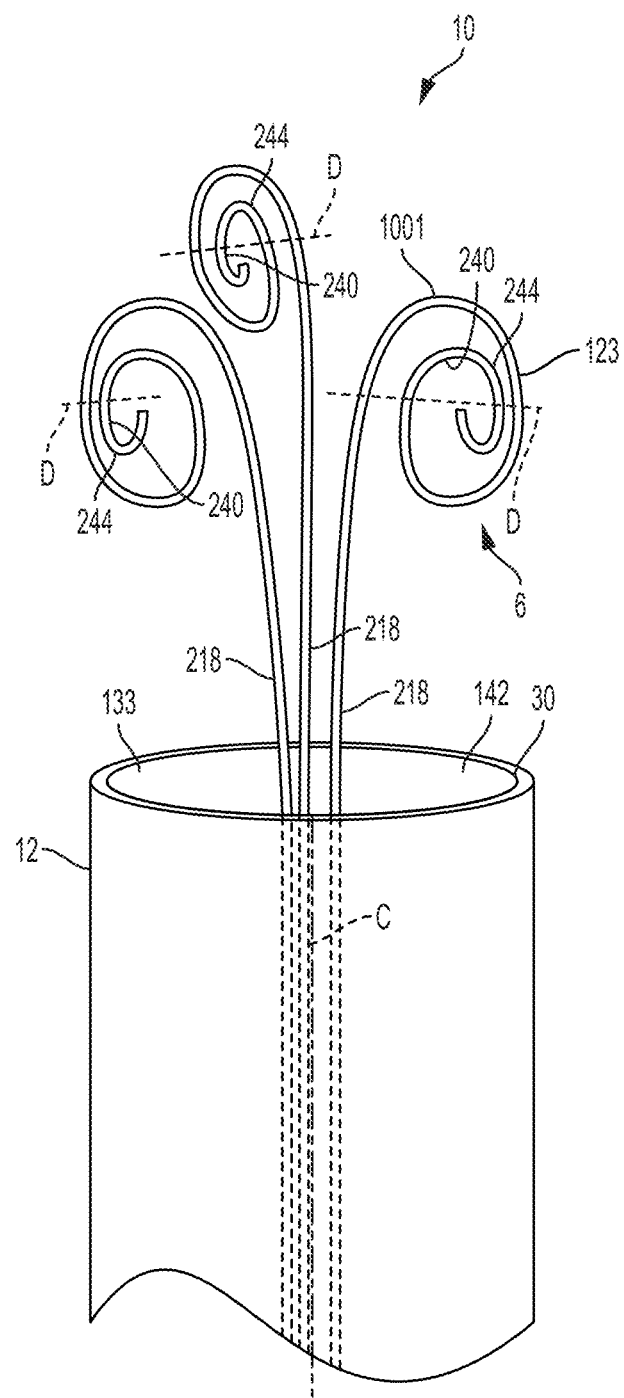
FIG. 1K is a perspective view of a retention portion of a bladder catheter, according to an example of the present invention.
Figure 1L:
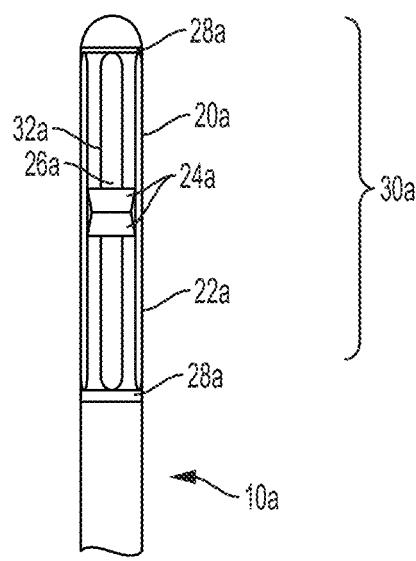
FIG. 1L is a side elevational view of a retention portion of a bladder catheter prior to deployment, according to an example of the present invention.
Figure 1M:
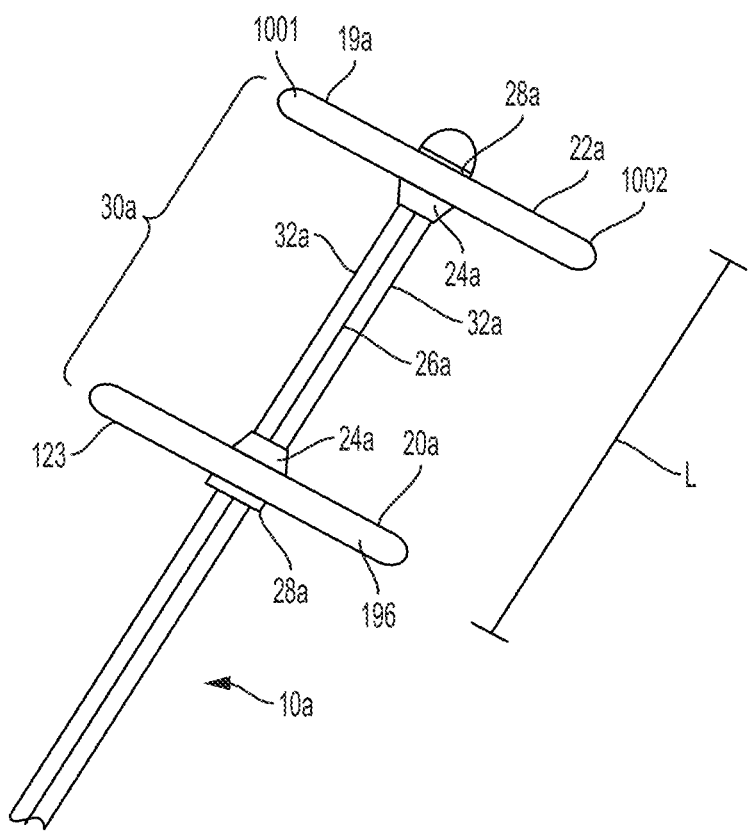
FIG. 1M is a side elevational view of the retention portion of FIG. 1L after deployment, according to an example of the present invention.
Figure 1N:
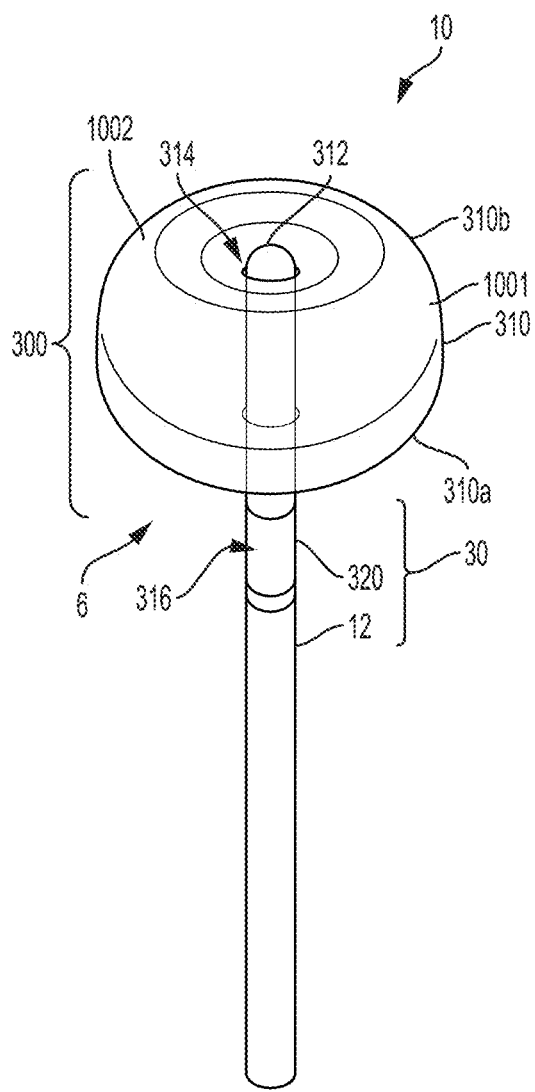
FIG. 1N is a perspective view of a retention portion of a bladder catheter, according to an example of the present invention.
Figure 1O:
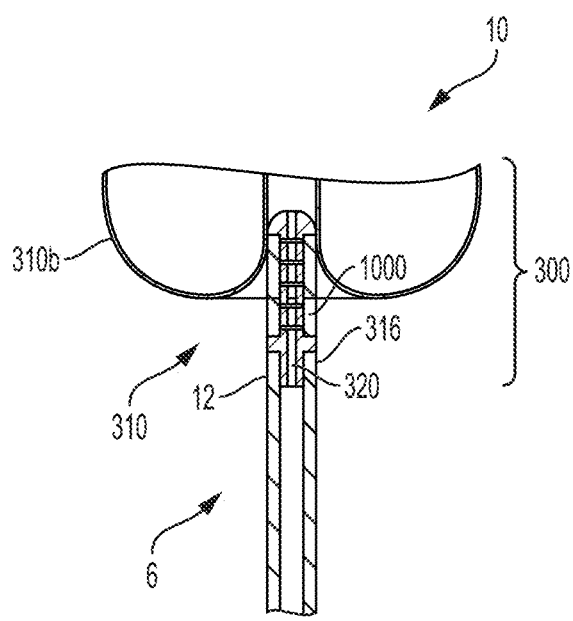
FIG. 1O is a cross-sectional view of a portion of the retention portion of FIG. 1N, according to an example of the present invention.
Figure 1P:
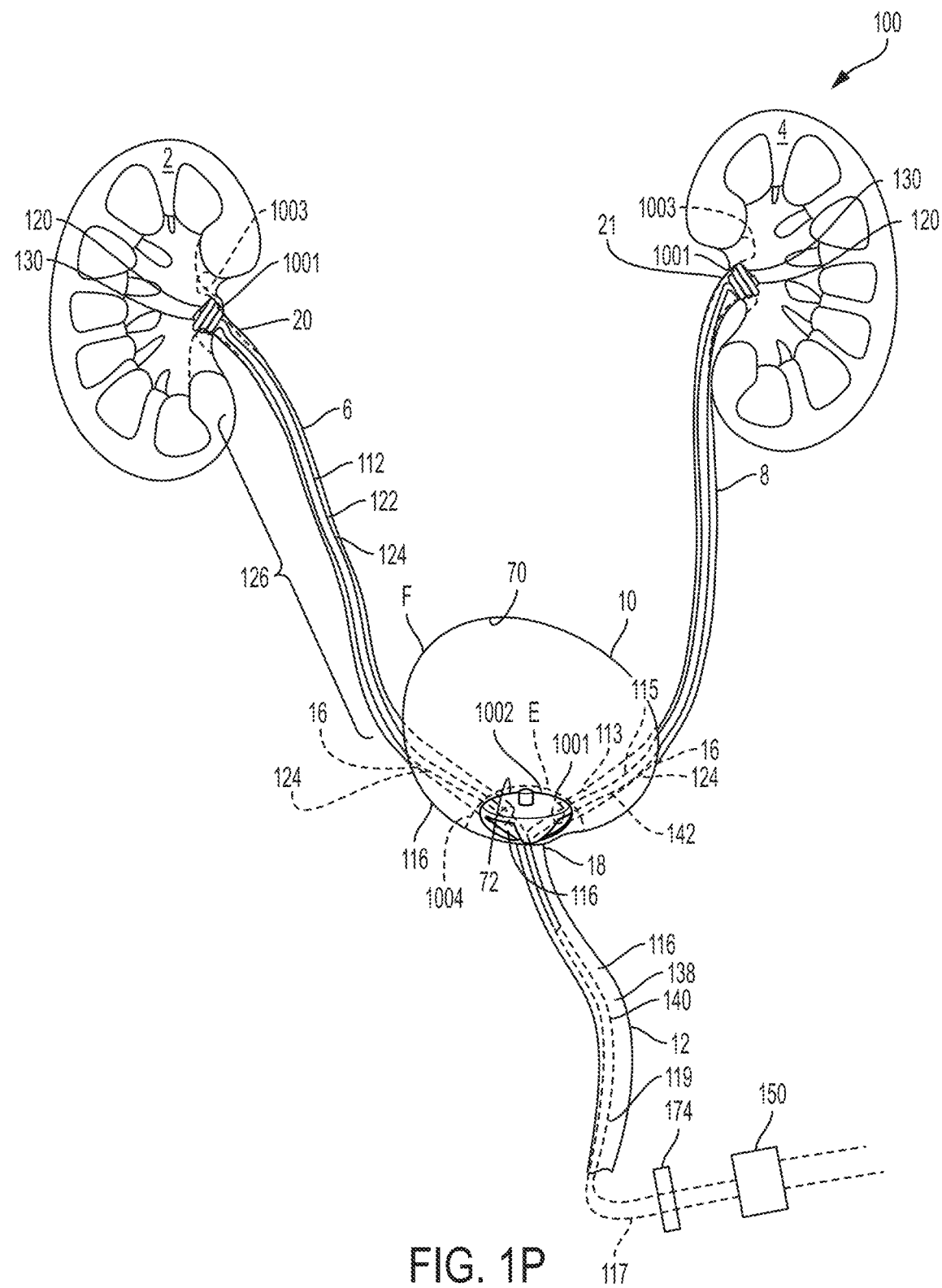
FIG. 1P is a schematic drawing of an indwelling portion of a system comprising a ureteral catheter and a bladder catheter deployed in a urinary tract of a patient, according to an example of the present invention.
Figure 1Q:
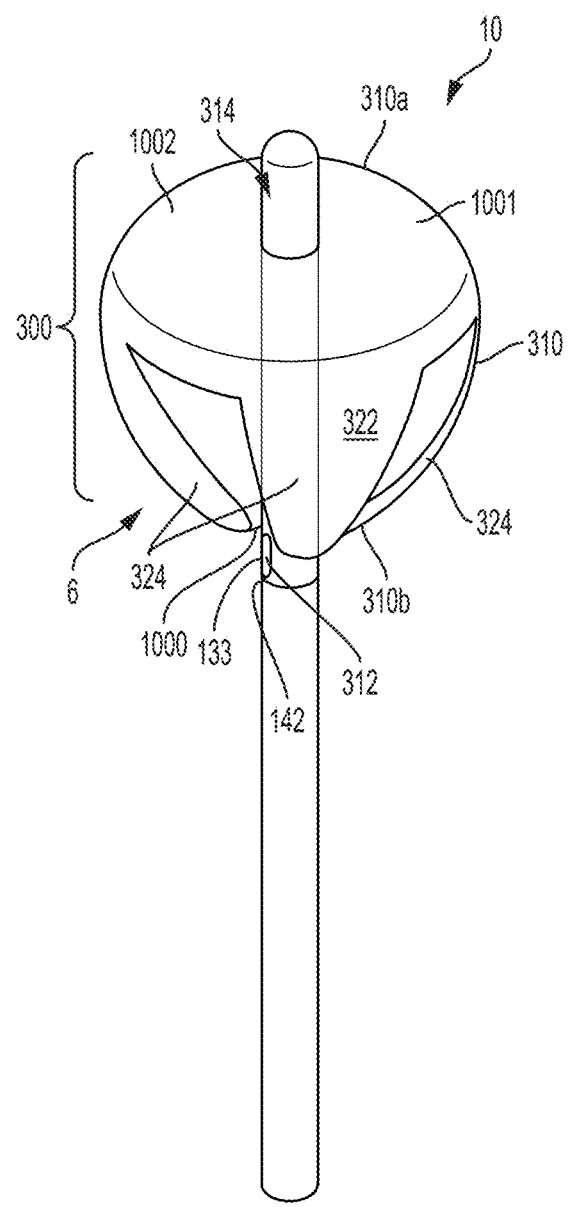
FIG. 1Q is a perspective view of a retention portion of a bladder catheter, according to an example of the present invention.
Figure 1R:
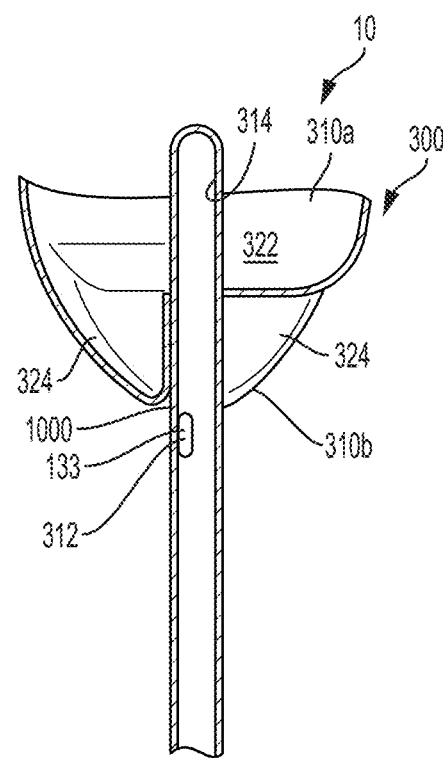
FIG. 1R is a cross-sectional view of a portion of the retention portion of FIG. 1Q, according to an example of the present invention.

Any of the ureteral catheters disclosed herein can be used as bladder catheters useful in the present methods and systems. For example, the bladder catheter can comprise a mesh as a bladder anchor, such as is shown in FIGS. 1A, 1B and 7B. In another example, the bladder catheter 116 can comprise a coil 36, 38, 40, 183, 184, 185, 334, 1210 as a bladder anchor, such as is shown in FIGS. 1C-1W and 7A. In another example, the bladder catheter 116 can comprise a mesh funnel 57 as a bladder anchor, such as is shown in FIG. 7B. In another example, the bladder catheter 116 can comprise a funnel 150 as a bladder anchor, such as is shown in FIG. 17. Regardless of the embodiment selected, the retention portion 123 creates an outer periphery 1002 or protective surface area 1001 to prevent the tissues 1003, 1004 from contracting or collapsing into the fluid column under negative pressure.

In some examples, the retention portion 123 comprises a coiled retention portion similar to the retention portions of the ureteral catheters described in connection with FIGS. 2A and 7A-14. In some examples such as are shown in FIGS. 1C-1E, 1U-1W, the coiled retention portion 123 can comprise a plurality of helical coils 36, 38, 40 or 438, 436, 432 arranged such that an outer periphery 1002 or outer region of the helical coils 36, 38, 40 or 438, 436, 432 contacts and supports bladder tissue 1004 to inhibit occlusion or blockage of protected drainage holes, ports or perforations 172 positioned in protected surface areas or inner surface areas of the helical coils 36, 38, 40 or 438, 436, 432.

The coiled retention portion 123 can comprise at least the first coil 36, 438 having an outer diameter D1 (see FIG. 1E), at least a second coil 38, 436 having an outer diameter D2, and at least a third coil 40, 432 having an outer diameter D3. The diameter D3 of the distal-most or third coil 40, 432 can be smaller than a diameter of either the first coil 36, 438 or the second coil 38, 436. Accordingly, a diameter of the coils 36, 38, 40 or 438, 436, 432, and/or a step distance or height between adjacent coils 36, 38, 40 or 438, 436, 432 can vary in a regular or irregular manner. In some examples, the plurality of coils 36, 38, 40 or 438, 436, 432 can form a tapered or reverse pyramid shape in which D1>D2>D3. In some examples, the coiled retention portion 123 can comprise a plurality of similarly sized coils or, for example, can include a plurality of proximal similarly sized coils and a distal-most coil having a smaller diameter than other coils of the plurality of coils. The diameter of the coils 36, 38, 40 or 438, 436, 432 and distance or height between adjacent coils is selected so that the retention portion 123 remains in the bladder for a desired period of time, such as hours, days or up to about 6 months. The coiled retention portion 123 can be large enough so that it remains in the bladder 10 and does not pass into the urethra until the catheter is ready to be removed from the bladder 10. For example, the outer diameter D1 of the proximal most or first coil 36 438 can range from about 2 mm to 80 mm. The outer diameter D2 of the second coil 38, 436 can range from about 2 mm to 60 mm. The distal-most or third coil 40, 432 can have an outer diameter D3 ranging from about 1 mm to 45 mm. The diameter of the coil tube can range from about 0.33 mm to 9.24 mm (about 1 Fr to about 28 Fr (French catheter scale).

The configurations, sizes and positions of the holes, ports or perforations 142, 172 can be any of the configurations, sizes and positions discussed above for the ureteral or other catheters. In some examples, holes, ports or perforations 142 are present on the outer periphery 1002 or protective surface area 1001 and protected holes, ports or perforations 172 are present on the protected surface areas or inner surface areas 1000. In some examples, the outer periphery 1002 or protective surface area 1001 is essentially free of or free of holes, ports or perforations 142, and the protected holes, ports or perforations 172 are present on the protected surface areas or inner surface areas 1000.

Figure 1U:
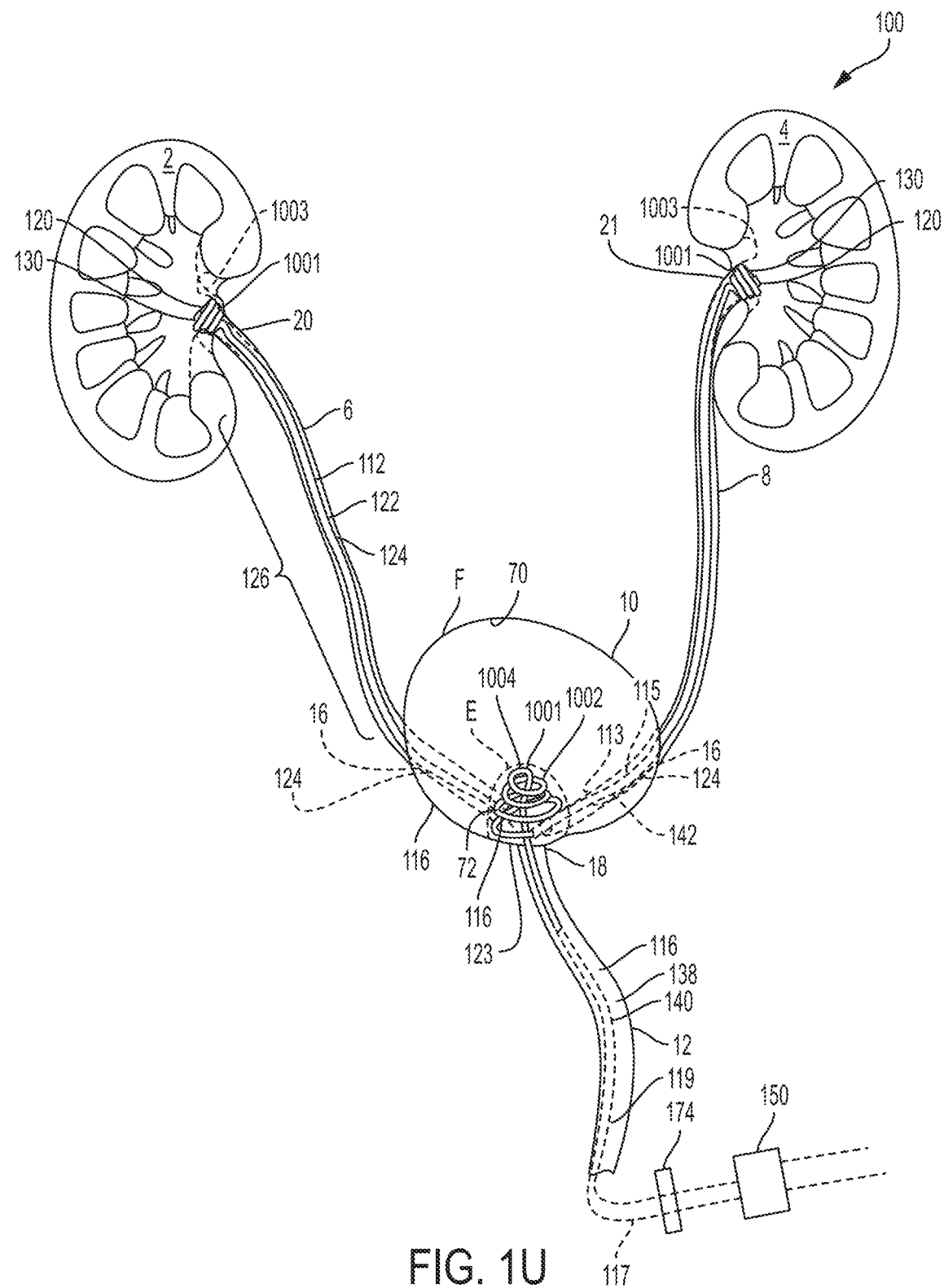
FIG. 1U is a schematic drawing of an indwelling portion of a system comprising a ureteral catheter and a bladder catheter deployed in a urinary tract of a patient, according to an example of the present invention.
Figure 1V:
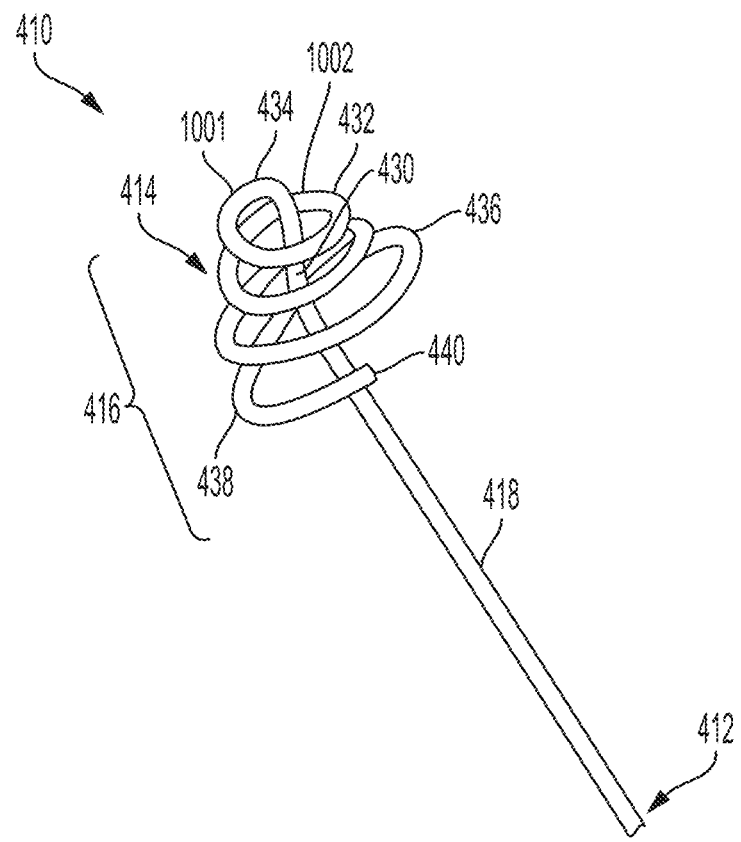
FIG. 1V is a perspective view of a retention portion of a bladder catheter, according to an example of the present invention.
Figure 1W:
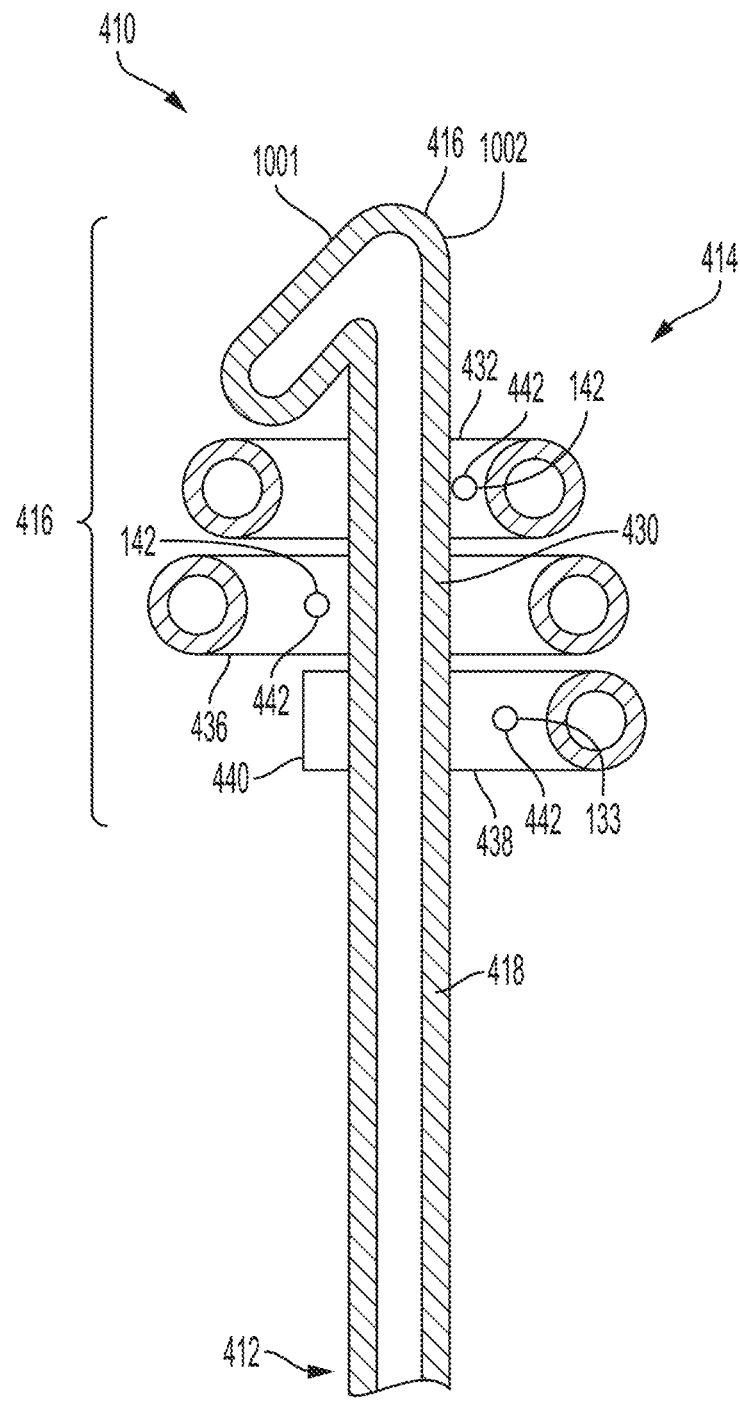
FIG. 1W is a cross sectional view of the retention portion of FIG. 1V, taken along line 1W-1W of FIG. 1V, according to an example of the present invention.

The retention portion 416 shown in FIGS. 1U-1W is a coiled retention portion comprising a plurality of coils wrapped around a substantially linear or straight portion 430 of the elongated tube 418. In some examples, the coiled retention portion 416 comprises a straight portion 430 and a distal-most coil 432 formed from a bend 434 of from about 90 degrees to 180 degrees in the elongated tube 418. The retention portion 416 further comprises one or more additional coils, such as a second or middle coil 436 and a third or proximal most coil 438, which are wrapped around the straight portion 430. The elongated tube 418 can further comprise a distal end 440 after the proximal most coil 438. The distal end 440 can be closed or can be open to receive urine or fluid from the bladder 10.

An area of two-dimensional slices 34 (shown in FIG. 1E) of the three-dimensional shape 32 defined by the deployed expandable retention portion 123 in a plane transverse to a central axis A of the expandable retention portion 16 can decrease towards the distal end 22 of the expanded or deployed retention portion 123, giving the retention portion 123 a pyramid or reversed conical shape. In some examples, a maximum cross-sectional area of the three-dimensional shape 32 defined by the deployed or expanded retention portion 123 in a plane transverse to the central axis A of the deployed or expanded retention portion 132 can range from about 100 mm$^2$ to 1500 mm$^2$, or about 750 mm$^2$.

Other examples of a catheter device 10 are shown in FIGS. 1F-1J. The retention portion 123 of the catheter device 10 comprises a basket shaped structure or support cap 212 of a bladder superior wall support 210 or outer periphery 1002, configured to be disposed within a distal portion of the tube 12 in a retracted position and to extend from the distal end of the tube 12 in a deployed position. The bladder superior wall support 210 comprises a support cap 212 configured to support a superior wall or bladder tissue 1004 and a plurality of support members, such as legs 214, connected to a proximal surface of the support cap 212. The legs 214 can be positioned so that the cap 212 is spaced apart from an open distal end of the drainage tube 12. For example, the legs 214 can be configured to maintain a gap, cavity, or space of distance D1 between an open distal end 30 of the tube 12 and the support cap 212. The distance D1 can range from about 1 mm to about 40 mm, or about 5 mm to about 40 mm. The height D2 of the bladder superior wall support 210 or retention portion can range from about 25 mm to about 75 mm, or about 40 mm. The maximum diameter of the support cap 212 can range from about 25 mm to about 60 mm in the deployed state, and preferably range from about 35 mm and 45 mm.

In some examples, the legs 214 comprise flexible tines, which can be formed from a flexible or shape memory material, such as a nickel titanium. The number of legs can range from about 3 to about 8. The length of each leg can range from about 25 mm to about 100 mm, or longer if the deployment mechanism is external to the patient's body. The width and/or thickness, e.g., diameter, of each leg can range from about 0.003 inches to about 0.035 inches.

In some examples, the support cap 212 can be a flexible cover 216 mounted to and supported by the legs 214. The flexible cover 216 can be formed from a flexible, soft and/or resilient material, such as silicone or Teflon®, for preventing fluid from passing through the cover 216, a porous material, or combinations thereof. In some examples, the flexible material is formed from a material which does not appreciably abrade, irritate, or damage the mucosal lining of the bladder wall or the urethra when positioned adjacent to the mucosal lining, such as silicone or Teflon® materials or porous materials. The thickness of the cover 216 can range from about 0.05 mm to about 0.5 mm. In some examples, the flexible cover 216 and legs 214 are sufficiently structurally rigid so that the cover 216 and legs 214 maintain their form when contacted by the superior wall or bladder tissue 1004. Accordingly, the legs 214 and flexible cover 216 prevent the bladder from collapsing and occluding perforations on the retention portion 6 and/or an open distal end 30 of the tube 12. Also, the legs 214 and flexible cover 216 effectively keep the trigone region and ureteral orifices open so that negative pressure can draw urine into the bladder and drainage tube 12. As discussed herein, if the bladder were permitted to collapse too far, flaps of tissue would extend over the ureter openings, thereby preventing negative pressure from being transmitted to the ureteral catheter(s), ureteral stent(s) and/or ureters and thereby inhibit drawing of urine into the bladder.

In some examples, the catheter device 10 further comprises a drainage tube 218. As shown in FIGS. 1G-1J, the drainage tube 218 can comprise an open distal end 220 positioned adjacent to or extending from the open distal end 30 of the tube 12. In some examples, the open distal end 220 of the drainage tube 218 is the only opening for drawing urine from the bladder into the interior of the drainage tube 218. In other examples, a distal portion of the drainage tube 218 may comprise perforations (not shown in FIGS. 1G-1I) or holes, ports or perforations 174 on a sidewall 222 thereof, as shown in FIG. 1J. The holes, ports or perforations 174 can provide additional spaces for drawing urine into the interior of the drainage tube 218, thereby ensuring that fluid collection can continue even if the open distal end 220 of the drainage tube 218 is occluded. Also, holes, ports or perforations 174 can increase surface area available for drawing fluid into the drainage tube 218, thereby increasing efficiency and/or fluid collection yield.

In some examples, a distal most portion of the support cap 212 can comprise a sponge or pad 224, such as a gel pad. The pad 224 can be positioned to contact and press against the superior bladder wall or bladder tissue 1004 for the purpose of preventing drainage, aspiration, or other trauma to the bladder 10 during negative pressure treatment.

With reference to FIG. 1J, the bladder superior wall support 210 comprises a support cap 212 and a plurality of legs 214. As in previously described examples, the bladder superior wall support 210 is capable of being moved between a retracted position, in which the support 210 is at least partially retracted in a conduit or tube 12, and a deployed position to support the superior wall of the bladder.

In some examples, the catheter device 10 also includes a drainage tube 218 extending from the open distal end 30 of the conduit or tube 12. Unlike in the previously-described examples, the support cap 212 shown in FIG. 4 comprises an inflatable balloon 226. The inflatable balloon 226 can be a substantially semi-spherical and can comprise a curved distal surface 228 configured to contact and support at least a portion of the superior bladder wall or bladder tissue 1004 when deployed.

In some examples, the drainage tube 218 comprises a perforated portion 230 extending between the open distal end 30 of the tube 12 and the support structure 212. The perforated portion 230 is positioned to draw fluid into an interior of the drainage tube 218 so that it can be removed from the bladder 100. Desirably, the perforated portion 230 is positioned so as not to be occluded either by the deployed support cap 212 or the bladder wall when negative pressure is applied thereto. The drainage tube 218 can comprise or be positioned adjacent to an inflation lumen 232 for providing fluid or gas to an interior 234 of the balloon 226 for inflating the balloon 226 from its contracted position to the deployed position. For example, as shown in FIG. 1J, the inflation lumen 232 can be disposed within the drainage tube 218.

Figure 6:
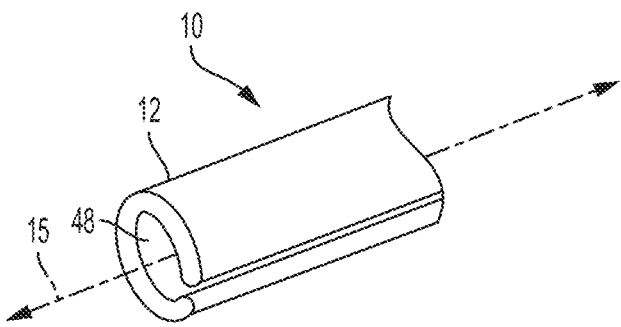
FIG. 6 is a perspective view of an example of a prior art ureteral stent according to FIG. 7 of US Patent Application Publication No. 2002/0183853 A1.

With reference to FIG. 1K, an exemplary retention portion 6, 123 of a urine collection catheter device 10 including multiple coiled drainage lumens, generally denoted as lumens 218, is illustrated. The retention portion 6 comprises the tube 12 having a distal open end 30. The drainage lumens 218 are positioned partially within the tube 12. In a deployed position, the draining lumens 218 are configured to extend from the open distal end 30 of the tube 12 and to conform to a coiled orientation. The drainage lumens 218 can be separate for the entire length of the catheter device 10, or may empty into a single drainage lumen defined by the tube 12. In some examples, as shown in FIG. 6, the drainage lumens 218 can be pigtail coils having one or more coils 244. Unlike in the previously described example, the pigtail coils 244 are coiled about an axis that is not coextensive with an axis C of an uncoiled portion of the tube. Instead, as shown in FIG. 6, the pigtail coils can be coiled about an axis D that is approximately perpendicular to the axis C of the tube 12. In some examples, the drainage lumens 218 can comprise holes, ports or perforations (not shown in FIG. 1K), similar to perforations 132, 133 in FIG. 9A or 9B, for drawing fluid from the bladder into an interior of the drainage lumens 218. In some examples, the perforations can be positioned on a radially inwardly facing side 240 and/or outwardly facing side of the coiled portions of the drainage lumens. As previously described, perforations positioned on radially inwardly facing sides of the drainage lumens 218 or tube 12 are less likely to be occluded by the bladder walls during application of negative pressure to the bladder. Urine can also be drawn directly into one or more drainage lumens defined by the tube 12. For example, rather than being drawing into the drainage lumen(s) 218 through the perforations 230, urine can be drawn directly through the open distal end 30 and into a drainage lumen defined by the tube 12.

With reference to FIGS. 1L and 1M, another example of a retention portion 123 is shown. A fluid receiving portion or distal end portion 30a of the catheter device 10a is shown in a contracted position in FIG. 1L, and in a deployed position in FIG. 1M. The distal end 30a includes opposing bladder wall supports 19a, 19b for supporting the superior and inferior bladder walls 1004. For example, the distal end portion 30a can comprise a proximal sheath 20a and a distal sheath 22a. Each sheath 20a, 22a extends between a slidable ring or collar 24a and stationary or mounted ring or collar 28a. The sheaths 20a, 22a are formed from a flexible, non-porous material, such as silicon or any of the materials discussed herein. The sheaths 20a, 22a are held together by one or more flexible wires or cables 26a. The sheaths 20a, 22a can also be connected by one or more rigid members, such as supports 32a. In some examples, the supports 32a can be tines formed from a flexible, shape-memory material, such as nickel titanium. The supports 32a are positioned to provide support for the proximal sheath 20a and to prevent the distal end 30a from collapsing when it is in the deployed position. In the contracted position, the collars 24a, 28a are positioned apart from one another, such that the sheaths 20a, 22a are stretched or folded against the cable 26a and supports 32a. In the deployed position, the slidable collars 24a are moved toward the stationary collars 28a, allowing the sheaths 20a. 22a to unfold from the central cables 26a and to form a substantially flat disk-shaped structure.

In use, the distal end 30a of the catheter device 10a is inserted into the bladder of a patient in the contracted position. Once inserted in the bladder, the distal sheath 22a is released by sliding the slidable collar 24a in a distal direction toward the stationary collar 28a. Once the distal sheath 22a is deployed, the proximal sheath 20a is released or deployed in a similar manner by sliding the slidable collar 24a in the proximal direction toward the respective stationary collar 28a. At this point, the proximal sheath 20a is floating within the bladder, and is not positioned or sealed against the inferior wall of the bladder. Pressure against the distal sheath 22a caused by collapsing of the bladder is transferred to the proximal sheath 20a through the supports 32a and causes the proximal sheath 20a to move toward the desired position adjacent to the opening of the urethra. Once the proximal sheath 20a is in place, a seal over the urethra opening may be created. The proximal sheath 20a assists in maintaining a negative pressure within the bladder and prevents air and/or urine from exiting the bladder through the urethra.

With reference to FIGS. 1N-1T, retention portions 123 comprising an inflatable support cap, such as an annular balloon 310, positioned to contact the superior wall of the bladder 10 to prevent the bladder 10 from contracting and occluding either fluid port(s) 312 of the catheter device 10 or the ureteral openings of the bladder. In some examples, a distal end portion 30 of the tube 12 extends through a central opening 314 of the balloon 310. The distal end portion 30 of the tube 12 can also contact the superior bladder wall.

Referring now to FIGS. 1N and 1O, in some examples, the tube 12 comprises a fluid access portion 316 positioned proximal to the balloon 310 and extending through a sidewall of the tube 12. The fluid access portion 316 can comprise a filter 318 (shown in FIG. 1O) disposed about a central lumen of the tube 12. In some examples, a sponge material 320 can be positioned over the filter 318 for increased absorbance of fluid within the bladder. For example, the sponge material 320 can be injection molded over the filter 318. In use, urine is absorbed by the sponge material 320 and, upon application of negative pressure through the tube 12, passes through the filter 318 and into the central lumen of the tube 12.

Referring now to FIGS. 1P-1R, in another example, the support cap, such as the annular balloon 310, comprises a substantially bulbous distal portion 322 configured to contact and support the superior bladder wall. The balloon 310 further comprises a plurality of proximally extending lobes 324. For example, the balloon 310 can comprise three lobes 324 spaced equidistantly around a portion of the tube 12 proximal to the balloon 310. As shown in FIG. 1R, the fluid ports 312 can be positioned between adjacent lobes 324. In this configuration, the lobes 324 and bulbous distal portion 322 contact the bladder wall, which prevents the bladder wall from blocking or occluding the fluid ports 312.

Referring now to FIGS. 1S and 1T, in another example, the annular balloon 310 is provided with a flattened and elongated shape. For example, the annular balloon 310 can have a substantially teardrop shaped radial cross section as shown in FIG. 1T, with a narrower portion 326 thereof positioned adjacent to the tube 12 and the enlarged or bulbous portion 328 positioned on the radially outwardly facing side thereof. The flatted annular balloon 310 is configured to span and optionally seal the periphery of the trigone region of the bladder such that when deployed in the bladder, the outer circumference of the balloon 310 extends radially beyond the ureteral openings. For example, when positioned in the patient's bladder, the central opening 314 of the balloon 310 can be configured to be positioned above the trigone region. Fluid port(s) 312 can be positioned proximal to the central portion balloon 310, as shown in FIG. 1T. Desirably, the fluid port(s) 312 are positioned between the central opening 314 of the balloon and the trigone region. When the bladder contracts from application of negative pressure, the bladder wall is supported by the outer circumference of the balloon 310 to avoid blocking the ureter openings. Accordingly, in this configuration, the balloon 310 contacts and prevents the bladder wall from blocking or occluding the fluid ports 312. In a similar manner, as discussed herein, the balloon 310 keeps the trigone region open so that urine can be drawn from the ureters into the bladder through the ureteral openings.

With reference to FIG. 41, in another example of a bladder catheter, an expandable cage 530 can anchor the bladder catheter in the bladder. The expandable cage 530 comprises a plurality of flexible members or tines extending longitudinally and radially outward from a catheter body of a bladder catheter which, in some examples, can be similar to those discussed above with respect to the retention portion of the ureteral catheter of FIG. 41. The members can be formed from a suitable elastic and shape memory material such as nitinol. In a deployed position, the members or tines are imparted with a sufficient curvature to define a spherical or ellipsoid central cavity. The cage is attached to an open distal open end of the catheter tube or body, to allow access to a drainage lumen defined by the tube or body. The cage is sized for positioning within the lower portion of the bladder and can define a diameter and length ranging from 1.0 cm to 2.3 cm, and preferably about 1.9 cm (0.75 in).

In some examples, the cage further comprises a shield or cover over distal portions of the cage to prevent or reduce the likelihood that tissue, namely, the distal wall of the bladder, will be caught or pinched as a result of contact with the cage or member. More specifically, as the bladder contracts, the inner distal wall of the bladder comes into contact with the distal side of the cage. The cover prevents the tissue from being pinched or caught, may reduce patient discomfort, and protect the device during use. The cover can be formed at least in part from a porous and/or permeable biocompatible material, such as a woven polymer mesh. In some examples, the cover encloses all or substantially all of the cavity. In some examples, the cover covers only about the distal ⅔, about the distal half, or about the distal third portion or any amount, of the cage 210.

The cage and cover are transitionable from a contracted position, in which the members are contracted tightly together around a central portion and/or around the bladder catheter 116 to permit insertion through a catheter or sheath to the deployed position. For example, in the case of a cage constructed from a shape memory material, the cage can be configured to transition to the deployed position when it is warmed to a sufficient temperature, such as body temperature (e.g., 37° C.). In the deployed position, the cage has a diameter D that is preferably wider than the urethral opening, and prevents patient motion from translating through the ureteral catheters 112, 114 to the ureters. The open arrangement of the members 212 or tines does not obstruct or occlude the distal opening 248 and/or drainage ports of the bladder catheter 216, making manipulation of the catheters 112, 114 easier to perform.

It is understood that any of the above-described bladder catheters may also be useful as ureteral catheters.

The bladder catheter is connected to the vacuum source, such as pump assembly 710 by, for example, flexible tubing 166 defining a fluid flow path.

Exemplary Fluid Sensors:

With reference again to FIGS. 1A, 1B, 1C, 1F, 1P, 1U, 2A, 2B, in some examples, the system or assembly 100, 700, 1100 further comprises one or more sensors 174 for monitoring physical parameters or fluid characteristics of fluid or urine being collected from the ureters 6, 8 and/or bladder 10. The one or more physiological sensors 174 associated with the patient can be configured to provide information representative of at least one physical parameter to a controller. As discussed herein in connection with FIG. 44, information obtained from the sensors 174 can be transmitted to a central data collection module or processor and used, for example, to control operation of an external device, such as the pump 710 (shown in FIG. 44). The sensors 174 can be integrally formed with one or more of the catheters 112, 114, 116 such as, for example, embedded in a wall of the catheter body or tube and in fluid communication with drainage lumens 124, 140. In other examples, one or more of the sensors 174 can be positioned in a fluid collection container 712 (shown in FIG. 44) or in internal circuitry of an external device, such as the pump 710.

Exemplary sensors 174 that can be used with the urine collection assembly 100 can comprise one or more of the following sensor types. For example, the catheter assembly 100 can comprise a conductance sensor or electrode that samples conductivity of urine. The normal conductance of human urine is about 5-10 mS/m. Urine having a conductance outside of the expected range can indicate that the patient is experiencing a physiological problem, which requires further treatment or analysis. The catheter assembly 100 can also comprise a flow meter for measuring a flow rate of urine through the catheter(s) 112, 114, 116. Flow rate can be used to determine a total volume of fluid excreted from the body. The catheter(s) 112, 114, 116 can also comprise a thermometer for measuring urine temperature. Urine temperature can be used to collaborate the conductance sensor. Urine temperature can also be used for monitoring purposes, as urine temperature outside of a physiologically normal range can be indicative of certain physiological conditions. In some examples, the sensors 174 can be urine analyte sensors configured to measure a concentration of creatinine and/or proteins in urine. For example, various conductivity sensors and optical spectrometry sensors may be used for determining analyte concentration in urine. Sensors based on color change reagent test strips may also be used for this purpose.

Method of Insertion of a System:

Having described the system 100 comprising the ureteral catheter(s) and/or ureteral stent(s) and bladder catheter, some examples of methods for insertion and deployment of the ureteral stent(s) or ureteral catheter(s) and bladder catheter will now be discussed in detail.

In some examples, a method for inducing negative pressure in a portion of a urinary tract of a patient is provided, the method comprising: deploying a ureteral catheter into a ureter of a patient to maintain patency of fluid flow between a kidney and a bladder of the patient, the ureteral catheter comprising a distal portion for insertion within the patient's kidney and a proximal portion; deploying a bladder catheter into the bladder of the patient, wherein the bladder catheter comprises a distal portion for insertion within the patient's bladder and a proximal portion for application of negative pressure, the proximal portion extending outside of the patient's body; and applying negative pressure to the proximal end of the bladder catheter to induce negative pressure in a portion of the urinary tract of the patient to remove fluid from the patient. In some examples, at least one of the ureteral catheter or the bladder catheter comprises (a) a proximal portion; and (b) a distal portion, the distal portion comprising a retention portion that comprises one or more protected drainage holes, ports or perforations and is configured to establish an outer periphery or protective surface area that inhibits mucosal tissue from occluding the one or more protected drainage holes, ports or perforations upon application of negative pressure through the catheter.

Figure 42A:
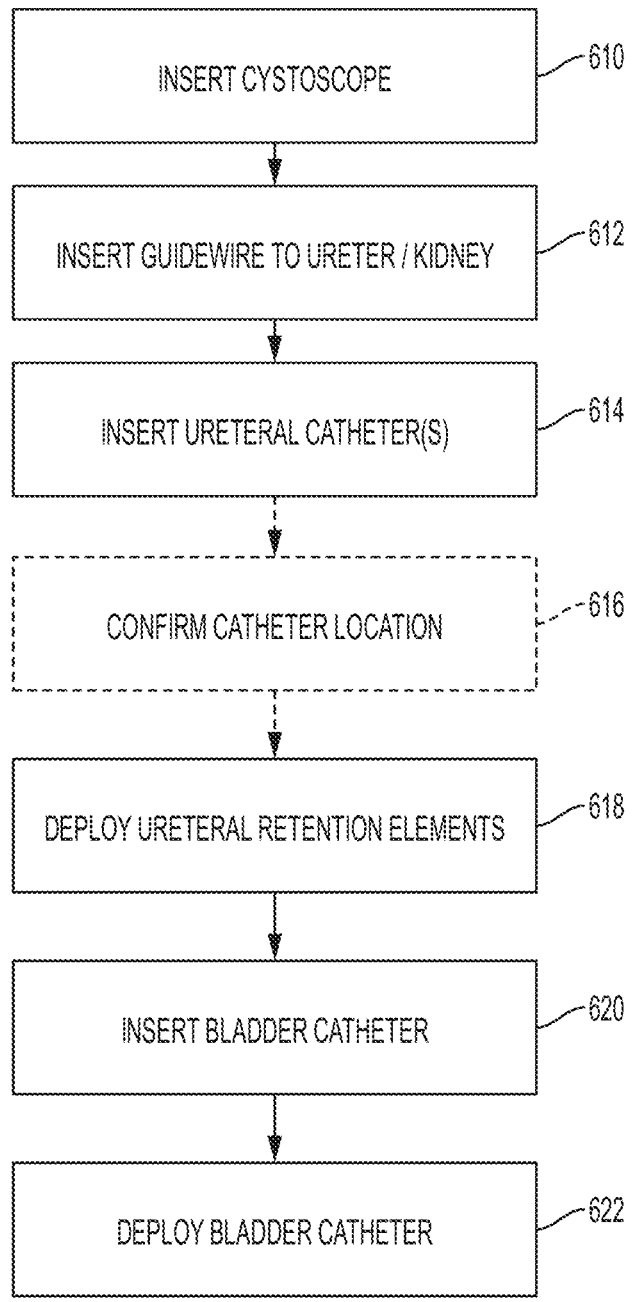
FIG. 42A is a flow chart illustrating a process for insertion and deployment of a system according to an example of the present invention.

With reference to FIG. 42A, an example of steps for positioning a system in a patient's body and, optionally, for inducing negative pressure in a patient's urinary tract, such as bladder, ureter and/or kidneys are illustrated. As shown at box 610, a medical professional or caregiver inserts a flexible or rigid cystoscope through the patient's urethra and into the bladder to obtain visualization of the ureteral orifices or openings. Once suitable visualization is obtained, as shown at box 612, a guidewire is advanced through the urethra, bladder, ureteral opening, ureter, and to a desired fluid collection position, such as the renal pelvis of the kidney. Once the guidewire is advanced to the desired fluid collection position, a ureteral stent or ureteral catheter of the present invention (examples of which are discussed in detail above) is inserted over the guidewire to the fluid collection position, as shown at box 614. In some examples, the location of the ureteral stent or ureteral catheter can be confirmed by fluoroscopy, as shown at box 616. Once the position of the distal end of the ureteral stent or ureteral catheter is confirmed, as shown at box 618, the retention portion of the ureteral catheter can be deployed. For example, the guidewire can be removed from the catheter, thereby allowing the distal end and/or retention portion to transition to a deployed position. In some examples, the deployed distal end portion of the catheter does not entirely occlude the ureter and/or renal pelvis, such that urine is permitted to pass outside the catheter and through the ureters into the bladder. Since moving the catheter can exert forces against urinary tract tissues, avoiding complete blockage of the ureters avoids application of force to the ureter sidewalls, which may cause injury.

After the ureteral stent or ureteral catheter is in place and deployed, the same guidewire can be used to position a second ureteral stent or second ureteral catheter in the other ureter and/or kidney using the same insertion and positioning methods described herein. For example, the cystoscope can be used to obtain visualization of the other ureteral opening in the bladder, and the guidewire can be advanced through the visualized ureteral opening to a fluid collection position in the other ureter. A second ureteral stent or second ureteral catheter can be drawn alongside the guidewire and deployed in the manner described herein. Alternatively, the cystoscope and guidewire can be removed from the body. The cystoscope can be reinserted into the bladder over the first ureteral catheter. The cystoscope is used, in the manner described above, to obtain visualization of the ureteral opening and to assist in advancing a second guidewire to the second ureter and/or kidney for positioning of the second ureteral stent or second ureteral catheter. Once the ureteral stents or catheters are in place, in some examples, the guidewire and cystoscope are removed. In other examples, the cystoscope and/or guidewire can remain in the bladder to assist with placement of the bladder catheter.

In some examples, once the ureteral catheters are in place, as shown at box 620, the medical professional, caregiver or patient can insert a distal end of a bladder catheter in a collapsed or contracted state through the urethra of the patient and into the bladder. The bladder catheter can be a bladder catheter of the present invention as discussed in detail above. Once inserted in the bladder, as shown at box 622, an anchor connected to and/or associated with the bladder catheter is expanded to a deployed position. In some examples, the bladder catheter is inserted through the urethra and into the bladder without using a guidewire and/or cystoscope. In other examples, the bladder catheter is inserted over the same guidewire used to position the ureteral stents or catheters.

In some examples, the ureteral stent or ureteral catheter is deployed and remains in the patient's body for at least 24 hours or longer. In some examples, the ureteral stent or ureteral catheter is deployed and remains in the patient's body for at least 30 days or longer. In some examples, the ureteral stent(s) or ureteral catheter(s) can be replaced periodically, for example every week or every month, to extend the length of therapy.

In some examples, the bladder catheter is replaced more often that the ureteral stent or ureteral catheter. In some examples, multiple bladder catheters are placed and removed sequentially during the indwell time for a single ureteral stent or ureteral catheter. For example, a physician, nurse, caregiver or patient can place the bladder catheter(s) in the patient at home or in any healthcare setting. Multiple bladder catheters can be provided to the healthcare professional, patient or caregiver in a kit, optionally with instructions for placement, replacement and optional connection of the bladder catheter(s) to the negative pressure source or drainage to a container, as needed. In some examples, negative pressure is applied each evening for a predetermined number of evenings (such as for 1 to 30 evenings or more). Optionally, the bladder catheter can be replaced each evening before application of negative pressure.

In some examples, the urine is permitted to drain by gravity or peristalsis from the urethra. In other examples, a negative pressure is induced in the bladder catheter to facilitate drainage of the urine. While not intending to be bound by any theory, it is believed that a portion of the negative pressure applied to the proximal end of the bladder catheter is transmitted to the ureter(s), renal pelvis or other portions of the kidney(s) to facilitate drainage of the fluid or urine from the kidney.

Figure 42B:
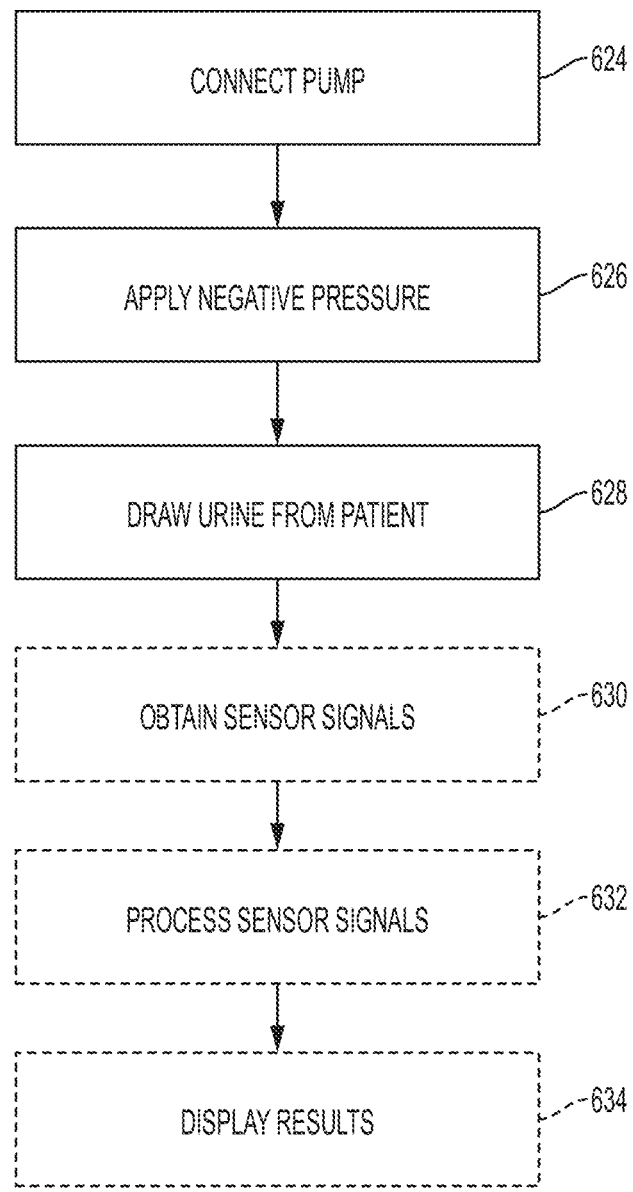
FIG. 42B is a flow chart illustrating a process for applying negative pressure using a system according to an example of the present invention.
Figure 43:
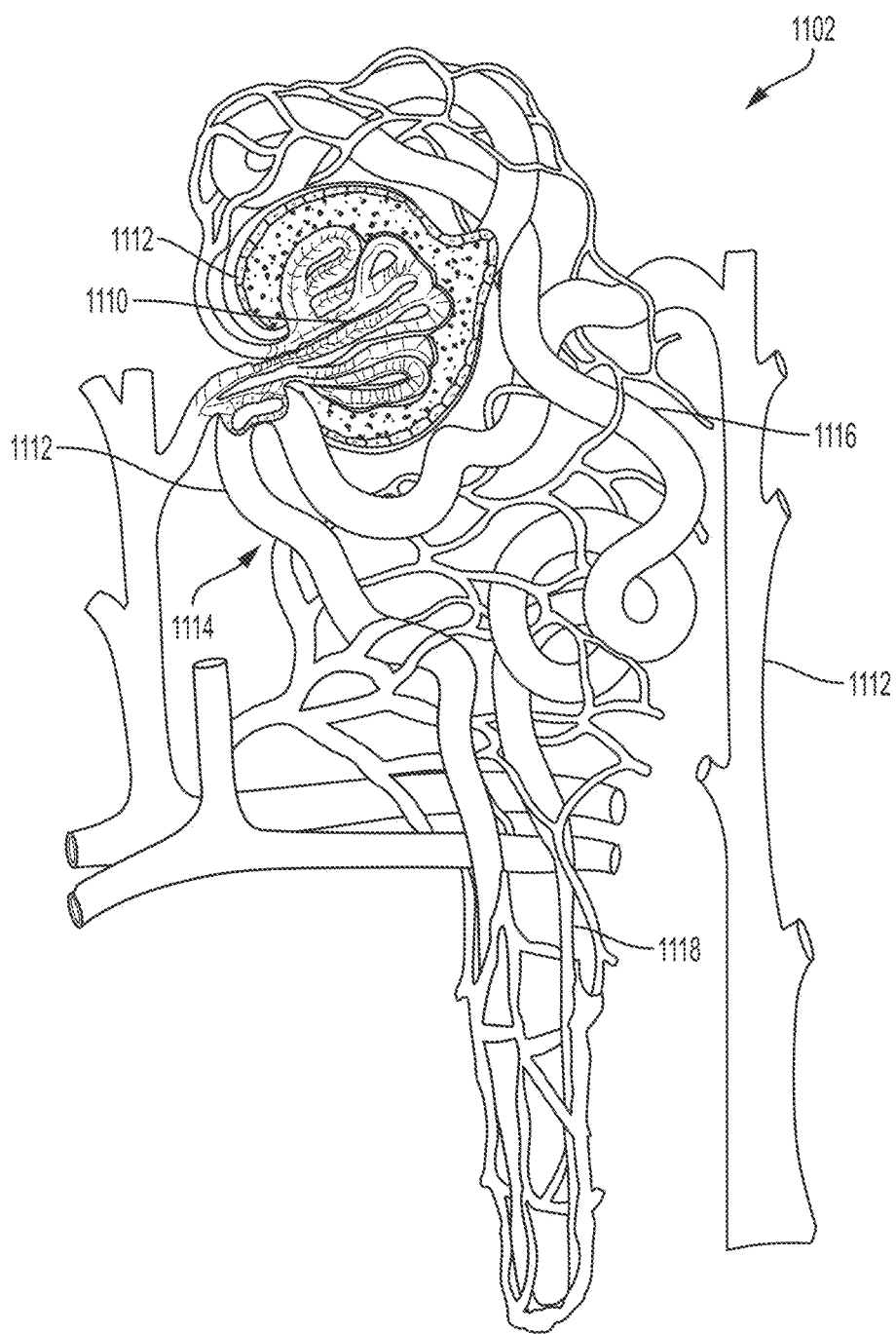
FIG. 43 is a schematic drawing of a nephron and surrounding vasculature showing a position of the capillary bed and convoluted tubules.

With reference to FIG. 42B, steps for using the system for inducement of negative pressure in the ureter(s) and/or kidney(s) are illustrated. As shown at box 624, after the indwelling portions of the ureteral stents or ureteral catheters and bladder catheters are correctly positioned and any anchoring/retention structures, if present, are deployed, the external proximal end of the bladder catheter is connected to a fluid collection or pump assembly. For example, the bladder catheter can be connected to a pump for inducing negative pressure at the patient's bladder, renal pelvis and/or kidney.

Once the bladder catheter and pump assembly are connected, negative pressure is applied to the renal pelvis and/or kidney and/or bladder through the drainage lumen of the bladder catheter, as shown at box 626. The negative pressure is intended to counter congestion mediated interstitial hydrostatic pressures due to elevated intra-abdominal pressure and consequential or elevated renal venous pressure or renal lymphatic pressure. The applied negative pressure is therefore capable of increasing flow of filtrate through the medullary tubules and of decreasing water and sodium re-absorption.

As a result of the applied negative pressure, as shown at box 628, urine is drawn into the bladder catheter at the drainage port(s) at the distal end thereof, through the drainage lumen of the bladder catheter, and to a fluid collection container for disposal. As the urine is being drawn to the collection container, at box 630, optional sensors disposed in the fluid collection system can provide a number of measurements about the urine that can be used to assess physical parameters, such as the volume of urine collected, as well as information about the physical condition of the patient and composition of the urine produced. In some examples, the information obtained by the sensors is processed, as shown at box 632, by a processor associated with the pump and/or with another patient monitoring device and, at box 634, is displayed to the user via a visual display of an associated feedback device.

Figure 44:
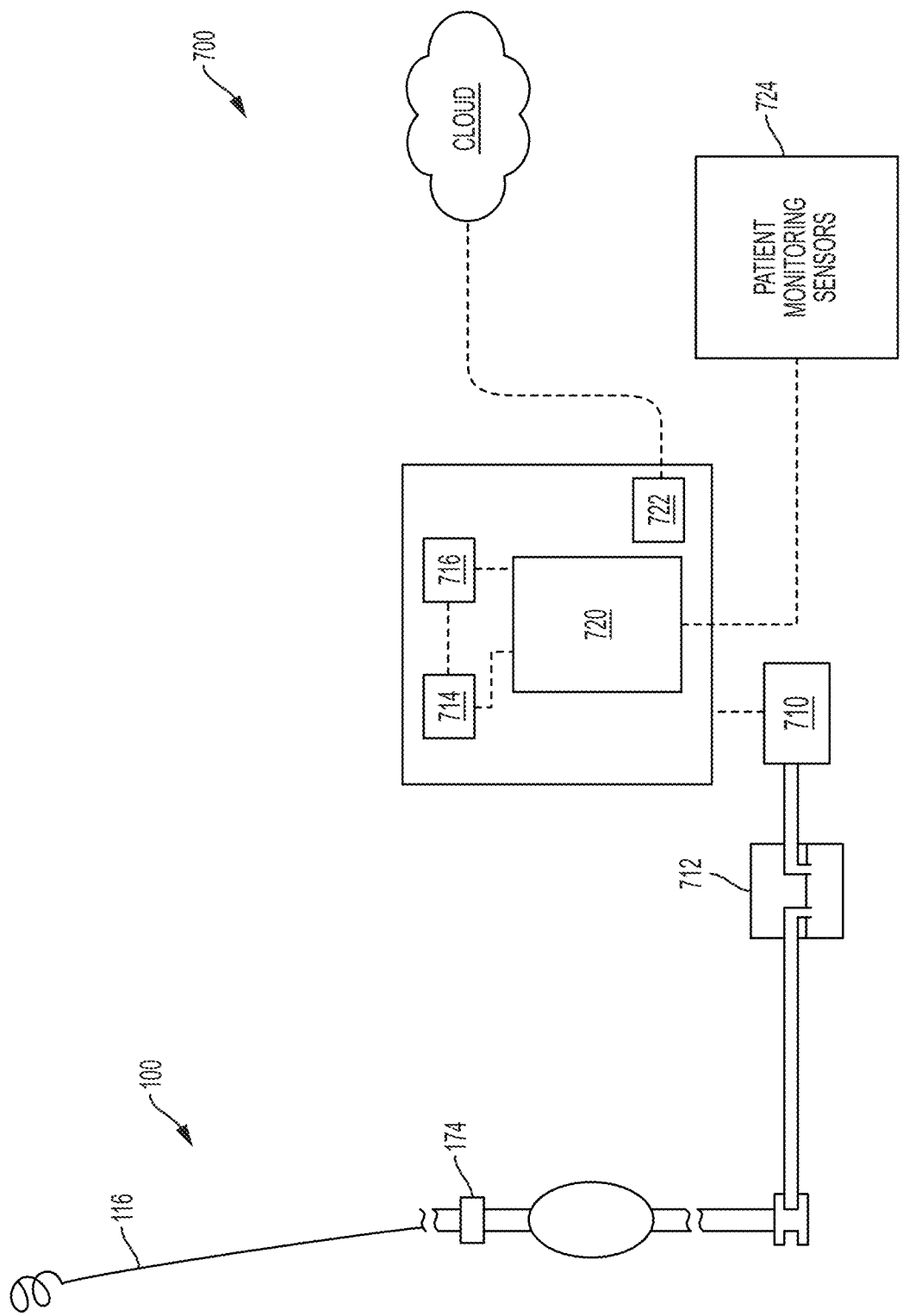
FIG. 44 is a schematic drawing of a system for inducing negative pressure to the urinary tract of a patient according to an example of the present invention.

Exemplary Fluid Collection System:

Having described an exemplary system and method of positioning such a system in the patient's body, with reference to FIG. 44, a system 700 for inducing negative pressure to a patient's bladder, ureter(s), renal pelvis and/or kidney(s) will now be described. The system 700 can comprise the ureteral stent(s) and/or ureteral catheter(s), bladder catheter or the system 100 described hereinabove. As shown in FIG. 44, the bladder catheter 116 of the system 100 is connected to one or more fluid collection containers 712 for collecting urine drawn from the bladder. The fluid collection container 712 connected to the bladder catheter 116 can be in fluid communication with an external fluid pump 710 for generating negative pressure in the bladder, ureter(s) and/or kidney(s) through the bladder catheter 116 and/or ureteral catheter(s) 112, 114. As discussed herein, such negative pressure can be provided for overcoming interstitial pressure and forming urine in the kidney or nephron. In some examples, a connection between the fluid collection container 712 and pump 710 can comprise a fluid lock or fluid barrier to prevent air from entering the bladder, renal pelvis or kidney in case of incidental therapeutic or non-therapeutic pressure changes. For example, inflow and outflow ports of the fluid container can be positioned below a fluid level in the container. Accordingly, air is prevented from entering medical tubing or the catheter through either the inflow or outflow ports of the fluid container 712. As discussed previously, external portions of the tubing extending between the fluid collection container 712 and the pump 710 can include one or more filters to prevent urine and/or particulates from entering the pump 710.

As shown in FIG. 44, the system 700 further comprises a controller 714, such as a microprocessor, electronically coupled to the pump 710 and having or associated with computer readable memory 716. In some examples, the memory 716 comprises instructions that, when executed, cause the controller 714 to receive information from sensors 174 located on or associated with portions of the assembly 100. Information about a condition of the patient can be determined based on information from the sensors 174. Information from the sensors 174 can also be used to determine and implement operating parameters for the pump 710.

In some examples, the controller 714 is incorporated in a separate and remote electronic device in communication with the pump 710, such as a dedicated electronic device, computer, tablet PC, or smart phone. Alternatively, the controller 714 can be included in the pump 710 and, for example, can control both a user interface for manually operating the pump 710, as well as system functions such as receiving and processing information from the sensors 174.

The controller 714 is configured to receive information from the one or more sensors 174 and to store the information in the associated computer-readable memory 716. For example, the controller 714 can be configured to receive information from the sensor 174 at a predetermined rate, such as once every second, and to determine a conductance based on the received information. In some examples, the algorithm for calculating conductance can also include other sensor measurements, such as urine temperature, to obtain a more robust determination of conductance.

The controller 714 can also be configured to calculate patient physical statistics or diagnostic indicators that illustrate changes in the patient's condition over time. For example, the system 700 can be configured to identify an amount of total sodium excreted. The total sodium excreted may be based, for example, on a combination of flow rate and conductance over a period of time.

With continued reference to FIG. 44, the system 700 can further comprise a feedback device 720, such as a visual display or audio system, for providing information to the user. In some examples, the feedback device 720 can be integrally formed with the pump 710. Alternatively, the feedback device 720 can be a separate dedicated or a multipurpose electronic device, such as a computer, laptop computer, tablet PC, smart phone, or other handheld electronic devices. The feedback device 720 is configured to receive the calculated or determined measurements from the controller 714 and to present the received information to a user via the feedback device 720. For example, the feedback device 720 may be configured to display current negative pressure (in mmHg) being applied to the urinary tract. In other examples, the feedback device 720 is configured to display current flow rate of urine, temperature, current conductance in mS/m of urine, total urine produced during the session, total sodium excreted during the session, other physical parameters, or any combination thereof.

In some examples, the feedback device 720 further comprises a user interface module or component that allows the user to control operation of the pump 710. For example, the user can engage or turn off the pump 710 via the user interface. The user can also adjust pressure applied by the pump 710 to achieve a greater magnitude or rate of sodium excretion and fluid removal.

Optionally, the feedback device 720 and/or pump 710 further comprise a data transmitter 722 for sending information from the device 720 and/or pump 710 to other electronic devices or computer networks. The data transmitter 722 can utilize a short-range or long-range data communications protocol. An example of a short-range data transmission protocol is Bluetooth®. Long-range data transmission networks include, for example, Wi-Fi or cellular networks. The data transmitter 722 can send information to a patient's physician or caregiver to inform the physician or caregiver about the patient's current condition. Alternatively, or in addition, information can be sent from the data transmitter 722 to existing databases or information storage locations, such as, for example, to include the recorded information in a patient's electronic health record (EHR).

With continued reference to FIG. 44, in addition to the urine sensors 174, in some examples, the system 700 can further comprise one or more patient monitoring sensors 724. Patient monitoring sensors 724 can include invasive and non-invasive sensors for measuring information about the patient's physical parameters, such as urine composition, as discussed in detail above, blood composition (e.g., hematocrit ratio, analyte concentration, protein concentration, creatinine concentration) and/or blood flow (e.g., blood pressure, blood flow velocity). Hematocrit is a ratio of the volume of red blood cells to the total volume of blood. Normal hematocrit is about 25% to 40%, and preferably about 35% and 40% (e.g., 35% to 40% red blood cells by volume and 60% to 65% plasma).

Non-invasive patient monitoring sensors 724 can include pulse oximetry sensors, blood pressure sensors, heart rate sensors, and respiration sensors (e.g., a capnography sensor). Invasive patient monitoring sensors 724 can include invasive blood pressure sensors, glucose sensors, blood velocity sensors, hemoglobin sensors, hematocrit sensors, protein sensors, creatinine sensors, and others. In still other examples, sensors may be associated with an extracorporeal blood system or circuit and configured to measure parameters of blood passing through tubing of the extracorporeal system. For example, analyte sensors, such as capacitance sensors or optical spectroscopy sensors, may be associated with tubing of the extracorporeal blood system to measure parameter values of the patient's blood as it passes through the tubing. The patient monitoring sensors 724 can be in wired or wireless communication with the pump 710 and/or controller 714.

In some examples, the controller 714 is configured to cause the pump 710 to provide treatment for a patient based information obtained from the urine analyte sensor 174 and/or patient monitoring sensors 724, such as blood monitoring sensors. For example, pump 710 operating parameters can be adjusted based on changes in the patient's blood hematocrit ratio, blood protein concertation, creatinine concentration, urine output volume, urine protein concentration (e.g., albumin), and other parameters. For example, the controller 714 can be configured to receive information about a blood hematocrit ratio or creatinine concentration of the patient from the patient monitoring sensors 724 and/or analyte sensors 174. The controller 714 can be configured to adjust operating parameters of the pump 710 based on the blood and/or urine measurements. In other examples, hematocrit ratio may be measured from blood samples periodically obtained from the patient. Results of the tests can be manually or automatically provided to the controller 714 for processing and analysis.

As discussed herein, measured hematocrit values for the patient can be compared to predetermined threshold or clinically acceptable values for the general population. Generally, hematocrit levels for females are lower than for males. In other examples, measured hematocrit values can be compared to patient baseline values obtained prior to a surgical procedure. When the measured hematocrit value is increased to within the acceptable range, the pump 710 may be turned off ceasing application of negative pressure to the ureter or kidneys. In a similar manner, the intensity of negative pressure can be adjusted based on measured parameter values. For example, as the patient's measured parameters begin to approach the acceptable range, intensity of negative pressure being applied to the ureter and kidneys can be reduced. In contrast, if an undesirable trend (e.g., a decrease in hematocrit value, urine output rate, and/or creatinine clearance) is identified, the intensity of negative pressure can be increased in order to produce a positive physiological result. For example, the pump 710 may be configured to begin by providing a low level of negative pressure (e.g., between about 0.1 mmHg and 10 mmHg). The negative pressure may be incrementally increased until a positive trend in patient creatinine level is observed. However, generally, negative pressure provided by the pump 710 will not exceed about 50 mmHg.

Figure 45A:
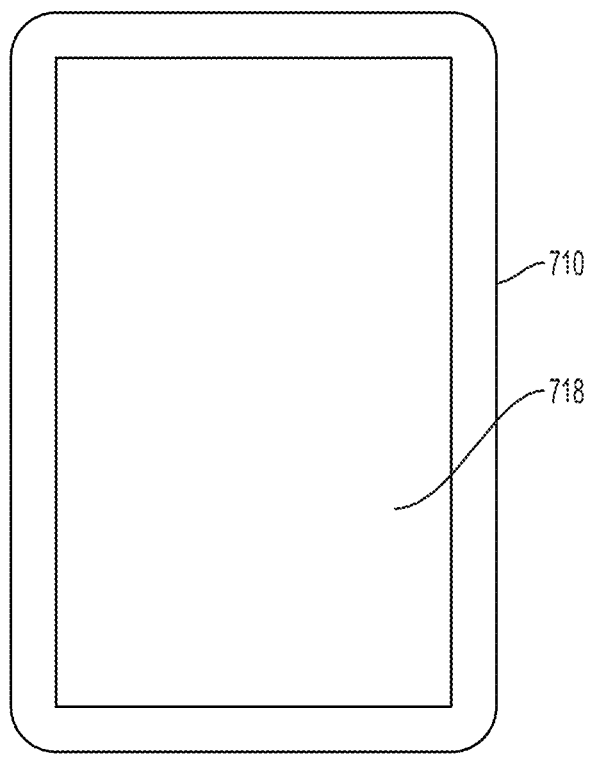
FIG. 45A is a plan view of a pump for use with the system of FIG. 44 according to an example of the present invention.
Figure 45B:
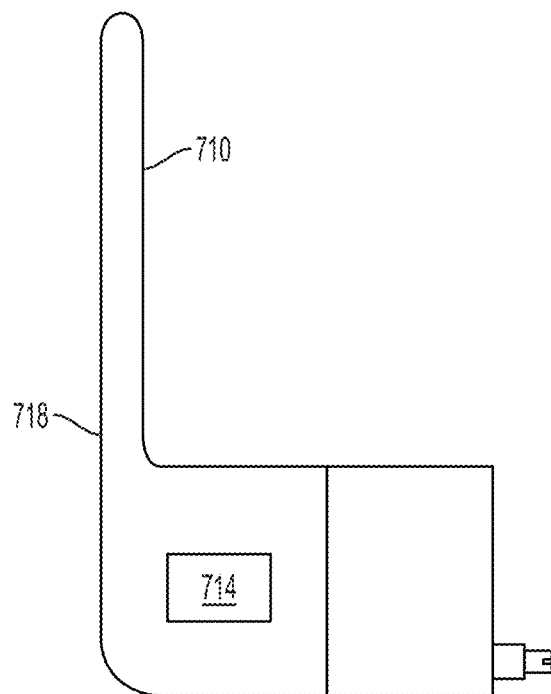
FIG. 45B is a side elevation view of the pump of FIG. 45A.
Figure 46:
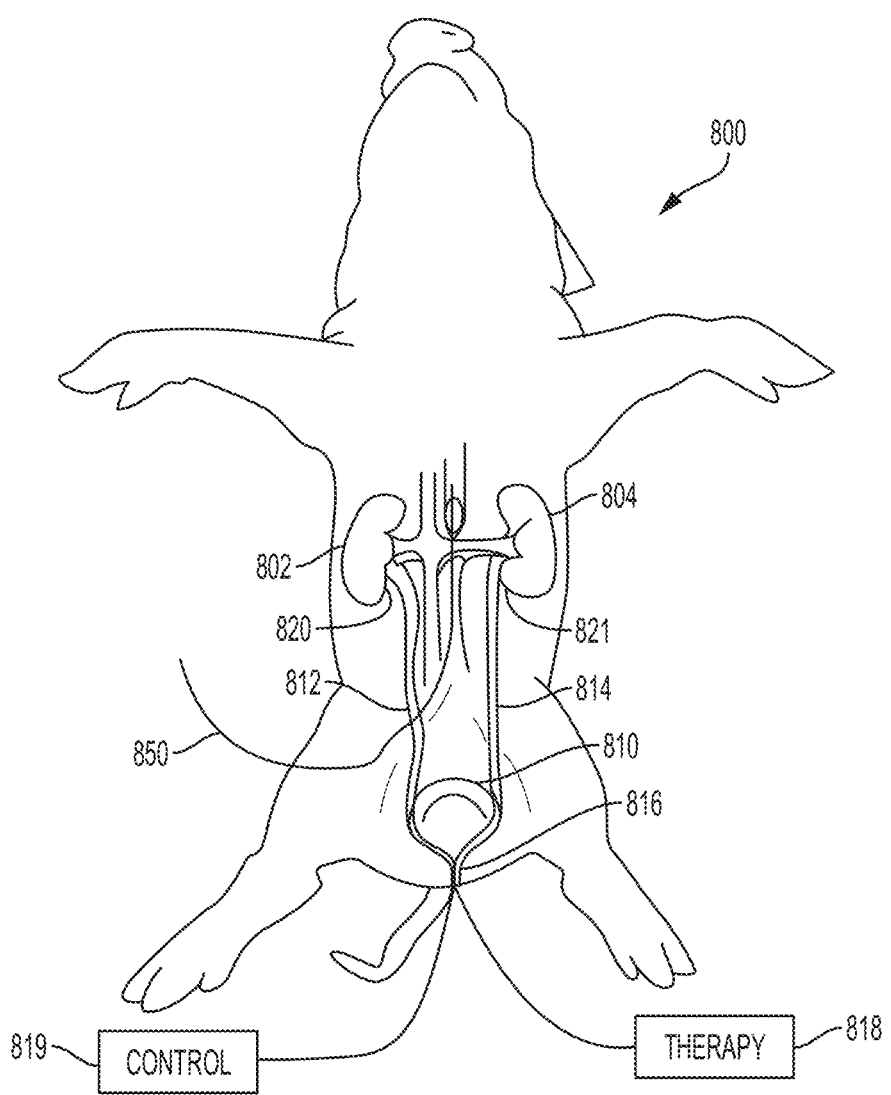
FIG. 46 is a schematic drawing of an experimental set-up for evaluating negative pressure therapy in a swine model according to the present invention.
Figure 47:
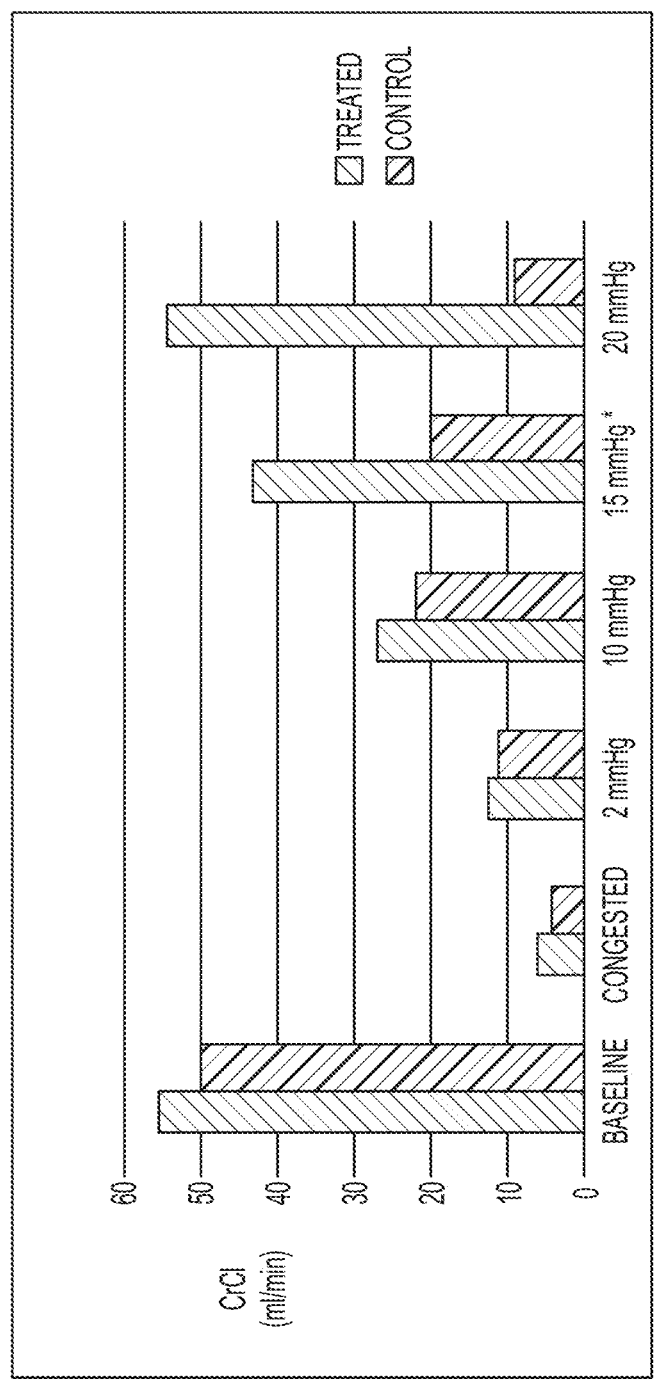
FIG. 47 is a graph of creatinine clearance rates for tests conducted using the experimental set-up shown in FIG. 21.

With reference to FIGS. 45A and 45B, an exemplary pump 710 for use with the system is illustrated. In some examples, the pump 710 is a micro-pump configured to draw fluid from the catheter(s) 112, 114 (shown, for example, in FIGS. 1A, 1B, 1C, 1F, 1P, 1U, 2A, 2B) and having a sensitivity or accuracy of about 10 mm Hg or less. Desirably, the pump 710 is capable of providing a range of flow of urine between 0.05 ml/min and 3 ml/min for extended periods of time, for example, for about 8 hours to about 24 hours per day, for one (1) to about 30 days or longer. At 0.2 ml/min, it is anticipated that about 300 mL of urine per day is collected by the system 700. The pump 710 can be configured to provide a negative pressure to the bladder of the patient, the negative pressure ranging from about 0.1 mmHg and about 150 mmHg, or about 0.1 mmHg to about 50 mmHg, or about 5 mmHg to about 20 mmHg (gauge pressure at the pump 710). For example, a micro-pump manufactured by Langer Inc. (Model BT100-2J) can be used with the presently disclosed system 700. Diaphragm aspirator pumps, as well as other types of commercially available pumps, can also be used for this purpose. Peristaltic pumps can also be used with the system 700. In other examples, a piston pump, vacuum bottle, or manual vacuum source can be used for providing negative pressure. In other examples, the system can be connected to a wall suction source, as is available in a hospital, through a vacuum regulator for reducing negative pressure to therapeutically appropriate levels.

In some examples, at least a portion of the pump assembly can be positioned within the patient's urinary tract, for example within the bladder. For example, the pump assembly can comprise a pump module and a control module coupled to the pump module, the control module being configured to direct motion of the pump module. At least one (one or more) of the pump module, the control module, or the power supply may be positioned within the patient's urinary tract. The pump module can comprise at least one pump element positioned within the fluid flow channel to draw fluid through the channel. Some examples of suitable pump assemblies, systems and methods of use are disclosed in U.S. Patent Application No. 62/550,259, entitled "Indwelling Pump for Facilitating Removal of Urine from the Urinary Tract", filed on Aug. 25, 2017, which is incorporated by reference herein in its entirety.

In some examples, the pump 710 is configured for extended use and, thus, is capable of maintaining precise suction for extended periods of time, for example, for about 8 hours to about 24 hours per day, or for 1 to about 30 days or longer, except for replacement time of bladder catheters. Further, in some examples, the pump 710 is configured to be manually operated and, in that case, includes a control panel 718 that allows a user to set a desired suction value. The pump 710 can also include a controller or processor, which can be the same controller that operates the system 700 or can be a separate processor dedicated for operation of the pump 710. In either case, the processor is configured for both receiving instructions for manual operation of the pump and for automatically operating the pump 710 according to predetermined operating parameters. Alternatively, or in addition, operation of the pump 710 can be controlled by the processor based on feedback received from the plurality of sensors associated with the catheter.

In some examples, the processor is configured to cause the pump 710 to operate intermittently. For example, the pump 710 may be configured to emit pulses of negative pressure followed by periods in which no negative pressure is provided. In other examples, the pump 710 can be configured to alternate between providing negative pressure and positive pressure to produce an alternating flush and pump effect. For example, a positive pressure of about 0.1 mmHg to 20 mmHg, and preferably about 5 mmHg to 20 mmHg can be provided followed by a negative pressure ranging from about 0.1 mmHg to 50 mmHg.

Percutaneous Urinary Catheters and Systems

Urine can also be removed from the urinary tract through percutaneous nephrostomy tubes or urinary bypass catheters deployed via percutaneous insertion in the renal pelvis and/or kidney of a patient. In some examples of the invention, such urinary bypass catheters can be adapted to provide negative and/or positive pressure therapy to a renal pelvis and/or kidney of a patient to facilitate urine production and to drain and/or conduct urine from the renal pelvis and/or kidney to an external fluid collection container. Urinary bypass catheters may be used, for example, to remove fluid (e.g., urine) from the body when portions of the urinary tract (e.g., the ureters or urethra) are blocked. Generally, such urinary bypass catheters are inserted into an abdomen of a patient at a percutaneous access site. Such catheters extend through the kidney and, optionally, into the renal pelvis. A common percutaneous access site for accessing the abdominal cavity and kidneys lies between about 0.5 cm and about 1.5 cm or approximately 1 cm below a tip of the twelfth rib and between about 0.5 cm and about 1.5 cm or approximately 1 cm medially therefrom. It is believed that such an access site provides easy access to a lower pole of the kidney and avoids injuring other abdominal organs (e.g., the colon, liver, and/or spleen). A physician inserting a urinary bypass catheter may also select other access sites on a patient's torso based on a patient's size and/or on other therapeutic concerns.

Exemplary Urinary Catheters

Deployable retention structures or portions of the bypass catheter are configured to maintain a distal portion and/or distal end of the catheter within the kidney, renal pelvis, and/or bladder. For example, any of the coils, funnels, expandable cages, balloons, and/or sponges described herein can be used us retention portions for maintaining an end of a catheter at a desired position within the urinary tract (e.g., within the renal pelvis, ureters, and/or kidneys).

Referring now to FIGS. 52A-54, an exemplary percutaneous nephrostomy tube or urinary bypass catheter 7010 will be discussed. It is understood, however, that any of the catheters discussed herein can be used in a similar manner as described below. The exemplary urinary bypass catheter 7010 is configured to be deployed in a urinary tract 7100 (shown in FIGS. 54, 55, and 57A-57E) of a patient. The catheter 7010 comprises an elongated tube 7018 extending from a proximal end 7020 to a distal end 7022. The elongated tube 7018 comprises a proximal portion 7012 configured to pass into an abdomen of the patient through a percutaneous opening or access site 7110 (shown in FIG. 54) and a distal portion 7014 comprising a retention portion 7016 configured to be deployed in a renal pelvis 7112, kidney 7102 (shown in FIG. 54), and/or bladder, of the patient. The percutaneous access site 7110 can be formed in a conventional manner, such as by inserting a tip of a needle through the skin into the abdomen.

The tube 7018 can be formed from and/or comprise one or more biocompatible polymer(s), such as polyurethane, polyvinyl chloride, polytetrafluoroethylene (PTFE), latex, silicone coated latex, silicone, polyglycolide or poly(glycolic acid) (PGA), Polylactide (PLA), Poly(lactide-co-glycolide), Polyhydroxyalkanoates, Polycaprolactone and/or Poly(propylene fumarate). Portions of the elongated tube 18 can also comprise and/or be impregnated with metal materials, such as copper, silver, gold, nickel-titanium alloy, stainless steel, and/or titanium. The elongated tube 7018 should be of sufficient length to extend from the renal pelvis 7112, through the kidney and percutaneous access site, and to the external fluid collection container. The tube 7018 size can range from about 1 Fr to about 9 Fr (French catheter scale), or about 2 Fr to 8 Fr, or can be about 4 Fr. In some examples, the tube 18 can have an external diameter ranging from about 0.33 mm to about 3.0 mm, or about 0.66 mm to 2.33 mm, or about 1.0 mm to 2.0 mm, and an internal diameter ranging from about 0.165 mm to about 2.40 mm, or about 0.33 mm to 2.0 mm, or about 0.66 mm to about 1.66 mm. In one example, the tube 7018 is 6 Fr and has an outer diameter of 2.0±0.1 mm. A length of the tube 7018 can range from about 30 cm to about 120 cm depending on the age (e.g., pediatric or adult) and size of the patient.

The retention portion 7016 of the bypass catheter 7010 can be integrally formed with the distal portion 7014 of the catheter 7010 or can be a separate structure mounted to the distal end 7022 of the elongated tube 7018 by a conventional fastener or adhesive. Many exemplary retention portions 7016 suitable for retaining the distal end 7022 of the elongated tube 7018 within the renal pelvis 7112 are provided in previous exemplary embodiments of ureteral catheters 7010. For example, retention portions 7016 comprising one or more of coils, funnels, cages, balloons, and/or sponges can be adapted for use with the bypass catheter 7010. In some cases, such retention portions 7016 can be adapted for use with urinary bypass catheters 7010 by, for example, inverting the retention portion(s) 7016 to account for the fact that a urinary bypass catheter 7010 enters the renal pelvis 7112 through the kidney 7102, rather than through the ureters.

Regardless of the embodiment selected, the retention portion 7016 creates an outer periphery or protected surface area to prevent urinary tract tissues from constricting or occluding a fluid column extending between nephrons of the kidney 7102 and a lumen of the elongated tube 7018. In some examples, such a retention portion 7016 could comprise an inwardly facing side or protected surface area 7024 comprising one or more drainage openings, perforations, and/or ports 7026 for receiving fluid, such as urine, produced by the kidneys 7102 and an outwardly facing side or protective surface area 7028, which can be free from or substantially free from the drainage ports 7026. Desirably, the inwardly facing side or protected surface area 7024 and the outwardly facing side or protective surface area 7028 are configured such that, when negative pressure is applied through the elongated tube 7018, the urine is drawn into a lumen of the tube 7018 through the one or more drainage ports 7026, while mucosal tissues, such as tissue of the ureters and/or renal pelvis 7112, are prevented from appreciably occluding the one or more drainage ports 7026. As in previously described ureteral catheters, sizes and spacing between the drainage ports 7026 may vary to achieve different distributions of negative pressure within the renal pelvis 7112 and/or kidney 7102, as are disclosed herein. In some examples, each of the one or more drainage ports 7026 has a diameter of about 0.0005 mm to about 2.0 mm, or about 0.05 mm to 1.5 mm, or about 0.5 mm to about 1.0 mm. In some examples, the drainage ports 7026 can be non-circular, and can have a surface area of about 0.0002 mm$^2$ to about 100 mm$^2$, or about 0.002 mm$^2$ to about 10 mm$^2$, or about 0.2 mm$^2$ to about 1.0 mm$^2$. The drainage ports 7026 can be spaced equidistantly along an axial length of the retention portion 7016. In other examples, drainage ports 7026 nearer to the distal end 7022 of the retention portion 7016 may be spaced more closely together to increase fluid flow through more distal drainage ports 7026, compared to examples where the ports 7026 are evenly spaced.

Figure 55:
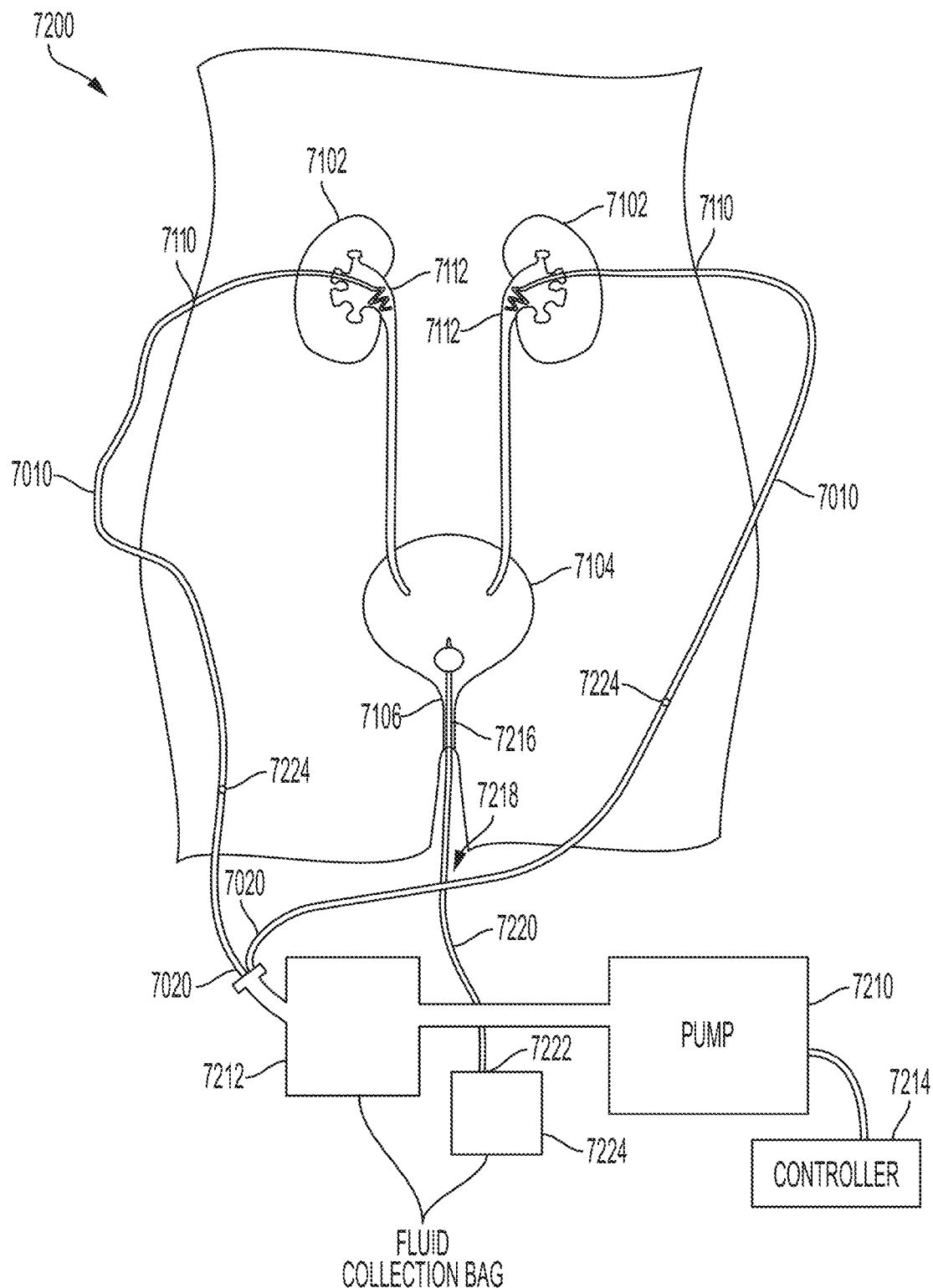

The proximal portion 7012 of the catheter 7010 generally extends from the kidney 7102 of the patient through the percutaneous access site 7110. The proximal portion 7012 of the catheter 7010 is free from or substantially free from perforations, openings, or drainage ports 7026 to avoid drawing fluids from the abdominal cavity into the elongated tube 7018. Also, the proximal end 7020 of the proximal portion 7012 can be configured to be connected to a fluid collection container and/or pump, as shown in FIG. 55.

Exemplary Retention Portion

As discussed above, the retention portion 7016 can be any structure suitable for maintaining the distal end 7022 of the elongated tube 7018 in the desired location within the urinary tract 7100. For example, a sufficiently sized retention portion 7016 can have an axial length L1 ranging from about 5 mm to about 100 mm, or from 20 mm to 80 mm, or about 50 mm.

In some examples, the retention portion 7016 comprises an expandable structure that transitions from a retracted state, when inserting or removing the catheter 7010 from the patient, to an expanded or deployed state configured to anchor and retain the retention portion 7016 in the renal pelvis 7112 and/or kidney 7102. In order to sufficiently retain the catheter 7010 in the desired location within the urinary tract 7100, in some examples, the retention portion 7016, when deployed, defines a three-dimensional shape 7032 (shown in FIG. 53) sized and positioned to maintain patency of the fluid column flowing between the kidney 7102 and the proximal end 7020 of the catheter 7010. Further, desirably, at least a portion of the fluid produced by the kidneys 7102 flows through the retention portion 7016 and tube 7018, rather than through the ureters. An area of two-dimensional slices 7034 (shown in FIG. 53) of the three-dimensional shape 7032 defined by the deployed expandable retention portion 7016 in a plane transverse to a central axis A of the expandable retention portion 7016 can decrease towards the distal end 7022 of the expandable retention portion 7016, giving the retention portion 7016 a pyramid or reversed conical shape. In some examples, a maximum cross-sectional area of the three-dimensional shape 7032 defined by the deployed expandable retention portion 7016 in a plane transverse to the central axis A of the expandable retention portion 7016 is less than or equal to about 500 mm$^2$, or less than or equal to about 350 mm$^2$, or from 100 mm$^2$ to 500 mm$^2$, or from 200 mm$^2$ to 350 mm$^2$.

In some examples, the retention portion 7016 comprises a coiled retention portion comprising an inverted helical coil. The coiled retention portion 7016 is similar to the retention portions of the ureteral catheters described in connection with FIGS. 8A-9E, except that the orientation of the coils is inverted since the retention portion 7016 is inserted into the renal pelvis through the kidney. The coiled retention portion 7016 can comprise a plurality of helical coils 7036, 7038, 7040 arranged such that an outer periphery or outer region of the helical coils 7036, 7038, 7040 contacts and supports tissues of the kidney 7102 and/or renal pelvis 7112 to inhibit occlusion or blockage of protected drainage holes, ports 7026 or perforations positioned in inwardly facing sides or protected surface areas of the helical coils 7036, 7038, 7040.

The coiled retention portion 7016 can comprise at least the first coil 7036 having a first diameter D1 (see FIG. 52B), at least a second coil 7038 having a second diameter D2, and at least a third coil 7040 having a third diameter D3. In order for the retention portion 7016 to fit within the renal pelvis 7112, the diameter D3 of the distal-most or third coil 7040 can be smaller than a diameter of either the first coil 7036 or the second coil 7038. Accordingly, a diameter of the coils 7036, 7038, 7040, and/or a step distance or height between adjacent coils 7036, 7038, 7040 can vary in a regular or irregular manner. In some examples, the plurality of coils 7036, 7038, 7040 can form a tapered or reverse pyramid shape in which D1>D2>D3. In some examples, the coiled retention portion 7016 can comprise a plurality of similarly sized coils or, for example, can include a plurality of proximal similarly sized coils and a distal-most coil having a smaller diameter than other coils of the plurality of coils.

The diameter of the coils 7036, 7038, 7040 and step distance or height between adjacent coils is selected so that the retention portion 7016 remains in the renal pelvis and/or kidney for a desired period of time. In particular, the coiled retention portion 7016 is desirably large enough so that it remains in the renal pelvis 7112 and does not pass either into the ureters or back into the kidney 7102 until the catheter 7010 is ready to be removed. For example, the outer diameter D1 of the proximal most or first coil 7036 can range from about 10 mm to about 30 mm, or about 15 mm to 25 mm, or be about 20 mm. The second coil 38 can have a diameter of about 5 mm to 25 mm, or about 10 mm to 20 mm, or can be about 15 mm. The distal-most or third coil 40 can have a diameter D3 ranging from about 1 mm to 20 mm, or about 5 mm to 15 mm, or can be about 10 mm.

Additional Exemplary Retention Portions

Figure 58A:
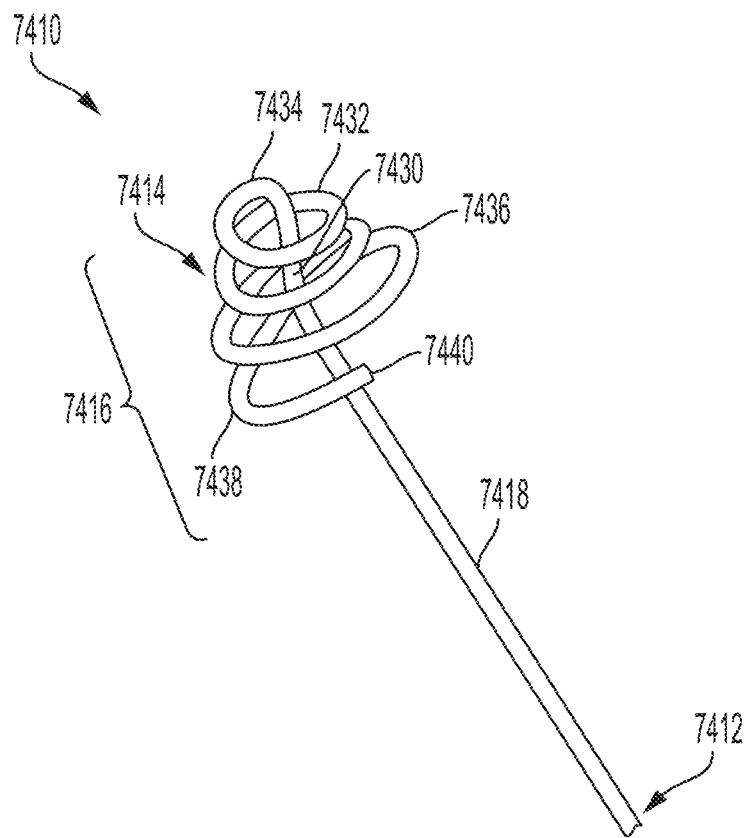
Figure 58B:
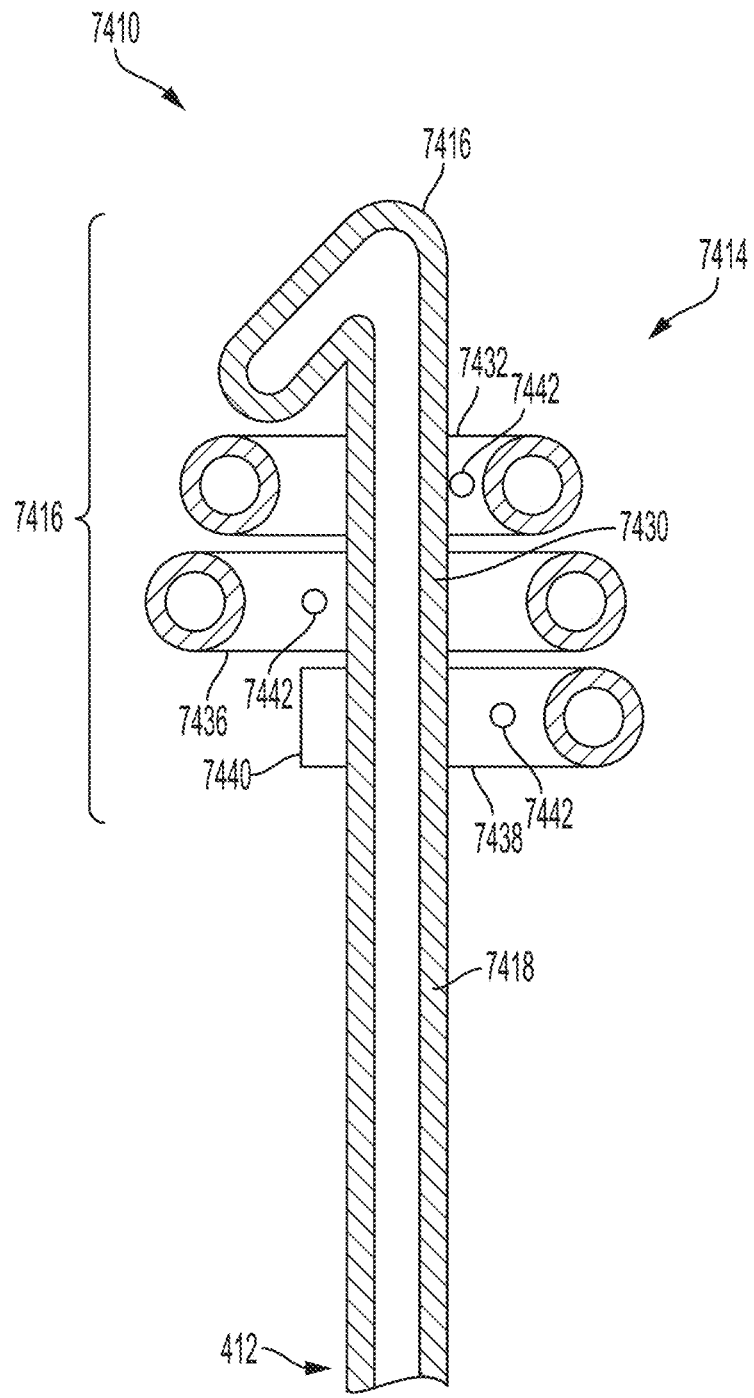

Another example of a ureteral catheter 7410 configured for percutaneous insertion into the renal pelvis of a patient is shown in FIGS. 58A and 58B. As in previous examples, the ureteral catheter 7410 is formed from an elongated tube 7418, and comprises a proximal portion 7412 and a distal portion 7414 comprising a retention portion 7416. The retention portion 7416 is a coiled retention portion comprising a plurality of coils wrapped around a substantially linear or straight segment or portion 7430 of the elongated tube 7418.

The coiled retention portion 416 further comprises a distal-most coil 7432 formed from a bend 7434 of from about 90 degrees to 180 degrees at a distal end of the straight segment or portion 7430 of the retention portion 7416. The retention portion 7416 further comprises one or more additional coils, such as a second or middle coil 7436 and a third or proximal most coil 7438, which are wrapped around the straight portion 7430 of the tube 7418. The elongated tube 7418 further comprises a distal end 7440 following the proximal most coil 7438. The distal end 7440 can be closed or can be open to receive urine from the patient's urinary tract.

As in previous examples, the size and orientation of the coils 7432, 7436, 7438 is selected so that the retention portion 7416 remains in the renal pelvis and does not pass into the ureter or retract back into the kidney. For example, the largest or proximal most coil 7438 can be about 10 mm to 30 mm in diameter, or about 15 mm to 25 mm in diameter, or about 20 mm in diameter. Coils 7436 and 7438 can have a smaller diameter of, for example, 5 mm to 25 mm, or about 10 mm to 20 mm, or about 15 mm. As in previous examples, the coiled retention portion 7416 can have a tapered appearance in which the coils 7432, 7436, 7438 become progressively narrower, giving the retention portion 7416 a reverse pyramid or reverse conical appearance.

Also as in previous examples, the retention portion 7416 further comprises openings or drainage ports 7442 positioned on a radially inward side or protected surface area of the coiled retention portion 7416. Since the coils 7432, 7436, 7438 extend around the straight portion 7430 and prevent tissue of the renal pelvis and/or kidneys from contacting the straight portion 7430, openings or drainage ports 7442 (shown in FIG. 54B) can also be positioned on the straight portion 7430 of the retention portion 7416. As in previous examples, the retention portion 7416 is inserted through the kidney and renal pelvis in a linear orientation over a guidewire. When the guidewire is removed, the retention portion 7416 adopts the coiled or deployed configuration.

Urine Collection System with Percutaneous Catheters

The urinary bypass catheter(s) 7010, 7410 can be used with systems for inducing negative pressure in a portion of a urinary tract 7100 of a patient. As shown in FIG. 55, an exemplary system 7200 comprises urinary bypass catheters 7010 deployed in the respective renal pelvis 7112 of each respective kidney 7102 of the patient. Proximal ends 7020 of the catheters 7010 are connected directly or indirectly to a pump 7210. For example, proximal ends 7020 of the catheters 7010 can be connected to fluid inflow ports of a rigid fluid collection container 7212. The pump 7210 can be connected to another port of the fluid collection container 7212 to induce negative pressure in the fluid collection container 7212 and catheters 7010 connected thereto. The pump 7210 can be similar to pumps in previously described examples and, particularly, can be configured to deliver gentle negative pressure to the urinary tract 7100 of the patient. The pump 7210 can be an external pump. In other examples, the pump 7210 can be an indwelling pump as described, for example, in PCT Appl. No. PCT/IB2018/056444 to Orr et al., entitled "Indwelling Pump for Facilitating Removal of Urine from the Urinary Tract." Generally, the applied negative pressure is a gentle negative pressure, such as a negative pressure of less than 50 mmHg. In other examples, negative pressure can be from 2 mmHg to 100 mmHg, or more, depending on therapeutic requirements of particular patients. The pump 7210 desirably has a sensitivity of 10 mmHg or less.

In some examples, the system 7200 further comprises a bladder catheter 7216 deployed within the patient's bladder 7104. The bladder catheter 7216 can be any suitable bladder catheter, as described in previous examples. The bladder catheter 7216 comprises an elongated tube 7218 comprising a proximal portion 7220, which extends through the urethra 7106 and from the patient. A proximal end 7222 of the proximal portion 7220 of the bladder catheter 7216 can be connected to the fluid collection container 7212. In other examples, the bladder catheter 7216 can be connected to a separate fluid collection container 7224, which is not connected to a pump 7210 for inducing negative pressure. In that case, fluid may pass from the patient's bladder 7104 through the bladder catheter 7216 by gravity.

In some examples, the system 7200 further comprises a controller 7214 electrically connected to the pump 7210 configured to actuate the pump 7210 and to control pump operating parameters. As in previous examples, the controller 7214 can be a microprocessor of the pump 7210 or a separate electronic device configured to provide operating instructions and/or operating parameters for the pump 7210. For example, the controller 7214 can be associated with a computer, laptop, tablet, smartphone, or similar electronic device.

The system can further comprise one or more physiological sensors 7226 associated with the patient, fluid collection container 7212, or catheter(s) 710, 7216. The physiological sensors 7226 can be configured to provide information representative of at least one physical parameter of the patient to the controller 7214. In that case, the controller 7214 can be configured to actuate or stop operation of the pump based on the at least one physical parameter.

Deployment Methods

Figure 56:
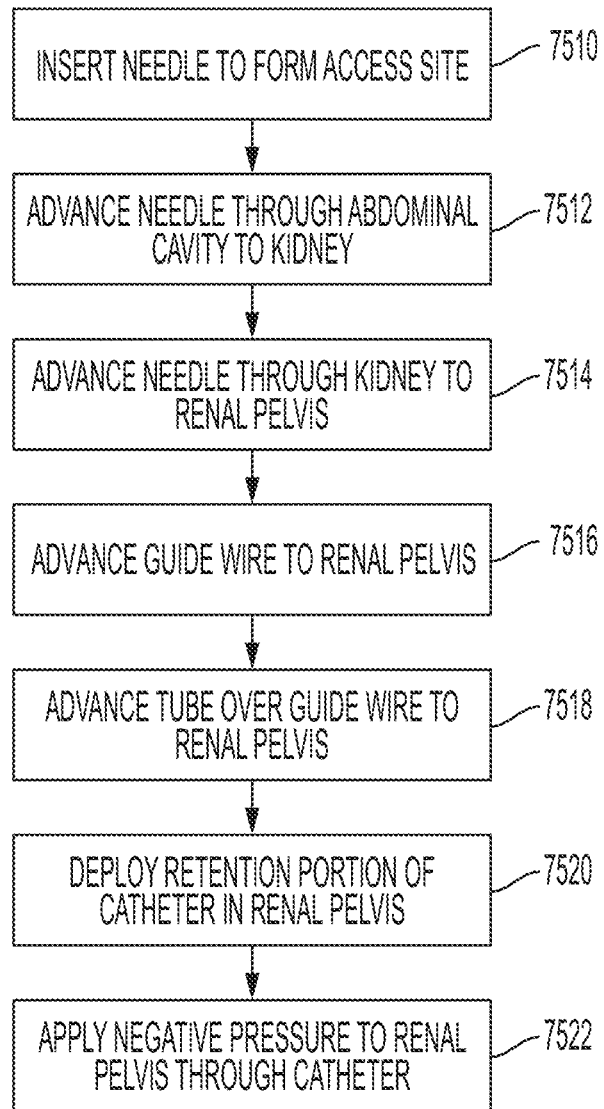

Having described aspects of a urinary bypass catheter 7010 and system 7200 for applying negative pressure to a patient, a method for insertion and/or deployment of the urinary bypass catheter will now be described in connection with the flow chart of FIG. 56. Schematic drawings showing different aspects of the catheter deployment method are shown in FIGS. 57A-57E. Initially, at box 7510, a needle 7312 (shown in FIGS. 57A-57C) of a conical tip catheter 7310 (shown in FIGS. 57A-57E) is inserted into an abdominal region of the patient, thereby creating a percutaneous access site. The catheter 7310 and needle 7312 should be of sufficient size to permit the urinary bypass catheter to pass through the catheter 7310. For example, the catheter 7310 can be about 3 Fr to about 10 Fr (French catheter scale), or from about 5 Fr to about 8 Fr, or about 6 Fr. In some examples, the catheter 7310 can have an external diameter ranging from about 0.5 mm to about 4 mm, and an internal diameter ranging from about 0.2 mm to about 3.5 mm. The needle 7312 can be from about 10 gauge to 30 gauge, or about 20 gauge to 25 gauge, and can have an outer diameter of from 0.3 mm to 3.5 mm, or about 0.5 mm to 1.0 mm. The needle 7312 can be any suitable length, such as from 10 mm to 50 mm, or about 30 mm.

Once the needle 7312 is inserted through the patient's skin, at 7512, the needle 7312 is advanced through the abdominal cavity and inserted into the kidney 7102. At 7514, the needle 7312 is advanced through the kidney 7102 and into the renal pelvis 7112, as shown in FIG. 57B. Once the needle 7312 is advanced to the renal pelvis 7112, at box 7516, a guidewire 7314 can be advanced to the renal pelvis 7112 through the needle 7312, as shown in FIG. 57C. Once the guidewire 7314 is in position, the needle 7312 can be retracted back through the catheter 7310. Next, at 7518, an elongated tube 7318 of the catheter 7310 can be inserted into the patient's abdominal cavity through the percutaneous access site and advanced to the renal pelvis over a guidewire 7314 and/or needle 7312, as shown in FIG. 57D. At 7520, once a distal end 7320 and retention portion 7322 of the elongated tube 7318 reach the renal pelvis, the retention portion 7322 can transition from its retracted state to the expanded or deployed state, as shown in FIG. 57E. As described herein, desirably, when deployed in the renal pelvis 7112, the retention portion 7322 maintains patency of fluid flow from the kidney 7102 into a lumen extending through at least a portion of the elongated tube 7318.

In some examples, deploying the retention portion 7322 can comprise retracting an outer tube or sheath in a proximal direction away from the retention portion 7322. Once the outer tube or sheath is removed, the retention portion 7322 automatically expands and returns to an unconstrained shape. In other examples, such as when the retention portion 7322 comprises a coiled retention portion, retracting the guidewire 7314 causes the retention portion 7322 to adopt the coiled or deployed configuration. Deploying the retention portion can also comprise, for example, blowing up a balloon or releasing a cage-like structure to protect the distal end of the elongated tube 7318.

In some examples, as shown in box 7522, negative pressure can be applied to the renal pelvis by attaching a proximal end of the elongated tube 7318 directly or indirectly to a fluid pump and actuating the pump to generate the negative pressure. For example, negative pressure can be applied continuously for a predetermined period of time. In other examples, negative pressure can be applied as pressure pulses provided for short duration at predetermined intervals. In some examples, the pump can alternate between providing negative pressure and positive pressure. It is believed that such alternating pressure therapy may further stimulate the kidneys resulting in increased urine production. In other examples, as described in greater detail above, negative pressure may be delivered to the renal pelvis through the elongated tube 7318 due to a pressure distribution or pressure gradient induced in the tube 7318, but without use of a pump or negative pressure source. For example, negative pressure sufficient to draw fluid, such as urine, into the tube 7318 may be created in distal portions of the tube 7318 in response to fluid flow through the tube 7318 by gravity. While not intending to be bound by theory, it is believed that the generated suction force is dependent on a vertical distance between the retention portion of the catheter and the proximal end of the catheter. Accordingly, the created negative pressure can be increased by increasing the vertical distance between the retention portion of the deployed catheter and the fluid collection container and/or proximal end of the catheter.

Exemplary Treatment Methods for Removing Excess Fluid

Figure 49:
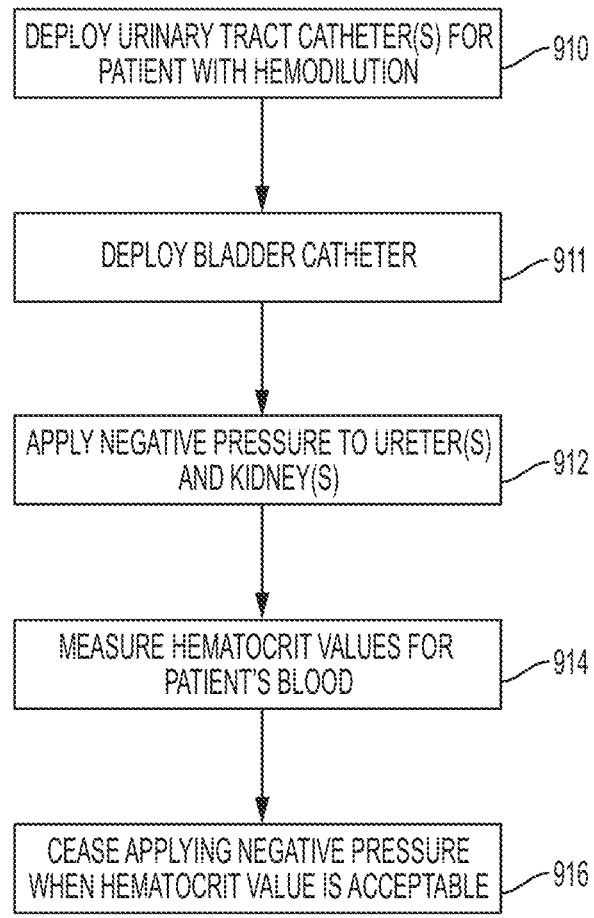
FIG. 49 is a flow chart illustrating a process for reducing creatinine and/or protein levels of a patient according to an example of the present invention.

Steps for removing excess fluid from a patient using the devices and systems described herein are illustrated in FIG. 49. As shown in FIG. 49, the treatment method comprises deploying a ureteral stent or a urinary tract catheter, such as a ureteral catheter, in the ureter and/or kidney of a patient such that flow of urine from the ureter and/or kidney, as shown at box 910. The catheter may be placed to avoid occluding the ureter and/or kidney. In some examples, a fluid collecting portion of the stent or catheter may be positioned in the renal pelvis of the patient's kidney. In some examples, a ureteral stent or ureteral catheter may be positioned in each of the patient's kidneys. In other examples, a urine collection catheter may be deployed in the bladder or ureter, as shown in box 911. In some examples, the ureteral catheter comprises one or more of any of the retention portions described herein. For example, the ureteral catheter can comprise a tube defining a drainage lumen comprising a helical retention portion and a plurality of drainage ports. In other examples, the catheter can include a funnel-shaped fluid collection and retention portion or a pigtail coil. Alternatively, a ureteral stent, having, for example, a pigtail coil, can be deployed.

As shown at box 912, the method further comprises applying negative pressure to at least one of the bladder, the ureter and/or kidney through the bladder catheter to induce or facilitate production of fluid or urine in the kidney(s) and to extract the fluid or urine from the patient. Desirably, negative pressure is applied for a period of time sufficient to reduce the patient's blood creatinine levels by a clinically significant amount.

Negative pressure may continue to be applied for a predetermined period of time. For example, a user may be instructed to operate the pump for the duration of a surgical procedure or for a time period selected based on physiological characteristics of the patient. In other examples, patient condition may be monitored to determine when sufficient treatment has been provided. For example, as shown at box 914, the method may further comprise monitoring the patient to determine when to cease applying negative pressure to the patient's bladder, ureter and/or kidneys. In some examples, a patient's hematocrit level is measured. For example, patient monitoring devices may be used to periodically obtain hematocrit values. In other examples, blood samples may be drawn periodically to directly measure hematocrit. In some examples, concentration and/or volume of urine expelled from the body through the bladder catheter may be monitored to determine a rate at which urine is being produced by the kidneys. In a similar manner, expelled urine output may be monitored to determine protein concentration and/or creatinine clearance rate for the patient. Reduced creatinine and protein concentration in urine may be indicative of over-dilution and/or depressed renal function. Measured values can be compared to the predetermined threshold values to assess whether negative pressure therapy is improving patient condition, and should be modified or discontinued. For example, as discussed herein, a desirable range for patient hematocrit may be between 25% and 40%. In other examples, as described herein, patient body weight may be measured and compared to a dry body weight. Changes in measured patient body weight demonstrate that fluid is being removed from the body. As such, a return to dry body weight represents that hemodilution has been appropriately managed and the patient is not over-diluted.

As shown at box 916, a user may cause the pump to cease providing negative pressure therapy when a positive result is identified. In a similar manner, patient blood parameters may be monitored to assess effectiveness of the negative pressure being applied to the patient's kidneys. For example, a capacitance or analyte sensor may be placed in fluid communication with tubing of an extracorporeal blood management system. The sensor may be used to measure information representative of blood protein, oxygen, creatinine, and/or hematocrit levels. Measured blood parameter values may be measured continuously or periodically and compared to various threshold or clinically acceptable values. Negative pressure may continue to be applied to the patient's bladder, kidney or ureter until a measured parameter value falls within a clinically acceptable range. Once a measured values fails within the threshold or clinically acceptable range, as shown at box 916, application of negative pressure may cease.

In some examples, there is provided a method of removing excess fluid from a patient for systemic fluid volume management associated with chronic edematous, hypertension, chronic kidney disease and/or acute heart failure. According to another aspect of the disclosure, a method for removing excess fluid for a patient undergoing a fluid resuscitation procedure, such as coronary graft bypass surgery, by removing excess fluid from the patient is provided. During fluid resuscitation, solutions such as saline solutions and/or starch solutions, are introduced to the patient's bloodstream by a suitable fluid delivery process, such as an intravenous drip. For example, in some surgical procedures, a patient may be supplied with between 5 and 10 times a normal daily intake of fluid. Fluid replacement or fluid resuscitation can be provided to replace bodily fluids lost through sweating, bleeding, dehydration, and similar processes. In the case of a surgical procedure such as coronary graft bypass, fluid resuscitation is provided to help maintain a patient's fluid balance and blood pressure within an appropriate rate. Acute kidney injury (AKI) is a known complication of coronary artery graft bypass surgery. AKI is associated with a prolonged hospital stay and increased morbidity and mortality, even for patients who do not progress to renal failure. See Kim, et al., Relationship between a perioperative intravenous fluid administration strategy and acute kidney injury following off-pump coronary artery bypass surgery: an observational study, *Critical Care* 19:350 (1995). Introducing fluid to blood also reduces hematocrit levels which has been shown to further increase mortality and morbidity. Research has also demonstrated that introducing saline solution to a patient may depress renal functional and/or inhibit natural fluid management processes. As such, appropriate monitoring and control of renal function may produce improved outcomes and, in particular, may reduce post-operative instances of AKI.

Figure 50:
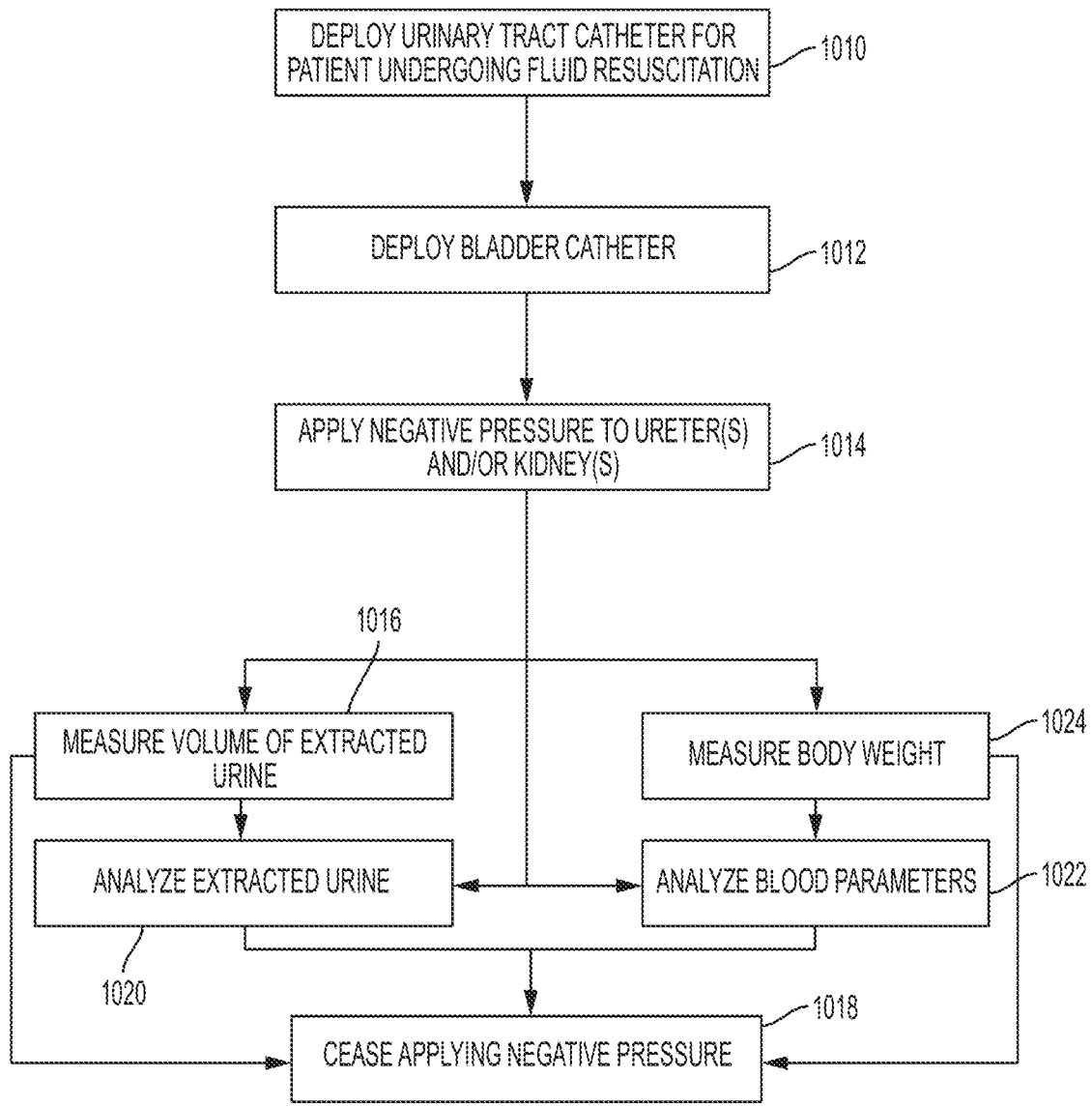
FIG. 50 is a flow chart illustrating a process for treating a patient undergoing fluid resuscitation according to an example of the present invention.
Figure 51:
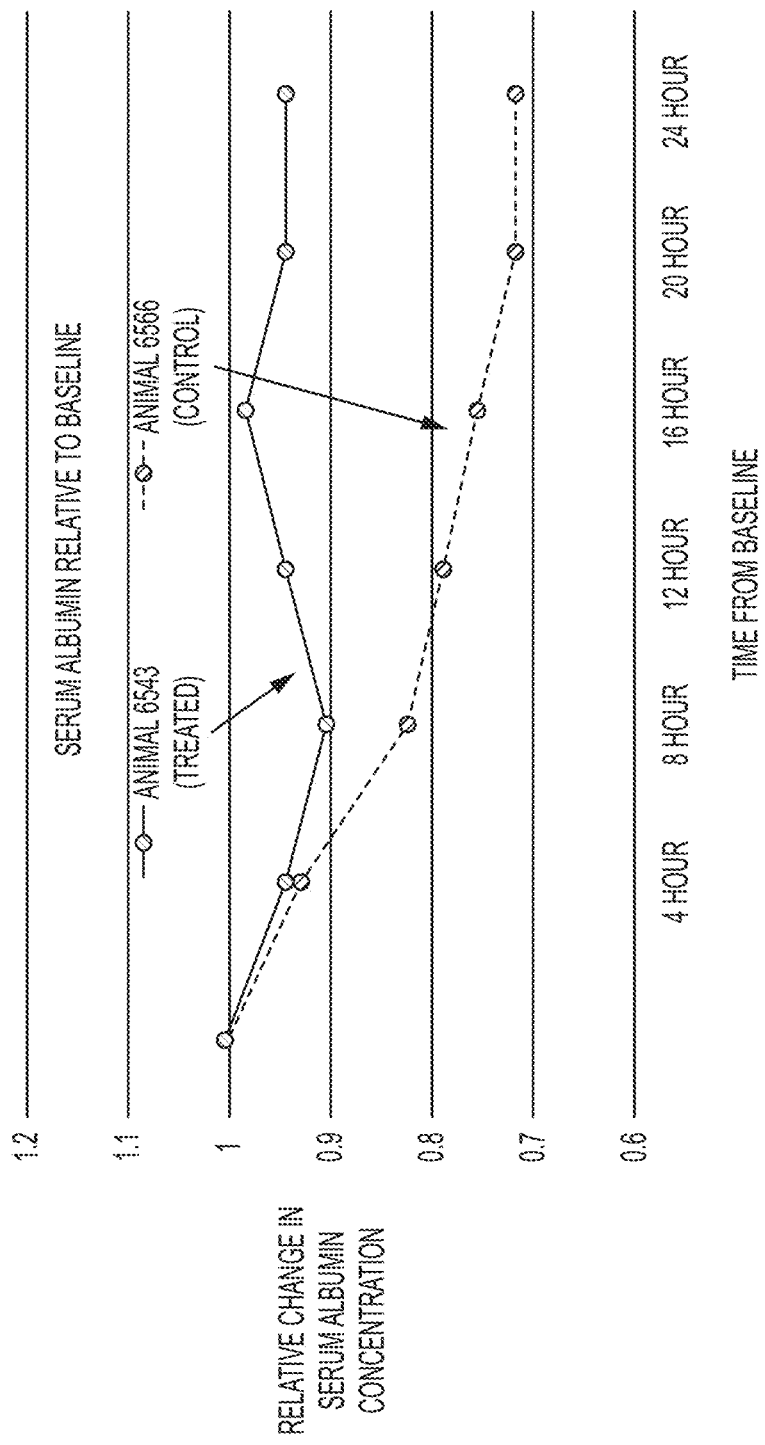
FIG. 51 is a graph of serum albumin relative to baseline for tests conduct on swine using the experimental method described herein.
Figure 52A:
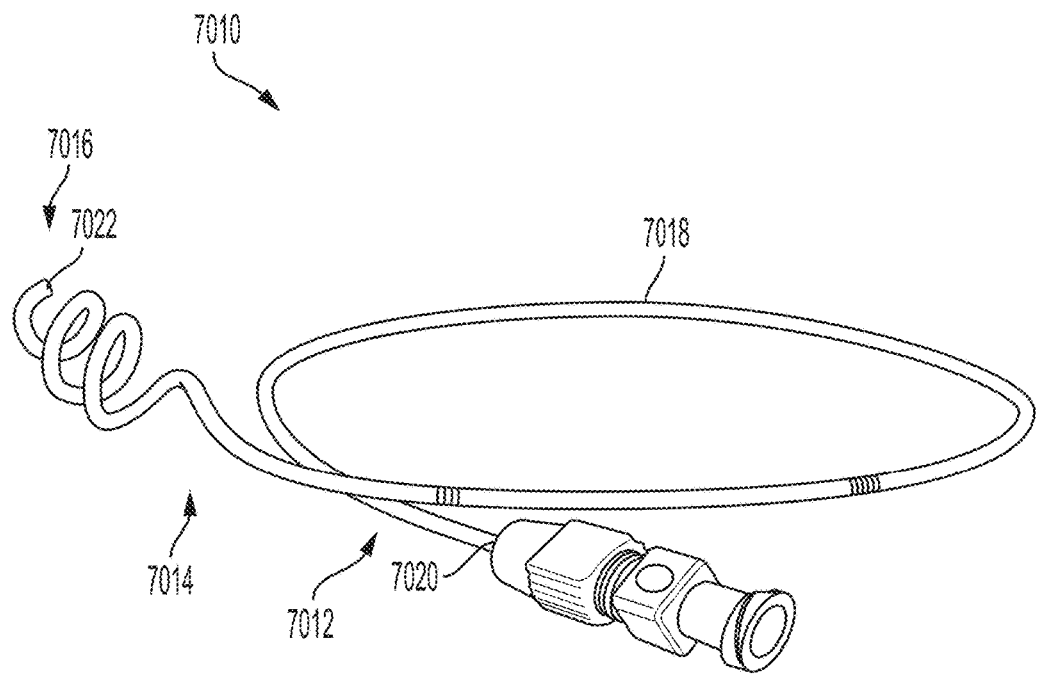
FIG. 52A is a perspective view of a catheter configured to be inserted to the renal pelvis through a percutaneous access site.
Figure 52B:
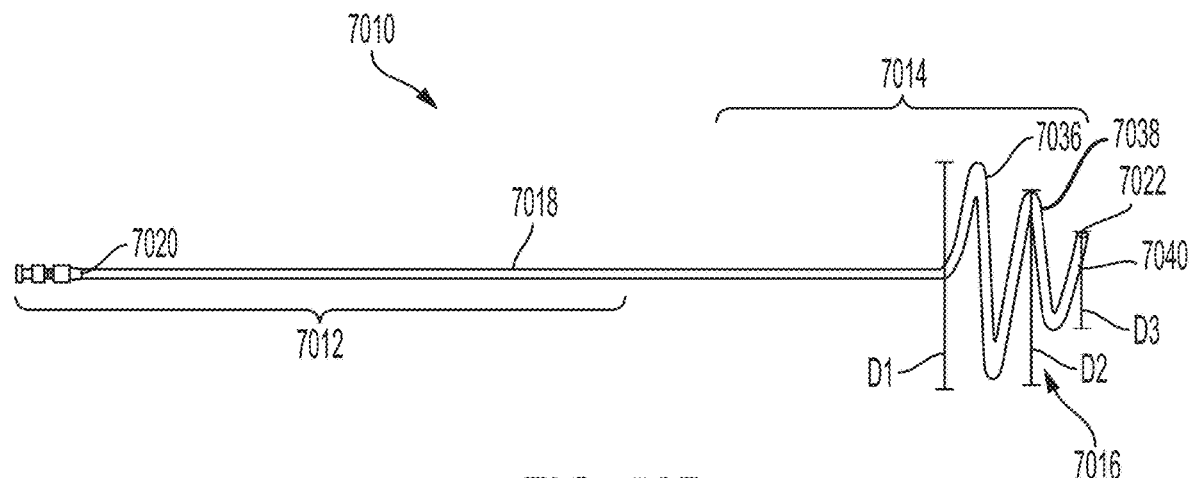
FIG. 52B is a side view of the catheter of FIG. 52A.
Figure 53:
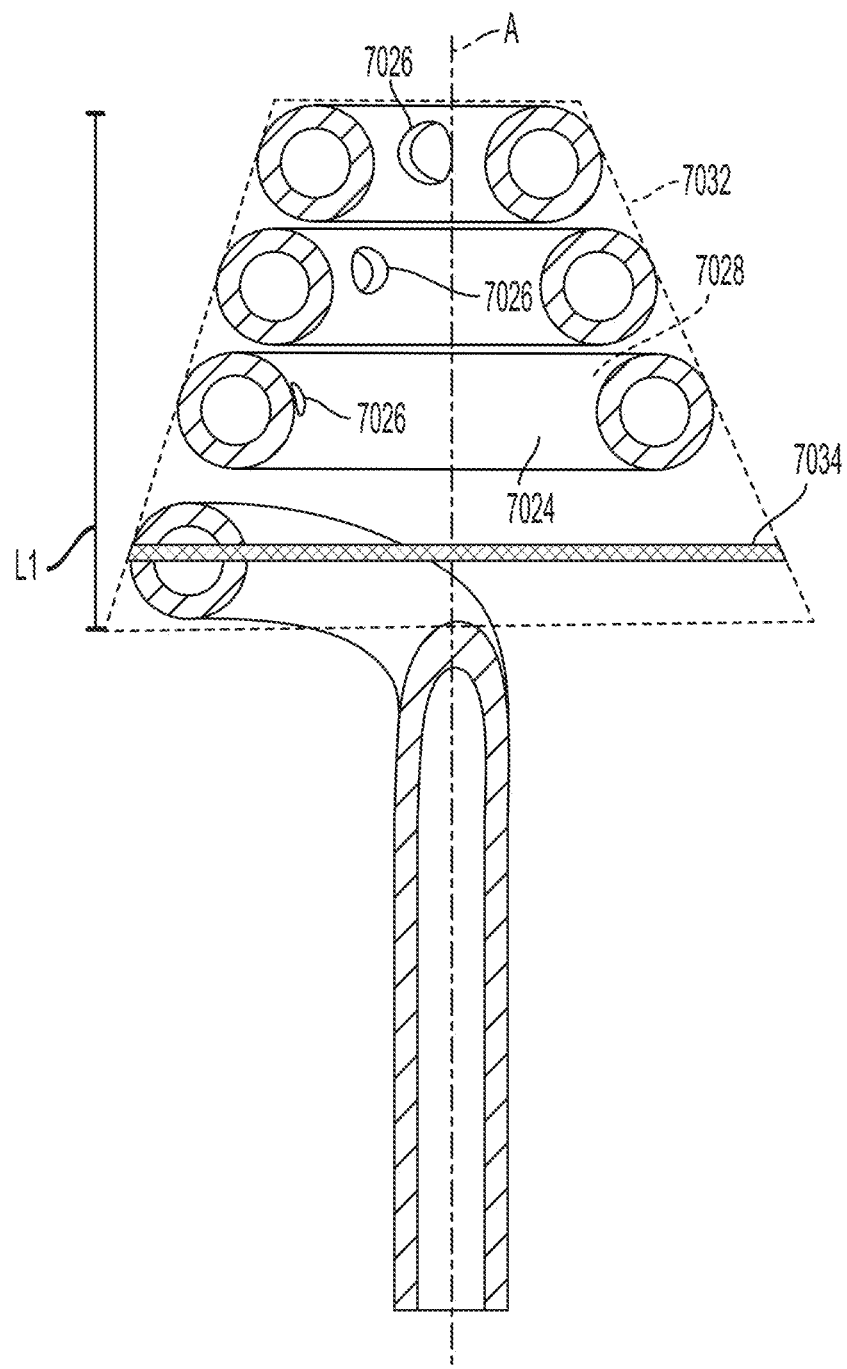
Figure 54:
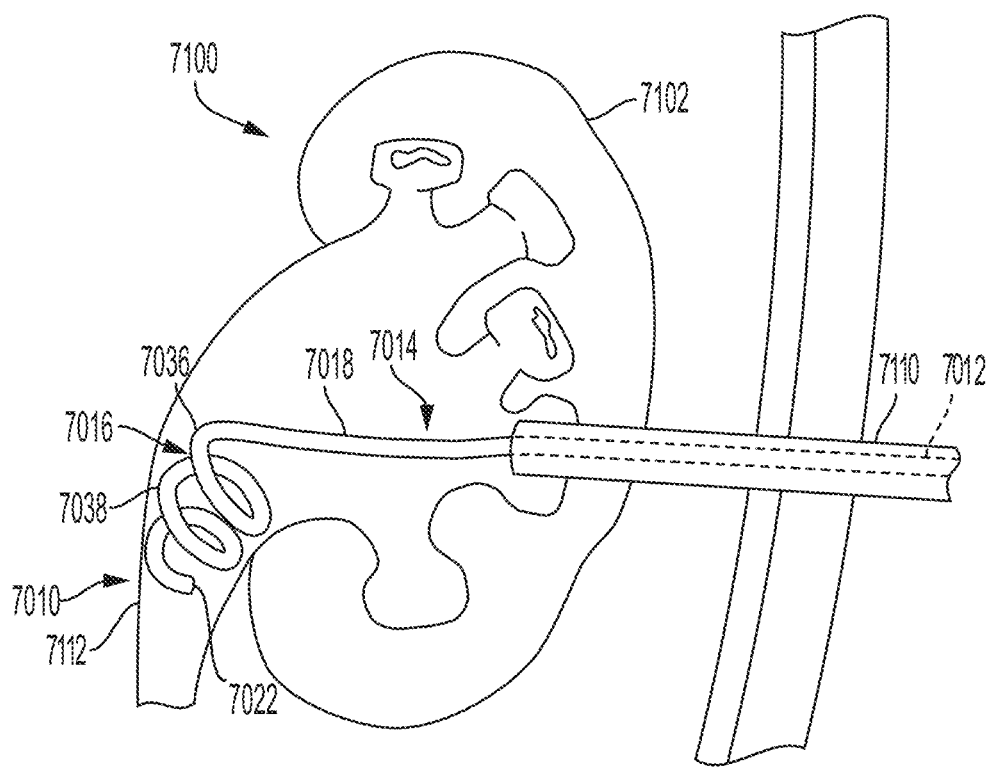

A method of treating a patient for removing excess fluid is illustrated in FIG. 50. As shown at box 1010, the method comprises deploying a ureteral stent or ureteral catheter in the ureter and/or kidney of a patient such that flow of urine from the ureter and/or kidney is not prevented by occlusion of the ureter and/or kidney. For example, a distal end of the ureteral stent or fluid collecting portion of the catheter may be positioned in the renal pelvis. In other examples, the catheter may be deployed in the kidney or ureter. The catheter can comprise one or more of the ureter catheters described herein. For example, the catheter can comprise a tube defining a drainage lumen and comprising a helical retention portion and a plurality of drainage ports. In other examples, the catheter can include a pigtail coil.

As shown at box 1012, a bladder catheter can be deployed in the patient's bladder. For example, the bladder catheter may be positioned to at least partially seal the urethra opening to prevent passage of urine from the body through the urethra. The bladder catheter can, for example, include an anchor for maintaining the distal end of the catheter in the bladder. As described herein, other arrangements of coils and helices, funnel, etc. may be used to obtain proper positioning of the bladder catheter. The bladder catheter can be configured to collect fluid which entered the patient's bladder prior to placement of the ureteral catheter(s), as well as fluid collected from the ureters, ureteral stents, and/or ureteral catheters during treatment. The bladder catheter may also collect urine which flows past the fluid collection portion(s) of the ureteral catheter and enters the bladder. In some examples, a proximal portion of the ureteral catheter may be positioned in a drainage lumen of the bladder catheter. In a similar manner, the bladder catheter may be advanced into the bladder using the same guidewire used for positioning of the ureteral catheter(s). In some examples, negative pressure may be provided to the bladder through the drainage lumen of the bladder catheter. In other examples, negative pressure may only be applied to the bladder catheter(s). In that case, the ureteral catheter drains into the bladder by gravity.

As shown at box 1014, following deployment of the ureteral stents and/or ureteral catheter(s) and the bladder catheter, negative pressure is applied to the bladder, ureter and/or kidney through the bladder catheter. For example, negative pressure can be applied for a period of time sufficient to extract urine comprising a portion of the fluid provided to the patient during the fluid resuscitation procedure. As described herein, negative pressure can be provided by an external pump connected to a proximal end or port of the bladder catheter. The pump can be operated continually or periodically dependent on therapeutic requirements of the patient. In some cases, the pump may alternate between applying negative pressure and positive pressure.

Negative pressure may continue to be applied for a predetermined period of time. For example, a user may be instructed to operate the pump for the duration of a surgical procedure or for a time period selected based on physiological characteristics of the patient. In other examples, patient condition may be monitored to determine when a sufficient amount of fluid has been drawn from the patient. For example, as shown at box 1016, fluid expelled from the body may be collected and a total volume of obtained fluid may be monitored. In that case, the pump can continue to operate until a predetermined fluid volume has been collected from the ureteral and/or bladder catheters. The predetermined fluid volume may be based, for example, on a volume of fluid provided to the patient prior to and during the surgical procedure. As shown at box 1018, application of negative pressure to the bladder, ureter and/or kidneys is stopped when the collected total volume of fluid exceeds the predetermined fluid volume.

In other examples, operation of the pump can be determined based on measured physiological parameters of the patient, such as measured creatinine clearance, blood creatinine level, or hematocrit ratio. For example, as shown at box 1020, urine collected form the patient may be analyzed by one or more sensors associated with the catheter and/or pump. The sensor can be a capacitance sensor, analyte sensor, optical sensor, or similar device configured to measure urine analyte concentration. In a similar manner, as shown at box 1022, a patient's blood creatinine or hematocrit level could be analyzed based on information obtain from the patient monitoring sensors discussed hereinabove. For example, a capacitance sensor may be placed in an existing extracorporeal blood system. Information obtained by the capacitance sensor may be analyzed to determine a patient's hematocrit ratio. The measured hematocrit ratio may be compared to certain expected or therapeutically acceptable values. The pump may continue to apply negative pressure to the patient's ureter and/or kidney until measured values within the therapeutically acceptable range are obtained. Once a therapeutically acceptable value is obtained, application of negative pressure may be stopped as shown at box 1018.

In other examples, as shown at box 2024, patient body weight may be measured to assess whether fluid is being removed from the patient by the applied negative pressure therapy. For example, a patient's measured bodyweight (including fluid introduced during a fluid resuscitation procedure) can be compared to a patient's dry body weight. As used herein, dry weights is defined as normal body weight measured when a patient is not over-diluted. For example, a patient who is not experiencing one or more of: elevated blood pressure, lightheadedness or cramping, swelling of legs, feet, arms, hands, or around the eyes, and who is breathing comfortably, likely does not have excess fluid. A weight measured when the patient is not experiencing such symptoms can be a dry body weight. Patient weight can be measured periodically until the measured weight approaches the dry body weight. When the measured weight approaches (e.g., is within between 5% and 10% of dry body weight), as shown at box 1018, application of negative pressure can be stopped.

The aforementioned details of treatment using the systems of the present invention can be used to treat a variety of conditions that can benefit from increased urine or fluid output or removal. For example, a method for preserving renal function by application of negative pressure to decrease interstitial pressure within tubules of the medullar region to facilitate urine output and to prevent venous congestion-induced nephron hypoxia in the medulla of the kidney is provided. The method comprises: deploying a ureteral stent or ureteral catheter into a ureter or kidney of a patient to maintain patency of fluid flow between a kidney and a bladder of the patient; deploying a bladder catheter into the bladder of the patient, wherein the bladder catheter comprises a distal end configured to be positioned in a patient's bladder, a drainage lumen portion having a proximal end, and a sidewall extending therebetween; and applying negative pressure to the proximal end of the catheter to induce negative pressure in a portion of the urinary tract of the patient for a predetermined period of time to remove fluid from the urinary tract of the patient.

In another example, a method for treatment of acute kidney injury due to venous congestion is provided. The method comprises: deploying a ureteral stent or ureteral catheter into a ureter or kidney of a patient to maintain patency of fluid flow between a kidney and a bladder of the patient; deploying a bladder catheter into the bladder of the patient, wherein the bladder catheter comprises a distal end configured to be positioned in a patient's bladder, a drainage lumen portion having a proximal end, and a sidewall extending therebetween; and applying negative pressure to the proximal end of the catheter to induce negative pressure in a portion of the urinary tract of the patient for a predetermined period of time to remove fluid from the urinary tract of the patient, thereby reducing venous congestion in the kidney to treat acute kidney injury.

In another example, a method for treatment of New York Heart Association (NYHA) Class III and/or Class IV heart failure through reduction of venous congestion in the kidney(s) is provided. The method comprises: deploying a ureteral stent or ureteral catheter into a ureter or kidney of a patient to maintain patency of fluid flow between a kidney and a bladder of the patient; deploying a bladder catheter into the bladder of the patient, wherein the bladder catheter comprises a distal end configured to be positioned in a patient's bladder, a drainage lumen portion having a proximal end, and a sidewall extending therebetween; and applying negative pressure to the proximal end of the catheter to induce negative pressure in a portion of the urinary tract of the patient for a predetermined period of time to remove fluid from the urinary tract of the patient to treat volume overload in NYHA Class III and/or Class IV heart failure.

In another example, a method for treatment of Stage 4 and/or Stage 5 chronic kidney disease through reduction of venous congestion in the kidney(s) is provided. The method comprises: deploying a ureteral stent or ureteral catheter into a ureter or kidney of a patient to maintain patency of fluid flow between a kidney and a bladder of the patient; deploying a bladder catheter into the bladder of the patient, wherein the bladder catheter comprises a distal end configured to be positioned in a patient's bladder, a drainage lumen portion having a proximal end, and a sidewall extending therebetween; and applying negative pressure to the proximal end of the catheter to induce negative pressure in a portion of the urinary tract of the patient to remove fluid from the urinary tract of the patient to reduce venous congestion in the kidney(s).

In some examples, a kit is provided for removing fluid from the urinary tract of a patient and/or inducing negative pressure in a portion of a urinary tract of a patient. The kit comprises: a ureteral stent or ureteral catheter comprising a drainage channel for facilitating flow of fluid from the ureter and/or kidney through the drainage channel of the ureteral stent or ureteral catheter towards the bladder of the patient; and a pump comprising a controller configured to induce a negative pressure in at least one of the ureter, kidney or bladder of the patient to draw urine through a drainage lumen of a catheter deployed in the patient's bladder. In some examples, the kit further comprises at least one bladder catheter. In some examples, the kit further comprises instructions for one or more of the following: inserting/deploying the ureteral stent(s) and/or ureteral catheter(s), inserting/deploying the bladder catheter, and operating the pump to draw urine through a drainage lumen of the bladder catheter deployed the patient's bladder.

In some examples, another kit comprises: a plurality of disposable bladder catheters, each bladder catheter comprising a drainage lumen portion having a proximal end, a distal end configured to be positioned in a patient's bladder, and a sidewall extending therebetween; and a retention portion extending radially outward from a portion of the distal end of the drainage lumen portion, and being configured to be extended into a deployed position in which a diameter of the retention portion is greater than a diameter of the drainage lumen portion; instructions for inserting/deploying the bladder catheter; and instructions for connecting the proximal end of the bladder catheter to a pump and for operating the pump to draw urine through the drainage lumen of the bladder catheter, for example by applying negative pressure to the proximal end of the bladder catheter.

In some examples, a kit is provided, the kit comprising: a plurality of disposable bladder catheters, each bladder catheter comprising (a) a proximal portion; and (b) a distal portion, the distal portion comprising a retention portion that comprises one or more protected drainage holes, ports or perforations and is configured to establish an outer periphery or protective surface area that inhibits mucosal tissue from occluding the one or more protected drainage holes, ports or perforations upon application of negative pressure through the catheter; instructions for deploying the bladder catheter; and instructions for connecting the proximal end of the bladder catheter to a pump and for operating the pump to draw urine through the drainage lumen of the bladder catheter.

Experimental Examples of Inducing Negative Pressure Using Ureteral Catheters:

Inducement of negative pressure within the renal pelvis of farm swine was performed for the purpose of evaluating effects of negative pressure therapy on renal congestion in the kidney. An objective of these studies was to demonstrate whether a negative pressure delivered into the renal pelvis significantly increases urine output in a swine model of renal congestion. In Example 1, a pediatric Fogarty catheter, normally used in embolectomy or bronchoscopy applications, was used in the swine model solely for proof of principle for inducement of negative pressure in the renal pelvis. It is not suggested that a Fogarty catheter be used in humans in clinical settings to avoid injury of urinary tract tissues. In Example 2, the ureteral catheter 112 shown in FIGS. 2A and 2B, and including a helical retention portion for mounting or maintaining a distal portion of the catheter in the renal pelvis or kidney, was used.

Example 1

Method

Four farm swine 800 were used for purposes of evaluating effects of negative pressure therapy on renal congestion in the kidney. As shown in FIG. 21, pediatric Fogarty catheters 812, 814 were inserted to the renal pelvis region 820, 821 of each kidney 802, 804 of the four swine 800. The catheters 812, 814 were deployed within the renal pelvis region by inflating an expandable balloon to a size sufficient to seal the renal pelvis and to maintain the position of the balloon within the renal pelvis. The catheters 812, 814 extend from the renal pelvis 802, 804, through a bladder 810 and urethra 816, and to fluid collection containers external to the swine.

Urine output of two animals was collected for a 15 minute period to establish a baseline for urine output volume and rate. Urine output of the right kidney 802 and the left kidney 804 were measured individually and found to vary considerably. Creatinine clearance values were also determined.

Renal congestion (e.g., congestion or reduced blood flow in the veins of the kidney) was induced in the right kidney 802 and the left kidney 804 of the animal 800 by partially occluding the inferior vena cava (IVC) with an inflatable balloon catheter 850 just above to the renal vein outflow. Pressure sensors were used to measure IVC pressure. Normal IVC pressures were 1-4 mmHg. By inflating the balloon of the catheter 850 to approximately three quarters of the IVC diameter, the IVC pressures were elevated to between 15-25 mmHg. Inflation of the balloon to approximately three quarters of IVC diameter resulted in a 50-85% reduction in urine output. Full occlusion generated IVC pressures above 28 mmHg and was associated with at least a 95% reduction in urine output.

One kidney of each animal 800 was not treated and served as a control ("the control kidney 802"). The ureteral catheter 812 extending from the control kidney was connected to a fluid collection container 819 for determining fluid levels. One kidney ("the treated kidney 804") of each animal was treated with negative pressure from a negative pressure source (e.g., a therapy pump 818 in combination with a regulator designed to more accurately control the low magnitude of negative pressures) connected to the ureteral catheter 814. The pump 818 was an Air Cadet Vacuum Pump from Cole-Parmer Instrument Company (Model No. EW-07530-85). The pump 818 was connected in series to the regulator. The regulator was an V-800 Series Miniature Precision Vacuum Regulator—⅛ NPT Ports (Model No. V-800-10-W/K), manufactured by Airtrol Components Inc.

The pump 818 was actuated to induce negative pressure within the renal pelvis 820, 821 of the treated kidney according to the following protocol. First, the effect of negative pressure was investigated in the normal state (e.g., without inflating the IVC balloon). Four different pressure levels (−2, −10, −15, and −20 mmHg) were applied for 15 minutes each and the rate of urine produced and creatinine clearance were determined. Pressure levels were controlled and determined at the regulator. Following the −20 mmHg therapy, the IVC balloon was inflated to increase the pressure by 15-20 mmHg. The same four negative pressure levels were applied. Urine output rate and creatinine clearance rate for the congested control kidney 802 and treated kidney 804 were obtained. The animals 800 were subject to congestion by partial occlusion of the IVC for 90 minutes. Treatment was provided for 60 minutes of the 90 minute congestion period.

Following collection of urine output and creatinine clearance data, kidneys from one animal were subjected to gross examination then fixed in a 10% neutral buffered formalin. Following gross examination, histological sections were obtained, examined, and magnified images of the sections were captured. The sections were examined using an upright Olympus BX41 light microscope and images were captured using an Olympus DP25 digital camera. Specifically, photomicrograph images of the sampled tissues were obtained at low magnification (20× original magnification) and high magnification (100× original magnification). The obtained images were subjected to histological evaluation. The purpose of the evaluation was to examine the tissue histologically and to qualitatively characterize congestion and tubular degeneration for the obtained samples.

Surface mapping analysis was also performed on obtained slides of the kidney tissue. Specifically, the samples were stained and analyzed to evaluate differences in size of tubules for treated and untreated kidneys. Image processing techniques calculated a number and/or relative percentage of pixels with different coloration in the stained images. Calculated measurement data was used to determine volumes of different anatomical structures.

Results

Urine Output and Creatinine Clearance

Urine output rates were highly variable. Three sources of variation in urine output rate were observed during the study. The inter-individual and hemodynamic variability were anticipated sources of variability known in the art. A third source of variation in urine output, upon information and belief believed to be previously unknown, was identified in the experiments discussed herein, namely, contralateral intra-individual variability in urine output.

Baseline urine output rates were 0.79 ml/min for one kidney and 1.07 ml/min for the other kidney (e.g., a 26% difference). The urine output rate is a mean rate calculated from urine output rates for each animal.

When congestion was provided by inflating the IVC balloon, the treated kidney urine output dropped from 0.79 ml/min to 0.12 ml/min (15.2% of baseline). In comparison, the control kidney urine output rate during congestion dropped from 1.07 ml/min to 0.09 ml/min (8.4% of baseline). Based on urine output rates, a relative increase in treated kidney urine output compared to control kidney urine output was calculated, according to the following equation:

(Therapy Treated/Baseline Treated)/(Therapy Control/Baseline Control)=Relative increase (0.12 ml/min/0.79 ml/min)/(0.09 ml/min/1.07 ml/min)=180.6%

Thus, the relative increase in treated kidney urine output rate was 180.6% compared to control. This result shows a greater magnitude of decrease in urine production caused by congestion on the control side when compared to the treatment side. Presenting results as a relative percentage difference in urine output adjusts for differences in urine output between kidneys.

Creatinine clearance measurements for baseline, congested, and treated portions for one of the animals are shown in FIG. 22.

Gross Examination and Histological Evaluation

Based on gross examination of the control kidney (right kidney) and treated kidney (left kidney), it was determined that the control kidney had a uniformly dark red-brown color, which corresponds with more congestion in the control kidney compared to the treated kidney. Qualitative evaluation of the magnified section images also noted increased congestion in the control kidney compared to the treated kidney. Specifically, as shown in Table 1, the treated kidney exhibited lower levels of congestion and tubular degeneration compared to the control kidney. The following qualitative scale was used for evaluation of the obtained slides.

| Lesion | Score |
|---|---|
| Congestion | |
| None: | 0 |
| Mild: | 1 |
| Moderate: | 2 |
| Marked: | 3 |
| Severe: | 4 |
| Tubular degeneration | |
| None: | 0 |
| Mild: | 1 |
| Moderate: | 2 |
| Marked: | 3 |
| Severe: | 4 |

TABLE 1

TABULATED RESULTS

| Animal ID/Organ/ Gross lesion | Slide number | Histologic lesions | | |
|---|---|---|---|---|
| | | Congestion | Tubular hyaline casts | Granulomas |
| 6343/Left Kidney/Nornal | R16-513-1 | 1 | 1 | 0 |
| 6343/Left Kidney/Normal with hemorrhagic streak | R16-513-2 | 1 | 1 | 0 |
| 6343/Right Kidney/Congestion | R16-513-3 | 2 | 2 | 1 |
| 6343/Right Kidney/Congestion | R16-513-4 | 2 | 1 | 1 |

As shown in Table 1, the treated kidney (left kidney) exhibited only mild congestion and tubular degeneration. In contrast, the control kidney (right kidney) exhibited moderate congestion and tubular degeneration. These results were obtained by analysis of the slides discussed below.

Figure 48A:
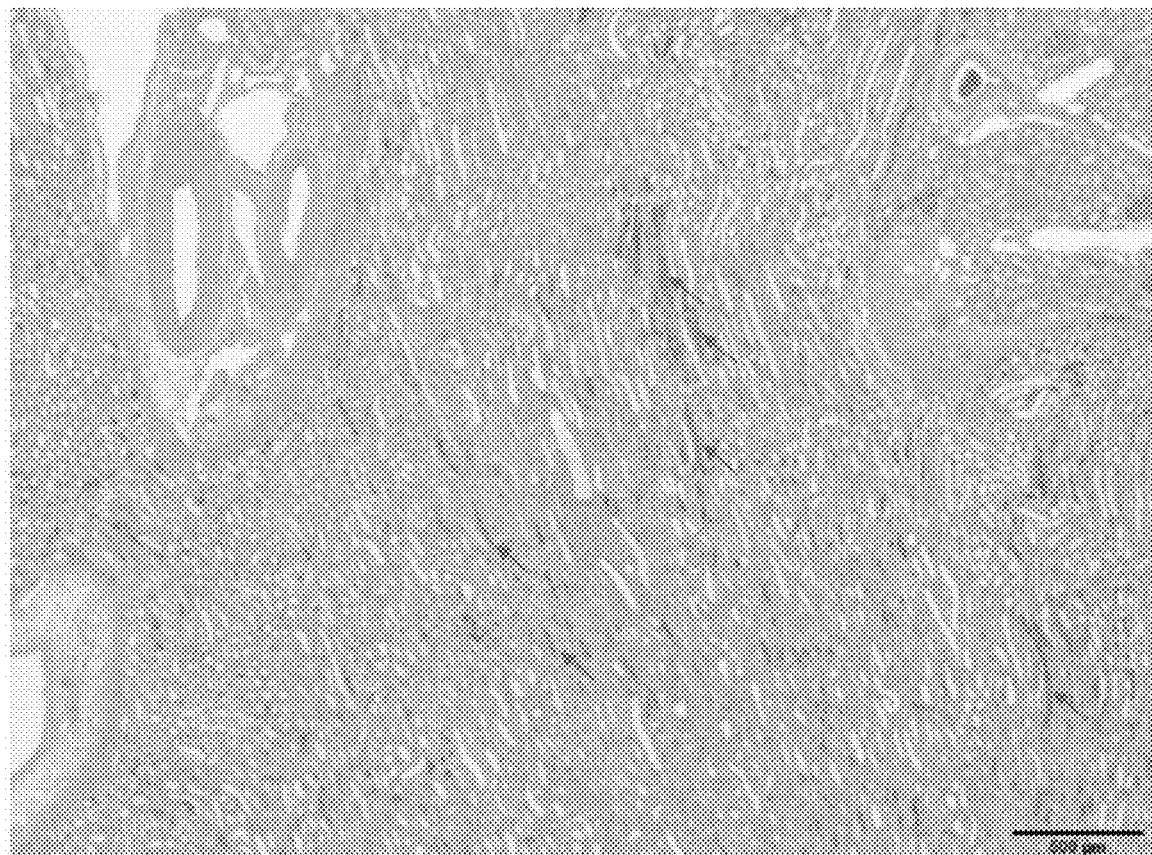
FIG. 48A is a low magnification photomicrograph of kidney tissue from a congested kidney treated with negative pressure therapy.
Figure 48B:
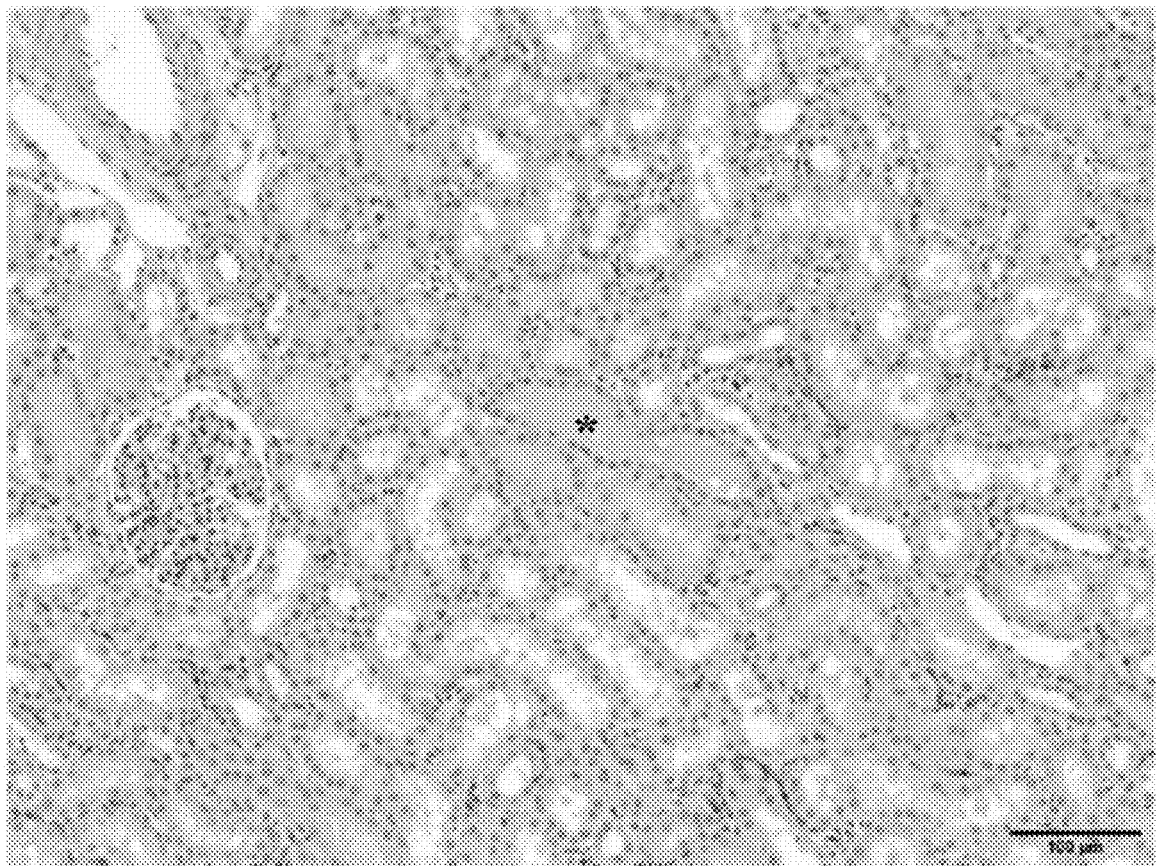
FIG. 48B is a high magnification photomicrograph of the kidney tissue shown in FIG. 48A.

FIGS. 48A and 48B are low and high magnification photomicrographs of the left kidney (treated with negative pressure) of the animal. Based on the histological review, mild congestion in the blood vessels at the corticomedullary junction was identified, as indicated by the arrows. As shown in FIG. 48B, a single tubule with a hyaline cast (as identified by the asterisk) was identified.

Figure 48C:
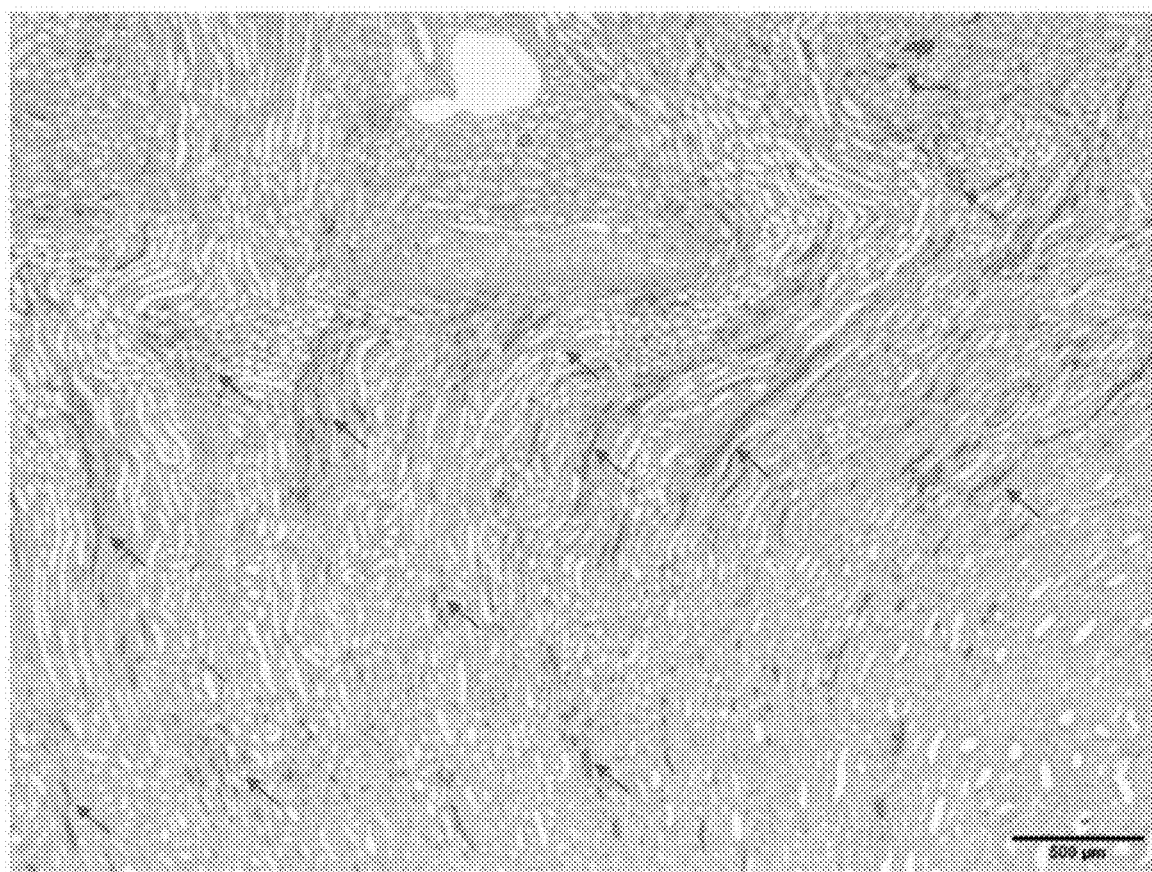
FIG. 48C is a low magnification photomicrograph of kidney tissue from a congested and untreated (e.g., control) kidney.
Figure 48D:
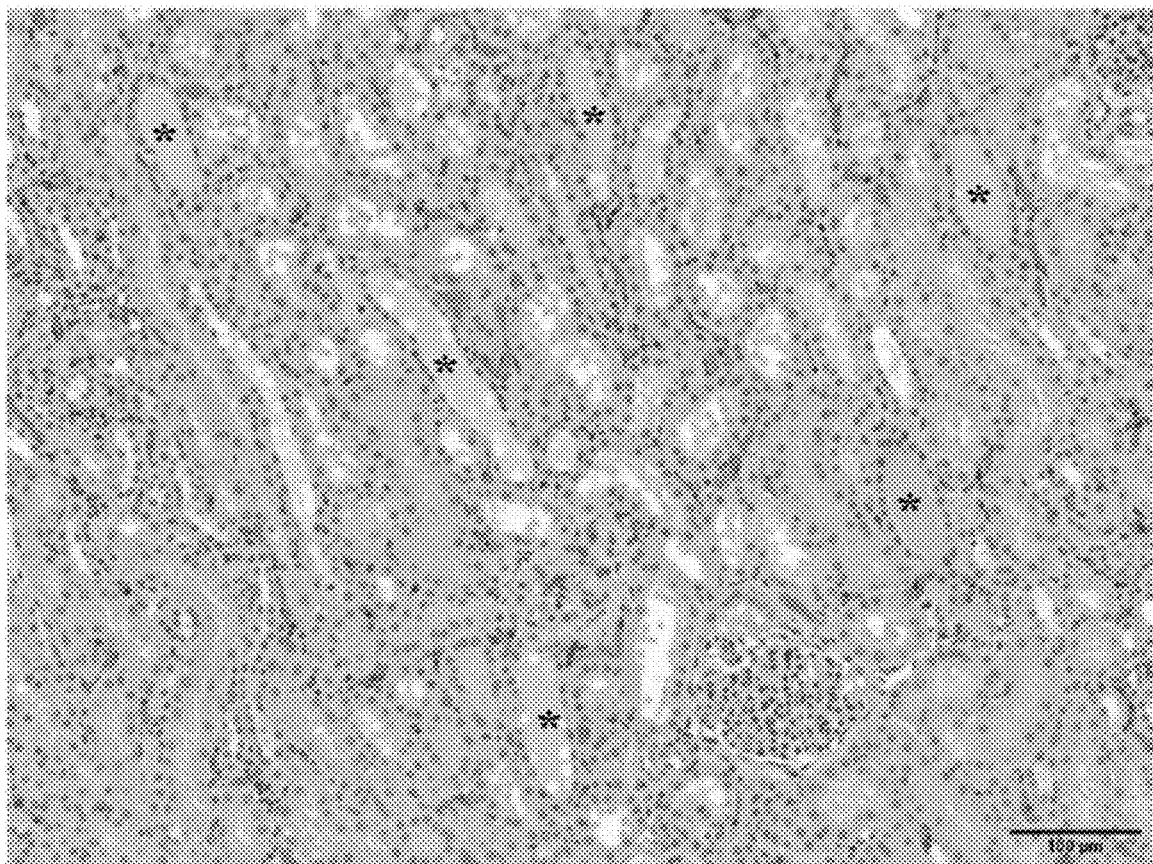
FIG. 48D is a high magnification photomicrograph of the kidney tissue shown in FIG. 23C

FIGS. 48C and 48D are low and high resolution photomicrographs of the control kidney (right kidney). Based on the histological review, moderate congestion in the blood vessel at the corticomedullary junction was identified, as shown by the arrows in FIG. 48C. As shown in FIG. 48D, several tubules with hyaline casts were present in the tissue sample (as identified by asterisks in the image). Presence of a substantial number of hyaline casts is evidence of hypoxia.

Surface mapping analysis provided the following results. The treated kidney was determined to have 1.5 times greater fluid volume in Bowman's space and 2 times greater fluid volume in tubule lumen. Increased fluid volume in Bowman's space and the tubule lumen corresponds to increased urine output. In addition, the treated kidney was determined to have 5 times less blood volume in capillaries compared to the control kidney. The increased volume in the treated kidney appears to be a result of (1) a decrease in individual capillary size compared to the control and (2) an increase in the number of capillaries without visible red blood cells in the treated kidney compared to the control kidney, an indicator of less congestion in the treated organ.

Summary

These results indicate that the control kidney had more congestion and more tubules with intraluminal hyaline casts, which represent protein-rich intraluminal material, compared to the treated kidney. Accordingly, the treated kidney exhibits a lower degree of loss of renal function. While not intending to be bound by theory, it is believed that as severe congestion develops in the kidney, hypoxemia of the organ follows. Hypoxemia interferes with oxidative phosphorylation within the organ (e.g., ATP production). Loss of ATP and/or a decrease in ATP production inhibits the active transport of proteins causing intraluminal protein content to increase, which manifests as hyaline casts. The number of renal tubules with intraluminal hyaline casts correlates with the degree of loss of renal function. Accordingly, the reduced number of tubules in the treated left kidney is believed to be physiologically significant. While not intending to be bound by theory, it is believed that these results show that damage to the kidney can be prevented or inhibited by applying negative pressure to a ureteral catheter inserted into the renal pelvis to facilitate urine output.

Example 2

Method

Four (4) farm swine (A, B, C, D) were sedated and anesthetized. Vitals for each of the swine were monitored throughout the experiment and cardiac output was measured at the end of each 30-minute phase of the study. Ureteral catheters, such as the ureteral catheter 112 shown in FIGS. 2A and 2B, were deployed in the renal pelvis region of the kidneys of each of the swine. The deployed catheters were a 6 Fr catheter having an outer diameter of 2.0±0.1 mm. The catheters were 54±2 cm in length, not including the distal retention portion. The retention portion was 16±2 mm in length. As shown in the catheter 112 in FIGS. 2A and 2B, the retention portion included two full coils and one proximal half coil. The outer diameter of the full coils, shown by line D1 in FIGS. 2A and 2B, was 18±2 mm. The half coil diameter D2 was about 14 mm. The retention portion of the deployed ureteral catheters included six drainage openings, plus an additional opening at the distal end of the catheter tube. The diameter of each of the drainage openings was 0.83±0.01 mm. The distance between adjacent drainage openings 132, specifically the linear distance between drainage openings when the coils were straightened, was 22.5±2.5 mm.

The ureteral catheters were positioned to extend from the renal pelvis of the swine, through the bladder, and urethra, and to fluid collection containers external to each swine. Following placement of the ureteral catheters, pressure sensors for measuring IVC pressure were placed in the IVC at a position distal to the renal veins. An inflatable balloon catheter, specifically a PTS® percutaneous balloon catheter (30 mm diameter by 5 cm length), manufactured by NuMED Inc. of Hopkinton, NY, was expanded in the IVC at a position proximal to the renal veins. A thermodilution catheter, specifically a Swan-Ganz thermodilution pulmonary artery catheter manufactured by Edwards Lifesciences Corp. of Irvine, CA, was then placed in the pulmonary artery for the purpose of measuring cardiac output.

Initially, baseline urine output was measured for 30 minutes, and blood and urine samples were collected for biochemical analysis. Following the 30-minute baseline period, the balloon catheter was inflated to increase IVC pressure from a baseline pressure of 1-4 mmHg to an elevated congested pressure of about 20 mmHg (+/−5 mmHg). A congestion baseline was then collected for 30 minutes with corresponding blood and urine analysis.

At the end of the congestion period, the elevated congested IVC pressure was maintained and negative pressure diuresis treatment was provided for swine A and swine C. Specifically, the swine (A, C) were treated by applying a negative pressure of −25 mmHg through the ureteral catheters with a pump. As in previously-discussed examples, the pump was an Air Cadet Vacuum Pump from Cole-Parmer Instrument Company (Model No. EW-07530-85). The pump was connected in series to a regulator. The regulator was a V-800 Series Miniature Precision Vacuum Regulator—⅛ NPT Ports (Model No. V-800-10-W/K), manufactured by Airtrol Components Inc. The swine were observed for 120 minutes, as treatment was provided. Blood and urine collection were performed every 30 minutes, during the treatment period. Two of the swine (B, D) were treated as congested controls (e.g., negative pressure was not applied to the renal pelvis through the ureteral catheters), meaning that the two swine (B, D) did not receive negative pressure diuresis therapy.

Following collection of urine output and creatinine clearance data for the 120-minute treatment period, the animals were sacrificed and kidneys from each animal were subjected to gross examination. Following gross examination, histological sections were obtained and examined, and magnified images of the sections were captured.

Results

Measurements collected during the Baseline, Congestion, and Treatment periods are provided in Table 2. Specifically, urine output, serum creatinine, and urinary creatinine measurements were obtained for each time period. These values allow for the calculation of a measured creatinine clearance as follows:

Creatinine Clearance: $CrCl =$ $$\text{Urine Output (ml/min)} * \frac{\text{Urinary Creatinine (mg/dl)}}{\text{Serum Creatinine (mg/dl)}}$$

In addition, Neutrophil gelatinase-associated lipocalin (NGAL) values were measured from serum samples obtained for each time period and Kidney Injury Molecule 1 (KIM-1) values were measured from the urine samples obtained for each time period. Qualitative histological findings determined from review of the obtained histological sections are also included in Table 2.

ciated with an 80% reduction in urine output rate (0.5 ml/min) and an 83% reduction in CrCl (30 ml/min). At 50 minutes into the congestion (20 minutes after the congestion baseline period), the animal experienced an abrupt drop in mean arterial pressure and respiration rate, followed by

TABLE 2

|  | Animal | | | |
|---|---|---|---|---|
|  | A | B | C | D |
|  | Treatment assignment | | | |
|  | Treatment | Control | Treatment | Control |
| Baseline: | | | | |
| Urine output (ml/min) | 3.01 | 2.63 | 0.47 | 0.98 |
| Serum creatinine (mg/dl) | 0.8 | 0.9 | 3.2 | 1.0 |
| Creatinine clearance (ml/min) | 261 | 172 | 5.4 | 46.8 |
| Serum NGAL (ng/ml) | 169 | * | 963 | 99 |
| Urinary KIM-1 (ng/ml) | 4.11 | * | 3.59 | 1.16 |
| Congestion: | | | | |
| Urine output (ml/min) | 0.06 (2%) | 0.53 (20%) | 0.12 (25%) | 0.24 (25%) |
| Serum creatinine (mg/dl) | 1.2 (150%) | 1.1 (122%) | 3.1 (97%) | 1.2 (120%) |
| Creatinine clearance (ml/min) | 1.0 (0.4%) | 30.8 (18%) | 1.6 (21%) | 16.2 (35%) |
| Serum NGAL (ng/ml) | 102 (60%) | * | 809 (84%) | 126 (127%) |
| Urinary KIM-1 (ng/ml) | 24.3 (591%) | * | 2.2 (61%) | 1.39 (120%) |
| Treatment: | | | | |
| Urine output (ml/min) | 0.54 (17%) |  | 0.47 (101%) | 0.35 (36%) |
| Serum creatinine (mg/dl) | 1.3 (163%) |  | 3.1 (97%) | 1.7 (170%) |
| Creatinine clearance (ml/min) | 30.6 (12%) | ** | 18.3 (341%) | 13.6 (29%) |
| Serum NGAL (ng/ml) | 197 (117%) |  | 1104 (115%) | 208 (209%) |
| Urinary KIM-1 (ng/ml) | 260 (6326%) |  | 28.7 (799%) | 233 (20000%) |
| Histological findings: | | | | |
| Blood volume in capillary space | 2.4% |  | 0.9% | 4.0% |
| Hyaline casts | Mild/Mod | ** | None | Mod |
| Degranulation | Mild/Mod |  | None | Mod |

Data are raw values (% baseline)
* not measured
** confounded by phenylephrine

Animal A: The animal weighed 50.6 kg and had a baseline urine output rate of 3.01 ml/min, a baseline serum creatinine of 0.8 mg/dl, and a measured CrCl of 261 ml/min. It is noted that these measurements, aside from serum creatinine, were uncharacteristically high relative to other animals studied. Congestion was associated with a 98% reduction in urine output rate (0.06 ml/min) and a >99% reduction in CrCl (1.0 ml/min). Treatment with negative pressure applied through the ureteral catheters was associated with urine output and CrCl of 17% and 12%, respectively, of baseline values, and 9× and >10×, respectively, of congestion values. Levels of NGAL changed throughout the experiment, ranging from 68% of baseline during congestion to 258% of baseline after 90 minutes of therapy. The final value was 130% of baseline. Levels of KIM-1 were 6 times and 4 times of baseline for the first two 30-minute windows after baseline assessment, before increasing to 68×, 52×, and 63× of baseline values, respectively, for the last three collection periods. The 2-hour serum creatinine was 1.3 mg/dl. Histological examination revealed an overall congestion level, measured by blood volume in capillary space, of 2.4%. Histological examination also noted several tubules with intraluminal hyaline casts and some degree of tubular epithelial degeneration, a finding consistent with cellular damage.

Animal B: The animal weighed 50.2 kg and had a baseline urine output rate of 2.62 ml/min and a measured CrCl of 172 ml/min (also higher than anticipated). Congestion was associated with an 80% reduction in urine output rate (0.5 ml/min) and an 83% reduction in CrCl (30 ml/min). At 50 minutes into the congestion (20 minutes after the congestion baseline period), the animal experienced an abrupt drop in mean arterial pressure and respiration rate, followed by tachycardia. The anesthesiologist administered a dose of phenylephrine (75 mg) to avert cardiogenic shock. Phenylephrine is indicated for intravenous administration when blood pressure drops below safe levels during anesthesia. However, since the experiment was testing the impact of congestion on renal physiology, administration of phenylephrine confounded the remainder of the experiment.

Animal C: The animal weighed 39.8 kg and had a baseline urine output rate of 0.47 ml/min, a baseline serum creatinine of 3.2 mg/dl, and a measured CrCl of 5.4 ml/min. Congestion was associated with a 75% reduction in urine output (0.12 ml/min) and a 79% reduction in CrCl (1.6 ml/min). It was determined that baseline NGAL levels were >5× the upper limit of normal (ULN). Treatment with negative pressure applied to the renal pelvis through the ureteral catheters was associated with a normalization of urine output (101% of baseline) and a 341% improvement in CrCl (18.2 ml/min). Levels of NGAL changed throughout the experiment, ranging from 84% of baseline during congestion to 47% to 84% of baseline between 30 and 90 minutes. The final value was 115% of baseline. Levels of KIM-1 decreased 40% from baseline within the first 30 minutes of congestion, before increasing to 8.7×, 6.7×, 6.6×, and 8× of baseline values, respectively, for the remaining 30-minute windows. Serum creatinine level at 2 hours was 3.1 mg/dl. Histological examination revealed an overall congestion level, measured by blood volume in capillary space, of 0.9%. The tubules were noted to be histologically normal.

Animal D: The animal weighed 38.2 kg and had a baseline urine output of 0.98 ml/min, a baseline serum creatinine of 1.0 mg/dl, and a measured CrCl of 46.8 ml/min. Congestion was associated with a 75% reduction in urine output rate (0.24 ml/min) and a 65% reduction in Cr Cl (16.2 ml/min). Continued congestion was associated with a 66% to 91% reduction of urine output and 89% to 71% reduction in CrCl. Levels of NGAL changed throughout the experiment, ranging from 127% of baseline during congestion to a final value of 209% of baseline. Levels of KIM-1 remained between 1× and 2× of baseline for the first two 30-minute windows after baseline assessment, before increasing to 190×, 219×, and 201× of baseline values for the last three 30-minute periods. The 2-hour serum creatinine level was 1.7 mg/dl. Histological examination revealed an overall congestion level 2.44× greater than that observed in tissue samples for the treated animals (A, C) with an average capillary size 2.33 times greater than that observed in either of the treated animals. The histological evaluation also noted several tubules with intraluminal hyaline casts as well as tubular epithelial degeneration, indicating substantial cellular damage.

Summary

While not intending to be bound by theory, it is believed that the collected data supports the hypothesis that venous congestion creates a physiologically significant impact on renal function. In particular, it was observed that elevation of the renal vein pressure reduced urine output by 75% to 98% within seconds. The association between elevations in biomarkers of tubular injury and histological damage is consistent with the degree of venous congestion generated, both in terms of magnitude and duration of the injury.

The data also appears to support the hypothesis that venous congestion decreases the filtration gradients in the medullary nephrons by altering the interstitial pressures. The change appears to directly contribute to the hypoxia and cellular injury within medullary nephrons. While this model does not mimic the clinical condition of AKI, it does provide insight into the mechanical sustaining injury.

The data also appears to support the hypothesis that applying negative pressure to the renal pelvis through ureteral catheters can increase urine output in a venous congestion model. In particular, negative pressure treatment was associated with increases in urine output and creatinine clearance that would be clinically significant. Physiologically meaningful decreases in medullary capillary volume and smaller elevations in biomarkers of tubular injury were also observed. Thus, it appears that by increasing urine output rate and decreasing interstitial pressures in medullary nephrons, negative pressure therapy may directly decrease congestion. While not intending to be bound by theory, by decreasing congestion, it may be concluded that negative pressure therapy reduces hypoxia and its downstream effects within the kidney in a venous congestion mediated AKI.

The experimental results appear to support the hypothesis that the degree of congestion, both in terms of the magnitude of pressure and duration, is associated with the degree of cellular injury observed. Specifically, an association between the degree of urine output reduction and the histological damage was observed. For example, treated Swine A, which had a 98% reduction in urine output, experienced more damage than treated Swine C, which had a 75% reduction in urine output. As would be expected, control Swine D, which was subjected to a 75% reduction in urine output without benefit of therapy for two and a half hours, exhibited the most histological damage. These findings are broadly consistent with human data demonstrating an increased risk for AKI onset with greater venous congestion. See e.g., Legrand, M. et al., Association between systemic hemodynamics and septic acute kidney injury in critically ill patients: a retrospective observational study. *Critical Care* 17:R278-86, 2013.

Example 3

Method

Inducement of negative pressure within the renal pelvis of farm swine using ureteral catheters was performed for the purpose of evaluating effects of negative pressure therapy on hemodilution of the blood. An objective of these studies was to demonstrate whether a negative pressure delivered into the renal pelvis significantly increases urine output in a swine model of fluid resuscitation.

Two pigs were sedated and anesthetized using ketamine, midazolam, isoflurane and propofol. One animal (#6543) was treated with a ureteral catheter and negative pressure therapy as described herein. The other, which received a Foley type bladder catheter, served as a control (#6566). Following placement of the ureteral catheters, the animals were transferred to a sling and monitored for 24 hours.

Fluid overload was induced in both animals with a constant infusion of saline (125 mL/hour) during the 24 hour follow-up. Urine output volume was measured at 15 minute increments for 24 hours. Blood and urine samples were collected at 4 hour increments. As shown in FIG. 21, a therapy pump 818 was set to induce negative pressure within the renal pelvis 820, 821 (shown in FIG. 21) of both kidneys using a pressure of −45 mmHg (+/−2 mmHg).

Results

Both animals received 7 L of saline over the 24 hour period. The treated animal produced 4.22 L of urine while the control produced 2.11 L. At the end of 24 hours, the control had retained 4.94 L of the 7 L administered, while the treated animal retained 2.81 L of the 7 L administered. FIG. 26 illustrates the change in serum albumin. The treated animal had a 6% drop in the serum albumin concentration over 24 hours, while the control animal had a 29% drop.

Summary

While not intending to be bound by theory, it is believed that the collected data supports the hypothesis that fluid overload induces clinically significant impact on renal function and, consequently induces hemodilution. In particular, it was observed that administration of large quantities of intravenous saline cannot be effectively removed by even healthy kidneys. The resulting fluid accumulation leads to hemodilution. The data also appears to support the hypothesis that applying negative pressure diuresis therapy using ureteral catheters to fluid overloaded animals can increase urine output, improve net fluid balance and decrease the impact of fluid resuscitation on development of hemodilution.

The preceding examples and embodiments of the invention have been described with reference to various examples. Modifications and alterations will occur to others upon reading and understanding the foregoing examples. Accordingly, the foregoing examples are not to be construed as limiting the disclosure.

What is claimed is:

1. A percutaneous urinary catheter configured to be deployed in a urinary tract, comprising:
  (a) a proximal portion; and
  (b) a distal portion comprising a retention portion configured to be deployed in a kidney and/or a renal pelvis, the retention portion comprising one or more drainage holes leading to one or more lumen(s) within the proximal portion, wherein the retention portion, when deployed, defines a three-dimensional shape sized and positioned to maintain patency of fluid flow between the kidney and/or renal pelvis and a proximal end of the catheter by inhibiting mucosal tissue from appreciably occluding the one or more drainage holes when negative pressure is applied through the catheter.

2. The percutaneous urinary catheter of claim 1, wherein the retention portion is configured to retain at least the distal portion of the catheter within the kidney and/or renal pelvis.

3. The percutaneous urinary catheter of claim 1, wherein a maximum outer diameter of the retention portion is greater than a diameter of a drainage lumen of the catheter.

4. The percutaneous urinary catheter of claim 1, wherein an area of a two-dimensional slice of the three-dimensional shape in a plane transverse to a central axis of the retention portion is greater than another slice of the three-dimensional shape in a plane transverse to a central axis of the retention portion towards a distal end of the retention portion.

5. The percutaneous urinary catheter of claim 1, wherein a maximum cross-sectional area of a two-dimensional slice of the three-dimensional shape in a plane transverse to a central axis of the retention portion is less than or equal to about 500 mm$^2$.

6. The percutaneous urinary catheter of claim 1, wherein the retention portion comprises a distal end sized to be positioned in the renal pelvis.

7. The percutaneous urinary catheter of claim 1, wherein the retention portion comprises at least a first coil having a first diameter and at least a second coil having a second diameter, the first diameter being greater than the second diameter.

8. The percutaneous urinary catheter of claim 7, wherein the first coil is closer to the proximal portion of the catheter than is the second coil.

9. The percutaneous urinary catheter of claim 1, wherein the retention portion comprises a plurality of coils, and wherein a distal-most coil of the plurality of coils has a smaller diameter than other coils of the plurality of coils.

10. The percutaneous urinary catheter of claim 9, wherein the retention portion comprises a straight portion extending through the retention portion, and wherein the plurality of coils are wrapped around the straight portion.

11. The percutaneous urinary catheter of claim 1, wherein the retention portion comprises a radially inwardly facing side comprising the one or more drainage holes, and a radially outwardly facing side that is essentially free of drainage holes.

12. The percutaneous urinary catheter of claim 1, wherein the retention portion is coextensive with other portions of the catheter.

13. The percutaneous urinary catheter of claim 1, wherein an axial length of the retention portion from a proximal end to a distal end thereof is from about 5 mm to about 100 mm.

14. The percutaneous urinary catheter of claim 1, wherein the one or more drainage holes have a diameter ranging from 0.0005 mm to about 2.0 mm.

15. The percutaneous urinary catheter of claim 1, wherein the catheter comprises an elongated tube extending from a proximal end of the proximal portion to a distal end of the distal portion.

16. The percutaneous urinary catheter of claim 15, wherein the elongated tube is from about 30 cm to about 60 cm in length.

17. The percutaneous urinary catheter of claim 15, wherein the elongated tube has an outer diameter of from about 1.0 mm to about 10.0 mm, and/or an inner diameter of about 0.5 mm to about 9.5 mm.

18. The percutaneous urinary catheter of claim 1, wherein a proximal end of the proximal portion of the catheter is configured to be connected to a negative pressure source for applying the negative pressure through the catheter.

19. The percutaneous urinary catheter of claim 1, wherein the proximal portion is essentially free of or free of drainage holes.

20. The percutaneous urinary catheter of claim 1, wherein the percutaneous urinary catheter is configured to be deployed in a urinary tract of a patient, wherein the patient is a human.

21. The percutaneous urinary catheter of claim 1, wherein the percutaneous urinary catheter is configured to be deployed in a urinary tract of a patient, wherein the patient is an animal.

22. The percutaneous urinary catheter of claim 1, wherein the percutaneous urinary catheter is configured to be deployed in a urinary tract of a patient, wherein the patient is a dog.

23. The percutaneous urinary catheter of claim 1, wherein the proximal portion is configured to pass through a percutaneous opening in the kidney or renal pelvis.

24. The percutaneous urinary catheter of claim 1, wherein the proximal portion is configured to pass through only a single percutaneous opening in the kidney or renal pelvis.

25. A system for inducing negative pressure in a portion of a urinary tract, the system comprising:
  (a) a percutaneous urinary catheter configured to be deployed in a urinary tract, comprising:
    (i) a proximal portion; and
    (ii) a distal portion comprising a retention portion configured to be deployed in a kidney and/or a renal pelvis, the retention portion comprising one or more drainage holes leading to one or more lumen(s) within the proximal portion,
  wherein the retention portion, when deployed, defines a three-dimensional shape sized and positioned to maintain patency of fluid flow between the kidney and/or renal pelvis and a proximal end of the catheter by inhibiting mucosal tissue from appreciably occluding the one or more drainage holes when negative pressure is applied through the catheter; and
  (b) a negative pressure source in fluid communication with the lumen, the negative pressure source being configured for inducing a negative pressure in a portion of the urinary tract to draw fluid through the lumen of the catheter.

26. The system of claim 25, wherein the negative pressure source is a pump.

27. The system of claim 26, wherein the pump is configured to generate positive or negative pressure in a proximal end of the lumen.

28. The system of claim 26, wherein the pump applies a negative pressure of about 100 mmHg or less to a proximal end of the lumen.

29. The system of claim 26, wherein the pump is configured to operate at one of three pressure levels, the pressure levels generating a negative pressure of 2 to 125 mmHg.

30. The system of claim 26, wherein the pump is configured to alternate between generating negative pressure and generating positive pressure.

31. The system of claim 26, wherein the pump has an accuracy of about 10 mmHg or less.

32. The system of claim 26, further comprising a controller configured to regulate the positive and/or negative pressure provided by the pump within a pressure range that facilitates increased urine production from the kidney.

33. The system of claim 32, further comprising one or more physiological sensors configured to provide information representative of at least one physical parameter to the controller, and wherein the controller is configured to actuate or cease operation of the pump based on the information representative of the at least one physical parameter.

34. A negative pressure therapy system for increasing urine production, the negative pressure therapy system comprising:
(a) a pump assembly, the pump assembly comprising:
  (i) a pump configured to provide positive or negative pressure to a kidney, and
  (ii) a controller configured to regulate the positive or negative pressure provided by the pump within a pressure range that facilitates increased urine production from the kidney,
(b) at least one percutaneous urinary catheter configured to be deployed in a urinary tract, comprising:
  (i) a proximal portion; and
  (ii) a distal portion comprising a retention portion configured to be deployed in a kidney and/or a renal pelvis, the retention portion comprising one or more drainage holes leading to one or more lumen(s) within the proximal portion,
wherein the retention portion, when deployed, defines a three-dimensional shape sized and positioned to maintain patency of fluid flow between the kidney and/or renal pelvis and a proximal end of the catheter by inhibiting mucosal tissue from appreciably occluding the one or more drainage holes when negative pressure is applied through the catheter.

35. A method for removing fluid from a urinary tract of a patient, the method comprising:
inserting a percutaneous urinary catheter through a percutaneous opening and into a kidney and/or renal pelvis; and
deploying a retention portion of the catheter within the kidney and/or renal pelvis to maintain patency of fluid flow from the kidney through at least a portion of the catheter, wherein the catheter comprises:
  (i) a proximal portion; and
  (ii) a distal portion comprising a retention portion configured to be deployed in the kidney and/or the renal pelvis, the retention portion comprising one or more drainage holes leading to one or more lumen(s) within the proximal portion, and
wherein the retention portion, when deployed, defines a three-dimensional shape sized and positioned to maintain patency of fluid flow between the kidney and/or renal pelvis and a proximal end of the catheter by inhibiting mucosal tissue from appreciably occluding the one or more drainage holes when negative pressure is applied through the catheter.

36. The method of claim 35, wherein inserting the percutaneous urinary catheter through the percutaneous opening comprises:
inserting a needle of the percutaneous catheter into a portion of the patient's body to create the percutaneous opening;
inserting the needle into a kidney and advancing the needle through the kidney to the renal pelvis; and
inserting an elongated tube of the percutaneous catheter over the needle, such that a distal end of the elongated tube advances from the kidney into the renal pelvis.

37. The method of claim 36, wherein inserting the percutaneous urinary catheter comprises inserting the needle of the percutaneous catheter into the abdominal region.

38. The method of claim 35, further comprising attaching a proximal end of the percutaneous urinary catheter directly or indirectly to a fluid pump and applying a negative pressure to a proximal end of the proximal portion of the urinary catheter by actuating the pump, thereby inducing the negative pressure in the kidney and/or renal pelvis.

\* \* \* \* \*